United States Patent
Andrews et al.

(10) Patent No.: US 12,404,304 B1
(45) Date of Patent: Sep. 2, 2025

(54) TELOMERASE REVERSE TRANSCRIPTASE (TERT) EXPRESSION ENHANCING COMPOUNDS AND METHODS FOR USING THE SAME

(71) Applicant: Sierra Sciences, LLC, Reno, NV (US)

(72) Inventors: William H. Andrews, Reno, NV (US); Christopher A. Foster, Carmichael, CA (US); Lancer K. Brown, Sparks, NV (US); Laura A. Briggs, Reno, NV (US); October Pawlik, Sparks, NV (US); Penelope Burke, Reno, NV (US); Federico C. A. Gaeta, Mountain View, CA (US); Beril Karakas, Reno, NV (US); Jessica Wheeler, Sparks, NV (US); Mieczyslaw A. Piatyszek, Morgan Hill, CA (US); Munirathnam Chaguturu, Lawrence, KS (US); Jian Zhang, Fremont, CA (US); Tom Kerley, Gardnerville, NV (US); Hamid Mohammadpour, Reno, NV (US)

(73) Assignee: Sierra Sciences, LLC, Reno, NV (US)

( * ) Notice: Subject to any disclaimer, the term of this patent is extended or adjusted under 35 U.S.C. 154(b) by 0 days.

(21) Appl. No.: 16/879,075

(22) Filed: May 20, 2020

Related U.S. Application Data

(63) Continuation of application No. 14/163,983, filed on Jan. 24, 2014, now abandoned, which is a continuation of application No. 12/727,086, filed on Mar. 18, 2010, now abandoned, which is a continuation-in-part of application No. 12/578,512, filed on Oct. 13, 2009, now abandoned, and a continuation-in-part of application No. 12/270,552, filed on Nov. 13, 2008, now abandoned.
(Continued)

(51) Int. Cl.
| | |
|---|---|
| C07D 413/14 | (2006.01) |
| C07D 215/06 | (2006.01) |
| C07D 231/22 | (2006.01) |
| C07D 279/02 | (2006.01) |
| C07D 401/04 | (2006.01) |
| C07D 401/06 | (2006.01) |
| C07D 401/12 | (2006.01) |
| C07D 403/04 | (2006.01) |
| C07D 405/06 | (2006.01) |
| C07D 409/06 | (2006.01) |
| C07D 413/04 | (2006.01) |
| C07D 417/04 | (2006.01) |
| C07D 417/12 | (2006.01) |
| C07D 417/14 | (2006.01) |
| C07D 471/04 | (2006.01) |
| C07D 487/04 | (2006.01) |
| C07D 493/08 | (2006.01) |
| C07D 498/04 | (2006.01) |
| C07D 513/04 | (2006.01) |
| C07H 17/04 | (2006.01) |
| C07K 9/00 | (2006.01) |
| C12N 15/01 | (2006.01) |

(52) U.S. Cl.
CPC ............ *C07K 9/003* (2013.01); *C07D 215/06* (2013.01); *C07D 231/22* (2013.01); *C07D 279/02* (2013.01); *C07D 401/04* (2013.01); *C07D 401/06* (2013.01); *C07D 401/12* (2013.01); *C07D 403/04* (2013.01); *C07D 405/06* (2013.01); *C07D 409/06* (2013.01); *C07D 413/04* (2013.01); *C07D 413/14* (2013.01); *C07D 417/04* (2013.01); *C07D 417/12* (2013.01); *C07D 417/14* (2013.01); *C07D 471/04* (2013.01); *C07D 487/04* (2013.01); *C07D 493/08* (2013.01); *C07D 498/04* (2013.01); *C07D 513/04* (2013.01); *C07H 17/04* (2013.01); *C12N 15/01* (2013.01)

(58) Field of Classification Search
CPC ........................... C07D 413/04; C07D 413/14
See application file for complete search history.

(56) References Cited

U.S. PATENT DOCUMENTS

| | | |
|---|---|---|
| 4,940,575 A | 7/1990 | Zysman et al. |
| 6,686,159 B2 | 2/2004 | Andrews et al. |
| (Continued) | | |

FOREIGN PATENT DOCUMENTS

| | | | | |
|---|---|---|---|---|
| WO | WO-0130771 A1 * | 5/2001 | ............. | A61P 35/00 |
| WO | WO2002016657 A1 | 2/2002 | | |
| (Continued) | | | | |

OTHER PUBLICATIONS

Imanishi et al.; "Oxidized Low-Density Lipoprotein Induces Endothelial Progenitor Cell Senescence, Leading to Cellular Dysfunction"; 2004; Clinical and Experimental Pharmacology and Physiology; 31: 407-413 (Year: 2004).*
(Continued)

*Primary Examiner* — Timothy P Thomas
(74) *Attorney, Agent, or Firm* — Todd Esker; Bret E. Field; Bozicevic, Field & Francis LLP

(57) ABSTRACT

Telomerase reverse transcriptase (TERT) expression enhancing compounds, and methods for using the same, are provided. In some embodiments, the compounds are azoles, such as such as pyrazoles, imidazoles, triazoles, tetrazoles, thiazoles, isothiazoles, oxazoles, and isoxazoles. In certain embodiments, the azole compound includes an acyl substituent which includes an amide, for example, an alkyl amide. Methods of interest include contacting cells with a TERT expression enhancing effective amount of compound to increase TERT expression in the cells. These compounds and methods find use in a variety of applications in which increased expression of telomerase reverse transcriptase is desired.

4 Claims, No Drawings
Specification includes a Sequence Listing.

Related U.S. Application Data

(60) Provisional application No. 61/182,931, filed on Jun. 1, 2009, provisional application No. 61/104,997, filed on Oct. 13, 2008, provisional application No. 60/988,043, filed on Nov. 14, 2007.

(56) References Cited

U.S. PATENT DOCUMENTS

| | | | |
|---|---|---|---|
| 7,211,435 | B2 | 5/2007 | Andrews et al. |
| 7,226,744 | B2 | 6/2007 | Andrews et al. |
| 7,279,328 | B1 | 10/2007 | Andrews et al. |
| 7,619,091 | B2 | 11/2009 | Barnham et al. |
| 2009/0143451 | A1* | 6/2009 | Andrews .............. A61K 31/422 435/375 |

FOREIGN PATENT DOCUMENTS

| | | | |
|---|---|---|---|
| WO | WO2002016658 | A1 | 2/2002 |
| WO | WO2002070668 | A2 | 9/2002 |
| WO | WO2002072787 | A2 | 9/2002 |
| WO | WO2002090570 | A2 | 11/2002 |
| WO | WO2002090571 | A2 | 11/2002 |
| WO | WO2002101010 | A2 | 12/2002 |
| WO | WO2003000916 | A2 | 1/2003 |
| WO | WO2003016474 | A2 | 2/2003 |
| WO | WO2004007461 | A1 | 1/2004 |
| WO | WO2007078113 | A1 | 7/2007 |
| WO | WO-2008046072 | A2 * | 4/2008 ........... A61K 31/415 |

OTHER PUBLICATIONS

He et al.; "Inhibition of Human Telomerase Reverse Transcriptase by Nonsteroidal Antiinflammatory Drugs in Colon Carcinoma"; Mar. 2006; Cancer; 106(6): 1243-9 (Year: 2006).*

Shin-Ya; "Novel Antitumor and Neuroprotective Substances Discovered by Characteristic Screenings Based on Specific Molecular Targets"; 2005; Biosci. Biotechnol. Biochem.; 69(5): 867-872 (Year: 2005).*

Akama et al.; WO 2001/030771 A1; English abstract supplied by CAPLUS Accession No. 2001:319884 (Year: 2001).*

Yuan et al.; "Mechanisms underlying the activation of TERT transcription and telomerase activity in human cancer: old actors and new players"; 2019; Oncogene; 38: 6172-6183; https://doi.org/10.1038/s41388-019-0872-9 (Year: 2019).*

Cannon, Chaper Nineteen in Burger's Medicinal Chemistry and Drug Discovery, Fifth Edition, vol. 1: Principles and Practice, Wiley-Interscience 1995, pp. 783-802.

He et al., Inhibition of Human Telomerase Reverse Transcriptase by Nonsteroidal Antiinflammatory Drugs in Colon Carcinoma; Mar. 2006; Cancer; 106(6): 1243-9.

Manishi et al., Oxidized Low-Density Lipoprotein Induces Endothelial Progenitor Cell Senescence, Leading to Cellular Dysfunction; 2004; Clinical and Experimental Pharmacology and Physiology; 31: 407-413.

Merriam Webster: Azole; http://merriam-webster.com/dictionary/azole; accessed Mar. 8, 2013.

Poma et al., The antitumor activities of curcumin and of its isoxazole analogue are not affected by multiple gene expression changes in an MDR model of the MCF-7 breast cancer cell line: analysis of the possible molecular basis, Int J Mol Med. Sep. 2007;20(3):329-35.

Chneider, J. et al., Small-molecule activation of neuronal cell fate:, Nature Chemical Biology 4, (2008) p. 408-410 (4).

Shin-Ya, Novel Antitumor and Neuroprotective Substances Discovered by Characteristic Screenings Based on Specific Molecular Targets; 2005; Biosci. Biotechnol. Biochem.; 69(5): 867-872.

Weuinrich et al., Reconstitution of human telomerase with the template RNA component hTR and the catalytic protein subunit hTRT, Nat Genet. Dec. 1997;17(4):498-502.

Wong et al., A yeast chemical genetic screen identifies inhibitors of human telomerase, Chem Biol. Mar. 21, 2013;20(3):333-40.

Zhu et al., Cellular senescence in human myoblasts is overcome by human telomerase reverse transcriptase and cyclindependent kinase 4: consequences in aging muscle and therapeutic strategies for muscular dystrophies; 2007; Aging Cell; 6: 515-523.

Burger's Medicinal Chemistry and Drug Discovery, Fifth Edition, vol. 1: Principles and Practice, Wiley-Interscience, pp. 783-802, 1995.

* cited by examiner

SEQUENCE LISTING

<160> NUMBER OF SEQ ID NOS: 4

<210> SEQ ID NO 1
<211> LENGTH: 41
<212> TYPE: DNA
<213> ORGANISM: Human

<400> SEQUENCE: 1
ggccccgccc tctcctcgcg gcgcgagttt caggcagcgc t     41

<210> SEQ ID NO 2
<211> LENGTH: 13
<212> TYPE: DNA
<213> ORGANISM: human

<400> SEQUENCE: 2

```
ggcgcgagtt tca                                                           13

<210> SEQ ID NO 3
<211> LENGTH: 10
<212> TYPE: DNA
<213> ORGANISM: human

<400> SEQUENCE: 3
cgcgagtttc                                                               10

<210> SEQ ID NO 4
<211> LENGTH: 21
<212> TYPE: DNA
<213> ORGANISM: human

<400> SEQUENCE: 4
ggcgcgagtt tcaggcagcg c                                                  21
```

TELOMERASE REVERSE TRANSCRIPTASE (TERT) EXPRESSION ENHANCING COMPOUNDS AND METHODS FOR USING THE SAME

CROSS-REFERENCE TO RELATED APPLICATIONS

This application is a continuation of United States application Ser. No. 14/163,983 filed Jan. 24, 2014, which application is a continuation of U.S. application Ser. No. 12/727,086 filed Mar. 18, 2010, which application is: (I) a continuation in part of U.S. application Ser. No. 12/578,512 filed Oct. 13, 2009, which application, pursuant to 35 U.S.C. § 119(e), claims priority to the filing date of United States Provisional Application Ser. No. 61/104,997 filed Oct. 13, 2008 and U.S. Provisional Application Ser. No. 61/182,931 filed Jun. 1, 2009; and (II) a continuation in part of United States application Ser. No. 12/270,552 filed Nov. 13, 2008, which application, pursuant to 35 U.S.C. § 119(e), claims priority to the filing date of U.S. Provisional Application Ser. No. 60/988,043 filed Nov. 14, 2007; the disclosures of which applications are herein incorporated by reference.

INTRODUCTION

Telomeres are regions of repetitive DNA found at the ends of the chromosomes of most eukaryotes. For example, human telomeres include many kilobases of (TTAGGG)n and are associated with various proteins. Small portions of these terminal sequences of telomeric DNA are lost from the tips of the chromosomes during the S phase of the cell cycle because of incomplete DNA replication. Many human cells progressively lose terminal sequences with cell division, a loss that correlates with the apparent absence of telomerase in these cells. The resulting telomere shortening limits cellular lifespan.

Telomerase is a ribonucleoprotein that synthesizes telomeric DNA. Telomerase is made up of two components: (1) an essential structural RNA component (TR or TER) (in humans the component is referred to as hTR or hTER), and (2) a catalytic protein (telomerase reverse transcriptase or TERT) (in humans the component is referred to as hTERT). Telomerase works by adding multiple DNA sequence repeats to the 3' end of DNA in the telomere region, where hTER serves as the template for nucleotide incorporation, and TERT as the catalyst. Both the catalytic protein component and the RNA template component of telomerase are activity-limiting components.

Because of its role in cellular senescence and immortalization, there is much interest in the regulation of telomerase activity.

SUMMARY

Telomerase reverse transcriptase (TERT) expression enhancing compounds, and methods for using the same, are provided. These compounds and methods find use in a variety of applications in which increased expression of telomerase reverse transcriptase is desired.

Definitions

When describing the compounds, pharmaceutical compositions containing such compounds and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope.

"Acyl" refers to a —C(O)R group, where R is hydrogen, alkyl, alkenyl, cycloalkyl, heterocycloalkyl, aryl, arylalkyl, heteroalkyl, heteroalkenyl, or heteroaryl as defined herein. Representative examples include, but are not limited to, formyl, acetyl, cyclohexylcarbonyl, cyclohexylmethylcarbonyl, benzoyl, benzylcarbonyl and the like.

"Acylamino" refers to a —NR'C(O)R group, where R' is hydrogen, alkyl, cycloalkyl, heterocycloalkyl, aryl, arylalkyl, heteroalkyl, heteroaryl, heteroarylalkyl and R is hydrogen, alkyl, alkoxy, cycloalkyl, heterocycloalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group —OC(O)H, —OC(O)-alkyl, —OC(O)-aryl or —OC(O)— cycloalkyl.

"Aliphatic" refers to hydrocarbyl organic compounds or groups characterized by a straight, branched or cyclic arrangement of the constituent carbon atoms and an absence of aromatic unsaturation. Aliphatics include, without limitation, alkyl, alkylene, alkenyl, alkynyl and alkynylene. Lower aliphatic groups typically have from 1 or 2 to 6 or 12 carbon atoms.

"Alkenyl" refers to monovalent olefinically unsaturated hydrocarbyl groups having up to about 11 carbon atoms, such as from 2 to 8 carbon atoms, and including from 2 to 6 carbon atoms, which can be straight-chained or branched and having at least 1 and including from 1 to 2 sites of olefinic unsaturation. Particular alkenyl groups include ethenyl (—CH=CH$_2$), n-propenyl (—CH$_2$CH=CH$_2$), isopropenyl (—C(CH$_3$)=CH$_2$), vinyl and substituted vinyl, and the like.

"Alkoxy" refers to the group —O-alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Alkoxycarbonyl" refers to a radical —C(O)-alkoxy where alkoxy is as defined herein.

"Alkoxycarbonylamino" refers to the group —NRC(O) OR' where R is hydrogen, alkyl, aryl or cycloalkyl, and R' is alkyl or cycloalkyl.

"Alkyl" refers to monovalent saturated aliphatic hydrocarbyl groups particularly having up to about 12 or 18 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "alkyl" also includes "cycloalkyls" as defined herein.

"Alkylene" refers to divalent saturated aliphatic hydrocarbyl groups particularly having up to about 12 or 18 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Alkynyl" refers to acetylenically unsaturated hydrocarbyl groups particularly having up to about 12 or 18 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Amino" refers to the radical —NH$_2$.

"Aminocarbonyl" refers to the group —C(O)NRR where each R is independently hydrogen, alkyl, aryl or cycloalkyl, or where the R groups are joined to form an alkylene group.

"Aminocarbonylamino" refers to the group —NRC(O)NRR where each R is independently hydrogen, alkyl, aryl or cycloalkyl, or where two R groups are joined to form an alkylene group.

"Aminocarbonyloxy" refers to the group —OC(O)NRR where each R is independently hydrogen, alkyl, aryl or cycloalky, or where the R groups are joined to form an alkylene group.

"Aralkyl" or "arylalkyl" refers to an alkyl group, as defined above, substituted with one or more aryl groups, as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some cases, an aryl group includes from 6 to 14 carbon atoms.

"Aryloxy" refers to —O-aryl groups wherein "aryl" is as defined herein.

"Azido" refers to a —N$_3$ group.

"Carbonyl" refers to —C(O)— groups, for example, a carboxy, an amido, an ester, a ketone, or an acyl substituent.

"Carboxyl" refers to a —C(O)OH group "Cyano" refers to a —CN group.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Heterocycloalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl.

"Halogen" refers to fluoro, chloro, bromo and iodo.

"Hetero" when used to describe a compound or a group present on a compound means that one or more carbon atoms in the compound or group have been replaced by, for example, a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, cycloalkenyl, e.g., heterocycloalkenyl, cycloheteroalkenyl, e.g., heterocyclohet-eroalkenyl and the like having from 1 to 5, and particularly from 1 to 3 heteroatoms. A heteroatom is any atom other than carbon or hydrogen and is typically, but not exclusively, nitrogen, oxygen, sulfur, phosphorus, boron, chlorine, bromine, or iodine.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. The heteroaryl group can be a 5-20 membered heteroaryl, or 5-10 membered heteroaryl. Particular heteroaryl groups are those derived from thiophen, pyrrole, benzothiophene, benzofuran, indole, pyridine, quinoline, imidazole, oxazole and pyrazine.

"Heterocycle" refers to organic compounds that contain a ring structure containing atoms in addition to carbon, such as sulfur, oxygen or nitrogen, as part of the ring. They may be either simple aromatic rings or non-aromatic rings. Examples include azoles, morpholine, piperazine, pyridine, pyrimidine and dioxane.

"Hydroxyl" refers to a —OH group.

"Nitro" refers to a —NO$_2$ group.

"Scaffold" refers to a molecular scaffold or core structure. For example, a scaffold may form the basis for a small molecule library where one or more substituents connected to the scaffold are variable.

"Stereoisomer" as it relates to a given compound refers to another compound having the same molecular formula, wherein the atoms making up the other compound differ in the way they are oriented in space, but wherein the atoms in the other compound are like the atoms in the given compound with respect to which atoms are joined to which other atoms (e.g. an enantiomer, a diastereomer, or a geometric isomer). See for example, Morrison and Boyd, Organic Chemistry, 1983, 4th ed., Allyn and Bacon, Inc., Boston, MA, p. 123.

"Substituted" refers to a group in which one or more hydrogen atoms are each independently replaced with the same or different substituent(s). "Substituted" groups particularly refer to groups having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$. Substituents of interest may include, but are not limited to, —X, —R$^8$ (with the proviso that R$^8$ is not hydrogen), —O—, =O, —OR$^8$, —SR$^8$, —S—, =S, —NR$^8$R$^9$, =NR$^8$, —CX$_3$, —CF$_3$, —CN, —OCN, —SCN, —NO, —NO$_2$, =N$_2$, —N$_3$, —S(O)$_2$O—, —S(O)$_2$OH, —S(O)$_2$R$^8$, —OS $(O_2)O—$, $—OS(O)_2R^8$, $—P(O)(O—)_2$, $—P(O)(OR^8)(O—)$, $—OP(O)(OR^8)(OR^9)$, $—C(O)R^8$, $—C(S)R^8$, $—C(O)OR^8$, $—C(O)NR^8R^9$, $—C(O)O—$, $—C(S)OR^8$, $—NR^1OC(O)NR^8R^9$, $vNR^{10}C(S)NR^8R^9$, $—NR^{11}C(NR^{10})NR^8R^9$ and $—C(NR^{10})NR^8R^9$, where each X is independently a halogen.

"Substituted acyl" includes those groups recited in the definition of "substituted" herein, and particularly refers to the group —C(O)R where R selected from the group consisting of hydrogen, alkyl, substituted alkyl, alkenyl, substituted alkenyl, alkynyl, substituted alkynyl, amino, substituted amino, aryl, arylalkyl, cycloalkyl, substituted cycloalkyl, heterocycloalkyl, heteroalkyl, or heteroaryl as defined herein.

"Substituted amino" includes those groups recited in the definition of "substituted" herein, and particularly refers to the group $—N(R)_2$ where each R is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group.

"Thioalkoxy" refers to the group —S-alkyl.
"Thioaryloxy" refers to the group —S-aryl.
"Thioketo" refers to the group =S.
"Thiol" refers to the group —SH.

The maximum number of heteroatoms in a stable, chemically feasible heterocyclic ring, whether it is aromatic or non aromatic, is determined by factors such as, the size of the ring, the degree of unsaturation and the valence of the heteroatoms. In general, a heterocyclic ring may have one to four heteroatoms so long as the heteroaromatic ring is chemically feasible and stable.

DETAILED DESCRIPTION

Telomerase reverse transcriptase (TERT) expression enhancing compounds, and methods for using the same, are provided. These compounds and methods find use in a variety of applications in which increased expression of telomerase reverse transcriptase is desired.

Before particular embodiments are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing the various aspects of the invention, the function and structure of various TERT expression enhancing compounds are described first in greater detail, followed by a description of methods and applications in which the compounds finds use.

TERT Expression Enhancing Compounds

As summarized above, aspects of the invention include TERT expression enhancing compounds. The TERT expression enhancing compounds are compounds that increase TERT expression in a cell upon contact with a cell or components thereof. In some instances, the types of cells in which the compounds of the invention exhibit activity are ones that include a TERT gene containing a Site C site in its promoter region, e.g., in the TERT gene minimal promoter. By increasing TERT expression is meant that the expression level of the TERT encoding mRNA is increased by 2-fold or more, such as by 5-fold or more and sometimes by 25-, 50-, or 100-fold or more and in certain embodiments 300-fold or more or higher, as compared to a control, i.e., expression in a comparable cell (such as a clone, cell from the same tissue, etc.) not contacted with the compound of interest (e.g., by using the assay described in Published United States Patent Application Publication No. US-2006-0199171-A1, the disclosure of which assay is herein incorporated by reference). Alternatively, in cases where expression of the TERT gene in a cell is so low that it is undetectable, the expression level of the TERT encoding mRNA is considered to be increased if expression is increased to a level that is easily detectable, e.g., by using the assay described in Published United States Patent Application Publication No. US-2006-0199171-A1, the disclosure of which assay is herein incorporated by reference.

In certain embodiments, the target cell in which TERT expression is increased is a normal cell, e.g., a somatic cell. In some of these embodiments, the compounds of the invention are used to increase the proliferative capacity of a cell. The term "proliferative capacity" as used herein refers to the number of divisions that a cell can undergo, and in some instances to the ability of the target cell to continue to divide where the daughter cells of such divisions are not transformed, i.e., they maintain normal response to growth and cell cycle regulation. As such, the compounds of the invention may find use in the delay of the occurrence of cellular senescence, among other applications. The compounds of the invention may delay the onset of cellular senescence by a factor of 1.2 or more, such as 2-fold or more, including 5-fold or more where in certain embodiments the delay is even greater, e.g., 10-, 20-, 50-fold or more or even higher, compared to a control.

In certain embodiments, the compounds of the invention modulate the interaction of a transcriptional repressor complex and a Site C site in the TERT promoter. By transcriptional repressor complex is meant a complex containing at least one factor (e.g., protein), wherein the complex binds specifically to a Site C site in the TERT promoter. For example, the transcriptional repressor complex can be a single protein that binds specifically to the Site C site in the TERT promoter (or minimal promoter). In contrast, the transcriptional repressor complex can contain a number of factors (e.g., proteins) that together bind specifically to the Site C site in the TERT promoter. In general, binding of the transcriptional repressor complex to a Site C site in the TERT promoter represses or reduces transcription of the TERT gene.

In certain embodiments, modulating the interaction of a transcriptional repressor complex and a Site C site means that the interaction is inhibited or reduced. In certain of these embodiments, the mechanism of activity of the compounds is by specific, direct interaction with the transcriptional repressor protein complex thereby preventing its binding to Site C in the TERT promoter. In certain embodiments, the binding of the compound to the transcriptional repressor complex competitively inhibits Site C DNA binding (meaning that the compound binds to the DNA-binding site of the transcriptional repressor complex) while in other embodiments the compound allosterically inhibits Site C DNA binding of the transcriptional repressor (meaning that it binds to a site other than to the DNA binding site of the transcriptional repressor). In certain embodiments, the compound binds to a member of the transcriptional repressor complex other than the DNA binding subunit to exert its inhibitory activity.

In certain embodiments, the compounds of the present invention reduce the repressive activity of a TERT transcriptional repressor complex of one or more factors (e.g., proteins), e.g., by inhibiting the binding of a transcriptional repressor to its cognate DNA binding site in the TERT minimal promoter. Of particular interest is the Site C DNA binding site within the −66 to −51 region of the TERT minimal promoter. This repressor site has been described in U.S. Pat. No. 6,686,159, which is incorporated herein by reference. In certain embodiments, the Site C sequence is:

```
                                          (SEQ ID NO: 1)
     GGCCCCGCCCTCTCCTCGCGGCGCGAGTTTCAGGCAGCGCT
```

In certain embodiments, the target Site C sequence is a portion or subsequence of the above sequence, such as:

```
                                          (SEQ ID NO: 2)
                    GGCGCGAGTTTCA;
```

```
                                          (SEQ ID NO: 3)
                      CGCGAGTTTC;
``` or

```
                                          (SEQ ID NO: 4)
               GGCGCGAGTTTCAGGCAGCGC.
```

Site C-binding transcriptional repressor complexes of interest include those described in U.S. patent application Ser. No. 11/088,001 filed on Mar. 22, 2005 entitled "Methods and Compositions for Modulating Telomerase Reverse Transcriptase (TERT) Expression", which is incorporated by reference herein in its entirety. As described therein, transcriptional repressor complexes that bind to Site C site include any known or later discovered members of LSF family including any homolog or any protein or polypeptide with at least 50%, at least 70%, or at least 90% of its amino acids identical to a member of LSF family, especially within its functional regions, e.g., its DNA binding domain or regions involved in protein-protein interaction. In general, LSF family is a family of proteins related to mammalian transcription factor LSF. Members of LSF family usually include LBP1a, LBP1b, LBP1c, LBP1d, LBP9, LBP32v1, LBP32v2, SOMv1, SOMv2, SOMv3, and BOM. LBP1d is a splice variant of LBP1c while LBP1a is a splice variant of LBP1 b. In addition, members the LSF family also include a splice variant of LBP1c, called LBP1c2, and a variant of BOM, called BOMv2, as well as any protein or polypeptide capable of binding to or interacting with one or more members related to LSF, e.g., YY1, NF-E4, Fe65, APP-CT, NFPB, and SP1.

In certain embodiments, the compounds of the invention increase the amount of telomerase expression from a level that is so low as to be undetectable to a level that is easily detectable, as determined by a quantitative RT-PCR assay, e.g., by an assay that determines the number of hTERT mRNA transcripts present in a cell after treatment with a compound of the invention, by measuring the Cycle Threshold value ($C_t$, a measure of the number of PCR cycles that are required to amplify a target cDNA) and correlating it to the number of hTERT mRNA transcripts present. In certain embodiments, the compounds of the invention may increase the number of hTERT mRNA transcripts per cell to a detectable level of 1 or more, such as 2 or more, 3 or more, 10 or more, 25 or more, 50 or more, 100 or more, 200 or more, 300 or more, 500 or more, or even higher.

In certain embodiments, the compounds of the invention have no significant effect of the viability of a cell, as determined by a cell viability assay, e.g., as determined by administering a compound of the invention to a cell and determining the number of viable cells in culture using a homogeneous method, such as the CellTiter-Glo® Luminescent Cell Viability Assay (Promega Corporation, Madison, WI.). The compounds of the invention may exhibit a % cell viability, as compared to a control (e.g., a DMSO control), of 15% or more, such as 20% or more, 30% or more, 40% or more, 50% or more, 60% or more, 70% or more, 80% or more, 90% or more, 100% or more, 120% or more, or even higher.

Structural Features

As reviewed above, aspects of the invention include TERT expression enhancing compounds. A TERT expression enhancing compound may include a scaffold component to which one or more substituents are bonded to produce a compound having TERT expression enhancing activity.

Scaffold components of interest include, but are not limited to: single 5- or 6-membered rings (e.g., see below, structures 5 or 6), two ortho-fused rings (e.g., structures 5:5, 5:6, or 6:6), three consecutive ortho-fused rings (e.g., 5:5:6, 6:5:6, 5:6:6 or 6:6:6), four consecutive ortho-fused rings (e.g., 5:6:6:5, 5:6:6:6, or 6:5:6:6), a linked ring system (e.g., 5-5, 5-6, 5-5-6, or 5-6-5) a bridged ring system (e.g., 5/5/6), or a spiro ring system (e.g., 5.6). A scaffold component may include a heterocyclic ring, a degree of unsaturation, and one or more suitable substituents that are determined by factors including the nature of the ring, the position of a heteroatom, the valence of the atoms and the degree of unsaturation.

Scaffold components of interest include, but are not limited to, the structures below, where these structures show various patterns of R substituents, and where each R substitutent is independently selected. These structures are provided as examples and as such are not meant to be limiting. Each of the individual embodiments described and illustrated herein has discrete components that may be separated from or combined with the components of any of the other several embodiments which have similar properties.

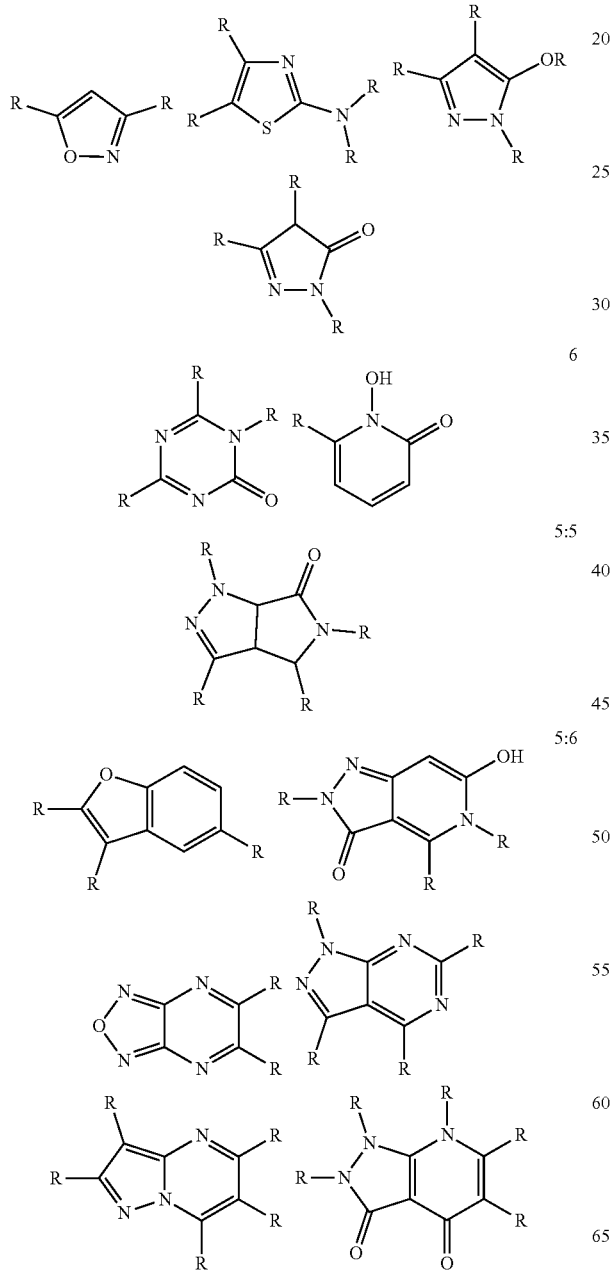

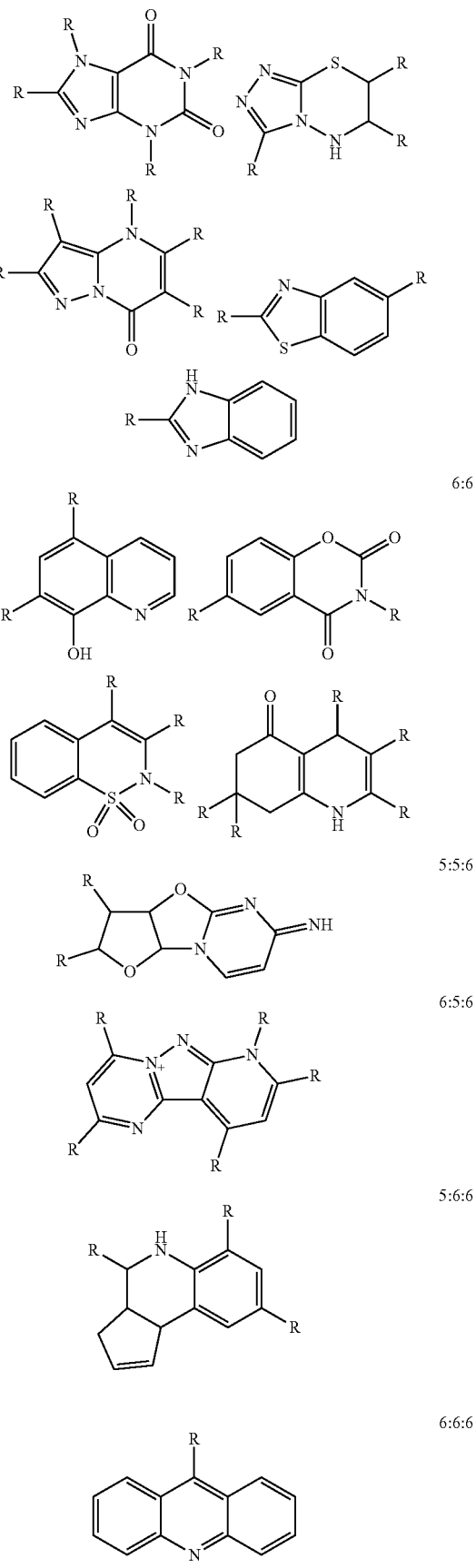

11
-continued

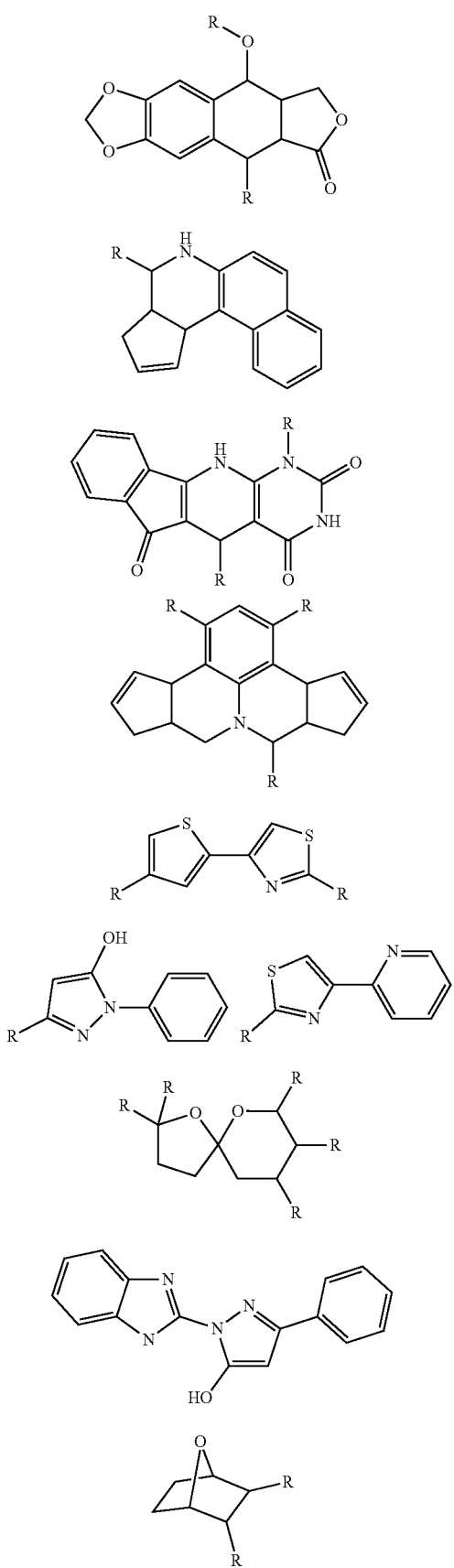

12
-continued

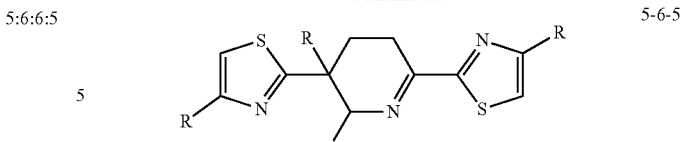

In certain embodiments a TERT expression enhancing compound may include two scaffold components that are connected by a linking group, where the linking group may connect the two scaffold components at any suitable position. The two scaffolds may be the same or different. In certain embodiments the linking group is a single bond. In certain embodiments the linking group is of 1 to 20 atoms in length, such as of 1 to 10, or 2 to 6 atoms in length. In certain cases the linking group may include a ring structure, and may include 1 or more heteroatoms, and/or may be optionally substituted. For example, a linking group may be a carbon chain, a chain including an ether moiety, a polyethyleneglycol (PEG) chain, a heterocycle group or a hydrocarbyl group.

The compounds of the invention may include one or more aromatic or heteroaromatic rings. In certain embodiments, the compounds may include from 5 to 30 carbon atoms, such as 7 to 25 carbon atoms, e.g., 10 to 15 carbon atoms.

In certain embodiments, a compound of the invention is not a polymeric molecule, e.g., a nucleic acid such as RNA, DNA or polynucleotide analog; a peptide, e.g., protein or fragment thereof, etc. In certain embodiments, a compound of the invention is not an hTERT expression regulatory RNA, e.g., an RNA with a base sequence complimentary to a target gene or gene expression vector.

In certain embodiments, a substituent may contribute to optical isomerism and/or stereo isomerism of a compound. Salts, solvates, hydrates, and prodrug forms of a compound are also of interest. All such forms are embraced by the present invention. Thus the compounds described herein include salts, solvates, hydrates, prodrug and isomer forms thereof, including the pharmaceutically acceptable salts, solvates, hydrates, prodrugs and isomers thereof. In certain embodiments, a compound may be a metabolized into a pharmaceutically active derivative.

The following are examples of compounds of the invention.

Quinolines

In certain embodiments, the compounds are quinolines, e.g., quinoline compounds substituted with substituents such as hydrogen, hydroxyl, halogen, alkyl, alkoxy, halogen, amino, thiol, cyano, nitro, —NHCONH$_2$, —NHCN, —NHCHO, —NHCOR, and —NHSO$_2$R, where R is hydrogen or C$_{1-6}$ alkyl. Substituent bonds to the quinoline may be to the carbons of the heterocyclic ring. In another embodiment, the bonds may be to the 5-, 7-, and 8-positions of the quinoline scaffold (Ia)

(Ia)

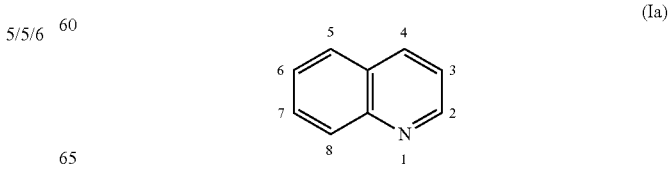

In another embodiment, the substituent on the 8-position of the quinoline core structure is a hydroxyl group. In another embodiment, the substituent on the 8-position of the quinoline core structure is a hydroxyl group and the substituent on the 5-position is a halogen. In another embodiment, the substituent on the 8-position of the quinoline core structure is a hydroxyl group and the substituent on the 7-position is a halogen. In another embodiment, the substituent on the 8-position of the quinoline core structure is a hydroxyl group and the substituents on the 5- and 7-positions are halogens.

One embodiment provides a use of a compound having the following structure:

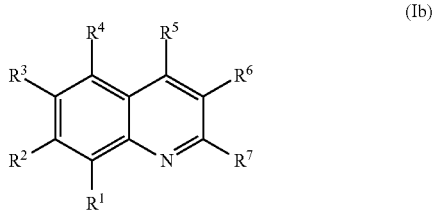

(Ib)

where $R^1$, $R^2$, $R^3$, and $R^4$ are independently selected from hydrogen, hydroxyl, halogen, alkyl, alkenyl, alkoxy, acyl, aryl, heterocycle, halogen, amino, thio, cyano, nitro, sulfonyl, sulfinyl, sulfonylamino, —NHCONH$_2$, —NHCN, —NHCHO, —NHCOR, and —NHSO$_2$R, where R is hydrogen or C$_{1-6}$ alkyl;

$R^5$, $R^6$, and $R^7$ are independently selected from hydrogen, alkyl, acyl, acylamino, acyloxy, amino, alkenyl, aryl, heterocyclyl and alkoxy; and at least three of $R^1$, $R^2$, $R^3$, and $R^4$ are not hydrogen;

or salt or stereoisomer thereof.

In a related embodiment, in formula (Ib), $R^1$ and $R^2$ can be cyclically linked.

In a related embodiment, in formula (Ib), any of $R^5$, $R^6$, and $R^7$ are independently selected from hydrogen, alkyl, acyl, acylamino, acyloxy, and amino.

In a related embodiment, in formula (Ib), any of $R^5$, $R^6$, and $R^7$ are independently selected from alkyl, acyl, acylamino, and acyloxy.

In a related embodiment, in formula (Ib), any of $R^5$, $R^6$, and $R^7$ are independently selected from alkyl, substituted alkyl, and acyl.

In a related embodiment, in formula (Ib), $R^7$ is selected from alkyl, acyl, acylamino, and acyloxy.

In a related embodiment, in formula (Ib), $R^7$ is selected from alkyl, and acyl.

In a related embodiment, in formula (Ib), $R^5$ and $R^6$ are hydrogen.

In a related embodiment, in formula (Ib), any of $R^1$, $R^2$, $R^3$, and $R^4$ are independently selected from hydrogen, hydroxyl, halogen, alkyl, alkoxy, halogen, amino, thiol, cyano, nitro, —NHCONH$_2$, —NHCN, —NHCHO, —NHCOR, and —NHSO$_2$R, where R is hydrogen or C$_{1-6}$ alkyl;

In a related embodiment, in formula (Ib), $R^1$ is selected from hydrogen, hydroxyl, alkyl, halogen, amino, thiol, —NHCONH$_2$, —NHCN, —NHCHO, —NHCOR, and —NHSO$_2$R, where R is hydrogen or C$_{1-6}$ alkyl.

In a related embodiment, in formula (Ib), $R^1$ is selected from hydrogen, hydroxyl, alkyl, —NHCONH$_2$, —NHCN, —NHCHO, —NHCOR, and —NHSO$_2$R, where R is hydrogen or C$_{1-6}$ alkyl.

In a related embodiment, in formula (Ib), $R^1$ is selected from hydrogen, hydroxyl, —CH$_2$OH, CH(CN)$_2$, —NHCONH$_2$, —NHCN, —NHCHO, —NHCOR, and —NHSO$_2$R, where R is hydrogen or C$_{1-6}$ alkyl.

In a related embodiment, in formula (Ib), $R^1$ is selected from hydrogen, hydroxyl, alkoxy, and halogen.

In a related embodiment, in formula (Ib), $R^1$ is hydroxyl.

In a related embodiment, in formula (Ib), any of $R^{2'}$ $R^3$, and $R^4$ are independently selected from hydrogen, halogen, alkyl, hydroxyl, alkoxy, amino, thiol, cyano, and nitro.

In a related embodiment, in formula (Ib), any of $R^2$, $R^3$, and $R^4$ are independently selected from hydrogen, halogen, alkyl, alkoxy, cyano, and nitro.

In a related embodiment, in formula (Ib), any of $R^2$, $R^3$, and $R^4$ are independently selected from hydrogen, halogen, alkoxy, substituted alkoxy, cyano, and nitro.

In a related embodiment, in formula (Ib), any of $R^2$, $R^3$, and $R^4$ are independently selected from hydrogen, fluoro, chloro, bromo, iodo, trifluoromethyl, alkoxy, cyano, nitro, —N(CN)$_2$, and C(CN)$_3$.

In a related embodiment, in formula (Ib), any of $R^2$, $R^3$, and $R^4$ are independently selected from hydrogen, fluoro, chloro, bromo, iodo, trifluoromethyl.

In a related embodiment, in formula (Ib), any of $R^2$, $R^3$, and $R^4$ are independently selected from hydrogen, fluoro, chloro, bromo, iodo.

In a related embodiment, in formula (Ib), $R^1$ is hydroxyl and any of $R^2$, $R^3$, and $R^4$ are independently selected from hydrogen, fluoro, chloro, bromo, iodo, trifluoromethyl, alkoxy, substituted alkoxy, cyano, nitro, —N(CN)$_2$, and C(CN)$_3$.

In a related embodiment, in formula (Ib), $R^1$ is hydroxyl and any of $R^2$, $R^3$, and $R^4$ are independently selected from hydrogen, fluoro, chloro, bromo, iodo, and trifluoromethyl.

In a related embodiment, in formula (Ib), $R^1$ is hydroxyl and any of $R^2$, $R^3$, and $R^4$ are independently selected from hydrogen, fluoro, chloro, bromo, and iodo.

One embodiment provides a use of a compound having the following structure:

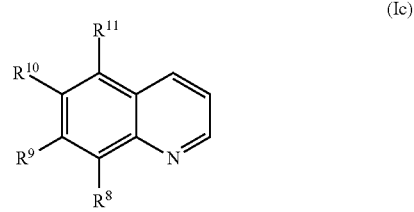

(Ic)

where $R^8$, $R^9$, $R^{10}$, and $R^{11}$ are independently selected from hydrogen, hydroxyl, halogen, alkyl, alkoxy, halogen, amino, thiol, cyano, nitro, —NHCONH$_2$, —NHCN, —NHCHO, —NHCOR, and —NHSO$_2$R, where R is hydrogen or C$_{1-6}$ alkyl; and at least three of $R^8$, $R^9$, $R^{10}$, and $R^{11}$ are not hydrogen;

or salt or stereoisomer thereof.

In a related embodiment, in formula (Ic), $R^8$ is selected from hydrogen, hydroxyl, alkyl, halogen, amino, thiol, —NHCONH$_2$, —NHCN, —NHCHO, —NHCOR, and —NHSO$_2$R, where R is hydrogen or C$_{1-6}$ alkyl.

In a related embodiment, in formula (Ic), $R^8$ is selected from hydrogen, hydroxyl, alkyl, —NHCONH$_2$, —NHCN, —NHCHO, —NHCOR, and —NHSO$_2$R, where R is hydrogen or C$_{1-6}$ alkyl.

In a related embodiment, in formula (Ic), $R^8$ is selected from hydrogen, hydroxyl, —CH$_2$OH, CH(CN)$_2$, —NHCONH$_2$, —NHCN, —NHCHO, —NHCOR, and —NHSO$_2$R, where R is hydrogen or $C_{1-6}$ alkyl.

In a related embodiment, in formula (Ic), $R^8$ is selected from hydrogen, hydroxyl, alkoxy, and halogen.

In a related embodiment, in formula (Ic), $R^8$ is hydroxyl.

In a related embodiment, in formula (Ic), any of $R^9$, $R^{10}$, and $R^{11}$ are independently selected from hydrogen, halogen, alkyl, hydroxyl, alkoxy, amino, thiol, cyano, and nitro.

In a related embodiment, in formula (Ic), any of $R^9$, $R^{10}$, and $R^{11}$ are independently selected from hydrogen, halogen, alkyl, alkoxy, cyano, and nitro.

In a related embodiment, in formula (Ic), $R^8$ is alkoxy, $R^9$ is alkyl, $R^{10}$ is hydrogen and $R^{11}$ is halogen; and where optionally $R^8$ and $R^9$ can be cyclically linked.

In a related embodiment, in formula (Ic), any of $R^9$, $R^{10}$, and $R^{11}$ are independently selected from hydrogen, halogen, alkoxy, cyano, and nitro.

In a related embodiment, in formula (Ic), any of $R^9$, $R^{10}$, and $R^{11}$ are independently selected from hydrogen, fluoro, chloro, bromo, iodo, trifluoromethyl, alkoxy, cyano, nitro, —N(CN)$_2$, and C(CN)$_3$.

In a related embodiment, in formula (Ic), any of $R^9$, $R_{10}$, and $R^{11}$ are independently selected from hydrogen, fluoro, chloro, bromo, iodo, trifluoromethyl.

In a related embodiment, in formula (Ic), any of $R^9$, $R_{10}$, and $R^{11}$ are independently selected from hydrogen, fluoro, chloro, bromo, iodo.

In a related embodiment, in formula (Ic), $R^8$ is hydroxyl and any of $R^9$, $R_{10}$, and $R^{11}$ are independently selected from hydrogen, fluoro, chloro, bromo, iodo, trifluoromethyl, alkoxy, substituted alkoxy, cyano, nitro, —N(CN)$_2$, and C(CN)$_3$.

In a related embodiment, in formula (Ic), $R^8$ is hydroxyl and any of $R^9$, $R_{10}$, and $R^{11}$ are independently selected from hydrogen, fluoro, chloro, bromo, iodo, and trifluoromethyl.

In a related embodiment, in formula (Ic), $R^8$ is hydroxyl and any of $R^9$, $R_{10}$, and $R^{11}$ are independently selected from hydrogen, fluoro, chloro, bromo, and iodo.

One embodiment provides a use of a compound of the structure of Formula (Ic) where $R^8$ is selected from hydrogen, hydroxyl, alkyl, substituted alkyl, alkoxy, halogen, amino, thiol, cyano, nitro, —NHCONH$_2$, —NHCN, —NHCHO, —NHCOR, and —NHSO$_2$R, where R is hydrogen or $C_{1-6}$ alkyl;

$R^9$, $R^{10}$, and $R^{11}$ are independently selected from hydrogen, halogen, alkyl, hydroxyl, alkoxy, amino, thiol, cyano, and nitro; and at least three of $R^8$, $R^9$, $R^{10}$, and $R^{11}$ are not hydrogen; or salt or stereoisomer thereof.

One embodiment provides a use of a compound having the following structure:

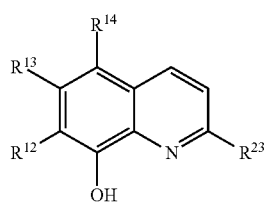

(Id)

where $R^{12}$, $R^{13}$, $R^{14}$ and $R^{23}$ are independently selected from hydrogen, hydroxyl, alkyl, alkoxy, halogen, amino, thiol, cyano, nitro, —NHCONH$_2$, —NHCN, —NHCHO, —NHCOR, and —NHSO$_2$R, where R is hydrogen or $C_{1-6}$ alkyl; and at least two of $R^2$, $R^3$, and $R^4$ are not hydrogen; or salt or stereoisomer thereof.

In a related embodiment, in formula (Id), any of $R^{12}$, $R^{13}$, and $R^{14}$ are independently selected from hydrogen, halogen, alkyl, hydroxyl, alkoxy, amino, substituted amino, thiol, cyano, and nitro.

In a related embodiment, in formula (Id), any of $R^{12}$, $R^{13}$, and $R^{14}$ are independently selected from hydrogen, halogen, alkyl, alkoxy, cyano, and nitro.

In a related embodiment, in formula (Id), any of $R^{12}$, $R^{13}$, and $R^{14}$ are independently selected from hydrogen, halogen, alkoxy, cyano, and nitro.

In a related embodiment, in formula (Id), any of $R^{12}$, $R^{13}$, and $R^{14}$ are independently selected from hydrogen, fluoro, chloro, bromo, iodo, trifluoromethyl, alkoxy, cyano, nitro, —N(CN)$_2$, and C(CN)$_3$.

In a related embodiment, in formula (Id), any of $R^{12}$, $R^{13}$, and $R^{14}$ are independently selected from hydrogen, fluoro, chloro, bromo, iodo, trifluoromethyl.

In a related embodiment, in formula (Id), any of $R^{12}$, $R^{13}$, and $R^{14}$ are independently selected from hydrogen, fluoro, chloro, bromo, iodo.

One embodiment provides a use of a compound of the structure of Formula (Id) where $R^{12}$, $R^{13}$, and $R^{14}$ are independently selected from hydrogen, halogen, alkyl, hydroxyl, alkoxy, amino, thiol, cyano, and nitro; and at least two of $R^{12}$, $R^{13}$, and $R^{14}$ are not hydrogen;

or salt or stereoisomer thereof.

One embodiment provides a use of a compound of the structure of Formula (Id) where $R^{12}$, $R^{13}$, and $R^{14}$ are independently selected from hydrogen, fluoro, chloro, bromo, iodo, trifluoromethyl, alkoxy, substituted alkoxy, cyano, nitro, —N(CN)$_2$, and C(CN)$_3$; and at least two of $R^{12}$, $R^{13}$, and $R^{14}$ are not hydrogen; or salt or stereoisomer thereof.

One embodiment provides a use of a compound described by the structure of one of compounds 1018 to 1021 and 1105, as found in Table 1; or a salt thereof.

One embodiment provides a use of a compound selected from Yodoxin (iodoquinol), 5,7-dibromo-8-hydroxyquinoline, 5-chloro-7-iodo-8-quinolinol (clioquinol), and 5,7-dichloro-8-hydroxyquinoline.

In certain embodiments, a compound is of the structure:

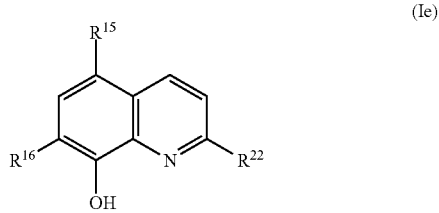

(Ie)

where $R^{15}$, $R^{16}$ and $R^{22}$ are independently selected from hydrogen, a halogen, a nitro, a hydrocarbyl, an aryl, an alkyl, a heterocycle, a carbonyl, an amino (—N(Z)Z'); a methylene-amino (—CH($R^{17}$)—N(Z)Z'), and a methylene-oxy (—CH($R^{17}$)—O$R^{18}$); where $R^{17}$, $R^{18}$, Z and Z' are independently selected from hydrogen, a hydrocarbyl, an aryl, an alkyl, an alkenyl, a heterocycle, a carbonyl, an acyl, a sulfonyl, and a sulfonate; and where optionally Z and Z' can be cyclically linked.

In particular embodiments, in formula (Ie), $R^{15}$ and $R^{16}$ are both halogen, e.g., iodo, bromo or chloro. In particular embodiments, in formula (Ie), $R^{15}$ is chloro and $R^{16}$ is bromo. In certain embodiments, in formula (Ie), $R^{15}$ and $R^{16}$ are independently selected from hydrogen, a halogen, a protected amino (—NH—P), an arylsulfonate (ArSO$_2$—), and a substituted methylene-amino group (—CH($R^{17}$)—N (Z)Z'), where $R^{17}$, Z and Z' are as described above. In particular embodiments, in formula (Ie), $R^{15}$ is a tosylamino (—NH-Ts), and $R^{16}$ is selected from hydrogen, a halogen, and an arylsulfonate (ArSO$_2$—), for example, 4-(CH$_3$)-PhSO$_2$—. In particular embodiments, in formula (Ie), $R^{16}$ is hydrogen and $R^{15}$ is a methylene-amino group (—CH ($R^{17}$)—N($R^{19}$)$R^{20}$), where $R^{17}$ is as described above and $R^{19}$ and $R^{20}$ are independently selected from hydrogen, a lower alkyl or a branched lower alkyl.

In certain embodiments a compound is of the structure:

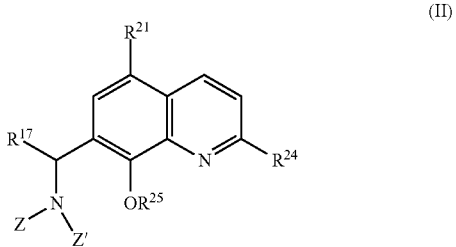

(II)

where $R^{21}$ and $R^{24}$ are independently selected from hydrogen, a hydroxyl, a halogen, a hydrocarbyl, an alkoxy, an aryloxy, a carbonyl, an aryl, an alkyl, a heterocycle, an amino, a thiol, a cyano, a nitro, a sulfonyl, and a sulfinyl;

$R^{25}$ is hydrogen or a hydrocarbyl; and $R^{17}$, Z and Z' are as described above; where optionally $R^{25}$ and Z' can be cyclically linked.

In certain embodiments, in formula (II), $R^{21}$ is hydrogen or a halogen and optionally, Z or Z' can be cyclically linked to $R^{17}$.

In certain embodiments a compound is of the structure:

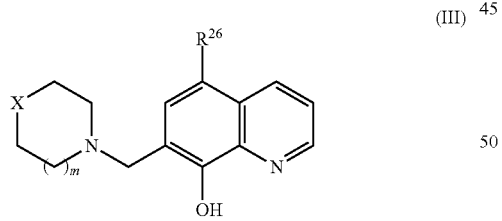

(III)

where $R^{26}$ is hydrogen, a hydrocarbyl, a carbonyl, an aryl, a methylene ether, a halogen, a nitro, or a heterocycle; and where m is 0 or 1; such that when m is 0, X is methylene (—CH$_2$—); and when m is 1, X is methylene (—CH(Z)—), oxy (—O—) or amino (—N(Z)—); where Z is as described above.

In certain embodiments, in formula (III), $R^{26}$ is hydrogen, a lower alkyl or a branched lower alkyl; m is 1 and X is amino (—N($R^{27}$)—), where $R^{27}$ is hydrogen, a lower alkyl or a branched lower alkyl.

In certain embodiments, a quinoline compound is described by a structure of one of compounds 1001 to 1105 and 1477 to 1482, as found in Table 1.

In another embodiment, a compound includes a dimer of quinolines, where the 8- and 8'-substituents are both hydroxyl, and the 7- and 7'-positions of the two quinolines are connected by a linker of 1 to 20 atoms in length, such as of 1 to 10, or 2 to 6 atoms in length; and where at least the 5 and 5'-positions may be independently, optionally substituted. In certain cases, the linker may include a ring structure, for example a N,N'-disubstituted piperidino heterocycle. In certain cases, the linker may be cyclic or acyclic, and may include 1 or more heteroatoms, and may be optionally substituted.

Pyrazols

In certain embodiments, the compounds are pyrazol compounds. As described herein, a pyrazol is a compound that includes a 5-membered heterocyclic ring including two adjacent N atoms.

In some embodiments, the pyrazol is substituted at up to 4 positions, such as at 0, 1, 2, 3 or 4 positions, where the substitutents are independently selected from hydrogen, a hydrocarbyl, a heterocycle, an alkoxy, an aryloxy, a carbonyl, a thiol, an amino, an oxo, a hydroxyl, and an aryl. In some embodiments, the pyrazol is a substituted 2,4-dihydro-pyrazol-3-one or 2H-pyrazol-3-ol.

In certain embodiments a pyrazol compound of the invention is described by one of the following structures:

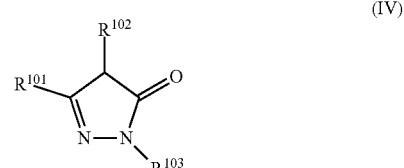

(IV)

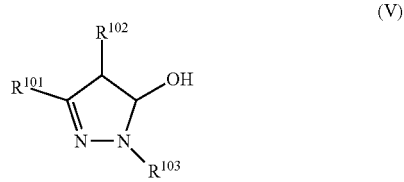

(V)

where $R^{101}$ and $R^{102}$ are independently selected from hydrogen, a hydrocarbyl, an aryl, an acyl, a carbonyl, a heterocycle, a hydroxyl, a halogen, an alkyl, an alkenyl, an alkoxy, an amino, a thio, a cyano, a nitro, a sulfonyl, a sulfinyl, a sulfonylamino, —NHCONH$_2$, —NHCN, —NHCHO, —NHCOR, and —NHSO$_2$R, where R is hydrogen or C$_{1-6}$ alkyl, where optionally $R^{101}$ and $R^{102}$ can be cyclically linked; and where $R^{103}$ is from hydrogen, a hydrocarbyl, an aryl, an acyl, a carbonyl, a heterocycle, an alkyl, an alkenyl, a sulfonyl, or a sulfoxide.

In certain embodiments, in formula (IV), $R^{102}$ may be connected to the pyrazol via a double bond, where optionally $R^{102}$ and $R^{101}$ can be cyclically linked.

In certain embodiments, in formulas (IV) or (V), $R^{101}$, $R^{102}$ and $R^{103}$ are independently selected from hydrogen, a hydrocarbyl, an aryl, an acyl, a carbonyl and a heterocycle.

In certain embodiments, in formula (IV) or (V), $R^{101}$, $R^{102}$ and $R^{103}$ are independently selected from hydrogen, a phenyl, a methylene-thio ($R^5$—S—CH$_2$—), a benzoyl, a 2-(1H-benzoimidazolyl) group, and substituted versions thereof; where $R^5$ is an aryl or a heterocycle.

In certain embodiments, in formula (IV) or (V), $R^{101}$ is an alkyl, for example a lower alkyl. In certain embodiments, in formulas (IV) or (V), $R^{102}$ is hydrogen or an arylacyl, for example a 4-halo-benzoyl. In certain embodiments, in formula (IV) or (V), $R^{103}$ is an aryl or a heterocycle, for example a 2-(1H-benzoimidazolyl).

In certain embodiments, in formulas (IV) or (V), $R^{102}$ is hydrogen; and $R^{101}$ and $R^{103}$ are independently selected from hydrogen, an alkyl, a phenyl, a methylene-thio ($R^5$—S—CH$_2$—), a 2-(1H-benzoimidazolyl) group, and substituted versions thereof; where $R^5$ is an aryl or a heterocycle.

In certain embodiments, in formulas (IV) or (V), $R^{102}$ is 4-halo-benzoyl; and $R^{101}$ and $R^{103}$ are independently selected from hydrogen, an alkyl, an aryl, a heterocycle, a phenyl, a methylene-thio ($R^5$—S—CH$_2$—), and a 2-(1H-benzoimidazolyl) group; where $R^5$ is an aryl or a heterocycle.

In certain embodiments, in formulas (IV) or (V), $R^{103}$ is of the structure:

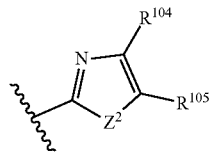

where $R^{104}$ and $R^{105}$ are independently selected from hydrogen, an alkyl, an aryl, an alkyloxycarbonyl group, where optionally $R^{104}$ and $R^{105}$ can be cyclically linked; and
$Z^2$ is O, S or NH.

In certain embodiments, in formulas (IV) or (V), $R^{103}$ is of the structure:

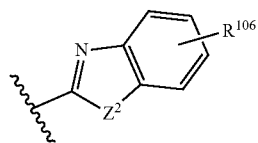

where $Z^2$ is O, S or NH; and
where $R^{106}$ is one or more groups, where each $R^{106}$ is independently selected from hydrogen, hydroxyl, halogen, alkyl, alkoxy, halogen, amino, thiol, cyano, nitro, —NHCONH$_2$, —NHCN, —NHCHO, —NHCOR, and —NHSO$_2$R, where R is hydrogen or $C_{1-6}$ alkyl.

In certain embodiments, in formulas (IV) or (V), $R^{102}$ has the structure of formula (XXXIVa), where the attachment to the structure of formula (XXXIVa) is made at the $R^{187}$ position. In particular embodiments, in formulas (IV) or (V), $R^{102}$ has the structure of formula (XXXIVa), where the attachment to the structure of formula (XXXIVa) is made at the $R^{187}$ position, and where $R^{101}$ is hydrogen or an alkyl (e.g., methyl), $R^{103}$ is aryl (e.g., phenyl), $R^{188}$ is hydrogen and $R^{186}$ is an alkyl or a methylene-phenoxy group (—CH$_2$—OPh).

In certain embodiments, a pyrazol compound is described by a structure of one of compounds 1106 to 1144 and 1483 to 1485, as found in Table 1.

Fused Pyrazols

In some embodiments, TERT expression enhancing compounds of the invention are fused pyrazol compounds. A fused pyrazol compound is a compound that includes a fused pyrazol, i.e. a pyrazol ring ortho-fused to a 5- or 6-membered ring. In some embodiments, a fused pyrazol is a pyrazol ortho-fused to a pyrimidine, a pyridine, or a pyrrol ring, such that the compound is a pyrazolopyrimidine, a pyrazolopyridine, or a pyrrolopyrazol. In certain embodiments, a fused pyrazol is a 4H-pyrazolo[1,5-a]pyrimidin-7-one, a 1,2-dihydro-7H-pyrazolo[3,4-b]pyridine-3,4-dione, a 3a,4,5,6a-tetrahydro-1H-pyrrolo[3,4-c]pyrazol-6-one, or substituted versions thereof.

In some embodiments, a fused pyrazol compound is described by the following structure:

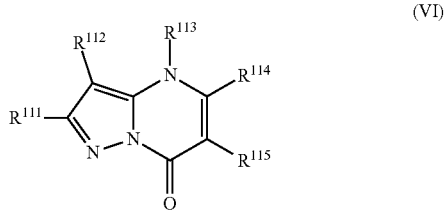

where $R^{111}$, $R^{112}$, $R^{114}$ and $R^{115}$ are independently selected from hydrogen, an amino, an alkoxy, an aryloxy, an aryl, an alkyl, a carbonyl, a halogen, a hydrocarbyl, a heterocycle, a hydroxyl, a sulfonyl, a sulfinyl, and a thio, where optionally $R^{114}$ and $R^{115}$ can be cyclically linked; and
where $R^{113}$ is hydrogen, an aryl, an alkyl, a carbonyl, a hydrocarbyl, a heterocycle, a sulfonyl, and a sulfoxide.

In certain embodiments, in formula (VI), $R^{111}$ is hydrogen, lower alkyl or a branched lower alkyl. In certain embodiments, in formula (VI), $R^{112}$ is an aryl, a carbonyl or a heterocycle. In certain embodiments, in formula (VI), $R^{114}$ and $R^{115}$ are independently selected from hydrogen, an aryl, an alkyl, a carbonyl, a heterocycle and a benzyl; and where optionally $R^{114}$ and $R^{115}$ can be cyclically linked. In certain embodiments, in formula (VI), $R^{113}$ is hydrogen.

In certain embodiments, a compound is described by the following structure:

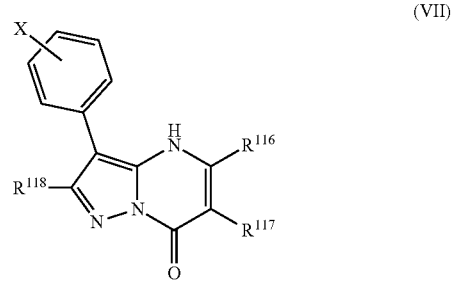

where X is one or more groups, each X independently selected from hydrogen, an alkyl, a hydroxyl, an alkoxy and a halogen;
where $R^{116}$ and $R^{117}$ are independently selected from hydrogen, an alkyl, a halogen, an aryl, a heterocycle, and a methylene-thio ($R^5$—S—CH$_2$—), where $R^5$ is an aryl or a heterocycle, where optionally $R^{116}$ and $R^{117}$ can be cyclically linked; and
where $R^{118}$ is hydrogen, an aryl, an heterocycle or a lower alkyl.

In certain embodiments, in formula (VII), $R^{116}$ and $R^{117}$ are independently selected from hydrogen, a lower alkyl, a branched lower alkyl, a phenyl or a benzyl.

In certain embodiments, a compound is described by one of the following structures:

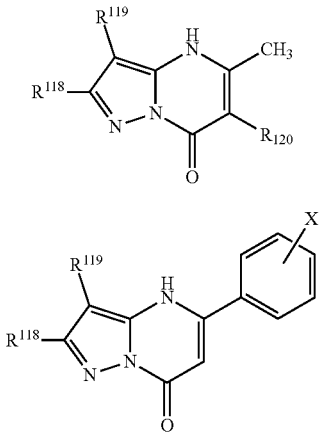

(VIIIa)

(VIIIb)

where X is hydrogen, an alkyl, a hydroxyl, an alkoxy or a halogen;

where $R^{118}$, $R^{119}$ and $R^{120}$ are independently selected from hydrogen, an alkyl, an aryl, a heterocycle, and a methylene-thio ($R^{121}$—S—CH$_2$—), where $R^{121}$ is an aryl or a heterocycle.

In certain embodiments, in formulas (VIIIa) and (VIIIb), $R^{118}$ is hydrogen, a lower alkyl, or a branched lower alkyl; and $R^{119}$ is an aryl or a heterocycle.

In certain embodiments, a fused pyrazol compound is described by a structure of one of compounds 1145 to 1169 and 1486, as found in Table 1.

Benzothiazole-Triazinone

In some embodiments, a TERT expression enhancing compound of the invention is a benzothiazole-triazinone compound. In some embodiments, a benzothiazole-triazinone compound is a substituted 4-(benzothiazol-2-ylamino)-1H-[1,3,5]triazin-2-one.

In some embodiments, a benzothiazole-triazinone compound is described by the following structure:

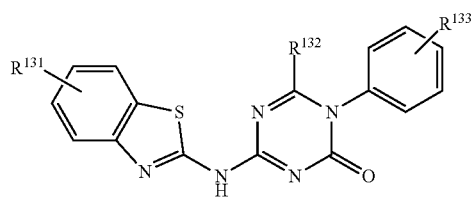

where $R^{131}$ and $R^{133}$ are one or more groups, each $R^{131}$ and each $R^{133}$ group are independently selected from hydrogen, an aryl, an alkyl, a carbonyl, an amino, an alkoxy, an aryloxy, a halogen, a hydrocarbyl, a heterocycle, or a hydroxyl; and where $R^{132}$ is hydrogen, an alkyl, an aryl, a hydrocarbyl, or a heterocycle.

In certain embodiments, a benzothiazole-triazinone compound is described by the structure of compound 1170, as found in Table 1.

Azoles

In certain embodiments, a TERT expression enhancing compound is an azole, e.g., an azole compound substituted with one or more substituents. The azole compounds of the invention may include a heterocycle with two or more hetero atoms selected from nitrogen, oxygen and sulfur. Examples include azole compounds such as pyrazoles, imidazoles, triazoles, tetrazoles, thiazoles, isothiazoles, oxazoles, and isoxazoles.

In some embodiments, an azole compound is an isoxazole. In certain embodiments, an azole compound includes a heterocycle substituent which includes a five-membered aromatic heterocycle, where the heterocycle includes at least one oxygen or sulfur atom. In some embodiments, a heterocycle substituent includes a thiophene group. In some embodiments, bonds to the heterocycle substituent are made to the 2-position of the heterocycle substituent.

In some embodiments, an azole compound includes an acyl substituent which includes an amide, for example, an alkyl amide. In certain embodiments, an alkyl amide substituent is a propylamide. In certain embodiments, bonds to the acyl substituent are made to the carbonyl carbon of the acyl substituent.

Thus in certain embodiments, a compound of the invention includes an azole of one of the following structures:

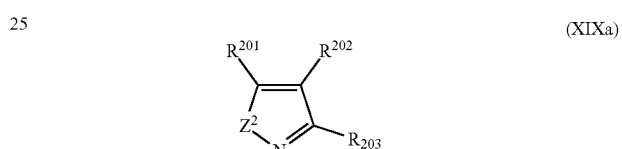

(XIXa)

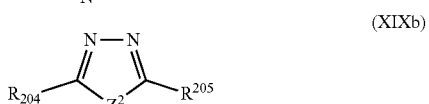

(XIXb)

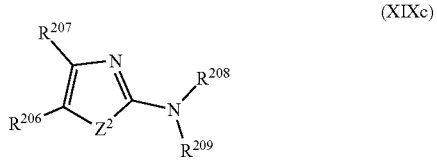

(XIXc)

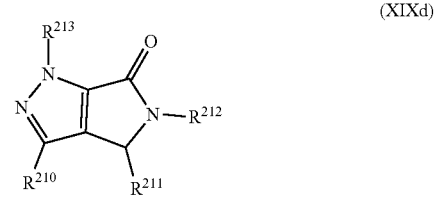

(XIXd)

where $Z^2$ is O or S; and where $R^{201}$, $R^{202}$, $R^{203}$, $R^{204}$, $R^{205}$, $R^{206}$, $R^{207}$, $R^{210}$ and $R^{21}$ are independently selected from hydrogen, an acyl, an amino, an aryl, an alkyl, a hydrocarbyl, a heterocycle, a thio, a straight-chain or branched $C_1$-$C_{20}$-alkyl or $C_2$-$C_{20}$-alkenyl (with or without asymmetric carbon atoms), and a halogen; and where $R^{208}$, $R^{209}$, $R^{212}$ and $R^{213}$ are independently selected from hydrogen, an acyl, an aryl, an alkyl, a hydrocarbyl, a heterocycle, and a straight-chain or branched $C_1$-$C_{20}$-alkyl or $C_2$-$C_{20}$-alkenyl (with or without asymmetric carbon atoms).

In certain embodiments, in formula (XIXa), at least one of $R^{201}$, $R^{202}$ and $R^{203}$ is a five-membered aromatic heterocycle having at least one oxygen or sulfur atom.

In certain cases, the substituents $R^{201}$, $R^{202}$, $R^{203}$, $R^{204}$, $R^{205}$, $R^{206}$, $R^{207}$, $R^{208}$, $R^{209}$, $R^{210}$, $R^{211}$, $R^{212}$ and $R^{213}$ contribute to optical isomerism and/or stereo isomerism.

Salts, solvates, hydrates, prodrug forms of the compounds also are possible. All such forms are embraced by the present invention. Thus the compounds of the subject invention include salts, solvates, hydrates, prodrug and isomer forms thereof, including the pharmaceutically acceptable salts, solvates, hydrates, prodrugs and isomers thereof.

In certain embodiments, in formula (XIXb), $Z^2$ is O, $R^{204}$ is an aryl or a heterocycle (e.g., a pyridyl), and $R^{205}$ is an aryl or a thioether (e.g., —SCH$_2$CONZ(Z') where Z and Z' as described above).

Of interest in certain embodiments are isoxazoles, such as a compound of formula (XIXa) where $Z^2$ is O.

In a related embodiment, the isoxazole of formula (XIXa) is a 3,5-substituted isozazole, where $R^{202}$ is hydrogen. Of interest is a 3,5-substituted isozazole of formula (XIXa) in which $R^{202}$ is hydrogen, and $R^{203}$ is an acyl, an amino, or a straight-chain or branched $C_1$-$C_{20}$-alkyl or $C_2$-$C_{20}$-alkenyl (with or without asymmetric carbon atoms), and $R^{201}$ is an aryl or a five-membered aromatic heterocycle having at least one oxygen or sulfur atom. In another related embodiment, an isoxazole compound of formula (XIXa) is a substituted 5-thiophen-2-yl-isoxazole where $R^{201}$ is 2-thiophenyl. In certain embodiments, in a 3,5-substituted isozazole of formula (XIXa), $R^{203}$ is an amido group (—CONZ(Z') where Z and Z' are as described above), and $R^{201}$ is an aryl (e.g., a phenyl).

Of interest are substituted 5-thiophen-2-yl-isoxazole compounds having a structure of formula (XXI):

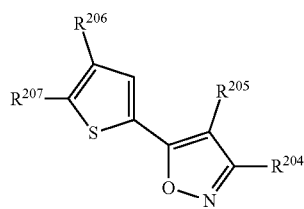

(XXI)

where $R^{204}$ and $R^{205}$ are independently selected from hydrogen, an acyl, an acyloxy, an aliphatic, an alkoxy, an amino, a cycloalkyl, an aryl, an aryloxy, a heteroaryl, a heterocycle, and a cyano, with the proviso that at least one of $R^{204}$ and $R^{205}$ is other than hydrogen; and $R^{206}$ and $R^{207}$ each independently is hydrogen, an acyl, an amino, a heterocycle, a sulfonyl, a halogen, or a straight-chain or branched $C_1$-$C_{15}$-alkyl or $C_2$-$C_{15}$-alkenyl or $C_1$-$C_{15}$-alkyloxy (with or without asymmetric carbon atoms).

In accordance with compounds of formula (XXI), $R^{204}$ may be optionally substituted by one or more substituents. Examples include substituents selected from the group consisting of heteroatom, halogen, cyano, nitro, azide, lower alkyl, lower alkoxy, lower alkoxy substituted by halogen, lower alkyl substituted by halogen, C(O)O-lower alkyl, lower alkylsulfonyl, —NR$^a$R$^b$, —C(O)—NR$^a$R$^b$, —C(O)-heterocycle, benzyloxy, heterocycle optionally substituted by hydroxy, halogen or lower alkyl, and heteroaryl optionally substituted by lower alkyl, where R$^a$ and R$^b$ are each independently hydrogen, lower alkylsulfonyl, —C(O)H, —(CH$_2$), —N(R$^c$)$_2$, —(CH$_2$)$_n$—O-lower alkyl, —(CH$_2$)$_n$—S-lower alkyl, —(CH$_2$)$_n$—S(O)$_2$-lower alkyl, heteroarylsulfonyl, lower alkyl, —(CH$_2$)$_n$-heterocycle optionally substituted by lower alkyl, —(CH$_2$)$_n$-cycloalkyl, —(CH$_2$)$_n$-heteroaryl, —(CH$_2$)$_n$—OH, or —(CO)—R$^d$, R$^c$ is hydrogen or a lower alkyl, R$^d$ is lower alkyl, cycloalkyl or heteroaryl, and n is 0, 1 or 2

In certain embodiments, the compound is a substituted 5-thiophen-2-yl-isoxazole of formula (XXI) in which $R^{204}$ is an acyl, an amino, a heterocycle, or a straight-chain or branched $C_1$-$C_{20}$-alkyl or $C_2$-$C_{20}$-alkenyl (with or without asymmetric carbon atoms), each of $R^{205}$ and $R^{206}$ is hydrogen, and $R^{207}$ is hydrogen, an acyl, an amino, a heterocycle, a sulfonyl group, a halogen, or a straight-chain or branched $C_1$-$C_{15}$-alkyl or $C_2$-$C_{15}$-alkenyl or $C_1$-$C_{15}$-alkyloxy (with or without asymmetric carbon atoms).

Compounds in particular embodiments include those where the compound is a substituted 5-thiophen-2-yl-isoxazole of formula (XXI), where $R^{205}$, $R^{206}$ and $R^{207}$ are each hydrogen, and $R^{204}$ is an acyl, an amino, a heterocycle, or a straight-chain or branched $C_1$-$C_{20}$-alkyl or $C_2$-$C_{20}$-alkenyl (with or without asymmetric carbon atoms).

In certain embodiments, the compound is a substituted 5-thiophen-2-yl-isoxazole of formula (XXI) in which $R^{205}$, $R^{206}$ and $R^{207}$ are each hydrogen, and $R^{204}$ is an acyl, such as a 5-thiophen-2-yl-isoxazole-3-acyl compound having a structure according to formula (XXII):

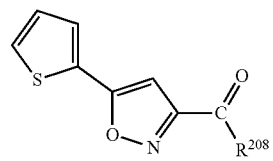

(XXII)

where $R^{208}$ is an amino, a straight-chain or branched $C_1$-$C_{15}$-alkyl or $C_2$-$C_{15}$-alkenyl or $C_1$-$C_{15}$-alkyloxy (with or without asymmetric carbon atoms), a cycloalkyl, an aryl, a heteroaryl, a heterocycle, or a cyano.

In accordance with compounds of formula (XXII), the $R^{208}$ group may be optionally substituted with one or more substituents. Examples of $R^{208}$ substituents include, but are not limited to, substituents selected from the group consisting of halogen, cyano, nitro, lower alkyl, lower alkoxy, lower alkoxy substituted by halogen, lower alkyl substituted by halogen, —C(O)O-lower alkyl, lower alkylsulfonyl, —NR$^a$R$^b$, —C(O)—NR$^a$R$^b$, —C(O)-heterocycle, benzyloxy, heterocycle optionally substituted by hydroxy, halogen or lower alkyl, and heteroaryl optionally substituted by lower alkyl, where R$^a$ and R$^b$ are each independently hydrogen, lower alkylsulfonyl, —C(O)H, —(CH$_2$), —N(R)$_2$, —(CH$_2$)$_n$—O-lower alkyl, —(CH$_2$)$_n$—S-lower alkyl, —(CH$_2$)$_n$—S(O)$_2$-lower alkyl, heteroarylsulfonyl, lower alkyl, —(CH$_2$)$_n$-heterocycle optionally substituted by lower alkyl, —(CH$_2$)$_n$-cycloalkyl, —(CH$_2$)$_n$-heteroaryl, —(CH$_2$)$_n$—OH, or —(CO)—R', wherein R' is lower alkyl, cycloalkyl or heteroaryl, and where n is 0, 1 or 2, and where R is hydrogen or lower alky.

In certain embodiments, the compound is a 5-thiophen-2-yl-isoxazole-3-carbonylamino compound of formula (XXII), where $R^{208}$ is an amino group that is substituted with a straight- or branched-chain alkyl or alkenyl group containing from one to six carbon atoms which is optionally substituted; or an amino group that is substituted with an aryl, heterocycle, cycloalkyl or heterocycloalkyl group containing from three to six carbon atoms which is optionally substituted. In a specific embodiment, the compound is a 5-thiophen-2-yl-isoxazole-3-carbonylamino compound of formula (XXII) in which $R^{208}$ is an amino group that is substituted with a straight- or branched-chain alkyl or alkenyl group containing from one to six carbon atoms which is optionally substituted. In another specific embodiment, the compound is a 5-thiophen-2-yl-isoxazole-3-carbonylamino compound of formula (XXII) in which $R^{208}$ is an amino group that is substituted with a straight- or branched-chain alkyl or alkenyl group containing from two to six carbon atoms which is optionally substituted.

Examples of substituted isoxazoles in accordance with one or more of the above structural formulae include, but are not limited to, N-butyl-5-thiophen-2-yl-1,2-oxazole-3-carboxamide; N-ethyl-5-thiophen-2-yl-1,2-oxazole-3-carboxamide; N-propyl-5-thiophen-2-yl-1,2-oxazole-3-carboxamide; N-prop-2-enyl-5-thiophen-2-yl-1,2-oxazole-3-carboxamide; N-butan-2-yl-5-thiophen-2-yl-1,2-oxazole-3-carboxamide; N-propan-2-yl-5-thiophen-2-yl-1,2-oxazole-3-carboxamide; N-(3-diethylaminopropyl)-5-thiophen-2-yl-1,2-oxazole-3-carboxamide; N-(2-methylpropyl)-5-thiophen-2-yl-1,2-oxazole-3-carboxamide; N-(cyclopropylmethyl)-5-thiophen-2-yl-1,2-oxazole-3-carboxamide; N-cyclopropyl-5-thiophen-2-yl-1,2-oxazole-3-carboxamide; N-[2-(cyclopropylamino)-2-oxoethyl]-5-thiophen-2-yl-1,2-oxazole-3-carboxamide; N-prop-2-ynyl-5-thiophen-2-yl-1,2-oxazole-3-carboxamide; N-[2-(tert-butylamino)-2-oxoethyl]-5-thiophen-2-yl-1,2-oxazole-3-carboxamide; N-[(4,6-dimethyl-2-oxo-1H-pyridin-3-yl)methyl]-5-thiophen-2-yl-1,2-oxazole-3-carboxamide; N-cyclohexyl-5-thiophen-2-yl-1,2-oxazole-3-carboxamide; N-cycloheptyl-5-thiophen-2-yl-1,2-oxazole-3-carboxamide; N-cyclopentyl-5-thiophen-2-yl-1,2-oxazole-3-carboxamide; N,N-diethyl-5-thiophen-2-yl-1,2-oxazole-3-carboxamide; N-(1-methylpiperidin-4-yl)-5-thiophen-2-yl-1,2-oxazole-3-carboxamide; 5-propyl-N-(thiophen-2-ylmethyl)-1,2-oxazole-3-carboxamide; N-(2-methoxyethyl)-5-thiophen-2-yl-1,2-oxazole-3-carboxamide; N-(1-methoxypropan-2-yl)-5-thiophen-2-yl-1,2-oxazole-3-carboxamide; 5-thiophen-2-yl-N-(2,2,2-trifluoroethyl)-1,2-oxazole-3-carboxamide; 5-thiophen-2-yl-N-(thiophen-2-ylmethyl)-1,2-oxazole-3-carboxamide; N-(2-dimethylamino-2-thiophen-2-ylethyl)-5-thiophen-2-yl-1,2-oxazole-3-carboxamide; N-(4-methylcyclohexyl)-5-thiophen-2-yl-1,2-oxazole-3-carboxamide; (4-methylpiperazin-1-yl)-(5-thiophen-2-yl-1,2-oxazol-3-yl)methanone; 2-[methyl-[(5-thiophen-2-yl-1,2-oxazol-3-yl)methyl]amino]-N-propan-2-ylacetamide; methyl-[2-oxo-2-(propan-2-ylamino)ethyl]-[(5-thiophen-2-yl-1,2-oxazol-3-yl)methyl]azanium; 2-[ethyl-[(5-thiophen-2-yl-1,2-oxazol-3-yl)methyl]amino]-N-propan-2-ylacetamide; ethyl-[2-oxo-2-(propan-2-ylamino)ethyl]-[(5-thiophen-2-yl-1,2-oxazol-3-yl)methyl]azanium; pyrrolidin-1-yl-(5-thiophen-2-yl-1,2-oxazol-3-yl)methanone; piperidin-1-yl-(5-thiophen-2-yl-1,2-oxazol-3-yl)methanone; 5-methyl-N-(thiophen-2-ylmethyl)-1,2-oxazole-3-carboxamide; N-[2-(benzoylamino)ethyl]-5-thiophen-2-yl-1,2-oxazole-3-carboxamide; (2-methylpiperidin-1-yl)-(5-thiophen-2-yl-1,2-oxazol-3-yl)methanone; azepan-1-yl-(5-thiophen-2-yl-1,2-oxazol-3-yl)methanone; 5-propan-2-yl-N-(thiophen-2-ylmethyl)-1,2-oxazole-3-carboxamide; thiomorpholin-4-yl-(5-thiophen-2-yl-1,2-oxazol-3-yl)methanone; 1-[4-[(5-thiophen-2-yl-1,2-oxazol-3-yl)methyl]piperazin-4-ium-1-yl]ethanone; N-cyclopropyl-2-[methyl-[(5-thiophen-2-yl-1,2-oxazol-3-yl)methyl]amino]acetamide; [2-(cyclopropylamino)-2-oxoethyl]-methyl-[(5-thiophen-2-yl-1,2-oxazol-3-yl)methyl]azanium; [2-(tert-butylamino)-2-oxoethyl]-ethyl-[(5-thiophen-2-yl-1,2-oxazol-3-yl)methyl]azanium; 4-[(5-thiophen-2-yl-1,2-oxazol-3-yl)methyl]piperazin-2-one; 4-[(5-thiophen-2-yl-1,2-oxazol-3-yl)methyl]piperazin-4-ium-2-one; N-ethyl-5-methyl-N-[2-oxo-2-(thiophen-2-ylmethylamino)ethyl]-1,2-oxazole-3-carboxamide; N-(2-phenylethyl)-5-thiophen-2-yl-1,2-oxazole-3-carboxamide; (2-ethylpiperidin-1-yl)-(5-thiophen-2-yl-1,2-oxazol-3-yl)methanone; 5-(2-methylpropyl)-N-(thiophen-2-ylmethyl)-1,2-oxazole-3-carboxamide; methyl 2-[(5-thiophen-2-yl1,2-oxazole-3-carbonyl)amino]acetate; N-(phenylmethyl)-5-thiophen-2-yl-1,2-oxazole-3-carboxamide; N-(1-phenylethyl)-5-thiophen-2-yl-1,2-oxazole-3-carboxamide; (2,6-dimethylpiperidin-1-yl)-(5-thiophen-2-yl-1,2-oxazol-3-yl)methanone; N-ethyl-5-[(thiophen-2-ylmethylamino)methyl]-1,2-oxazole-3-carboxamide; N-methyl-1-(5-thiophen-2-yl-1,2-oxazol-3-yl)methanamine; N-[2-(azepan-1-yl)-2-thiophen-2-ylethyl]-5-thiophen-2-yl-1,2-oxazole-3-carboxamide; N-methyl-N-phenyl-5-thiophen-2-yl-1,2-oxazole-3-carboxamide; N-(2-piperidin-1-yl-2-thiophen-2-ylethyl)-5-thiophen-2-yl-1,2-oxazole-3-carboxamide; (4-methylpiperidin-1-yl)-(5-thiophen-2-yl-1,2-oxazol-3-yl)methanone; N-[2-[(4-fluorophenyl)amino]-2-oxoethyl]-N-methyl-5-thiophen-2-yl-1,2-oxazole-3-carboxamide; N-[(2-fluorophenyl)methyl]-5-thiophen-2-yl-1,2-oxazole-3-carboxamide; N,N-dicyclohexyl-5-thiophen-2-yl-1,2-oxazole-3-carboxamide; N-phenyl-5-thiophen-2-yl-1,2-oxazole-3-carboxamide; 5-cyclopropyl-N-(thiophen-2-ylmethyl)-1,2-oxazole-3-carboxamide; N-tert-butyl-2-[ethyl-[(5-thiophen-2-yl-1,2-oxazol-3-yl)methyl]amino]acetamide; N-(oxolan-2-ylmethyl)-5-thiophen-2-yl-1,2-oxazole-3-carboxamide; N-(2-morpholin-4-ylethyl)-5-thiophen-2-yl-1,2-oxazole-3-carboxamide; N-(3-morpholin-4-ylpropyl)-5-thiophen-2-yl-1,2-oxazole-3-carboxamide; N-[(4-fluorophenyl)methyl]-5-thiophen-2-yl-1,2-oxazole-3-carboxamide; 5-phenyl-N-(thiophen-2-ylmethyl)-1,2-oxazole-3-carboxamide; N-[2-[(3-fluoro-4-methylbenzoyl)amino]ethyl]-5-thiophen-2-yl-1,2-oxazole-3-carboxamide; N-[(4-acetamidophenyl)methyl]-5-thiophen-2-yl-1,2-oxazole-3-carboxamide; N-[2-(4-methylpiperidin-1-yl)-2-thiophen-2-ylethyl]-5-thiophen-2-yl-1,2-oxazole-3-carboxamide; N-(2-dimethylamino-2-thiophen-2-ylethyl)-5-phenyl-1,2-oxazole-3-carboxamide; N-(4-fluorophenyl)-5-thiophen-2-yl-1,2-oxazole-3-carboxamide; N-(2-fluorophenyl)-5-thiophen-2-yl-1,2-oxazole-3-carboxamide; N-(4-acetamidophenyl)-5-thiophen-2-yl-1,2-oxazole-3-carboxamide; 5-(4-fluorophenyl)-N-(thiophen-2-ylmethyl)-1,2-oxazole-3-carboxamide; N-(2-methylsulfanylphenyl)-5-thiophen-2-yl-1,2-oxazole-3-carboxamide; 5-[(3-cyclopentylpropanoyl-(thiophen-2-ylmethyl)amino)methyl]-N-(2-methylpropyl)-1,2-oxazole-3-carboxamide; N-(2-methylpropyl)-5-[(thiophen-2-ylmethylamino)methyl]-1,2-oxazole-3-carboxamide; N-ethyl-5-[(pentan-3-yl-(thiophene-2-carbonyl)amino)methyl]-1,2-oxazole-3-carboxamide; ethyl 4-(5-thiophen-2-yl1,2-oxazole-3-carbonyl)piperazine-1-carboxylate; N-[3-(methylcarbamoyl)phenyl]-5-thiophen-2-yl-1,2-oxazole-3-carboxamide; N-(3-acetamidophenyl)-5-thiophen-2-yl-1,2-oxazole-3-carboxamide; N-[2-[(5Z)—2,4-dioxo-5-(thiophen-2-ylmethylidene)-1,3-thiazolidin-3-yl]ethyl]-5-methyl-1,2-oxazole-3-carboxamide; N-(2,4-difluorophenyl)-5-thiophen-2-yl-1,2-oxazole-3-carboxamide; N-(2,5-difluorophenyl)-5-thiophen-2-yl-1,2-oxazole-3-carboxamide; N-cyclopropyl-2-[4-[(5-thiophen-2-yl-1,2-oxazol-3-yl)methyl]piperazin-1-yl]acetamide; 1-[4-[(5-thiophen-2-yl-1,2-oxazol-3-yl)methyl]piperazin-1-yl]ethanone; 2-[ethyl-[(5-phenyl-1,2-oxazol-3-yl)methyl]amino]-N-(thiophen-2-ylmethyl)acetamide; ethyl-[2-oxo-2-(thiophen-2-ylmethylamino)ethyl]-[(5-phenyl-1,2-oxazol-3-yl)methyl]azanium; N-ethyl-N-[(4-methyl-1,2,5-oxadiazol-3-yl)methyl]-5-thiophen-2-yl-1,2-oxazole-3-carboxamide; morpholin-4-yl-(5-thiophen-2-yl-1,2-oxazol-3-yl)methanone; 5-(4-methylphenyl)-N-(thiophen-2-ylmethyl)-1,2-oxazole-3-carboxamide; methyl 3-amino-5-(3-phenyl-1,2-oxazol-5-yl)thiophene-2-carboxylate; 2-[[4-[5-(5-ethylthiophen-2-yl)-1,2-oxazol-3-yl]phenyl]sulfonylamino]-3-methylbutanoic acid; 3-methyl-2-[[4-

[5-(5-methylthiophen-2-yl)-1,2-oxazol-3-yl]phenyl]sulfonylamino]butanoic acid; (2R)-3-methyl-2-[[4-[5-(5-methylthiophen-2-yl)-1,2-oxazol-3-yl]phenyl]sulfonylamino]butanoic acid; [3-methyl-5-(5-methylthiophen-2-yl)-1,2-oxazol-4-yl]carbamate; 5-(3-methyl-1,2-oxazol-5-yl)-N-[[5-oxo-1-[4-(2-oxopiperidin-1-yl)phenyl]pyrrolidin-3-yl]methyl]thiophene-2-carboxamide; 2-[2-methyl-5-(3-methyl-1,2-oxazol-5-yl)thiophen-3-yl]sulfonyl-3,4-dihydro-1H-isoquinoline; 2-[5-(3,4-dimethyl-1,2-oxazol-5-yl)-2-methylthiophen-3-yl]sulfonyl-3,4-dihydro-1H-isoquinoline; 1-(2-chlorophenyl)ethyl N-[3-methyl-5-(5-methylthiophen-2-yl)-1,2-oxazol-4-yl]carbamate; 3-(5-heptylthiophen-2-yl)-5-(5-propylthiophen-2-yl)-1,2-oxazole; 3-(4-octoxyphenyl)-5-[5-[(E)-pent-1-enyl]thiophen-2-yl]-1,2-oxazole; 5-(5-butylthiophen-2-yl)-3-(4-octylphenyl)-1,2-oxazole; 5-(5-butylthiophen-2-yl)-3-(4-octoxyphenyl)-1,2-oxazole; 3-(5-butylthiophen-2-yl)-5-(5-nonylthiophen-2-yl)-1,2-oxazole; 3-(5-decylthiophen-2-yl)-5-(5-pentylthiophen-2-yl)-1,2-oxazole; 3-(5-heptylthiophen-2-yl)-5-(5-nonylthiophen-2-yl)-1,2-oxazole; and 3-(5-heptylthiophen-2-yl)-5-(5-pentylthiophen-2-yl)-1,2-oxazole.

In certain embodiments, the compound is a substituted 5-thiophen-2-yl-isoxazole-3-carboxylic acid propylamide (also referred to as N-propyl-5-(2-thienyl)isoxazole-3-carboxamide), of the structure of compound 1188, as found in Table 1.

In certain embodiments, compounds of the invention range in molecular weight from about 100 to about 700 daltons, including from about 125 to about 600 daltons such as from about 150 to about 450. In certain embodiments, compounds of the invention may contain from about 4 to about 50 carbon atoms and contain at least one other type of atom, including but not limited to nitrogen, oxygen, sulfur, bromine, fluorine, and/or chlorine atoms. As discussed above, the non-carbon atoms can be present as part of an aromatic ring structure, a substituent of the aromatic ring group, as part of a non-aromatic ring structure, or as another structural element.

In certain embodiments a compound is a substituted 5-thiophen-2-yl-isoxazole, of the structure of Formula (XXI) where $R^{204}$ and $R^{205}$ are independently selected from hydrogen, an acyl, an acyloxy, an aliphatic, an alkoxy, an amino, a cycloalkyl, an aryl, an aryloxy, a heteroaryl, a heterocycle, and cyano, with the proviso that at least one of $R^{204}$ and $R^{205}$ is other than hydrogen; and $R^{206}$ and $R^{207}$ each independently is hydrogen, acyl, amino, heterocycle, sulfonyl, halogen, straight-chain or branched $C_1$-$C_{15}$-alkyl or $C_2$-$C_{15}$-alkenyl or $C_1$-$C_{15}$-alkoxy (with or without asymmetric carbon atoms); and where the 5-thiophen-2-yl-isoxazole compound is NOT 5-thiophen-2-yl-isoxazole-3-carboxylic acid propylamide.

In particular embodiments, a compound is of one of the structures:

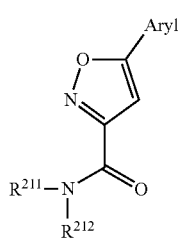

(XXIIIa)

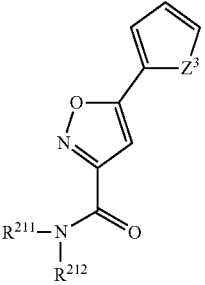

(XXIIIb)

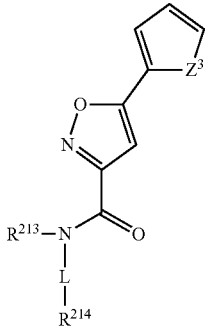

(XXIV)

where $R^{21}$, $R^{212}$, $R^{213}$, and $R^{214}$ are independently selected from hydrogen, an aryl, an alkyl, an allyl, a carbonyl, a hydrocarbyl, a heterocycle;

where $Z^3$ is O or S;

where Aryl is an aryl group, for example, a 4-fluorophenyl group; and where L is a linking group.

In particular embodiments, in formulas (XXIIIa) and (XXIIIb), $R^{211}$ and $R^{212}$ are independently selected from hydrogen, a lower alkyl, a branched lower alkyl, an allyl and a cycloalkyl. In particular embodiments, in formulas (XXIIIa) an (XXIIIb), $R^{211}$ is hydrogen and $R^{212}$ is a chain of about 1 to 10 atoms, such as 1 to 4 atoms; where the chain may optionally include 1, 2 or 3 ether bonds, and may be optionally substituted; and where $R^{212}$ is NOT propyl.

In certain embodiments, in formula (XXIV), L is a linker of up to about 10 atoms in length, and $R^{214}$ is an aryl, a cycloalkyl or a heterocycle.

In particular embodiments, in formula (XXIV), L is a $C_1$-$C_6$ alkyl chain (for example, a $C_1$-$C_3$ chain), a linker of 1 to 6 atoms in length where one of the atoms is an oxygen; or a single bond; and $R^{214}$ is a cyclopropyl, a cyclopentyl, a tetrahydrofuranyl, a morpholino or a phenyl. In some cases the linker may be optionally substituted.

In some embodiments an azole compound is a 2-aminothiazole compound of formula (XIXc). In certain embodiments, in formula (XIXc), $Z^2$ is S, and $R^{206}$, $R^{207}$ are independently selected from hydrogen, an amino, an alkoxy, an aryloxy, an aryl, a carbonyl, a halogen, a hydrocarbyl, a heterocycle, a hydroxyl, a sulfonyl, a sulfinyl, and a thio; and $R^{208}$, and $R^{209}$ are independently selected from hydrogen, an aryl, a carbonyl, a hydrocarbyl, a heterocycle, and a sulfonyl.

In certain embodiments, in formula (XIXc), $R^{206}$ is hydrogen.

In certain embodiments, an azole compound is a compound described by one of the following structures:

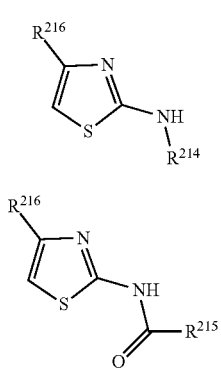

(XVI)

(XVII)

where $R^{216}$ is an aryl, or a heterocycle and $R^{214}$ is hydrogen, an alkoxy, an aryloxy, an aryl, an alkyl, a carbonyl, a hydrocarbyl, a heterocycle or a sulfonyl; and $R^{215}$ is hydrogen, an alkoxy, an aryloxy, an aryl, an alkyl, a hydrocarbyl or a heterocycle.

In certain embodiments, in formulas (XVI) or (XVII), $R^{216}$ is a heterocycle, and $R^{214}$ and $R^{215}$ are independently selected from an alkyl, an aryl, a heterocycle, and an arylsulfonylmethylene (ArSO$_2$CH$_2$—). In certain embodiments, in formulas (XVII) and (XVIII), $R^{216}$ is a pyridyl, a pyrrole or a phenyl; and $R^{214}$ and $R^{215}$ are independently selected from a pyridyl, a phenyl, a pyrrole, an ortho-fused 2-ring heterocycle (for example a benzothiazolyl or a benzodioxine), an amidosulfonylphenyl (Z(Z')NSO$_2$Ph- where Z and Z' are as described above), or an arylsulfonylmethylene (for example, PhSO$_2$CH$_2$— or 4-F-PhSO$_2$CH$_2$—).

In certain embodiments, in formula (XIXd), $R^{210}$ and $R^{211}$ are independently selected from hydrogen, an amino, an alkoxy, an aryloxy, an aryl, a carbonyl, a halogen, a hydrocarbyl, a heterocycle, a hydroxyl, a sulfonyl, a sulfinyl, and a thio; and $R^{212}$ and $R^{213}$ are independently selected from hydrogen, an aryl, a carbonyl, a hydrocarbyl, a heterocycle, and a sulfonyl.

In certain embodiments, in formula (XIXd), $R^{210}$, $R^{21}$ and $R^{212}$ are independently selected from hydrogen, an aryl and a heterocycle. In certain embodiments, in formula (XIXd), $R^{210}$ is a heterocycle, for example a 2-thiophene-yl or a 2-furan-yl; and $R^{211}$ and $R^{212}$ are independently an aryl, for example a substituted phenyl. In certain embodiments, in formula (XIXd), $R^{210}$ is a 2-thiophene-yl or 2-furan-yl; and $R^{211}$ and $R^{212}$ are independently a substituted phenyl.

In certain embodiments, an azole compound is described by the structure of one of compounds 1171 to 1208, 1487 to 1525, as found in Table 1.

Benzothiazines

Also of interest as TERT expression enhancing compounds are benzothiazines. Benzothiazine compounds of interest include, for example, a 2H-benzo[e][1,2]thiazine-1,1-dioxide compound. In some embodiments, a benothiazine compound is a substituted benzothiazine, for example, a substituted 2H-benzo[e][1,2]thiazine-1,1-dioxide; where the 2H-benzo[e][1,2]thiazine-1,1-dioxide may be substituted at up to 7 positions, such as at 0, 1, 2, 3, 4, 5, 6 or 7 positions. In some embodiments, the oxidation state of the S atom may be reduced, for example, S may be present as either —SO$_2$— or —SO— or —S—.

In some embodiments, a benzothiazine compound is a compound described by the structure:

where the substituents $R^{301}$, $R^{302}$, $R^{304}$, $R^{305}$, $R^{306}$ and $R^{307}$ are independently selected from hydrogen, an amino, an alkoxy, an aryloxy, an aryl, a carbonyl, a halogen, a hydrocarbyl, a heterocycle, a hydroxyl, a sulfonyl, a sulfinyl, and a thio; and where $R^{303}$ is hydrogen, an aryl, an alkyl, a carbonyl, a hydrocarbyl, a heterocycle, or a sulfonyl.

In certain embodiments, a compound is described by one of the following structures:

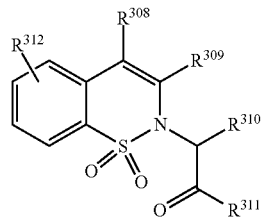

(XII)

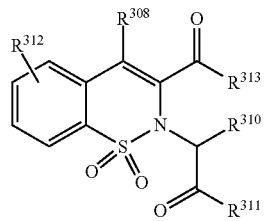

(XIII)

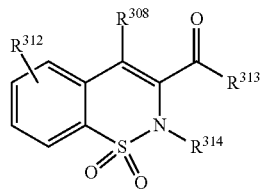

(XIV)

where $R^{308}$, $R^{309}$, $R^{310}$, $R^{31}$ and $R^{313}$ are independently selected from hydrogen, an amino, an alkoxy, an aryloxy, an aryl, a carbonyl, a halogen, a hydrocarbyl, a heterocycle, a hydroxyl, a sulfonyl, a sulfinyl, and a thio;

where $R^{314}$ is hydrogen, an aryl, a carbonyl, an ester, an alkyl, an allyl, a hydrocarbyl, a heterocycle, or a sulfonyl; and where, $R^{312}$ is one or more groups, where each $R^{312}$ is independently selected from hydrogen, an amino, an alkoxy, an aryloxy, an aryl, a carbonyl, a halogen, a nitro, a cyano, a hydrocarbyl, a heterocycle, a hydroxyl, a sulfoxide and a thio.

In certain embodiments, in formulas (XII)—(XIV), $R^{308}$ is hydrogen, hydroxyl, or a heterocycle. In certain embodiments, in formulas (XII)—(XIV), $R^{309}$, $R^{313}$ and $R^{311}$ are independently an aryl. In certain embodiments, in formulas (XII)—(XIV), $R^{308}$ is hydrogen, a hydroxyl, or a heterocycle, for example a N-piperidino; and $R^{309}$, $R^{313}$ and $R^{311}$ are independently an aryl, for example a phenyl. In certain embodiments, in formulas (XII)—(XIV), $R^{308}$ is hydrogen or N-piperidino; and $R^{309}$, $R^{313}$ and $R^{311}$ are independently hydrogen or a phenyl.

In certain embodiments, a benzothiazine compound is described by the structure of one of compounds 1209 to 1218, as found in Table 1.

Bridged Cyclohexanes

Also of interest as TERT expression enhancing compounds are bridged cyclohexanes. A bridged cyclohexane is a compound that includes a cyclohexane ring bridged by any suitable bridging group, such as 1,4-bridged by any suitable group, for example by an oxo (—O—) bridge. In some embodiments, a bridged cyclohexane compound is a 7-oxa-bicyclo[2.2.1]heptane substituted at up to 4 positions, such as at 0, 1, 2, 3 or 4 positions. In certain embodiments, a bridged cyclohexane compound is described by one of the following structures:

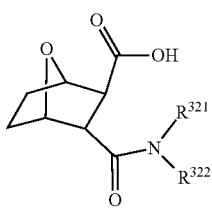

(XVIIIa)

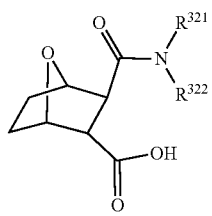

(XVIIIb)

where $R^{321}$ and $R^{322}$ are independently selected from hydrogen, an aryl, an alkyl, a hydrocarbyl, and a heterocycle, where optionally $R^{321}$ and $R^{322}$ are cyclically linked. In certain embodiments, in formulas (XVIIIa) and (XVIIIb), $R^{321}$ is hydrogen or a lower alkyl and $R^{322}$ is a phenyl, a heterocycle-substituted lower alkyl, or a substituted piperidino. In certain embodiments, in formulas (XVIII) and (XVIIIb), $R^{321}$ and $R^{322}$ are cyclically linked thereby comprising a substituted piperidino.

In certain embodiments, a bridged cyclohexane compound may be an isomer of one of formulas (XVIIIa) and (XVIIIb).

In certain embodiments, a bridged cyclohexane compound is described by the structure of one of compounds 1219 to 1223, as found in Table 1.

Naphthofuranones

In some embodiments, TERT expression enhancing compounds of interest are napthofuranones. In some embodiments, a naphthofuranone compound comprises a substituted hydroxy-tetrahydro-naphtho[2,3-c]furan-1-one scaffold. In some embodiments, a napthofuranone compound is described by the following structure:

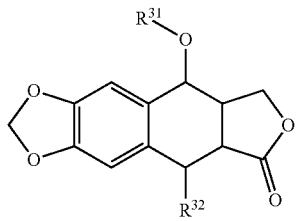

where $R^{31}$ is hydrogen, an aryl, a carbonyl, a hydrocarbyl, a sugar, a heterocycle or a sulfonyl; and where $R^{32}$ is hydrogen, an amino, an alkoxy, an aryloxy, an aryl, a carbonyl, a halogen, a hydrocarbyl, a heterocycle, a hydroxyl, a sulfonyl, a sulfinyl, and a thio.

In certain embodiments, in formula (XXVII), $R^{31}$ is a sugar, or a substituted sugar derivative; and $R^{32}$ is an aryl or a heterocycle. In certain embodiments, in formula (XXVII), $R^{31}$ is a glucose derivative and $R^{32}$ is a phenol.

In certain embodiments, a napthofuranone compound is described by the structure of one of compounds 1224 and 1225, as found in Table 1.

Tetrahydrofuro-Oxazolo-Pyrimidinols

In some embodiments, TERT expression enhancing compounds of interest are tetrahydrofuro-oxazolo-pyrimidinols. In some embodiments, a tetrahydrofuro-oxazolo-pyrimidinol compound comprises a substituted 2-hydroxymethyl-6-imino-2,3,3a,9a-tetrahydro-6H-furo[2',3':4,5]oxazolo[3,2-a]pyrimidin-3-ol scaffold. In some embodiments, a tetrahydrofuro-oxazolo-pyrimidinol compound is described by the following structure:

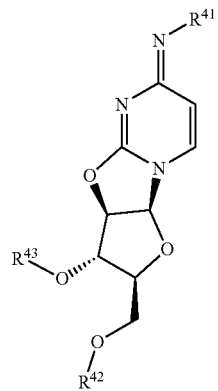

where $R^{41}$, $R^{42}$ and $R^{43}$ are independently selected from hydrogen, an alkyl, an aryl, an acyl, a carbonyl, a hydrocarbyl, a heterocycle, a sulfonyl and a sulfoxide.

In certain embodiments, a tetrahydrofuro-oxazolo-pyrimidinol compound is described by the structure of compound 1226, as found in Table 1.

Aza-Fluorene

In some embodiments, TERT expression enhancing compounds of interest are aza-fluorenes. In some embodiments, an aza-fluorene compound comprises a substituted 1H-1,5,9-triaza-8a-azonia-fluorene scaffold. In some embodiments, an aza-fluorene compound is described by the following structure:

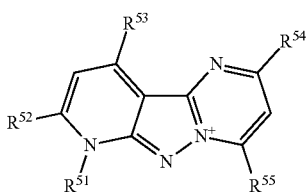

where $R^{51}$, $R^{52}$, $R^{53}$, $R^{54}$, and $R^{55}$ are independently selected from hydrogen, an aryl, a carbonyl, a hydrocarbyl, a heterocycle, a lower alkyl, a phenyl, a sulfonyl and a sulfoxide.

In certain embodiments, an aza-fluorene compound is described by the structure of compound 1227, as found in Table 1.

Oxadiazolo-Pyrazine

In some embodiments, TERT expression enhancing compounds of interest are oxadiazolo-pyrazines. In some embodiments, an oxadiazolo-pyrazine compound comprises a substituted [1,2,5]oxadiazolo[3,4-b]pyrazine scaffold. In some embodiments, an oxadiazolo-pyrazine compound is described by the following structure:

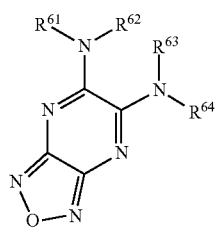

where $R^{61}$, $R^{62}$, $R^{63}$ and $R^{64}$ are independently selected from hydrogen, an alkyl, an aryl, an acyl, a carbonyl, a hydrocarbyl, a heterocycle, a sulfonyl and a sulfoxide.

In certain embodiments, an oxadiazolo-pyrazine compound is described by the structure of one of compounds 1228 to 1231, as found in Table 1.

Tetrahydro-Benzothiophene

In some embodiments, TERT expression enhancing compounds of interest are tetrahydro-benzothiophenes. In some embodiments, a tetrahydro-benzothiophene compound comprises a substituted 4,5,6,7-tetrahydro-benzo[b]thiophene. In some embodiments, a tetrahydro-benzothiophene compound is described by the following structure:

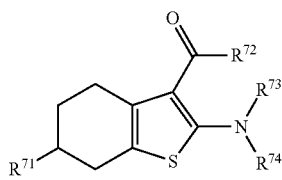

where $R^{71}$, $R^{72}$, $R^{73}$ and $R^{74}$ are independently selected from hydrogen, an alkyl, an aryl, an acyl, a carbonyl, a hydrocarbyl, a heterocycle, a sulfonyl and a sulfoxide.

In certain embodiments, a tetrahydro-benzothiophene compound is described by the structure of one of compounds 1232 and 1233, as found in Table 1.

Pyrimidinediones

In some embodiments, a TERT expression enhancing compound of the invention is a pyrimidinedione compound. In some embodiments, a pyrimidinedione compound comprises a substituted 1H-pyrimidine-2,4-dione. In some embodiments, a pyrimidinedione compound is described by the following structure:

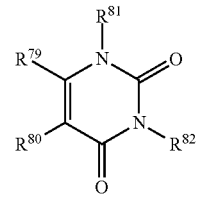

where $R^{79}$, $R^{80}$, $R^{81}$ and $R^{82}$ are independently selected from hydrogen, an aryl, a carbonyl, a sulfonyl, a hydrocarbyl and a heterocycle; where optionally $R^{79}$ and $R^{80}$ are cyclically linked to provide a second ring ortho-fused to the pyrimidinedione ring; and where the ortho-fused second ring may be optionally substituted.

In some embodiments, a compound is described by one of one of the following structures:

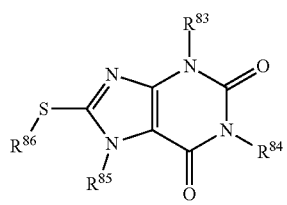

(XXVa)

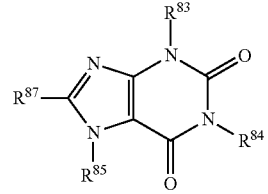

(XXVb)

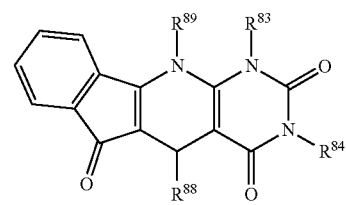

(XXVI)

where $R^{87}$, $R^{88}$ are independently selected from hydrogen, an aryl, a carbonyl, a hydrocarbyl, an alkyl and a heterocycle;

where $R^{83}$, $R^{84}$, $R^{85}$, $R^{86}$ and $R^{89}$ are independently selected from hydrogen, an aryl, an alkyl, a carbonyl, an acyl, a sulfonyl, a sulfoxide, a hydrocarbyl and a heterocycle. In certain embodiments, in formulas (XXVa) (XXVb) or (XXVI), $R^{83}$ and $R^{84}$ are independently hydrogen or a lower alkyl. In certain embodiments, in formulas (XXVa) or (XXVb), $R^{85}$ is hydrogen or a lower alkyl; and $R^{86}$ or $R^{87}$ includes a linker of about 1 to 6 atoms in length connected to an aryl or a heterocycle. In certain embodiments, in formula (XXVb), $R^4$ is a heterocycle-substituted thiomethylene (Het-$CH_2$—S—), or an aryl-substituted methylene-thio (Ar—CH$_2$—S—). In certain embodiments, in formula (XXVI), R$^{88}$ is an aryl or a heterocycle and R$^{89}$ is hydrogen or a lower alkyl.

In certain embodiments, a pyrimidinedione compound is described by the structure of one of compounds 1235 and 1234, as found in Table 1.

Benzofurans

In some embodiments, a TERT expression enhancing compound of the invention is a benzofuran compound. In some embodiments, a benzofuran compound is described by the following structure:

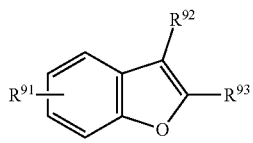

where R$^{91}$, is one or more groups, where each R$^{91}$ is independently selected from hydrogen, an amino (—NZZ'), an alkoxy, an aryloxy, an aryl, a carbonyl, an acyl, a halogen, a hydrocarbyl, a heterocycle, a hydroxyl, a sulfonyl, a sulfinyl, a sulfoxide and a thio; where R$^{92}$ and R$^{93}$ are independently selected from hydrogen, an amino (—NZZ'), an alkoxy, an aryloxy, an aryl, a carbonyl, an acyl a halogen, a hydrocarbyl, a heterocycle, a hydroxyl, a sulfonyl, a sulfinyl, a sulfoxide and a thio; and where optionally R$^{92}$ and R$^{93}$ can be cyclically linked.

In some embodiments, a benzofuran compound is described by the following structure:

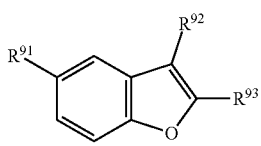

where R$^{91}$, R$^{92}$ and R$^{93}$ are defined above.

In certain embodiments, a benzofuran compound is described by the structure of one of compounds 1236 to 1239, as found in Table 1.

Dihydro-Triazolo-Thiadiazines

In some embodiments, a TERT expression enhancing compound of the invention is a dihydro-triazolo-thiadiazine compound. In some embodiments, a dihydro-triazolo-thiadiazine compound comprises a substituted 6,7-dihydro-5H-[1,2,4]triazolo[3,4-b][1,3,4]thiadiazine. In some embodiments, a dihydro-triazolo-thiadiazine compound is described by the following structure:

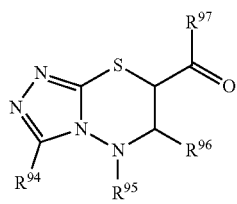

where R$^{94}$, and R$^{96}$ are independently selected from hydrogen, an amino, an alkoxy, an aryloxy, an aryl, a carbonyl, a halogen, a hydrocarbyl, a heterocycle, a hydroxyl, a sulfonyl, a sulfinyl, and a thio; and where R$^{95}$ is hydrogen, an aryl, a carbonyl, a hydrocarbyl, a heterocycle, or a sulfonyl; and where R$^{97}$ is from hydrogen, an amino, an alkoxy, an aryloxy, an aryl, a hydrocarbyl, a heterocycle, and a hydroxyl.

In certain embodiments, a dihydro-triazolo-thiadiazine compound is described by the structure of compound 1240, as found in Table 1.

Benzo-Oxazine-Diones

In some embodiments, a TERT expression enhancing compound of the invention is a benzo-oxazine-dione compound. In some embodiments, a benzo-oxazine-dione compound comprises a substituted benzo[e][1,3]oxazine-2,4-dione. In some embodiments, a benzo-oxazine-dione compound is described by the following structure:

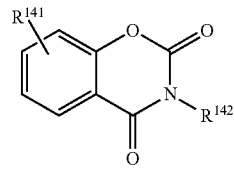

where R$^{141}$ is one or more groups, where each R$^{141}$ independently selected from hydrogen, an amino, an alkoxy, an aryloxy, an aryl, a carbonyl, a halogen, a hydrocarbyl, a heterocycle, a hydroxyl, a sulfonyl, a sulfinyl, and a thio; and where R$^{142}$ is hydrogen, an aryl, a carbonyl, a hydrocarbyl, a heterocycle, or a sulfonyl.

In certain embodiments, a benzo-oxazine-dione compound is described by a structure of one of compounds 1241 to 1242, as found in Table 1.

Dihydro-Pyridines

In some embodiments, a TERT expression enhancing compound of the invention is a dihydro-pyridine compound. In some embodiments, a dihydro-pyridine compound comprises a substituted 1,4-dihydro-pyridine or 4,6,7,8-tetrahydro-1H-quinolin-5-one. In some embodiments, a dihydro-pyridine compound is described by one of the following structures:

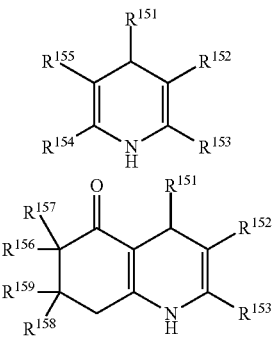

where R$^{151}$, R$^{152}$, R$^{153}$, R$^{154}$, R$^{155}$, R$^{156}$, R$^{157}$, R$^{158}$ and R$^{159}$ are independently selected from hydrogen, an amino, an alkoxy, an aryloxy, an aryl, an alkyl, a carbonyl, an ester, a cyano, a halogen, a hydrocarbyl, a heterocycle, a hydroxyl, a sulfonyl, a sulfinyl, and a thio; and where optionally R$^{154}$ and R$^{155}$ can be cyclically linked.

In certain embodiments, a dihydro-pyridine compound is described by the structure of one of compounds 1243 to 1248, as found in Table 1.

Pyrazolo-Pyrimidines

In some embodiments, a TERT expression enhancing compound of the invention is a pyrazolo-pyrimidine compound. In some embodiments, a pyrazolo-pyrimidine compound comprises a 1,3,4-substituted 1H-pyrazolo[3,4-d]pyrimidine. In some embodiments, a pyrazolo-pyrimidine compound is described by the following structure:

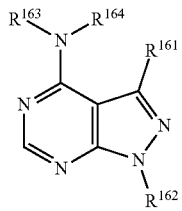

where $R^{161}$ is selected from hydrogen, an amino, an alkoxy, an aryloxy, an aryl, a carbonyl, a halogen, a hydrocarbyl, a heterocycle, a hydroxyl, a sulfonyl, a sulfinyl, and a thio; where $R^{162}$, $R^{163}$ and $R^{164}$ are independently selected from hydrogen, an aryl, a carbonyl, a hydrocarbyl, an alkyl, a heterocycle, and a sulfonyl; and where optionally $R^{163}$ and $R^{164}$ can be cyclically linked.

In certain embodiments, a pyrazolo-pyrimidine compound is described by the structure of compound 1249, as found in Table 1.

Hydroxy-Pyridinones

In some embodiments, a TERT expression enhancing compound of the invention is a hydroxy-pyridinone compound. In some embodiments, a hydroxy-pyridinone compound comprises a substituted 1-hydroxy-1H-pyridin-2-one. In some embodiments, a hydroxy-pyridinone compound is described by the following structure:

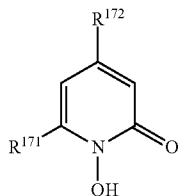

where $R^{171}$ and $R^{172}$ are selected from hydrogen, an amino, an alkoxy, an aryloxy, an aryl, a carbonyl, a halogen, a hydrocarbyl, an alkyl, a heterocycle, a hydroxyl, a sulfonyl, a sulfinyl, and a thio.

In certain embodiments, a hydroxy-pyridinone compound is described by the structure of compound 1250, as found in Table 1.

Benzenesulfonyl-Piperidines

In some embodiments, a TERT expression enhancing compound of the invention is a benzenesulfonyl-piperidine compound. In some embodiments, a benzenesulfonyl-piperidine compound comprises a substituted 1-benzenesulfonyl-piperidin-4-ol. In some embodiments, a benzenesulfonyl-piperidine compound is described by the following structure:

(XXX)

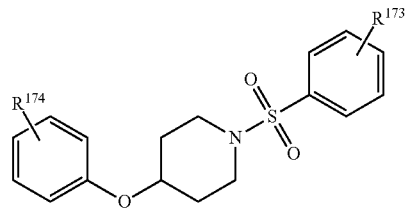

where $R^{173}$ and $R^{174}$ are each independently one or more groups, where each $R^{173}$ and each $R^{174}$ are independently selected from hydrogen, an amino, an alkoxy, an aryloxy, an aryl, a carbonyl, a cyano, a halogen, a nitro, a hydrocarbyl, a heterocycle, a hydroxyl, a sulfonyl, a sulfinyl, a sulfoxide and a thio.

In certain embodiments, a compound is of formula (XXX) where $R^{174}$ is an aryl or a heterocycle.

In certain embodiments, a benzenesulfonyl-piperidine compound is described by the structure of compound 1251, as found in Table 1.

Benzo-Azole

In some embodiments, a TERT expression enhancing compound of the invention is a benzo-azole compound. In some embodiments, a benzo-azole compound comprises a substituted 1H-benzoimidazole or benzothiazole. In some embodiments, a benzo-azole compound is described by the following structure:

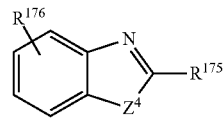

where $R^{176}$ is one or more groups;
where $R^{175}$ and each $R^{176}$ group are independently selected from hydrogen, an amino, an alkoxy, an aryloxy, an aryl, a carbonyl, a cyano, a halogen, a hydrocarbyl, a heterocycle, a hydroxyl, a sulfonyl, a sulfinyl, a sulfoxide and a thio; and where $Z^4$ is $NR^{177}$ or S, where $R^{177}$ is hydrogen, an aryl, a carbonyl, a hydrocarbyl, a heterocycle, a sulfoxide or a sulfonyl.

In certain embodiments, a benzo-azole compound is described by the structure of one of compounds 1252 to 1253, as found in Table 1.

Pyridin-2-Yl-Pyridazines

In some embodiments, a TERT expression enhancing compound of the invention is a pyridin-2-yl-pyridazine compound. In some embodiments, a pyridin-2-yl-pyridazine compound comprises a substituted 3-pyridin-2-yl-pyridazine. In some embodiments, a pyridin-2-yl-pyridazine compound is described by the following structure:

(XXXII)

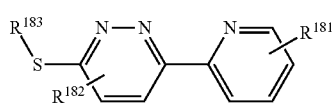

where $R^{181}$ and $R^{182}$ are independently selected from hydrogen, an amino, an alkoxy, an aryloxy, an aryl, a carbonyl, a cyano, a halogen, a hydrocarbyl, a heterocycle, a hydroxyl, a sulfonyl, a sulfinyl, and a thio; and where $R^{183}$ is hydrogen, an aryl, a carbonyl, a hydrocarbyl, a heterocycle, or a sulfonyl.

In certain embodiments, in formula (XXXII) $R^{183}$ is a benzyl or a Ar—NHCO—CH$_2$— group where Ar is an aryl.

In certain embodiments, a pyridin-2-yl-pyridazine compound is described by the structure of one of compounds 1254 to 1260, as found in Table 1.

Thieno-Triazolo-Pyrimidine

In some embodiments, a TERT expression enhancing compound of the invention is a thieno-triazolo-pyrimidine compound. In some embodiments, a thieno-triazolo-pyrimidine compound comprises a substituted thieno[2,3-e][1,2,3]triazolo[1,5-a]pyrimidine. In some embodiments, a thieno-triazolo-pyrimidine compound is described by the following structure:

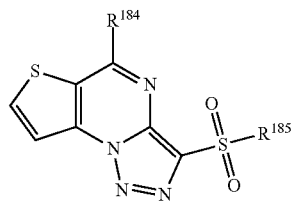

where $R^{184}$ and $R^{185}$ are independently selected from hydrogen, an amino, an alkoxy, an aryloxy, an aryl, a carbonyl, a halogen, a hydrocarbyl, a heterocycle, and a hydroxyl.

In certain embodiments, a thieno-triazolo-pyrimidine compound is described by the structure of compound 1261, as found in Table 1.

Hydrazos

In some embodiments, a TERT expression enhancing compound of the invention is a hydrazo compound. In some embodiments, a hydrazo compound is described by one of the following structures:

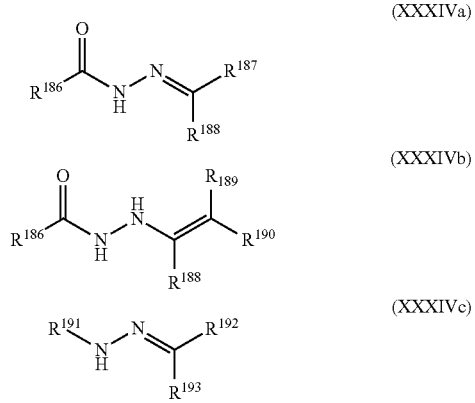

where $R^{186}$, $R^{187}$, $R^{188}$, $R^{189}$, $R^{190}$, $R^{191}$, $R^{192}$ and $R^{193}$ are independently selected from hydrogen, an alkyl, an aryl, an alkenyl, a carbonyl, a halogen, a hydrocarbyl, a heterocycle, and a hydroxyl.

In certain embodiments, in formula (XXXIVb), $R^{189}$ and $R^{190}$ are cyclically linked.

In certain embodiments, in formula (XXXIVa) or (XXXIVb), $R^{186}$ is an aryl, a phenyl, a benzyl or a heterocycle.

In certain embodiments, in formula (XXXIVa), $R^{188}$ is hydrogen or methyl, and $R^{186}$ and $R^{187}$ are independently, a cycloalkyl, an aryl, a phenyl, a naphthyl, a benzyl or a heterocycle.

In certain embodiments, in formula (XXXIVa), $R^{188}$ is hydrogen or methyl; and $R^{186}$ is a phenyl-cyclopropyl, a heterocycle, a phenyl or a naphthyl, and $R^{187}$ is a phenyl or a naphthyl.

In certain embodiments, in formula (XXXIVa), $R^{187}$ has the structure of formula (IV) or (V), where the attachment to the structure of formula (IV) or (V) is made at the $R^{102}$ position, i.e., in formula (IV) or (V), $R^{102}$ has the structure of formula (XXXIVa) substituted at $R^{187}$. In particular embodiments, in formula (XXXIVa), $R^{187}$ has the structure of formula (IV) or (V), where the attachment to the structure of formula (IV) or (V) is made at the $R^{102}$ position, where $R^{101}$ is hydrogen or an alkyl (e.g., methyl), $R^{103}$ is aryl (e.g., phenyl), and $R^{186}$ is an alkyl or a methylene-phenoxy group (—CH$_2$—OPh).

In certain embodiments, a hydrazo compound is described by the structure of one of compounds 1262 to 1294, 1464, 1465, 1483, 1485, and 1526 to 1531, as found in Table 1.

Pyrazol-1-Yl-Pyrimidinones

In some embodiments, a TERT expression enhancing compound of the invention is a pyrazol-1-yl-pyrimidinone compound. In some embodiments, a pyrazol-1-yl-pyrimidinone compound is a substituted 2-pyrazol-1-yl-3H-pyrimidin-4-one.

In some embodiments, a pyrazol-1-yl-pyrimidinone compound is described by the following structure:

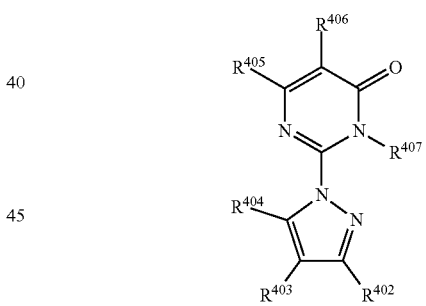

where $R^{402}$, $R^{403}$, $R^{404}$, $R^{405}$ and $R^{406}$ are independently selected from hydrogen, an amino, an alkoxy, an aryloxy, an aryl, an alkyl, a carbonyl, a halogen, a hydrocarbyl, a heterocycle, a hydroxyl, a sulfonyl, a sulfinyl, and a thio; and where $R^{407}$ is hydrogen, an aryl, an alkyl, a carbonyl, a hydrocarbyl, a heterocycle, or a sulfonyl.

In certain embodiments, a pyrazol-1-yl-pyrimidinone compound is described by a structure of Table 1, for example, one of structures 1295 to 1297.

Thieno-Pyridazinone

In some embodiments, a TERT expression enhancing compound of the invention is a thieno-pyridazinone compound. In some embodiments, a thieno-pyridazinone compound is a substituted 2H-thieno[3,4-d]pyridazin-1-one.

In some embodiments, a thieno-pyridazinone compound is described by the following structure:

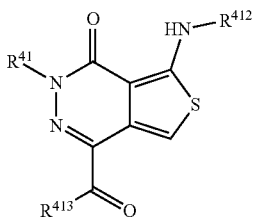

where $R^{41}$ and $R^{412}$ are independently selected from hydrogen, an aryl, an alkyl, a carbonyl, an acyl, a hydrocarbyl, a heterocycle, or a sulfonyl; and where $R^{413}$ is hydrogen, an amino, an alkoxy, an aryloxy, an aryl, a hydrocarbyl, a heterocycle, or a hydroxyl.

where $R^{414}$ and $R^{415}$ are each independently one or more groups, where each $R^{414}$ and $R^{415}$ are independently selected from hydrogen, an amino, an alkoxy, an aryloxy, an aryl, a carbonyl, a halogen, a hydrocarbyl, a heterocycle, a hydroxyl, a sulfonyl, a sulfinyl, and a thio; and where $R^{416}$ is hydrogen, an amino, an alkoxy, an aryloxy, an aryl, a hydrocarbyl, a heterocycle, or a hydroxyl.

In certain embodiments, a thieno-pyridazinone compound is described by the structure of one of compounds 1298 to 1300, as found in Table 1.

Thiadiazolamines

In some embodiments, a TERT expression enhancing compound of the invention is a thiadiazolamine compound. In some embodiments, a thiadiazolamine compound is a substituted [1,3,4]thiadiazol-2-ylamine. In some embodiments, a thiadiazolamine compound is described by one of the following structures:

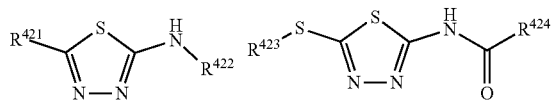

where $R^{421}$ and $R^{422}$ are independently selected from hydrogen, an amino, an alkoxy, an aryloxy, an aryl, a carbonyl, a halogen, a hydrocarbyl, a heterocycle, a hydroxyl, a sulfonyl, a sulfinyl, and a thio; where $R^{423}$ is hydrogen, an alkyl, an aryl, a hydrocarbyl, or a heterocycle; and where $R^{424}$ is hydrogen, an amino, an alkoxy, an aryloxy, an aryl, a hydrocarbyl, a heterocycle, or a hydroxyl.

In certain embodiments, a thiadiazolamine compound is described by the structure of one of compounds 1301 to 1303, as found in Table 1.

Pentaaza-Indacenes

In some embodiments, a TERT expression enhancing compound of the invention is a pentaaza-indacene compound. In some embodiments, a pentaaza-indacene compound is a substituted 6H-1,3,3a,5,6-pentaaza-as-indacene. In some embodiments, a pentaaza-indacene compound is described by the following structure:

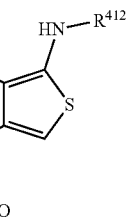

where $R^{432}$, $R^{433}$ and $R^{434}$ are independently selected from hydrogen, an amino, an alkoxy, an aryloxy, an aryl, a carbonyl, a halogen, a hydrocarbyl, a heterocycle, a hydroxyl, a sulfonyl, a sulfinyl, and a thio; and where $R^{431}$ is hydrogen, an aryl, a carbonyl, an alkyl, a hydrocarbyl, a heterocycle, a sulfoxide or a sulfonyl.

In certain embodiments, a pentaaza-indacene compound is described by the structure of compound 1304, as found in Table 1.

Chromenones

In some embodiments, a TERT expression enhancing compound of the invention is a chromen-2-one compound. In some embodiments, a chromenone compound is a substituted chromen-2-one. In some embodiments, a chromenone compound is described by the following structure:

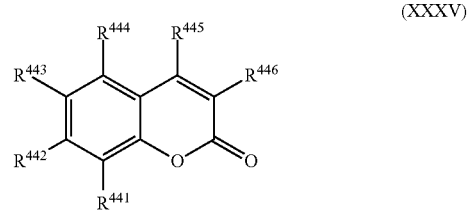

where $R^{441}$, $R^{442}$, $R^{443}$, $R^{444}$, $R^{445}$ and $R^{446}$ are independently selected from hydrogen, an amino, an alkoxy, an aryloxy, an aryl, a carbonyl, a halogen, a hydrocarbyl, a heterocycle, a hydroxyl, a sulfonyl, a sulfinyl, a sulfoxide and a thio.

In certain embodiments, in formula (XXXV), $R^{441}$, $R^{442}$, $R^{444}$ and $R^{445}$ are hydrogen, and $R^{443}$ and $R^{446}$ are independently selected from an amino, an alkoxy, an aryloxy, an aryl, a carbonyl, a halogen, a hydrocarbyl, a heterocycle, a hydroxyl, a sulfonyl, a sulfinyl, a sulfoxide and a thio.

In certain embodiments, in formula (XXXV), $R^{441}$, $R^{443}$, $R^{444}$ and $R^{445}$ are hydrogen, and $R^{442}$ and $R^{446}$ are independently selected from an amino, an alkoxy, an aryloxy, an aryl, a carbonyl, a halogen, a hydrocarbyl, a heterocycle, a hydroxyl, a sulfonyl, a sulfinyl, a sulfoxide and a thio.

In certain embodiments, in formula (XXXV), $R^{443}$, $R^{444}$ and $R^{446}$ are hydrogen, and $R^{441}$, $R^{442}$ and $R^{445}$ are independently selected from an amino, an alkoxy, an aryloxy, an aryl, a carbonyl, a halogen, a hydrocarbyl, a heterocycle, a hydroxyl, a sulfonyl, a sulfinyl, a sulfoxide and a thio.

In certain embodiments, in formula (XXXV), $R^{441}$, $R^{444}$ and $R^{446}$ are hydrogen, $R^{442}$ is an acyloxy or arylsulfonate, $R^{443}$ is a halogen, and $R^{445}$ is an alkyl.

In certain embodiments, in formula (XXXV), $R^{443}$ and $R^{444}$ are hydrogen, $R^{441}$ is a lower alkyl, $R^{442}$ is an acyloxy or arylsulfonate, and $R^{445}$ and $R^{446}$ are independently selected from an alkyl, where optionally $R^{445}$ and $R^{446}$ are cyclically linked.

In certain embodiments, in formula (XXXV), $R^{441}$, $R^{443}$ and $R^{444}$ are hydrogen, and $R^{442}$, $R^{445}$ and $R^{446}$ are independently selected from an amino, an alkoxy, an aryloxy, an aryl, a carbonyl, a halogen, a hydrocarbyl, a heterocycle, a hydroxyl, a sulfonyl, a sulfinyl, a sulfoxide and a thio.

In certain embodiments, in formula (XXXV), $R^{441}$, $R^{442}$, $R^{443}$, $R^{444}$ and $R^{445}$ are hydrogen and $R^{446}$ is an amino, an alkoxy, an aryloxy, an aryl, a carbonyl, a halogen, a hydrocarbyl, a heterocycle, a hydroxyl, a sulfonyl, a sulfinyl, a sulfoxide or a thio.

In certain embodiments, a chromenone compound is described by the structure of one of compounds 1305 to 1311, 1532 and 1533, as found in Table 1.

N-Phenyl-Benzamides and N-Phenyl-Phenylsulfonamide

In some embodiments, a TERT expression enhancing compound of the invention is a substituted N-phenyl-benzamide or N-phenyl-phenylsulfonamide compound. In some embodiments, a N-phenyl-benzamide or N-phenyl-phenylsulfonamide compound is described by the following structures:

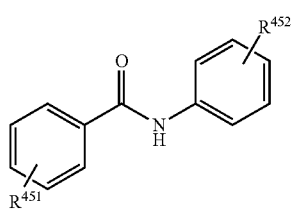

(XXXVIa)

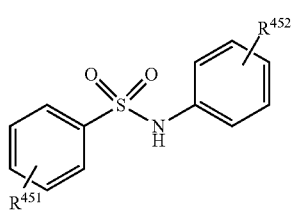

(XXXVIb)

where $R^{451}$ and $R^{452}$ are each independently one or more groups, where each $R^{451}$ and each $R^{452}$ are independently selected from hydrogen, an alkoxy, a halogen, a nitro, a hydrocarbyl, a heterocycle, a hydroxyl.

In certain embodiments, in formula (XXXVIa) or (XXXVIb), $R^{451}$ is one or more groups, each independently selected from benzyloxy, methyl, methoxy, trifluoromethyl, nitro, hyrdroxyl, iodo, fluoro, acetoxy, phenylsulfinamido (PhSO$_2$NH—), and $R^{452}$ is one or more groups, each independently selected from nitro, a carboxylmethyleneoxy (e.g., —OCH$_2$CO$_2$Me), benzimidazolyl, a piperidinyl (e.g., N-methylsulfonyl-piperidinyl), fluoro, methyl, nitro, hydroxyl, and an alkylaminocarbonyl (e.g., PhCH$_2$CH$_2$NHCO—).

In certain embodiments, a N-phenyl-benzamide or N-phenyl-phenylsulfonamide compound is described by the structure of one of compounds 1318, 1330, 1334, 1335, 1338, 1385, 1386, 1414, 1420, 1424, 1534 to 1539, as found in Table 1.

Diphenylthioureas

In some embodiments, a TERT expression enhancing compound of the invention is a substituted diphenylthiourea compound. In some embodiments, a diphenylthiourea compound is described by the following structure:

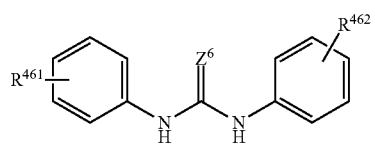

(XXXVII)

where $Z^6$ is O or S, $R^{461}$ and $R^{462}$ are each independently one or more groups, where each $R^{461}$ and each $R^{462}$ are independently selected from hydrogen, an alkyl, an aryl, an alkoxy, an aryloxy, an acyl, a halogen, a nitro, a heterocycle, a hydroxyl.

In certain embodiments, in formula (XXXVII), $Z^6$ is S, $R^{461}$ and $R^{462}$ are each independently one or more groups, where each $R^{461}$ and each $R^{462}$ are independently selected from chloro, bromo, acetyl, nitro, trifluoromethyl, phenoxy, pyridylmethylene and a benzothioazolyl group.

In certain embodiments, a diphenylurea compound is described by the structure of one of compounds 1344, 1345, 1439, 1442, 1443, 1449 and 1540, as found in Table 1.

Additional Compounds

In certain embodiments, a compound of the invention is described by the structure of one of compounds 1312 to 1476, 1541 to 1557, as found in Table 1, or a substituted version thereof.

In certain embodiments, a compound of the invention is a compound selected from the group consisting of quinolines, pyrazols, fused pyrazols, benzothiazole-triazinones, azoles, benzothiazines, bridged cyclohexanes, naphthofuranones, tetrahydrofuro-oxazolo-pyrimidinols, aza-fluorenes, oxadiazolo-pyrazines, tetrahydro-benzothiophenes, pyrimidinediones, benzofurans, dihydro-triazolo-thiadiazines, benzo-oxazine-diones, dihydro-pyridines, pyrazolo-pyrimidines, hydroxy-pyridinones, benzenesulfonyl-piperidines, benzo-azole, pyridin-2-yl-pyridazines, thieno-triazolo-pyrimidine, hydrazos, pyrazol-1-yl-pyrimidinones, thieno-pyridazinones, thiadiazolamines, pentaaza-indacenes, chromenones, N-phenyl-benzamides, N-phenyl-phenylsulfonamides, diphenylthioureas, and compounds 1312 to 1476 and 1541 to 1557 of Table 1, with the proviso that the compound does not comprise a triphenylmethyl, a triphenylamino, a tiphenylphosphine, or a Ph$_3$Z group where Z is Ar, Si or Ge.

In certain embodiments, a compound of the invention is not a triaryl compound of the general structure:

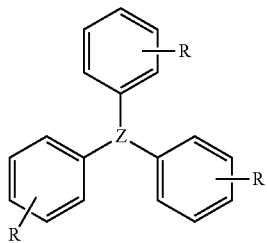

where Z is C, N, P, Ar, Si or Ge, and R is H or one or more independently selected substituent groups, where optionally one or more R groups forms a fused ring with the main aromatic ring.

Table 1 Compounds

TABLE 1

Compounds 1001 to 1557

| Structure | Compound number | Mol Weight | Formula |
|---|---|---|---|
| 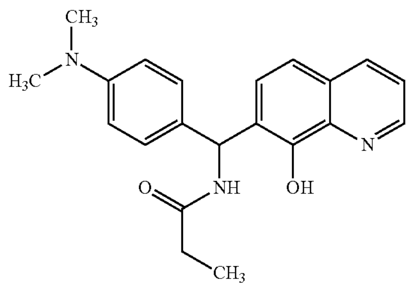 [SMILES: CCC(=O)NC(c1ccc(N(C)C)cc1)c1ccc2cccnc2c1O] | 1001 | 349.43 | C21H23N3O2 |
| 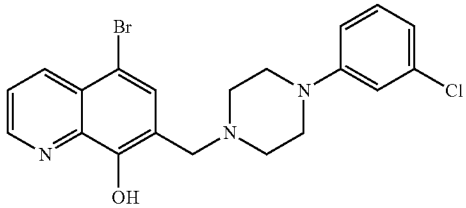 [SMILES: Oc1c(CN2CCN(c3cccc(Cl)c3)CC2)cc(Br)c2cccnc12] | 1002 | 432.74 | C20H19BrClN3O |
| 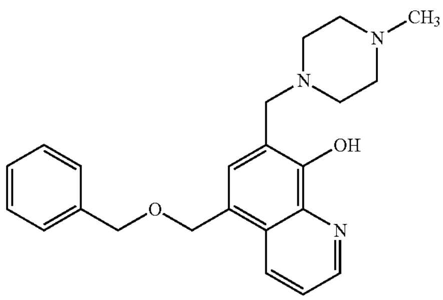 [SMILES: CN1CCN(Cc2cc(COCc3ccccc3)c3cccnc3c2O)CC1] | 1003 | 377.48 | C23H27N3O2 |
| 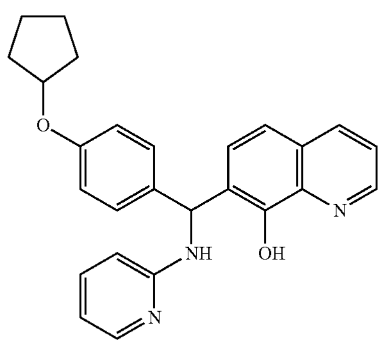 [SMILES: Oc1c(C(Nc2ccccn2)c2ccc(OC3CCCC3)cc2)ccc2cccnc12] | 1004 | 411.50 | C26H25N3O2 |
| 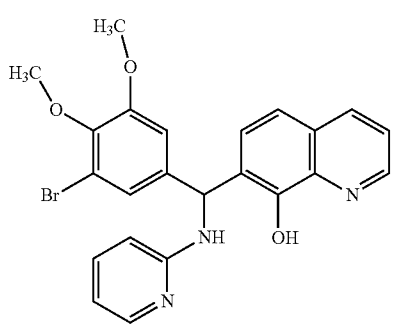 [SMILES: COc1cc(C(Nc2ccccn2)c2ccc3cccnc3c2O)cc(Br)c1OC] | 1005 | 466.33 | C23H20BrN3O3 |

TABLE 1-continued

Compounds 1001 to 1557

| Structure | Compound number | Mol Weight | Formula |
|---|---|---|---|
| 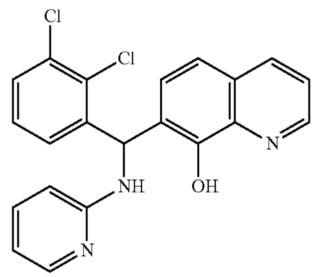 [SMILES: Oc1c(C(Nc2ccccn2)c2cccc(Cl)c2Cl)ccc2cccnc12] | 1006 | 396.27 | C21H15Cl2N3O |
| 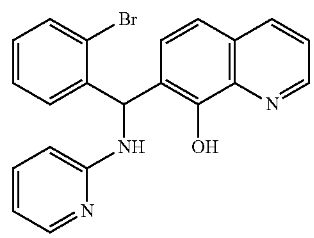 [SMILES: Oc1c(C(Nc2ccccn2)c2ccccc2Br)ccc2cccnc12] | 1007 | 406.27 | C21H16BrN3O |
| 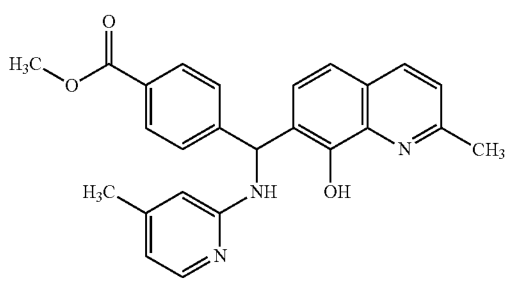 | 1008 | 413.47 | C25H23N3O3 |
| 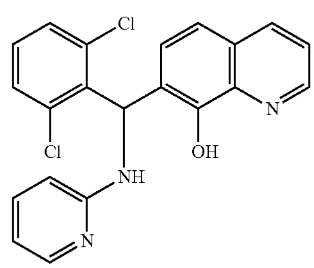 [SMILES: Oc1c(C(Nc2ccccn2)c2c(Cl)cccc2Cl)ccc2cccnc12] | 1009 | 396.27 | C21H15Cl2N3O |
| 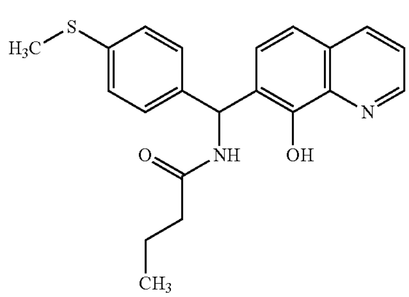 [SMILES: CCCC(=O)NC(c1ccc(SC)cc1)c1ccc2cccnc2c1O] | 1010 | 366.48 | C21H22N2O2S |

TABLE 1-continued

Compounds 1001 to 1557

| Structure | Compound number | Mol Weight | Formula |
|---|---|---|---|
| 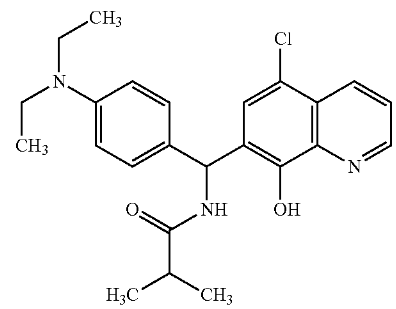 [SMILES: CCN(CC)c1ccc(C(NC(=O)C(C)C)c2cc(Cl)c3cccnc3c2O)cc1] | 1011 | 425.95 | C24H28ClN3O2 |
| 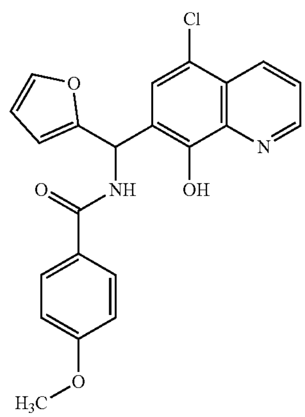 [SMILES: COc1ccc(C(=O)NC(c2ccco2)c2cc(Cl)c3cccnc3c2O)cc1] | 1012 | 408.83 | C22H17ClN2O4 |
| 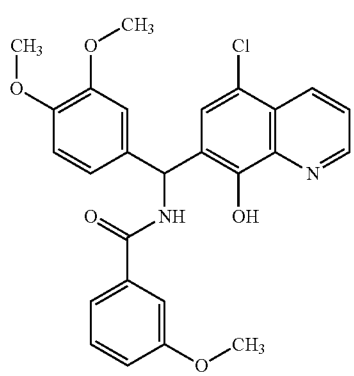 [SMILES: COc1cccc(C(=O)NC(c2ccc(OC)c(OC)c2)c2cc(Cl)c3cccnc3c2O)c1] | 1013 | 478.92 | C26H23ClN2O5 |
| 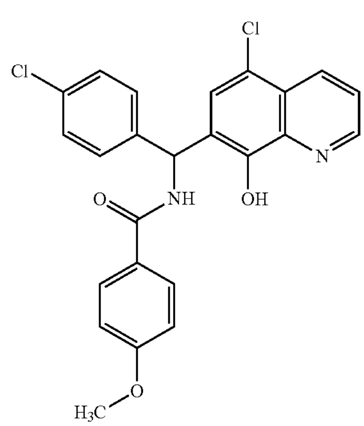 [SMILES: COc1ccc(C(=O)NC(c2ccc(Cl)cc2)c2cc(Cl)c3cccnc3c2O)cc1] | 1014 | 453.32 | C24H18Cl2N2O3 |

TABLE 1-continued

Compounds 1001 to 1557

| Structure | Compound number | Mol Weight | Formula |
|---|---|---|---|
| (structure) | 1015 | 444.91 | C26H21ClN2O3 |
| (structure) | 1016 | 444.91 | C26H21ClN2O3 |
| (structure) | 1017 | 444.91 | C26H21ClN2O3 |
| (structure) | 1018 | 396.95 | C9H5I2NO |

TABLE 1-continued
Compounds 1001 to 1557
| Structure | Compound number | Mol Weight | Formula |
|---|---|---|---|
| 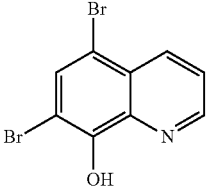 [SMILES: Oc1c(Br)cc(Br)c2cccnc12] | 1019 | 302.95 | C9H5Br2NO |
| 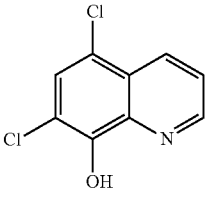 [SMILES: Oc1c(Cl)cc(Cl)c2cccnc12] | 1020 | 214.05 | C9H5Cl2NO |
| 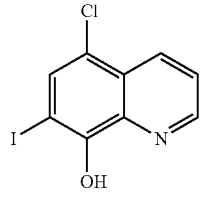 [SMILES: Oc1c(I)cc(Cl)c2cccnc12] | 1021 | 305.50 | C9H5ClINO |
| 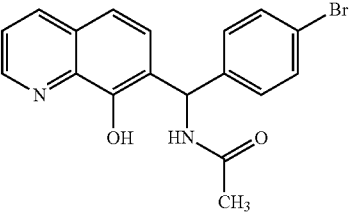 [SMILES: CC(=O)NC(c1ccc(Br)cc1)c1ccc2cccnc2c1O] | 1022 | 371.23 | C18H15BrN2O2 |
| 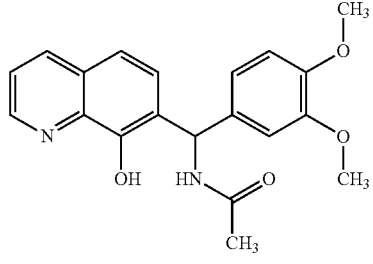 [SMILES: COc1ccc(C(NC(C)=O)c2ccc3cccnc3c2O)cc1OC] | 1023 | 352.38 | C20H20N2O4 |
| 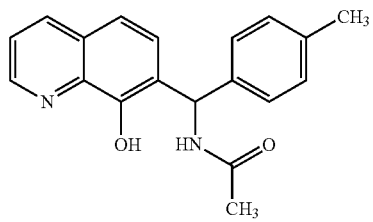 [SMILES: CC(=O)NC(c1ccc(C)cc1)c1ccc2cccnc2c1O] | 1024 | 306.36 | C19H18N2O2 |

TABLE 1-continued

Compounds 1001 to 1557

| Structure | Compound number | Mol Weight | Formula |
|---|---|---|---|
| 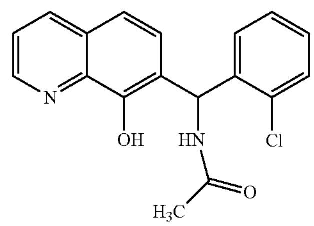 [SMILES: CC(=O)NC(c1ccccc1Cl)c1ccc2cccnc2c1O] | 1025 | 326.78 | C18H15ClN2O2 |
| 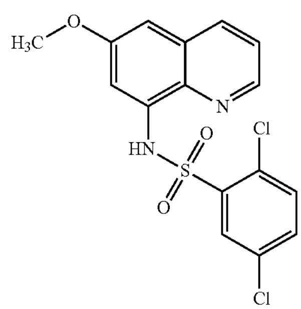 [SMILES: COc1cc(NS(=O)(=O)c2cc(Cl)ccc2Cl)c2ncccc2c1] | 1026 | 383.25 | C16H12Cl2N2O3S |
| 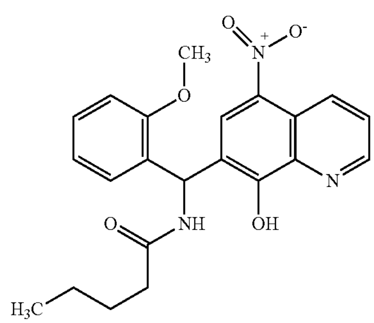 | 1027 | 409.44 | C22H23N3O5 |
| 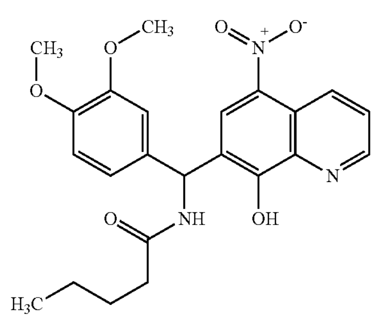 | 1028 | 411.41 | C21H21N3O6 |
| 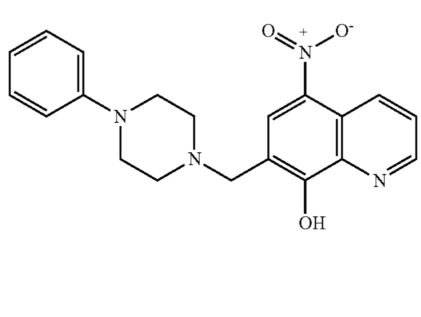 | 1029 | 364.40 | C20H20N4O3 |

TABLE 1-continued

Compounds 1001 to 1557

| Structure | Compound number | Mol Weight | Formula |
|---|---|---|---|
| 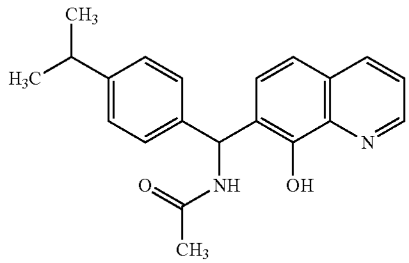 [SMILES: CC(=O)NC(c1ccc(C(C)C)cc1)c1ccc2cccnc2c1O] | 1030 | 334.41 | C21H22N2O2 |
| 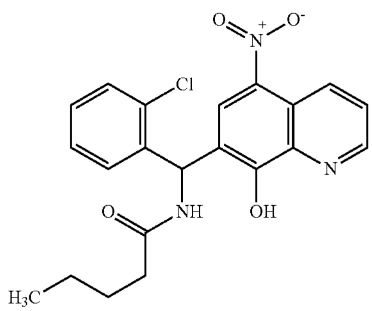 | 1031 | 413.85 | C21H20ClN3O4 |
| 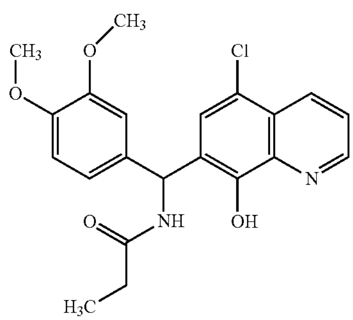 [SMILES: CCC(=O)NC(c1ccc(OC)c(OC)c1)c1cc(Cl)c2cccnc2c1O] | 1032 | 400.86 | C21H21ClN2O4 |
| 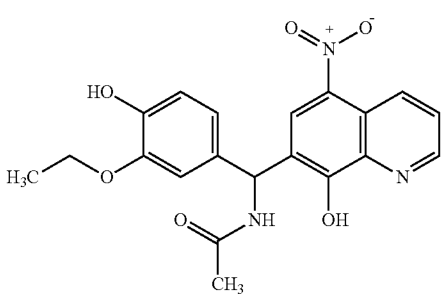 | 1033 | 397.38 | C20H19N3O6 |
| 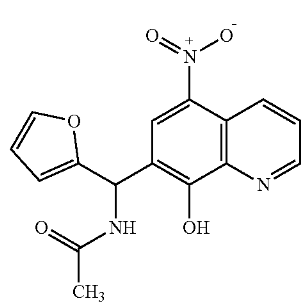 | 1034 | 327.29 | C16H13N3O5 |

TABLE 1-continued

Compounds 1001 to 1557

| Structure | Compound number | Mol Weight | Formula |
|---|---|---|---|
| 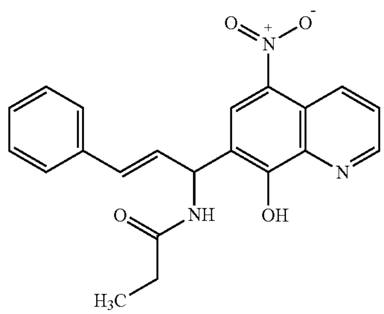 | 1035 | 377.39 | C21H19N3O4 |
| 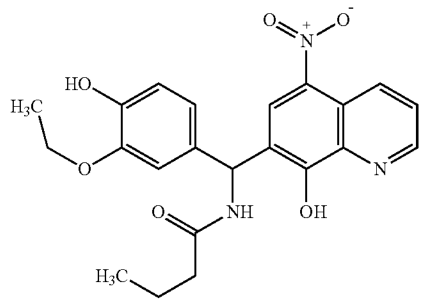 | 1036 | 425.43 | C22H23N3O6 |
| 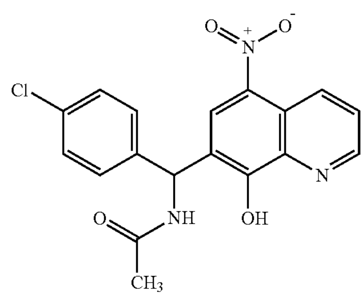 | 1037 | 371.77 | C18H14ClN3O4 |
| 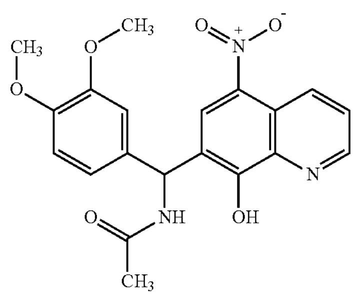 | 1038 | 386.83 | C20H19ClN2O4 |
| 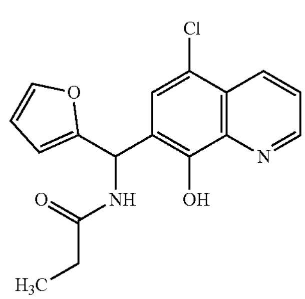 [SMILES: CCC(=O)NC(c1ccco1)c1cc(Cl)c2cccnc2c1O] | 1039 | 330.77 | C17H15ClN2O3 |

TABLE 1-continued

Compounds 1001 to 1557

| Structure | Compound number | Mol Weight | Formula |
|---|---|---|---|
| 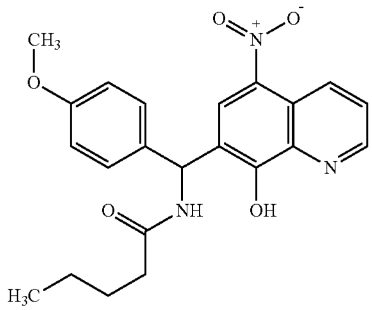 | 1040 | 409.44 | C22H23N3O5 |
| 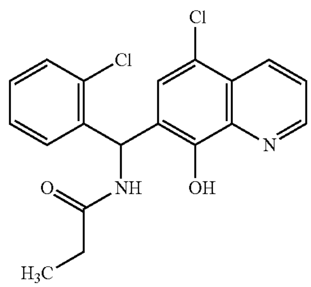 [SMILES: CCC(=O)NC(c1ccccc1Cl)c1cc(Cl)c2cccnc2c1O] | 1041 | 375.25 | C19H16Cl2N2O2 |
| 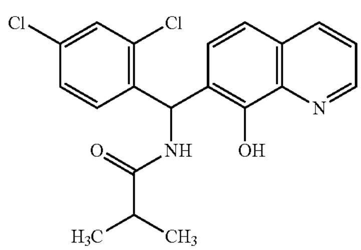 [SMILES: CC(C)C(=O)NC(c1ccc(Cl)cc1Cl)c1ccc2cccnc2c1O] | 1042 | 389.27 | C20H18Cl2N2O2 |
| 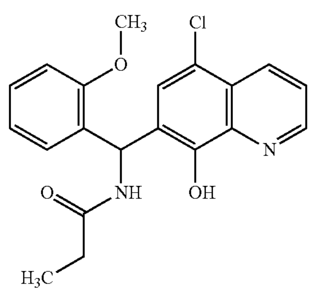 [SMILES: CCC(=O)NC(c1ccccc1OC)c1cc(Cl)c2cccnc2c1O] | 1043 | 370.83 | C20H19ClN2O3 |
| 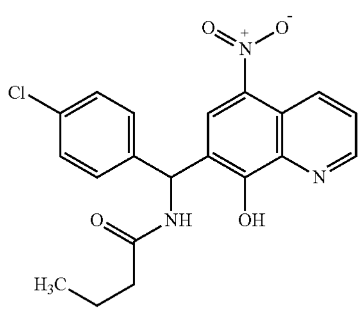 | 1044 | 399.83 | C20H18ClN3O4 |

TABLE 1-continued

Compounds 1001 to 1557

| Structure | Compound number | Mol Weight | Formula |
|---|---|---|---|
| 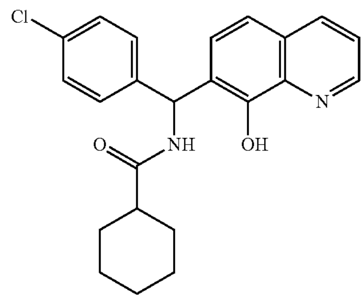 [SMILES: O=C(NC(c1ccc(Cl)cc1)c1ccc2cccnc2c1O)C1CCCCC1] | 1045 | 394.89 | C23H23ClN2O2 |
| 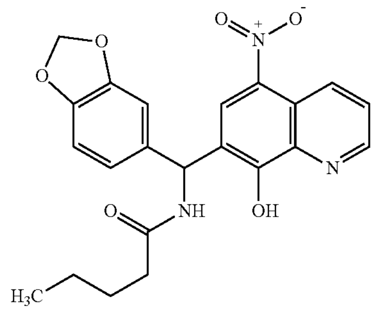 | 1046 | 423.42 | C22H21N3O6 |
| 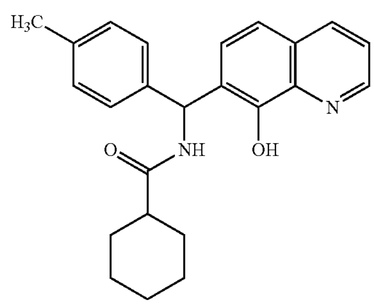 [SMILES: Cc1ccc(C(NC(=O)C2CCCCC2)c2ccc3cccnc3c2O)cc1] | 1047 | 374.48 | C24H26N2O2 |
| 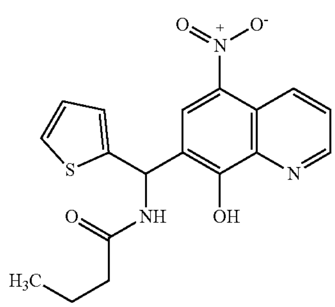 | 1048 | 371.41 | C18H17N3O4S |
| 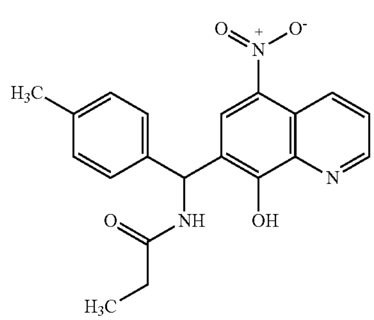 | 1049 | 365.38 | C20H19N3O4 |

TABLE 1-continued

Compounds 1001 to 1557

| Structure | Compound number | Mol Weight | Formula |
|---|---|---|---|
| 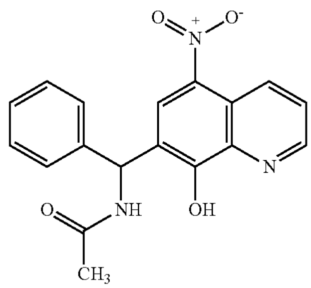 | 1050 | 337.33 | C18H15N3O4 |
| 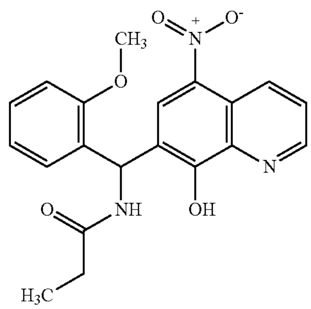 | 1051 | 381.38 | C20H19N3O5 |
| 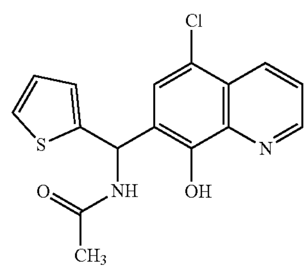 [SMILES: CC(=O)NC(c1cccs1)c1cc(Cl)c2cccnc2c1O] | 1052 | 332.80 | C16H13ClN2O2S |
| 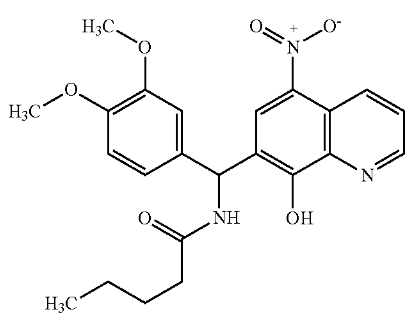 | 1053 | 439.46 | C23H25N3O6 |
| 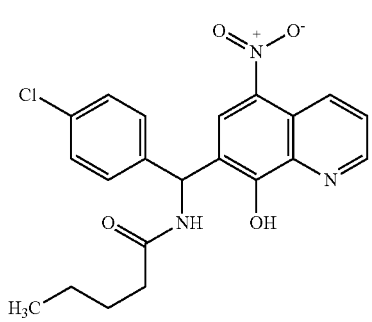 | 1054 | 413.85 | C21H20ClN3O4 |

TABLE 1-continued

Compounds 1001 to 1557

| Structure | Compound number | Mol Weight | Formula |
|---|---|---|---|
| 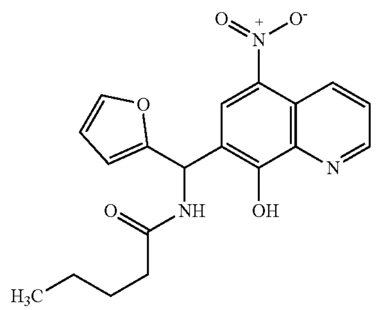 | 1055 | 369.37 | C19H19N3O5 |
| 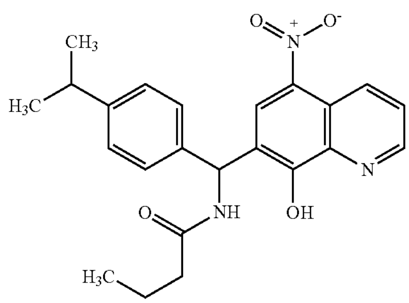 | 1056 | 407.46 | C23H25N3O4 |
| 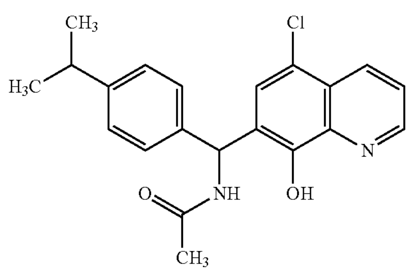 [SMILES: CC(=O)NC(c1ccc(C(C)C)cc1)c1cc(Cl)c2cccnc2c1O] | 1057 | 368.86 | C21H21ClN2O2 |
| 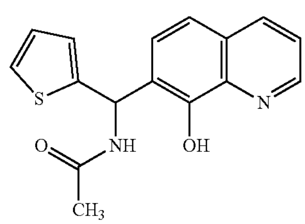 [SMILES: CC(=O)NC(c1cccs1)c1ccc2cccnc2c1O] | 1058 | 298.36 | C16H14N2O2S |
| 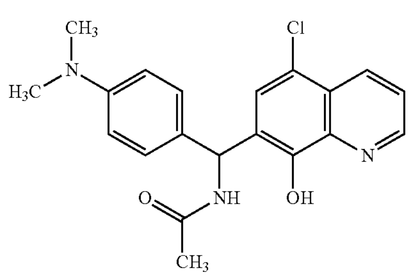 [SMILES: CC(=O)NC(c1ccc(N(C)C)cc1)c1cc(Cl)c2cccnc2c1O] | 1059 | 369.85 | C20H20ClN3O2 |

TABLE 1-continued

Compounds 1001 to 1557

| Structure | Compound number | Mol Weight | Formula |
|---|---|---|---|
| 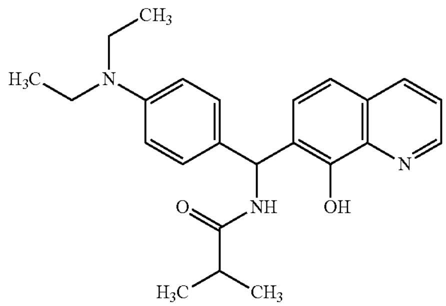 [SMILES: CCN(CC)c1ccc(C(NC(=O)C(C)C)c2ccc3cccnc3c2O)cc1] | 1060 | 391.51 | C24H29N3O2 |
| 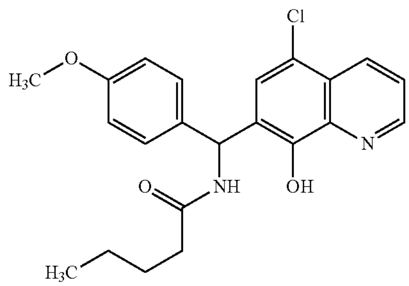 [SMILES: CCCCC(=O)NC(c1ccc(OC)cc1)c1cc(Cl)c2cccnc2c1O] | 1061 | 398.88 | C22H23ClN2O3 |
| 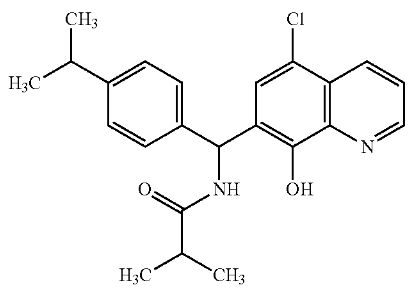 [SMILES: CC(C)C(=O)NC(c1ccc(C(C)C)cc1)c1cc(Cl)c2cccnc2c1O] | 1062 | 396.91 | C23H25ClN2O2 |
| 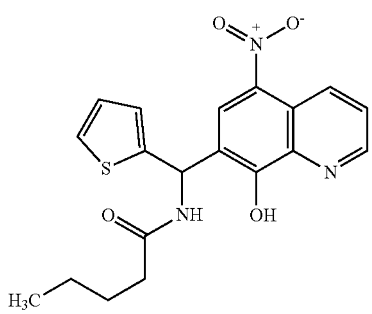 | 1063 | 385.44 | C19H19N3O4S |
| 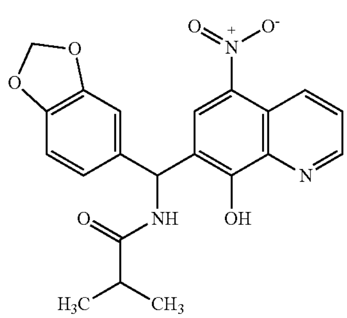 | 1064 | 409.39 | C21H19N3O6 |

TABLE 1-continued

Compounds 1001 to 1557

| Structure | Compound number | Mol Weight | Formula |
|---|---|---|---|
| 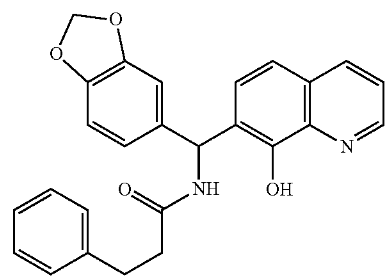 [SMILES: O=C(CCc1ccccc1)NC(c1ccc2c(c1)OCO2)c1ccc2cccnc2c1O] | 1065 | 426.46 | C26H22N2O4 |
| 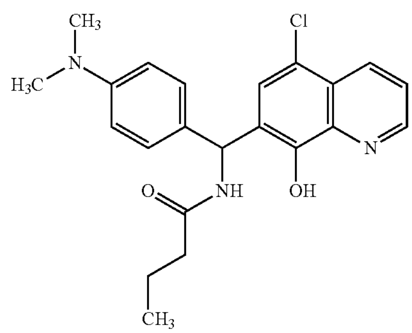 [SMILES: CCCC(=O)NC(c1ccc(N(C)C)cc1)c1cc(Cl)c2cccnc2c1O] | 1066 | 397.90 | C22H24ClN3O2 |
| 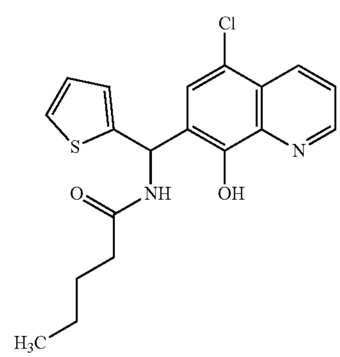 [SMILES: CCCCC(=O)NC(c1cccs1)c1cc(Cl)c2cccnc2c1O] | 1067 | 374.88 | C19H19ClN2O2S |
| 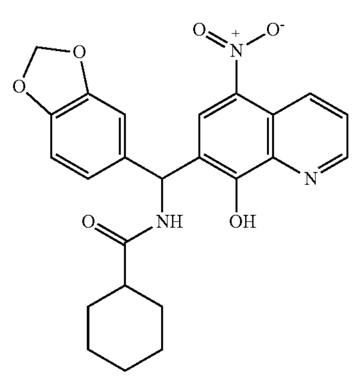 | 1068 | 449.46 | C24H23N3O6 |

TABLE 1-continued

Compounds 1001 to 1557

| Structure | Compound number | Mol Weight | Formula |
|---|---|---|---|
| 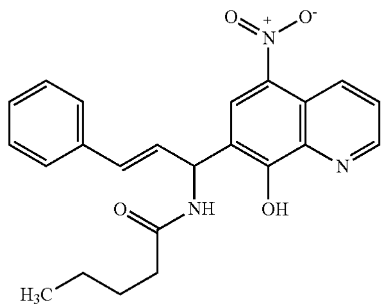 | 1069 | 405.45 | C23H23N3O4 |
| 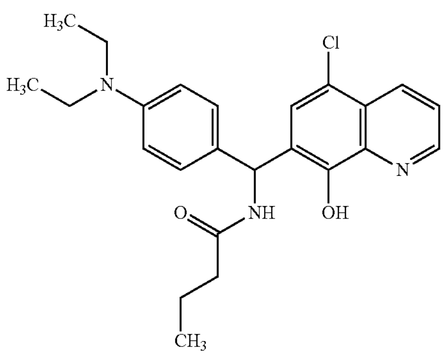 [SMILES: CCCC(=O)NC(c1ccc(N(CC)CC)cc1)c1cc(Cl)c2cccnc2c1O] | 1070 | 425.95 | C24H28ClN3O2 |
| 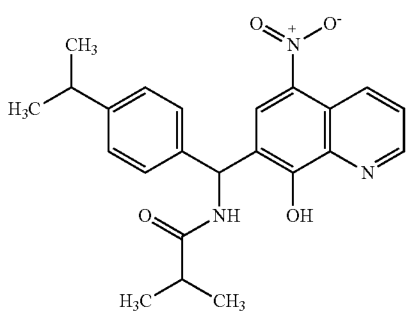 | 1071 | 407.46 | C23H25N3O4 |
| 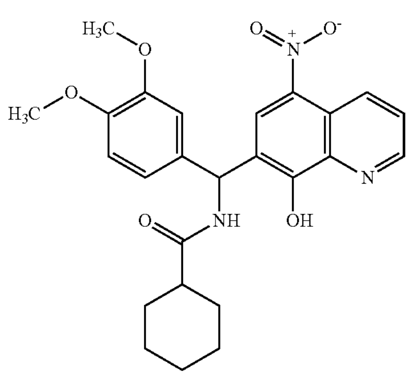 | 1072 | 465.50 | C25H27N3O6 |

TABLE 1-continued

Compounds 1001 to 1557

| Structure | Compound number | Mol Weight | Formula |
|---|---|---|---|
| 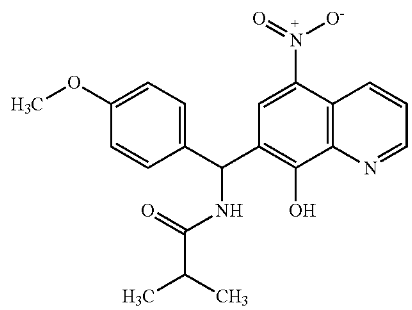 | 1073 | 395.41 | C21H21N3O5 |
| 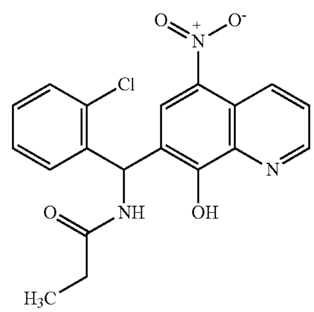 | 1074 | 385.80 | C19H16ClN3O4 |
| 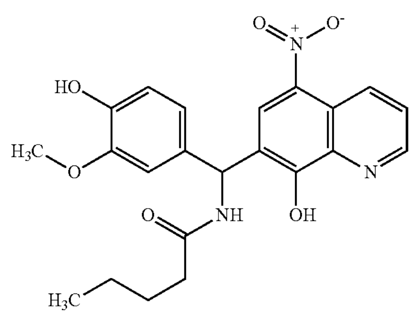 | 1075 | 439.46 | C23H25N3O6 |
| 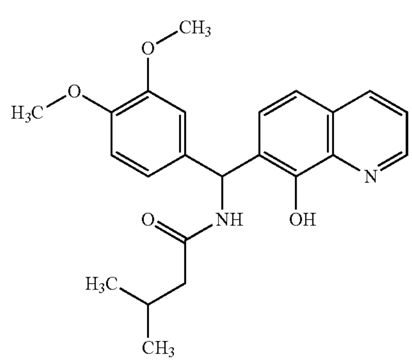 [SMILES: COc1ccc(C(NC(=O)CC(C)C)c2ccc3cccnc3c2O)cc1OC] | 1076 | 394.46 | C23H26N2O4 |

TABLE 1-continued
Compounds 1001 to 1557
| Structure | Compound number | Mol Weight | Formula |
|---|---|---|---|
| 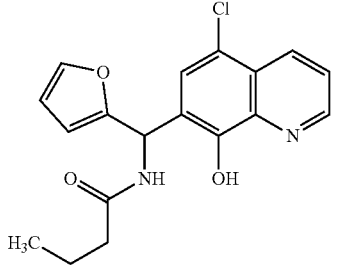 [SMILES: CCCC(=O)NC(c1ccco1)c1cc(Cl)c2cccnc2c1O] | 1077 | 344.79 | C18H17ClN2O3 |
| 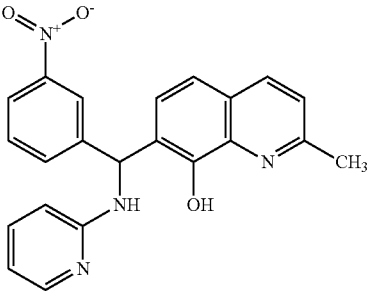 [SMILES: Cc1ccc2ccc(C(Nc3ccccn3)c3cccc([N+](=O)[O-])c3)c(O)c2n1] | 1078 | 386.40 | C22H18N4O3 |
| 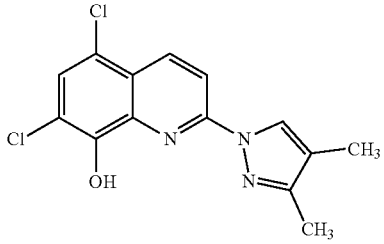 [SMILES: Cc1cn(-c2ccc3c(Cl)cc(Cl)c(O)c3n2)nc1C] | 1079 | 308.16 | C14H11Cl2N3O |
| 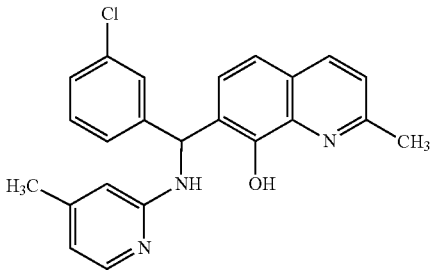 | 1080 | 389.88 | C23H20ClN3O |
| 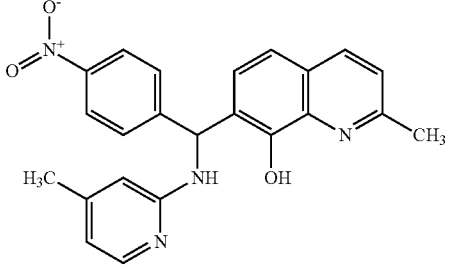 [SMILES: Cc1ccnc(NC(c2ccc([N+](=O)[O-])cc2)c2ccc3ccc(C)nc3c2O)c1] | 1081 | 400.43 | C23H20N4O3 |

TABLE 1-continued
Compounds 1001 to 1557
| Structure | Compound number | Mol Weight | Formula |
|---|---|---|---|
| 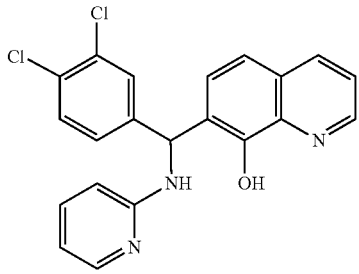 [SMILES: Oc1c(C(Nc2ccccn2)c2ccc(Cl)c(Cl)c2)ccc2cccnc12] | 1082 | 396.27 | C21H15Cl2N3O |
| 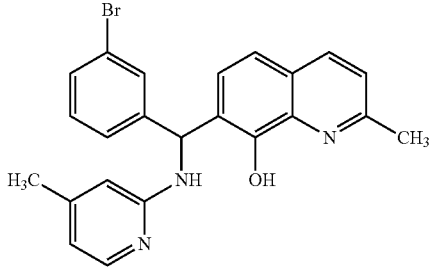 | 1083 | 434.33 | C23H20BrN3O |
| 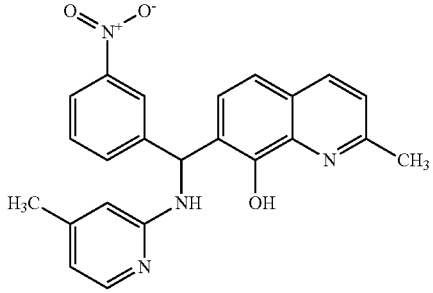 | 1084 | 400.43 | C23H20N4O3 |
| 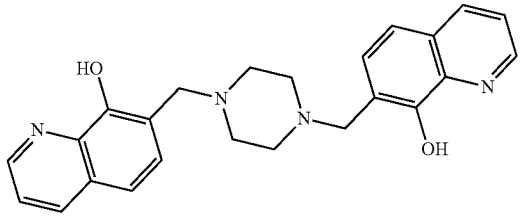 [SMILES: Oc1c(CN2CCN(Cc3ccc4cccnc4c3O)CC2)ccc2cccnc12] | 1085 | 400.47 | C24H24N4O2 |
| 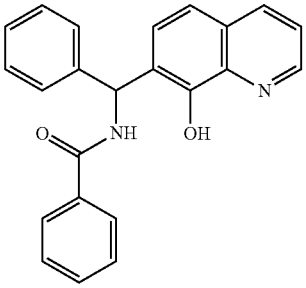 [SMILES: O=C(NC(c1ccccc1)c1ccc2cccnc2c1O)c1ccccc1] | 1086 | 354.40 | C23H18N2O2 |

TABLE 1-continued
Compounds 1001 to 1557
| Structure | Compound number | Mol Weight | Formula |
|---|---|---|---|
| 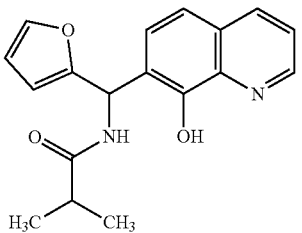 [SMILES: CC(C)C(=O)NC(c1ccco1)c1ccc2cccnc2c1O] | 1087 | 310.35 | C18H18N2O3 |
| 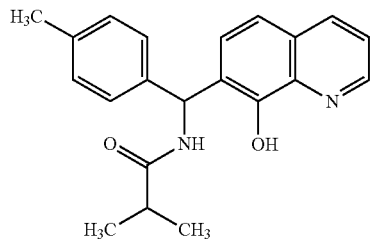 [SMILES: Cc1ccc(C(NC(=O)C(C)C)c2ccc3cccnc3c2O)cc1] | 1088 | 334.41 | C21H22N2O2 |
| 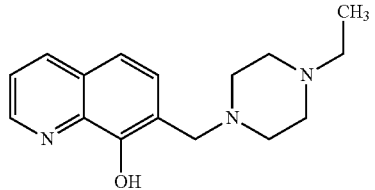 [SMILES: CCN1CCN(Cc2ccc3cccnc3c2O)CC1] | 1089 | 271.36 | C16H21N3O |
| 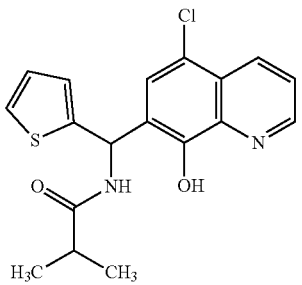 [SMILES: CC(C)C(=O)NC(c1cccs1)c1cc(Cl)c2cccnc2c1O] | 1090 | 360.86 | C18H17ClN2O2S |
| 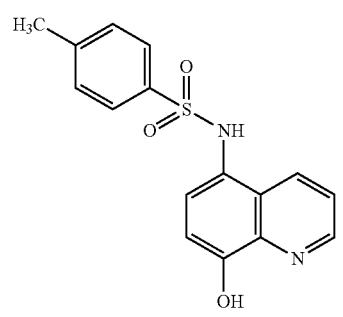 [SMILES: Cc1ccc(S(=O)(=O)Nc2ccc(O)c3ncccc23)cc1] | 1091 | 314.36 | C16H14N2O3S |

TABLE 1-continued
Compounds 1001 to 1557
| Structure | Compound number | Mol Weight | Formula |
|---|---|---|---|
| 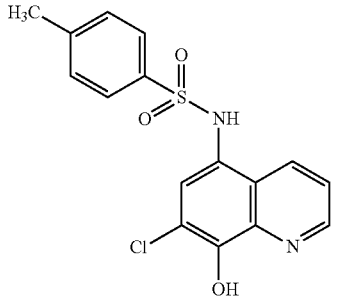 [SMILES: Cc1ccc(S(=O)(=O)Nc2cc(Cl)c(O)c3ncccc23)cc1] | 1092 | 348.80 | C16H13ClN2O3S |
| 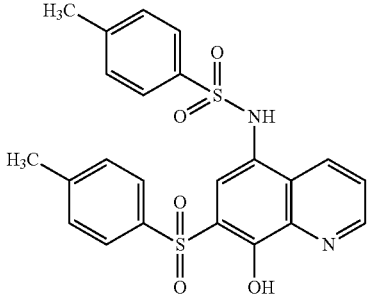 [SMILES: Cc1ccc(S(=O)(=O)Nc2cc(S(=O)(=O)c3ccc(C)cc3)c(O)c3ncccc23)cc1] | 1093 | 468.55 | C23H20N2O5S2 |
| 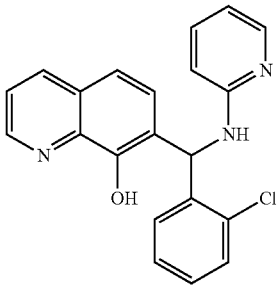 [SMILES: Oc1c(C(Nc2ccccn2)c2ccccc2Cl)ccc2cccnc12] | 1094 | 361.82 | C21H16ClN3O |
| 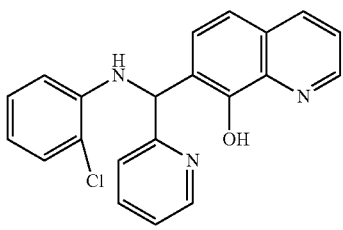 [SMILES: Oc1c(C(Nc2ccccc2Cl)c2ccccn2)ccc2cccnc12] | 1095 | 361.82 | C21H16ClN3O |
| 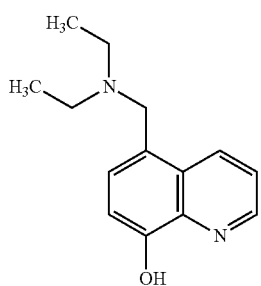 [SMILES: CCN(CC)Cc1ccc(O)c2ncccc12] | 1096 | 230.31 | C14H18N2O |

TABLE 1-continued

Compounds 1001 to 1557

| Structure | Compound number | Mol Weight | Formula |
|---|---|---|---|
| (structure) | 1097 | 272.34 | C16H20N2O2 |
| (structure) | 1098 | 286.37 | C17H22N2O2 |
| (structure) | 1099 | 300.40 | C18H24N2O2 |
| (structure) | 1100 | 314.42 | C19H26N2O2 |
| (structure) | 1101 | 329.44 | C19H27N3O2 |

TABLE 1-continued

Compounds 1001 to 1557

| Structure | Compound number | Mol Weight | Formula |
|---|---|---|---|
| 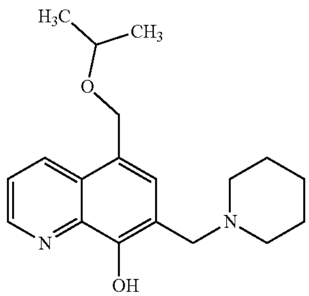 [SMILES: CC(C)OCc1cc(CN2CCCCC2)c(O)c2ncccc12] | 1102 | 314.42 | C19H26N2O2 |
| 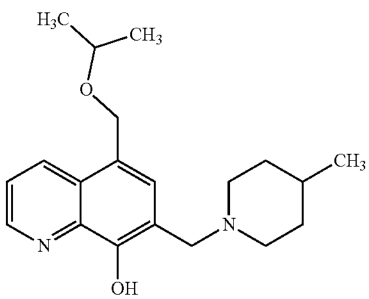 [SMILES: CC1CCN(Cc2cc(COC(C)C)c3cccnc3c2O)CC1] | 1103 | 328.45 | C20H28N2O2 |
| 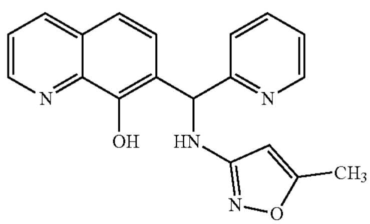 [SMILES: Cc1cc(NC(c2ccccn2)c2ccc3cccnc3c2O)no1] | 1104 | 332.36 | C19H16N4O2 |
| 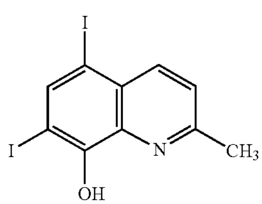 | 1105 | 410.98 | C10H7I2NO |
| 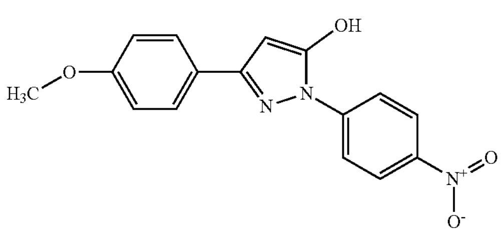 [SMILES: COc1ccc(-c2cc(O)n(-c3ccc([N+](=O)[O-])cc3)n2)cc1] | 1106 | 311.29 | C16H13N3O4 |
| 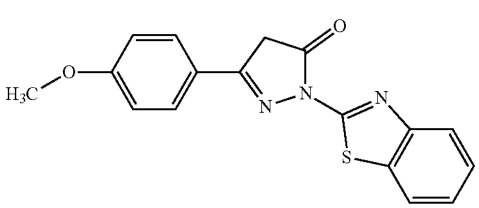 [SMILES: COc1ccc(C2=NN(c3nc4ccccc4s3)C(=O)C2)cc1] | 1107 | 323.37 | C17H13N3O2S |

TABLE 1-continued
Compounds 1001 to 1557
| Structure | Compound number | Mol Weight | Formula |
|---|---|---|---|
| 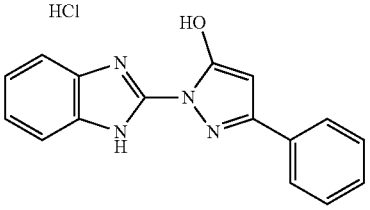 [SMILES: Cl ; Oc1cc(-c2ccccc2)nn1-c1nc2ccccc2[nH]1] | 1108 | 312.75 | C16H13ClN4O |
| 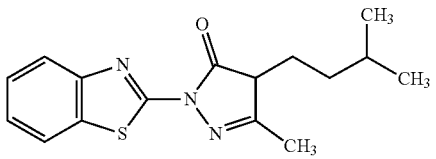 | 1109 | 301.41 | C16H19N3OS |
| 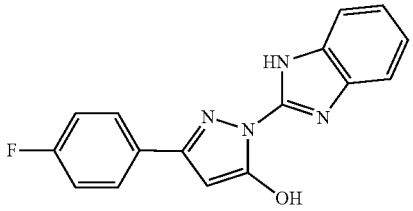 [SMILES: Oc1cc(-c2ccc(F)cc2)nn1-c1nc2ccccc2[nH]1] | 1110 | 294.28 | C16H11FN4O |
| 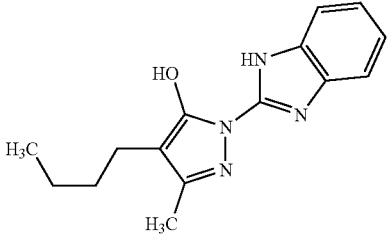 [SMILES: CCCCc1c(C)nn(-c2nc3ccccc3[nH]2)c1O] | 1111 | 270.33 | C15H18N4O |
| 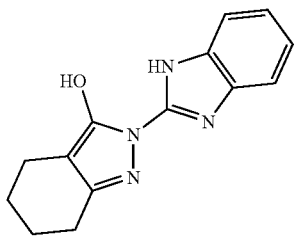 [SMILES: Oc1c2c(nn1-c1nc3ccccc3[nH]1)CCCC2] | 1112 | 254.29 | C14H14N4O |
| 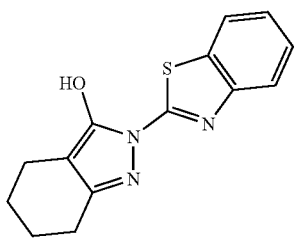 [SMILES: Oc1c2c(nn1-c1nc3ccccc3s1)CCCC2] | 1113 | 271.34 | C14H13N3OS |

TABLE 1-continued

Compounds 1001 to 1557

| Structure | Compound number | Mol Weight | Formula |
|---|---|---|---|
| 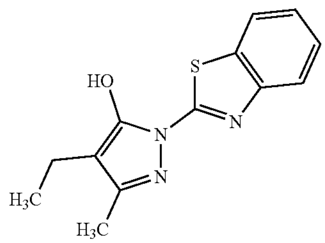 [SMILES: CCc1c(C)nn(-c2nc3ccccc3s2)c1O] | 1114 | 259.33 | C13H13N3OS |
| 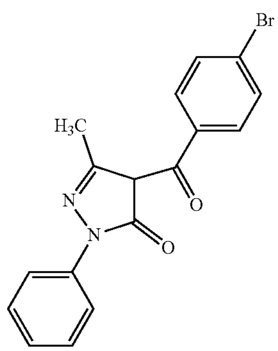 [SMILES: CC1=NN(c2ccccc2)C(=O)C1C(=O)c1ccc(Br)cc1] | 1115 | 357.20 | C17H13BrN2O2 |
| 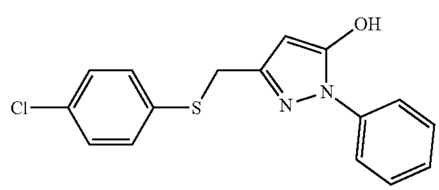 [SMILES: Oc1cc(CSc2ccc(Cl)cc2)nn1-c1ccccc1] | 1116 | 316.80 | C16H13ClN2OS |
| 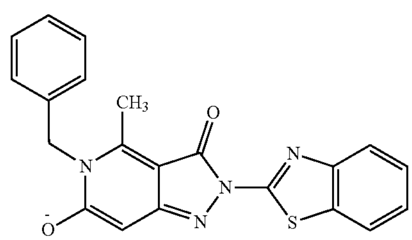 [SMILES: Cc1c2c(=O)n(-c3nc4ccccc4s3)nc-2cc(O)n1Cc1ccccc1] | 1117 | 387.43 | C21H15N4O2S |
| 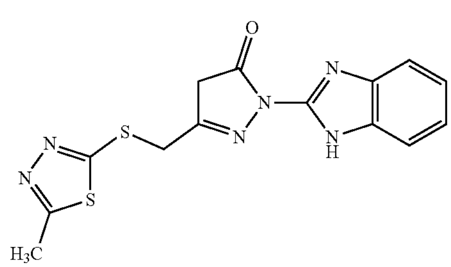 [SMILES: Cc1nnc(SCC2=NN(c3nc4ccccc4[nH]3)C(=O)C2)s1] | 1118 | 344.42 | C14H12N6OS2 |

TABLE 1-continued
Compounds 1001 to 1557
| Structure | Compound number | Mol Weight | Formula |
|---|---|---|---|
| 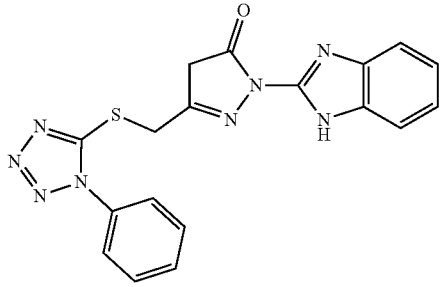 [SMILES: O=C1CC(CSc2nnnn2-c2ccccc2)=NN1c1nc2ccccc2[nH]1] | 1119 | 390.42 | C18H14N8OS |
| 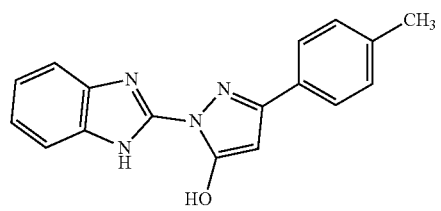 [SMILES: Cc1ccc(-c2cc(O)n(-c3nc4ccccc4[nH]3)n2)cc1] | 1120 | 290.32 | C17H14N4O |
| 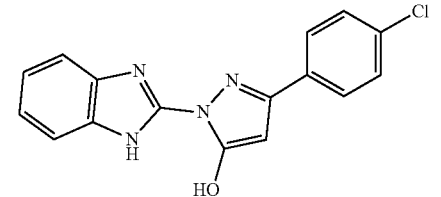 [SMILES: Oc1cc(-c2ccc(Cl)cc2)nn1-c1nc2ccccc2[nH]1] | 1121 | 310.74 | C16H11ClN4O |
| 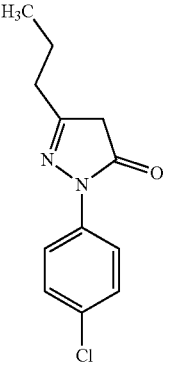 | 1122 | 236.70 | C12H13ClN2O |
| 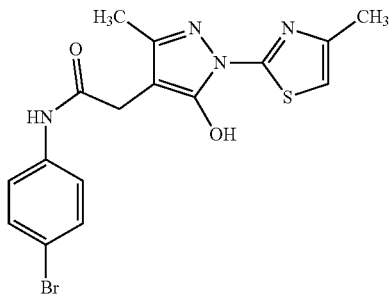 [SMILES: Cc1csc(-n2nc(C)c(CC(=O)Nc3ccc(Br)cc3)c2O)n1] | 1123 | 407.29 | C16H15BrN4O2S |

TABLE 1-continued

Compounds 1001 to 1557

| Structure | Compound number | Mol Weight | Formula |
|---|---|---|---|
| 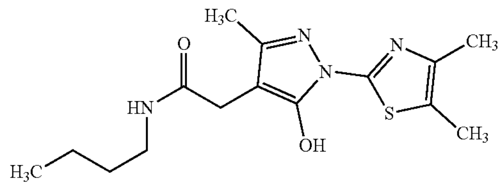 [SMILES: CCCCNC(=O)Cc1c(C)nn(-c2nc(C)c(C)s2)c1O] | 1124 | 322.43 | C15H22N4O2S |
| 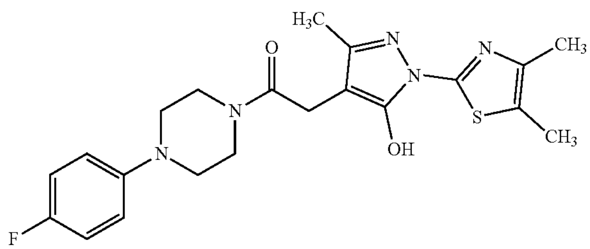 [SMILES: Cc1nc(-n2nc(C)c(CC(=O)N3CCN(c4ccc(F)cc4)CC3)c2O)sc1C] | 1125 | 429.51 | C21H24FN5O2S |
| 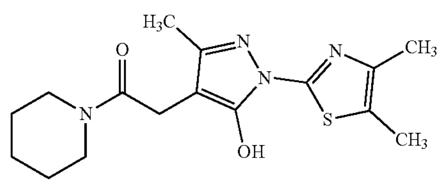 [SMILES: Cc1nc(-n2nc(C)c(CC(=O)N3CCCCC3)c2O)sc1C] | 1126 | 334.44 | C16H22N4O2S |
| 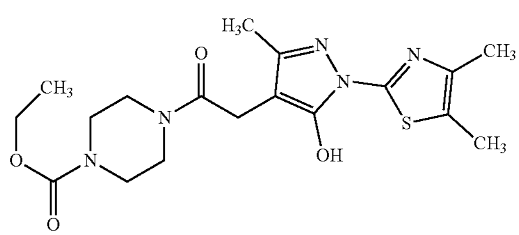 [SMILES: CCOC(=O)N1CCN(C(=O)Cc2c(C)nn(-c3nc(C)c(C)s3)c2O)CC1] | 1127 | 407.49 | C18H25N5O4S |
| 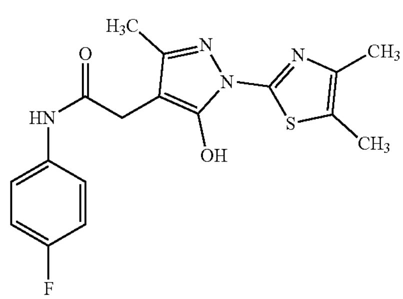 [SMILES: Cc1nc(-n2nc(C)c(CC(=O)Nc3ccc(F)cc3)c2O)sc1C] | 1128 | 360.41 | C17H17FN4O2S |
| 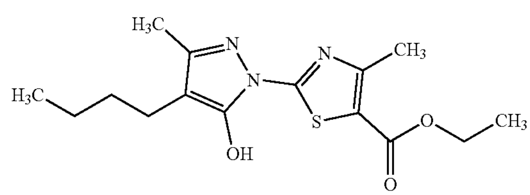 [SMILES: CCCCc1c(C)nn(-c2nc(C)c(C(=O)OCC)s2)c1O] | 1129 | 323.41 | C15H21N3O3S |
| 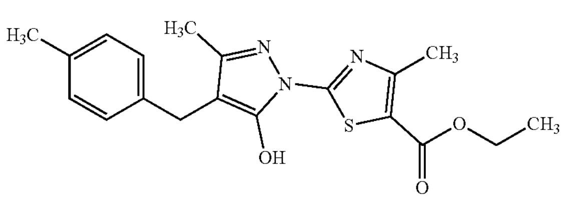 [SMILES: CCOC(=O)c1sc(-n2nc(C)c(Cc3ccc(C)cc3)c2O)nc1C] | 1130 | 371.45 | C19H21N3O3S |

TABLE 1-continued

Compounds 1001 to 1557

| Structure | Compound number | Mol Weight | Formula |
|---|---|---|---|
| 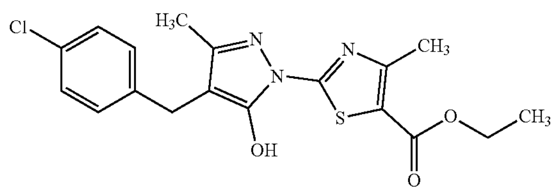 [SMILES: CCOC(=O)c1sc(-n2nc(C)c(Cc3ccc(Cl)cc3)c2O)nc1C] | 1131 | 391.87 | C18H18ClN3O3S |
| 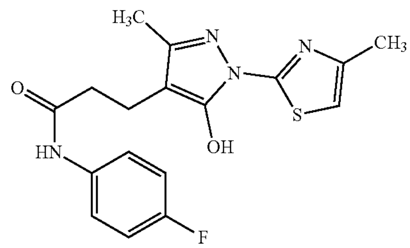 [SMILES: Cc1csc(-n2nc(C)c(CCC(=O)Nc3ccc(F)cc3)c2O)n1] | 1132 | 360.41 | C17H17FN4O2S |
| 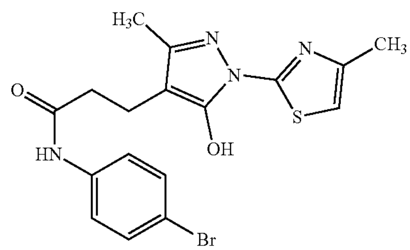 | 1133 | 421.31 | C17H17BrN4O2S |
| 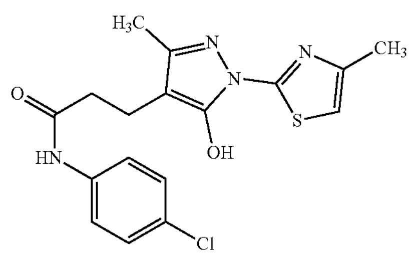 [SMILES: Cc1csc(-n2nc(C)c(CCC(=O)Nc3ccc(Cl)cc3)c2O)n1] | 1134 | 376.86 | C17H17ClN4O2S |
| 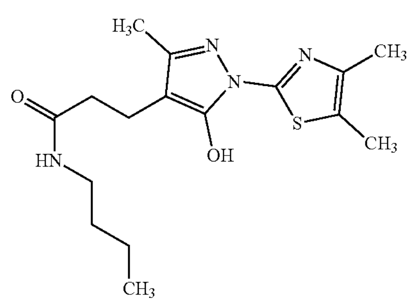 [SMILES: CCCCNC(=O)CCc1c(C)nn(-c2nc(C)c(C)s2)c1O] | 1135 | 336.45 | C16H24N4O2S |
| 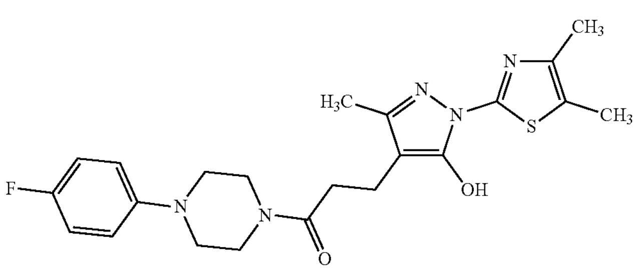 [SMILES: Cc1nc(-n2nc(C)c(CCC(=O)N3CCN(c4ccc(F)cc4)CC3)c2O)sc1C] | 1136 | 443.54 | C22H26FN5O2S |

TABLE 1-continued
Compounds 1001 to 1557
| Structure | Compound number | Mol Weight | Formula |
|---|---|---|---|
| 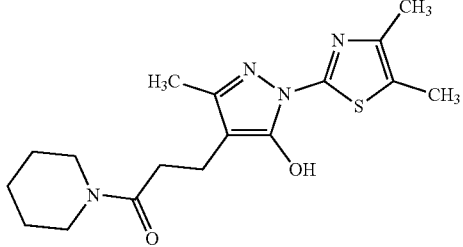 [SMILES: Cc1nc(-n2nc(C)c(CCC(=O)N3CCCCC3)c2O)sc1C] | 1137 | 348.46 | C17H24N4O2S |
| 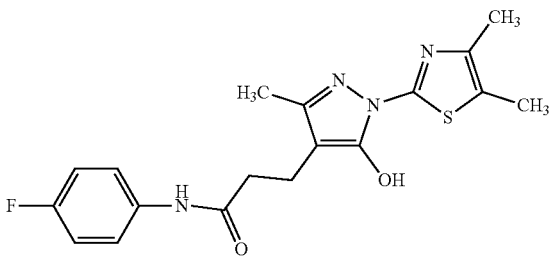 [SMILES: Cc1nc(-n2nc(C)c(CCC(=O)Nc3ccc(F)cc3)c2O)sc1C] | 1138 | 374.43 | C18H19FN4O2S |
| 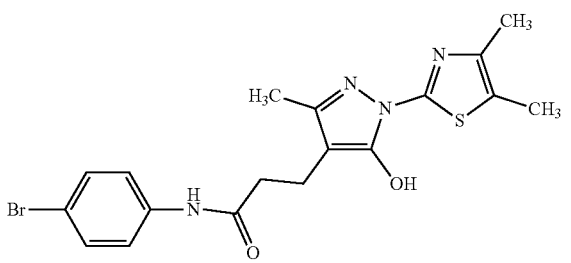 [SMILES: Cc1nc(-n2nc(C)c(CCC(=O)Nc3ccc(Br)cc3)c2O)sc1C] | 1139 | 435.34 | C18H19BrN4O2S |
| 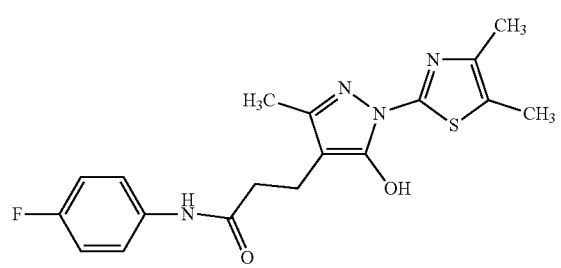 [SMILES: Cc1nc(-n2nc(C)c(CCC(=O)Nc3ccc(F)cc3)c2O)sc1C] | 1140 | 390.89 | C18H19ClN4O2S |
| 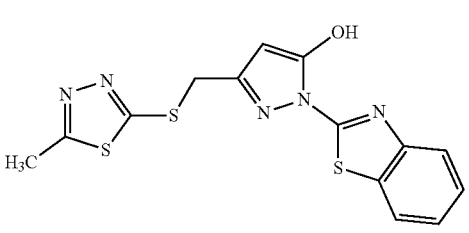 [SMILES: Cc1nnc(SCc2cc(O)n(-c3nc4ccccc4s3)n2)s1] | 1141 | 361.46 | C14H11N5OS3 |
| 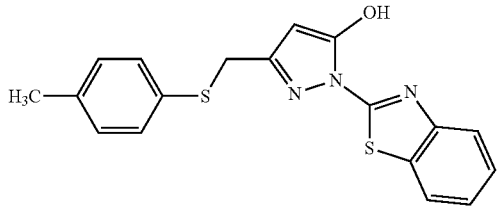 [SMILES: Cc1ccc(SCc2cc(O)n(-c3nc4ccccc4s3)n2)cc1] | 1142 | 336.41 | C18H16N4OS |

TABLE 1-continued

Compounds 1001 to 1557

| Structure | Compound number | Mol Weight | Formula |
|---|---|---|---|
| 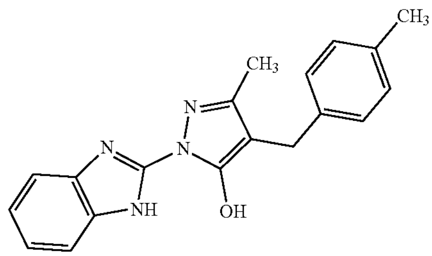 [SMILES: Cc1ccc(Cc2c(C)nn(-c3nc4ccccc4[nH]3)c2O)cc1] | 1143 | 318.37 | C19H18N4O |
| 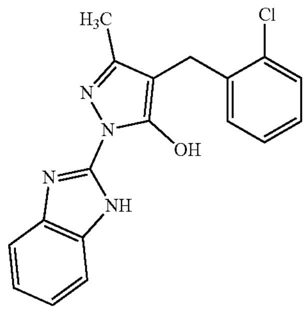 [SMILES: Cc1nn(-c2nc3ccccc3[nH]2)c(O)c1Cc1ccccc1Cl] | 1144 | 338.79 | C18H15ClN4O |
| 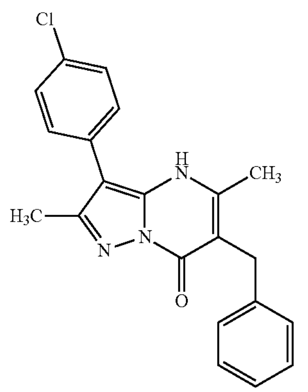 [SMILES: Cc1nn2c(=O)c(Cc3ccccc3)c(C)[nH]c2c1-c1ccc(Cl)cc1] | 1145 | 363.84 | C21H18ClN3O |
| 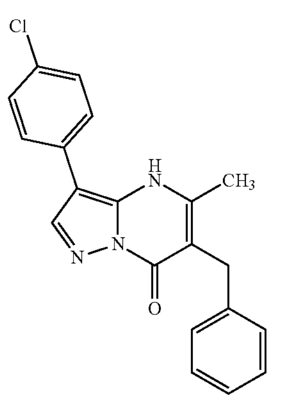 [SMILES: Cc1[nH]c2c(-c3ccc(Cl)cc3)cnn2c(=O)c1Cc1ccccc1] | 1146 | 349.81 | C20H16ClN3O |

TABLE 1-continued

Compounds 1001 to 1557

| Structure | Compound number | Mol Weight | Formula |
|---|---|---|---|
| 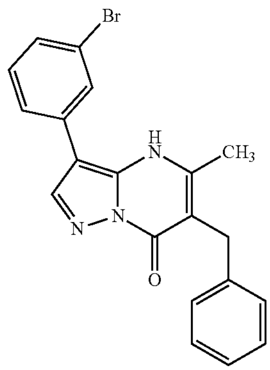 [SMILES: Cc1[nH]c2c(-c3cccc(Br)c3)cnn2c(=O)c1Cc1ccccc1] | 1147 | 394.27 | C20H16BrN3O |
| 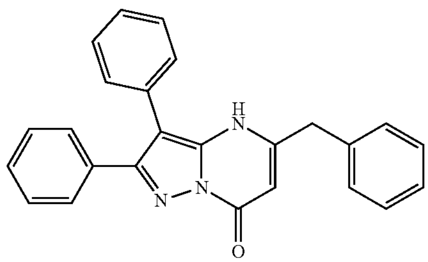 [SMILES: O=c1cc(Cc2ccccc2)[nH]c2c(-c3ccccc3)c(-c3ccccc3)nn12] | 1148 | 377.44 | C25H19N3O |
| 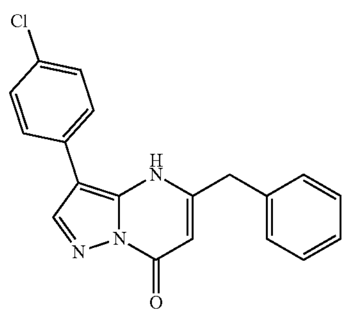 [SMILES: O=c1cc(Cc2ccccc2)[nH]c2c(-c3ccc(Cl)cc3)cnn12] | 1149 | 335.79 | C19H14ClN3O |
| 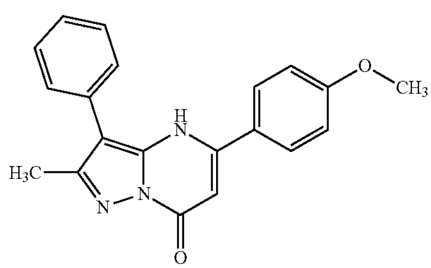 [SMILES: COc1ccc(-c2cc(=O)n3nc(C)c(-c4ccccc4)c3[nH]2)cc1] | 1150 | 331.37 | C20H17N3O2 |
| 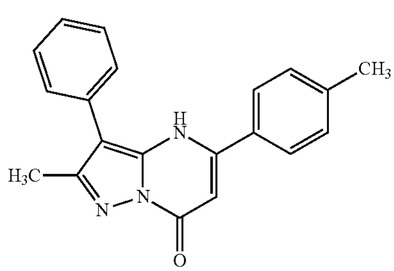 [SMILES: Cc1ccc(-c2cc(=O)n3nc(C)c(-c4ccccc4)c3[nH]2)cc1] | 1151 | 315.37 | C20H17N3O |

TABLE 1-continued
Compounds 1001 to 1557
| Structure | Compound number | Mol Weight | Formula |
|---|---|---|---|
| 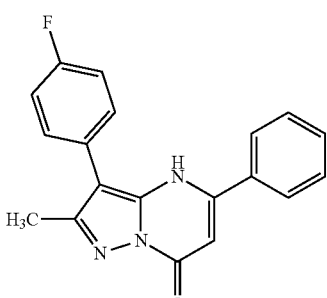 | 1152 | 319.33 | C19H14FN3O |
| 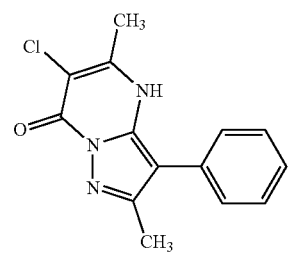 [SMILES: Cc1nn2c(=O)c(Cl)c(C)[nH]c2c1-c1ccccc1] | 1153 | 273.72 | C14H12ClN3O |
| 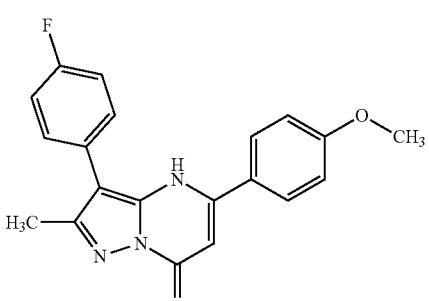 | 1154 | 349.36 | C20H16FN3O2 |
| 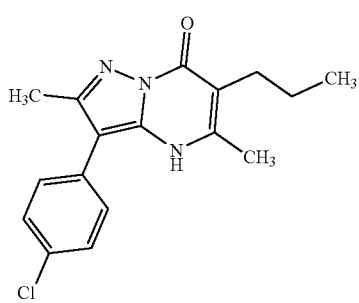 [SMILES: CCCc1c(C)[nH]c2c(-c3ccc(Cl)cc3)c(C)nn2c1=O] | 1155 | 315.80 | C17H18ClN3O |
| 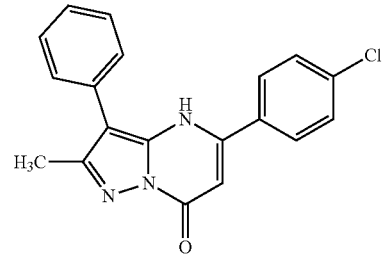 [SMILES: Cc1nn2c(=O)cc(-c3ccc(Cl)cc3)[nH]c2c1-c1ccccc1] | 1156 | 335.79 | C19H14ClN3O |

TABLE 1-continued
Compounds 1001 to 1557
| Structure | Compound number | Mol Weight | Formula |
|---|---|---|---|
| 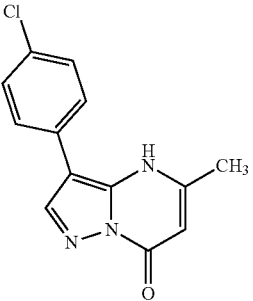 [SMILES: Cc1cc(=O)n2ncc(-c3ccc(Cl)cc3)c2[nH]1] | 1157 | 259.69 | C13H10ClN3O |
| 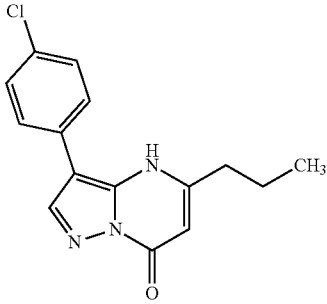 [SMILES: CCCc1cc(=O)n2ncc(-c3ccc(Cl)cc3)c2[nH]1] | 1158 | 287.74 | C15H14ClN3O |
| 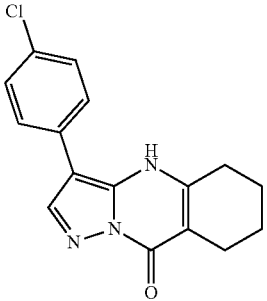 [SMILES: O=c1c2c([nH]c3c(-c4ccc(Cl)cc4)cnn13)CCCC2] | 1159 | 299.76 | C16H14ClN3O |
| 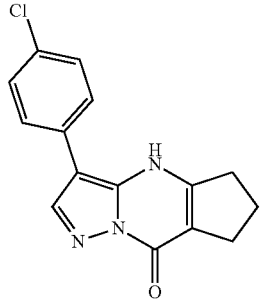 [SMILES: O=c1c2c([nH]c3c(-c4ccc(Cl)cc4)cnn13)CCC2] | 1160 | 285.73 | C15H12ClN3O |
| 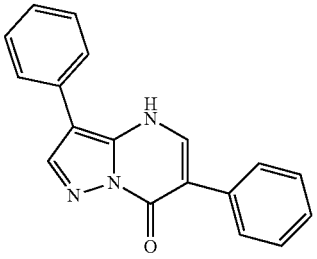 [SMILES: O=c1c(-c2ccccc2)c[nH]c2c(-c3ccccc3)cnn12] | 1161 | 287.32 | C18H13N3O |

TABLE 1-continued

Compounds 1001 to 1557

| Structure | Compound number | Mol Weight | Formula |
|---|---|---|---|
| 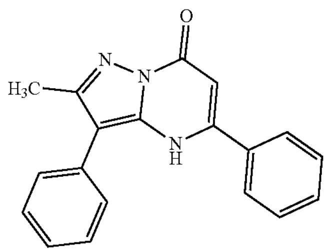 [SMILES: Cc1nn2c(=O)cc(-c3ccccc3)[nH]c2c1-c1ccccc1] | 1162 | 301.34 | C19H15N3O |
| 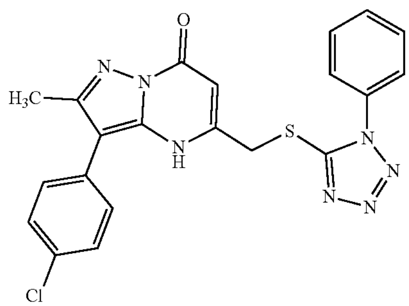 [SMILES: Cc1nn2c(=O)cc(CSc3nnnn3-c3ccccc3)[nH]c2c1-c1ccc(Cl)cc1] | 1163 | 449.92 | C21H16ClN7OS |
| 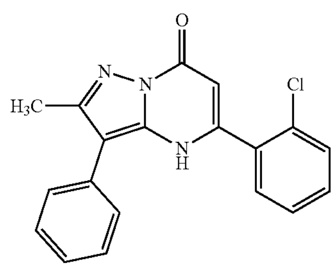 [SMILES: Cc1nn2c(=O)cc(-c3ccccc3Cl)[nH]c2c1-c1ccccc1] | 1164 | 335.79 | C19H14ClN3O |
| 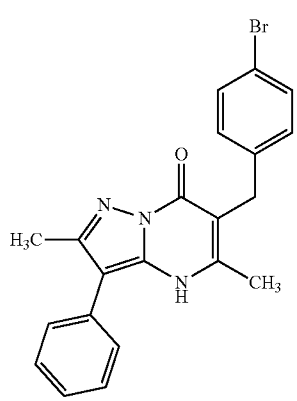 [SMILES: Cc1nn2c(=O)c(Cc3ccc(Br)cc3)c(C)[nH]c2c1-c1ccccc1] | 1165 | 408.29 | C21H18BrN3O |

TABLE 1-continued

Compounds 1001 to 1557

| Structure | Compound number | Mol Weight | Formula |
|---|---|---|---|
| 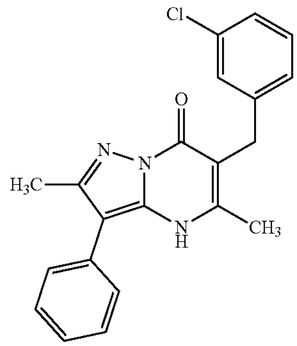 [SMILES: Cc1nn2c(=O)c(Cc3cccc(Cl)c3)c(C)[nH]c2c1-c1ccccc1] | 1166 | 363.84 | C21H18ClN3O |
| 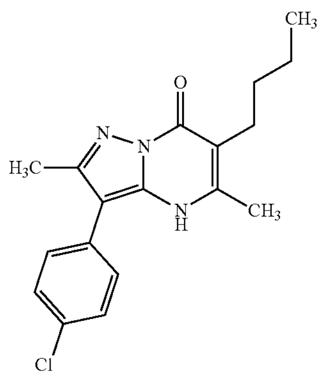 [SMILES: CCCCc1c(C)[nH]c2c(-c3ccc(Cl)cc3)c(C)nn2c1=O] | 1167 | 329.82 | C18H20ClN3O |
| 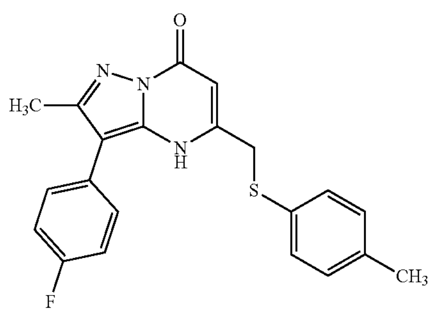 [SMILES: Cc1ccc(SCc2cc(=O)n3nc(C)c(-c4ccc(F)cc4)c3[nH]2)cc1] | 1168 | 379.45 | C21H18FN3OS |
| 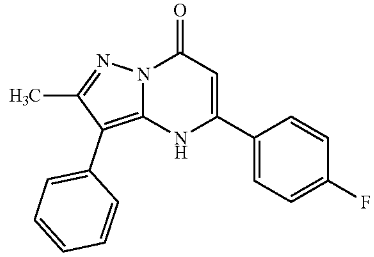 [SMILES: Cc1nn2c(=O)cc(-c3ccc(F)cc3)[nH]c2c1-c1ccccc1] | 1169 | 319.33 | C19H14FN3O |

TABLE 1-continued

Compounds 1001 to 1557

| Structure | Compound number | Mol Weight | Formula |
|---|---|---|---|
| 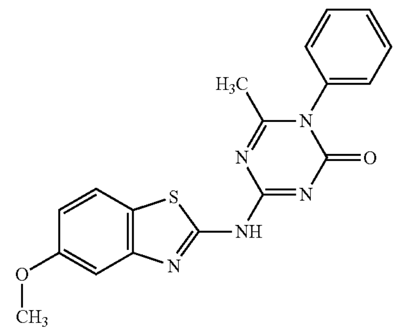 [SMILES: COc1ccc2sc(Nc3nc(C)n(-c4ccccc4)c(=O)n3)nc2c1] | 1170 | 365.41 | C18H15N5O2S |
| 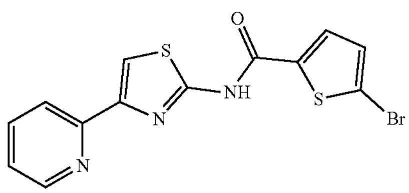 [SMILES: O=C(Nc1nc(-c2ccccn2)cs1)c1ccc(Br)s1] | 1171 | 366.26 | C13H8BrN3OS2 |
| 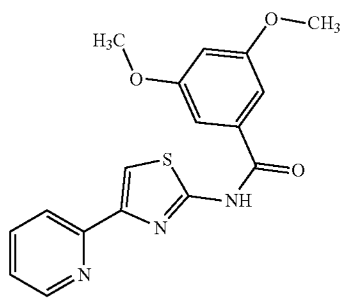 [SMILES: COc1cc(OC)cc(C(=O)Nc2nc(-c3ccccn3)cs2)c1] | 1172 | 341.38 | C17H15N3O3S |
| 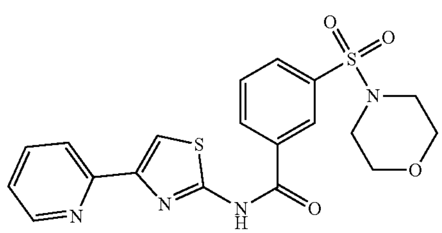 [SMILES: O=C(Nc1nc(-c2ccccn2)cs1)c1cccc(S(=O)(=O)N2CCOCC2)c1] | 1173 | 430.50 | C19H18N4O4S2 |
| 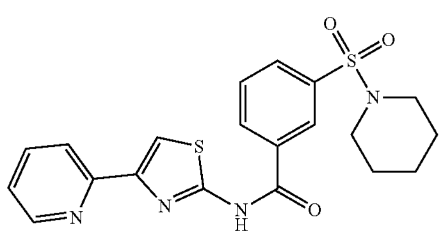 | 1174 | 428.53 | C20H20N4O3S2 |
| 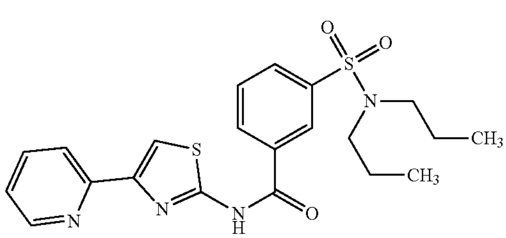 [SMILES: CCCN(CCC)S(=O)(=O)c1cccc(C(=O)Nc2nc(-c3ccccn3)cs2)c1] | 1175 | 444.57 | C21H24N4O3S2 |

TABLE 1-continued

Compounds 1001 to 1557

| Structure | Compound number | Mol Weight | Formula |
|---|---|---|---|
| 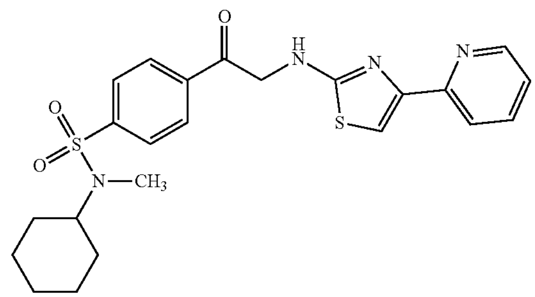 [SMILES: CN(C1CCCCC1)S(=O)(=O)c1ccc(C(=O)CNc2nc(-c3ccccn3)cs2)cc1] | 1176 | 456.58 | C22H24N4O3S2 |
| 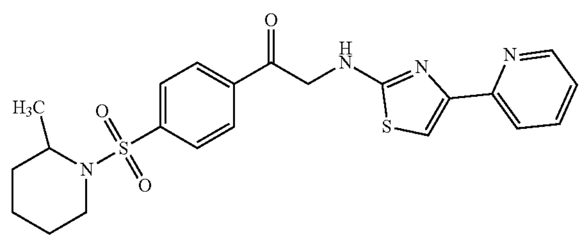 [SMILES: CC1CCCCN1S(=O)(=O)c1ccc(C(=O)CNc2nc(-c3ccccn3)cs2)cc1] | 1177 | 442.55 | C21H22N4O3S2 |
| 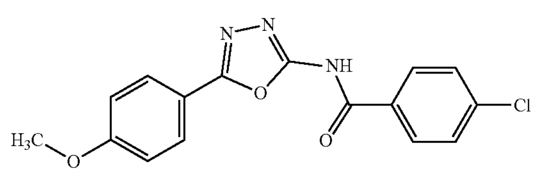 [SMILES: COc1ccc(-c2nnc(NC(=O)c3ccc(Cl)cc3)o2)cc1] | 1178 | 329.74 | C16H12ClN3O3 |
| 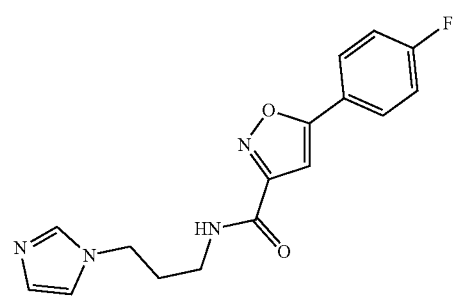 [SMILES: O=C(NCCCn1ccnc1)c1cc(-c2ccc(F)cc2)on1] | 1179 | 314.31 | C16H15FN4O2 |
| 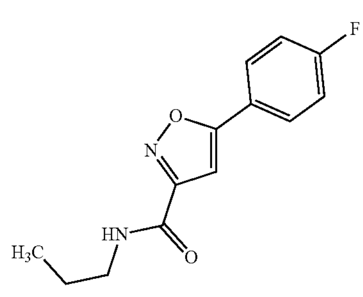 [SMILES: CCCNC(=O)c1cc(-c2ccc(F)cc2)on1] | 1180 | 248.25 | C13H13FN2O2 |

TABLE 1-continued

Compounds 1001 to 1557

| Structure | Compound number | Mol Weight | Formula |
|---|---|---|---|
| 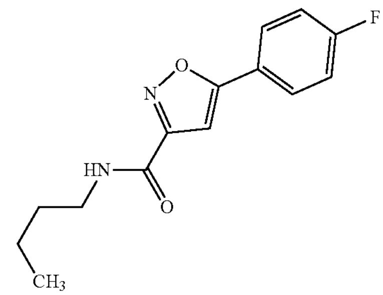 [SMILES: CCCCNC(=O)c1cc(-c2ccc(F)cc2)on1] | 1181 | 262.28 | C14H15FN2O2 |
| 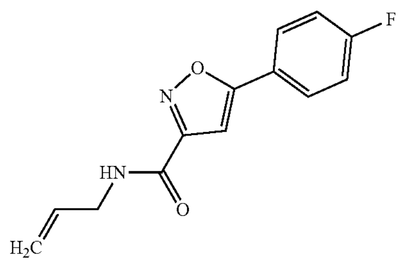 [SMILES: C=CCNC(=O)c1cc(-c2ccc(F)cc2)on1] | 1182 | 246.24 | C13H11FN2O2 |
| 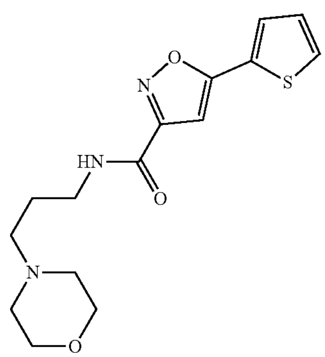 [SMILES: O=C(NCCCN1CCOCC1)c1cc(-c2cccs2)on1] | 1183 | 321.39 | C15H19N3O3S |
| 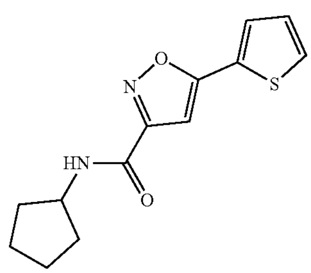 [SMILES: O=C(NC1CCCC1)c1cc(-c2cccs2)on1] | 1184 | 262.33 | C13H14N2O2S |
| 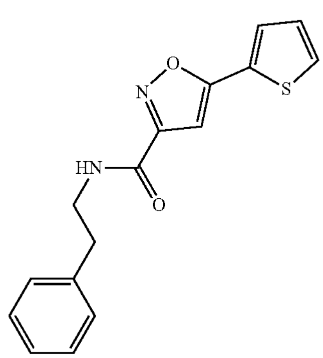 [SMILES: O=C(NCCc1ccccc1)c1cc(-c2cccs2)on1] | 1185 | 298.36 | C16H14N2O2S |

TABLE 1-continued

Compounds 1001 to 1557

| Structure | Compound number | Mol Weight | Formula |
|---|---|---|---|
| 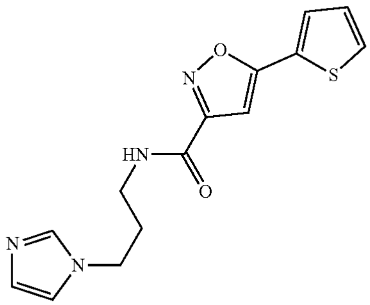 [SMILES: O=C(NCCCn1ccnc1)c1cc(-c2cccs2)on1] | 1186 | 302.35 | C14H14N4O2S |
| 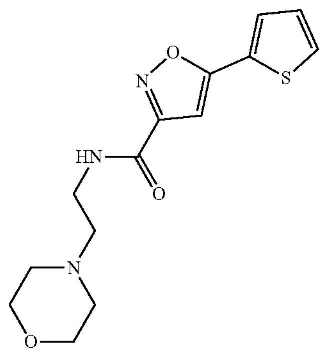 [SMILES: O=C(NCCN1CCOCC1)c1cc(-c2cccs2)on1] | 1187 | 307.37 | C14H17N3O3S |
| 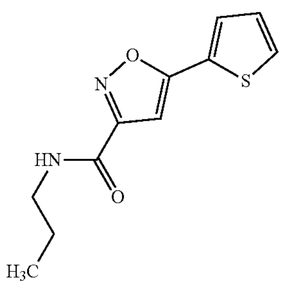 [SMILES: CCCNC(=O)c1cc(-c2cccs2)on1] | 1188 | 236.29 | C11H12N2O2S |
| 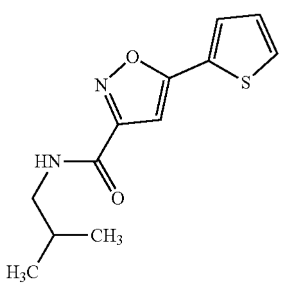 [SMILES: CC(C)CNC(=O)c1cc(-c2cccs2)on1] | 1189 | 250.32 | C12H14N2O2S |
| 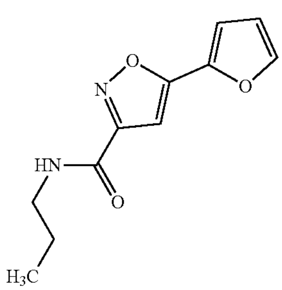 [SMILES: CCCNC(=O)c1cc(-c2ccco2)on1] | 1190 | 220.22 | C11H12N2O3 |

TABLE 1-continued

Compounds 1001 to 1557

| Structure | Compound number | Mol Weight | Formula |
|---|---|---|---|
| 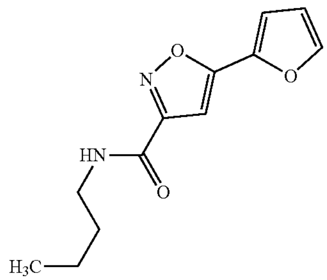 [SMILES: CCCCNC(=O)c1cc(-c2ccco2)on1] | 1191 | 234.25 | C12H14N2O3 |
| 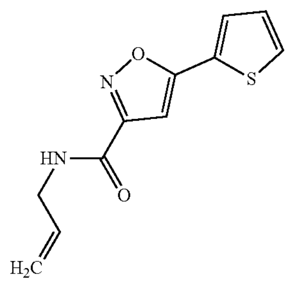 [SMILES: C=CCNC(=O)c1cc(-c2cccs2)on1] | 1192 | 234.27 | C11H10N2O2S |
| 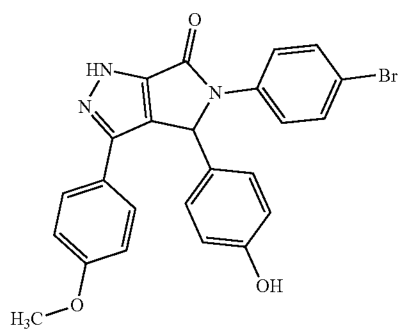 [SMILES: COc1ccc(-c2n[nH]c3c2C(c2ccc(O)cc2)N(c2ccc(Br)cc2)C3=O)cc1] | 1193 | 476.32 | C24H18BrN3O3 |
| 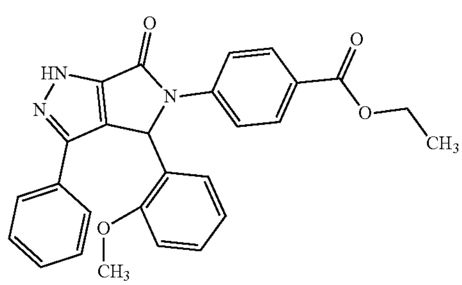 [SMILES: CCOC(=O)c1ccc(N2C(=O)c3[nH]nc(-c4ccccc4)c3C2c2ccccc2OC)cc1] | 1194 | 453.49 | C27H23N3O4 |
| 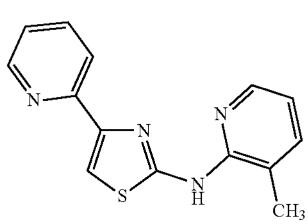 [SMILES: Cc1cccnc1Nc1nc(-c2ccccn2)cs1] | 1195 | 268.34 | C14H12N4S |

TABLE 1-continued

Compounds 1001 to 1557

| Structure | Compound number | Mol Weight | Formula |
|---|---|---|---|
| 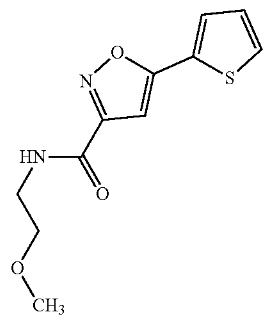 [SMILES: COCCNC(=O)c1cc(-c2cccs2)on1] | 1196 | 252.29 | C11H12N2O3S |
| 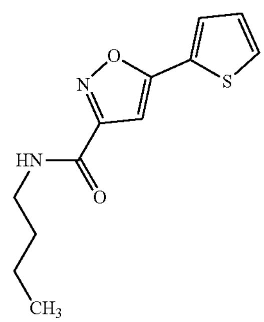 [SMILES: CCCCNC(=O)c1cc(-c2cccs2)on1] | 1197 | 250.32 | C12H14N2O2S |
| 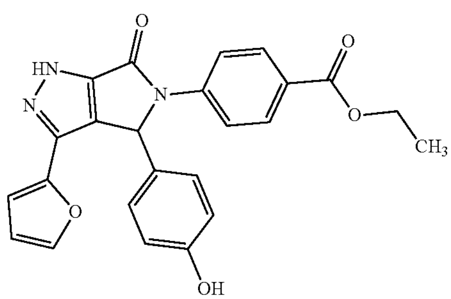 [SMILES: CCOC(=O)c1ccc(N2C(=O)c3[nH]nc(-c4ccco4)c3C2c2ccc(O)cc2)cc1] | 1198 | 429.42 | C24H19N3O5 |
| 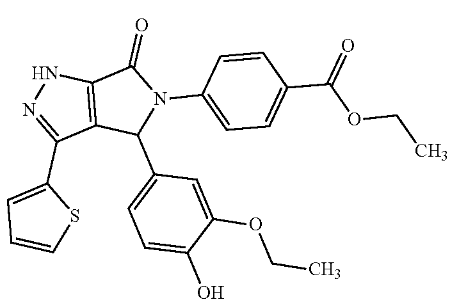 [SMILES: CCOC(=O)c1ccc(N2C(=O)c3[nH]nc(-c4cccs4)c3C2c2ccc(O)c(OCC)c2)cc1] | 1199 | 489.54 | C26H23N3O5S |

TABLE 1-continued

Compounds 1001 to 1557

| Structure | Compound number | Mol Weight | Formula |
|---|---|---|---|
| 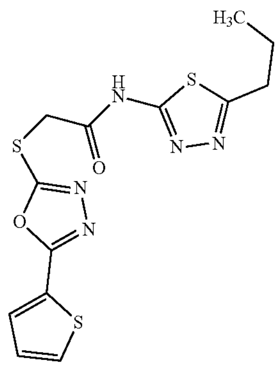 [SMILES: CCCc1nnc(NC(=O)CSc2nnc(-c3cccs3)o2)s1] | 1200 | 367.47 | C13H13N5O2S3 |
| 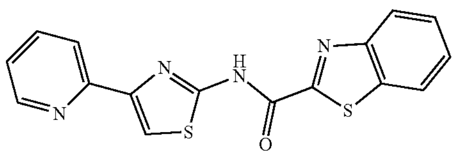 [SMILES: O=C(Nc1nc(-c2ccccn2)cs1)c1nc2ccccc2s1] | 1201 | 338.41 | C16H10N4OS2 |
| 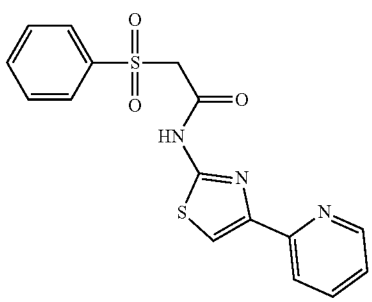 [SMILES: O=C(CS(=O)(=O)c1ccccc1)Nc1nc(-c2ccccn2)cs1] | 1202 | 359.42 | C16H13N3O3S2 |
| 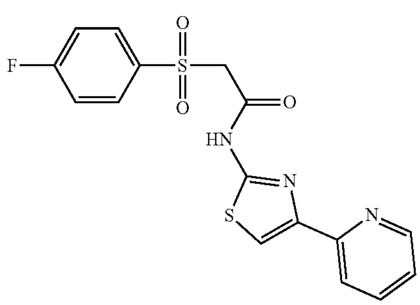 [SMILES: O=C(CS(=O)(=O)c1ccc(F)cc1)Nc1nc(-c2ccccn2)cs1] | 1203 | 377.41 | C16H12FN3O3S2 |
| 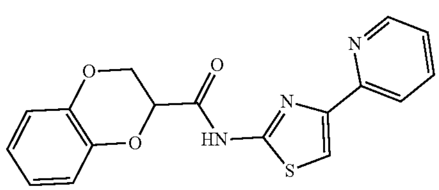 [SMILES: O=C(Nc1nc(-c2ccccn2)cs1)C1COc2ccccc2O1] | 1204 | 339.37 | C17H13N3O3S |
| 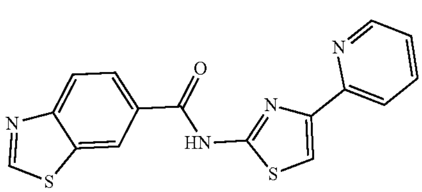 [SMILES: O=C(Nc1nc(-c2ccccn2)cs1)c1ccc2ncsc2c1] | 1205 | 338.41 | C16H10N4OS2 |

TABLE 1-continued

Compounds 1001 to 1557

| Structure | Compound number | Mol Weight | Formula |
|---|---|---|---|
| 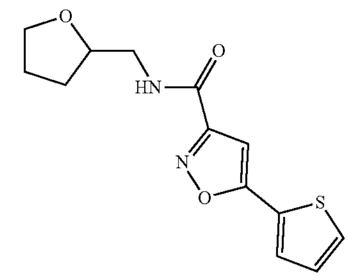 [SMILES: O=C(NCC1CCCO1)c1cc(-c2cccs2)on1] | 1206 | 278.33 | C13H14N2O3S |
| 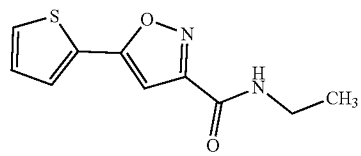 | 1207 | 222.26 | C10H10N2O2S |
| 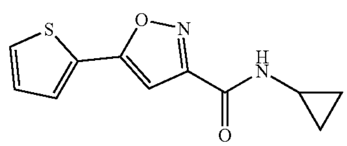 [SMILES: O=C(NC1CC1)c1cc(-c2cccs2)on1] | 1208 | 234.27 | C11H10N2O2S |
| 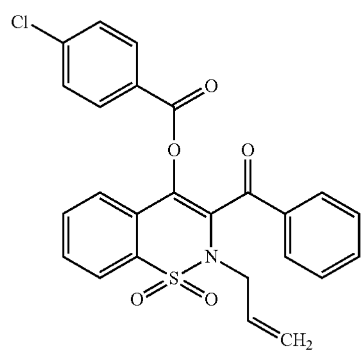 [SMILES: C=CCN1C(C(=O)c2ccccc2)=C(OC(=O)c2ccc(Cl)cc2)c2ccccc2S1(=O)=O] | 1209 | 479.93 | C25H18ClNO5S |
| 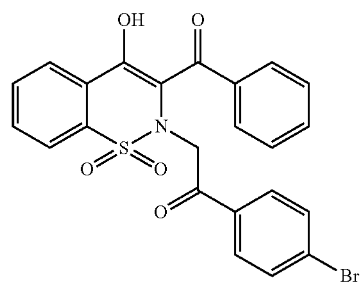 [SMILES: O=C(CN1C(C(=O)c2ccccc2)=C(O)c2ccccc2S1(=O)=O)c1ccc(Br)cc1] | 1210 | 498.35 | C23H16BrNO5S |

TABLE 1-continued

Compounds 1001 to 1557

| Structure | Compound number | Mol Weight | Formula |
|---|---|---|---|
| 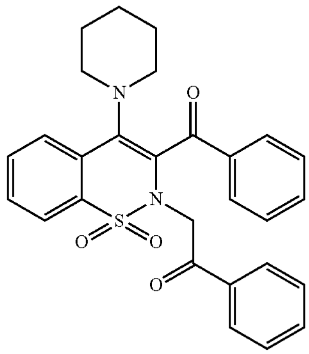 [SMILES: O=C(CN1C(C(=O)c2ccccc2)=C(N2CCCCC2)c2ccccc2S1(=O)=O)c1ccccc1] | 1211 | 486.58 | C28H26N2O4S |
| 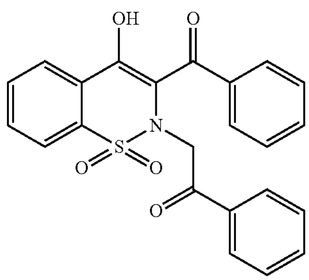 [SMILES: O=C(CN1C(C(=O)c2ccccc2)=C(O)c2ccccc2S1(=O)=O)c1ccccc1] | 1212 | 419.45 | C23H17NO5S |
| 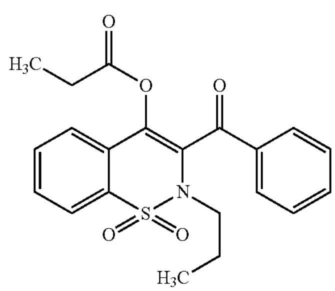 [SMILES: CCCN1C(C(=O)c2ccccc2)=C(OC(=O)CC)c2ccccc2S1(=O)=O] | 1213 | 399.46 | C21H21NO5S |
| 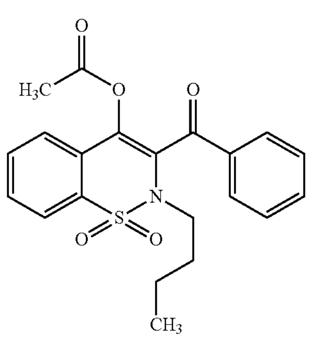 [SMILES: CCCCN1C(C(=O)c2ccccc2)=C(OC(C)=O)c2ccccc2S1(=O)=O] | 1214 | 399.46 | C21H21NO5S |

TABLE 1-continued

Compounds 1001 to 1557

| Structure | Compound number | Mol Weight | Formula |
|---|---|---|---|
| 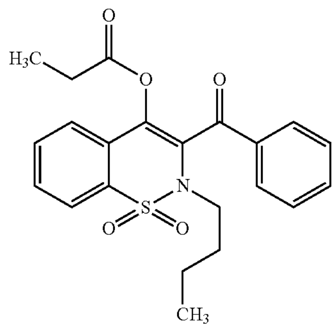 [SMILES: CCCCN1C(C(=O)c2ccccc2)=C(OC(=O)CC)c2ccccc2S1(=O)=O] | 1215 | 413.49 | C22H23NO5S |
| 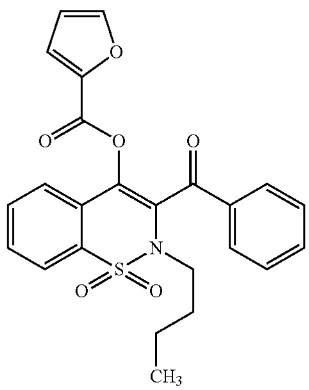 [SMILES: CCCCN1C(C(=O)c2ccccc2)=C(OC(=O)c2ccco2)c2ccccc2S1(=O)=O] | 1216 | 451.49 | C24H21NO6S |
| 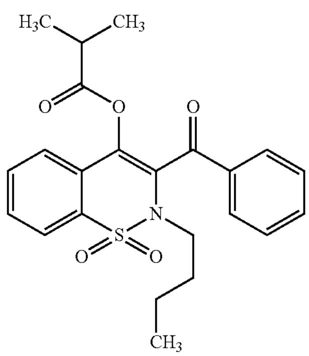 [SMILES: CCCCN1C(C(=O)c2ccccc2)=C(OC(=O)C(C)C)c2ccccc2S1(=O)=O] | 1217 | 427.51 | C23H25NO5S |
| 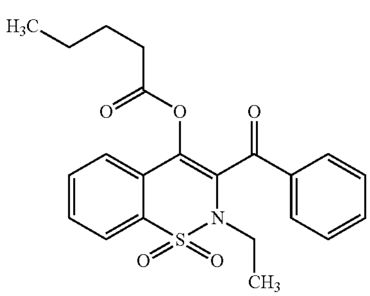 [SMILES: CCCCC(=O)OC1=C(C(=O)c2ccccc2)N(CC)S(=O)(=O)c2ccccc21] | 1218 | 413.49 | C22H23NO5S |

TABLE 1-continued

Compounds 1001 to 1557

| Structure | Compound number | Mol Weight | Formula |
|---|---|---|---|
| 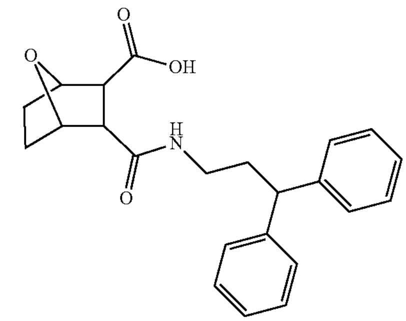 [SMILES: O=C(O)C1C2CCC(O2)C1C(=O)NCCC(c1ccccc1)c1ccccc1] | 1219 | 379.45 | C23H25NO4 |
| 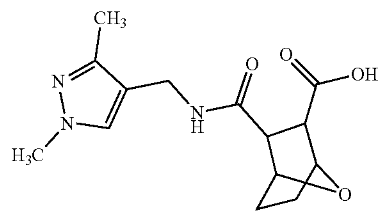 [SMILES: Cc1nn(C)cc1CNC(=O)C1C2CCC(O2)C1C(=O)O] | 1220 | 293.32 | C14H19N3O4 |
| 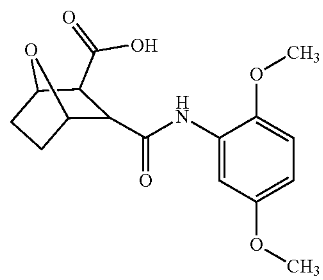 [SMILES: COc1ccc(OC)c(NC(=O)C2C3CCC(O3)C2C(=O)O)c1] | 1221 | 321.33 | C16H19NO6 |
| 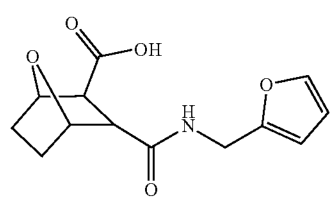 [SMILES: O=C(O)C1C2CCC(O2)C1C(=O)NCc1ccco1] | 1222 | 265.26 | C13H15NO5 |
| 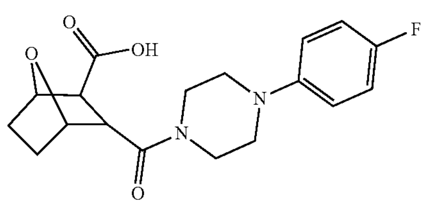 [SMILES: O=C(O)C1C2CCC(O2)C1C(=O)N1CCN(c2ccc(F)cc2)CC1] | 1223 | 348.37 | C18H21FN2O4 |

TABLE 1-continued

Compounds 1001 to 1557

| Structure | Compound number | Mol Weight | Formula |
|---|---|---|---|
| 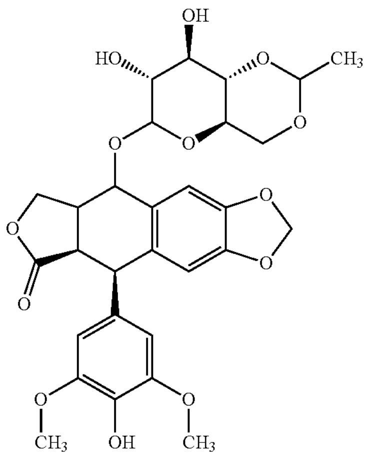 | 1224 | 588.56 | C29H32O13 |
| 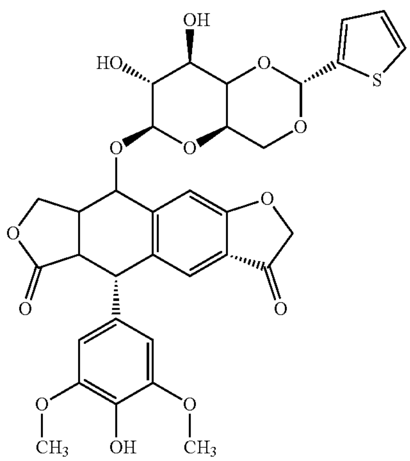 | 1225 | 656.65 | C32H32O13S |
| 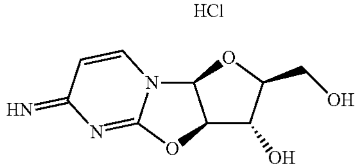 [SMILES: Cl ; N=c1ccn2c(n1)O[C@@H]1[C@@H](O)[C@H](CO)O[C@@H]12] | 1226 | 261.66 | C9H12ClN3O4 |
| 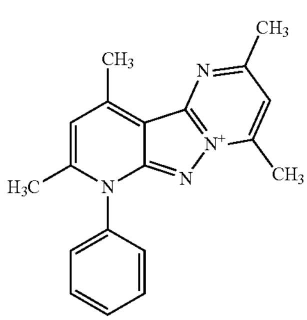 | 1227 | 303.38 | C19H19N4 |

TABLE 1-continued

Compounds 1001 to 1557

| Structure | Compound number | Mol Weight | Formula |
|---|---|---|---|
| 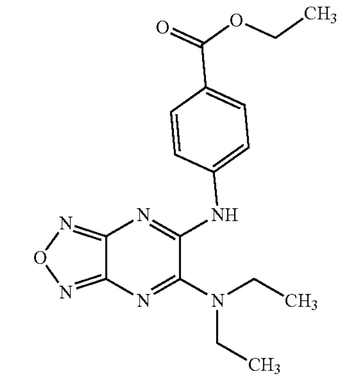 [SMILES: CCOC(=O)c1ccc(Nc2nc3nonc3nc2N(CC)CC)cc1] | 1228 | 356.38 | C17H20N6O3 |
| 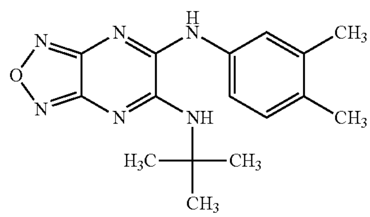 [SMILES: Cc1ccc(Nc2nc3nonc3nc2NC(C)(C)C)cc1C] | 1229 | 312.37 | C16H20N6O |
| 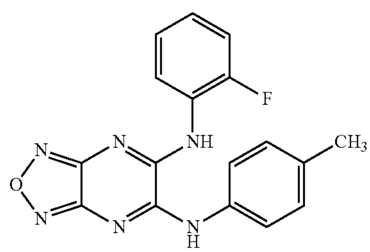 [SMILES: Cc1ccc(Nc2nc3nonc3nc2Nc2ccccc2F)cc1] | 1230 | 336.32 | C17H13FN6O |
| 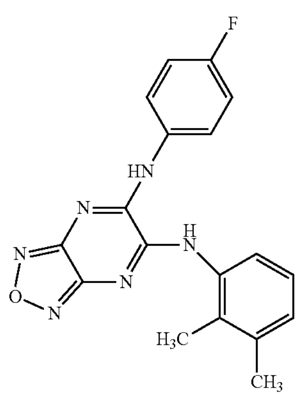 [SMILES: Cc1cccc(Nc2nc3nonc3nc2Nc2ccc(F)cc2)c1C] | 1231 | 350.35 | C18H15FN6O |

TABLE 1-continued

Compounds 1001 to 1557

| Structure | Compound number | Mol Weight | Formula |
|---|---|---|---|
| 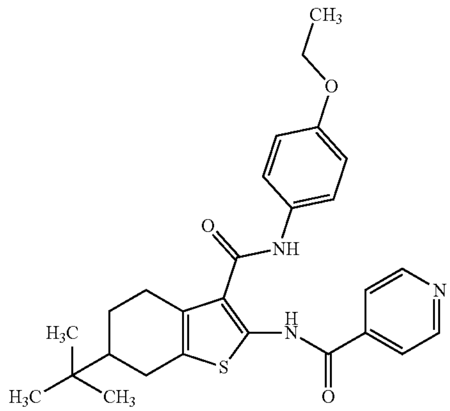 [SMILES: CCOc1ccc(NC(=O)c2c(NC(=O)c3ccncc3)sc3c2CCC(C(C)(C)C)C3)cc1] | 1232 | 477.62 | C27H31N3O3S |
| 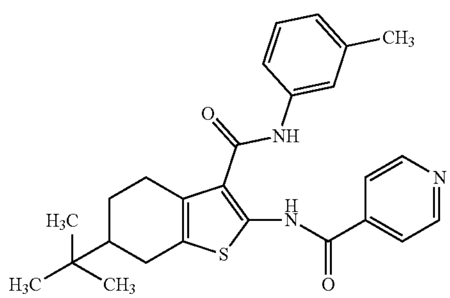 [SMILES: Cc1cccc(NC(=O)c2c(NC(=O)c3ccncc3)sc3c2CCC(C(C)(C)C)C3)c1] | 1233 | 447.59 | C26H29N3O2S |
| 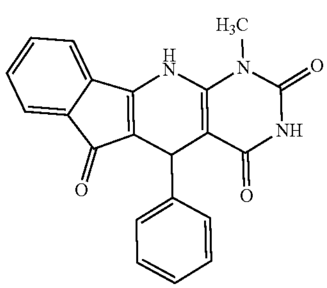 [SMILES: Cn1c2c(c(=O)[nH]c1=O)C(c1ccccc1)C1=C(N2)c2ccccc2C1=O] | 1234 | 357.36 | C21H15N3O3 |
| 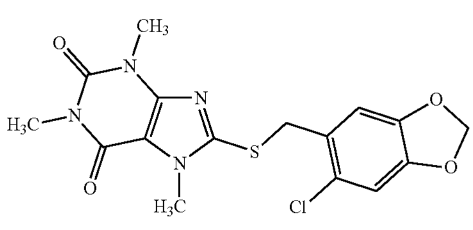 [SMILES: Cn1c(=O)c2c(nc(SCc3cc4c(cc3Cl)OCO4)n2C)n(C)c1=O] | 1235 | 394.83 | C16H15ClN4O4S |

TABLE 1-continued

Compounds 1001 to 1557

| Structure | Compound number | Mol Weight | Formula |
|---|---|---|---|
| 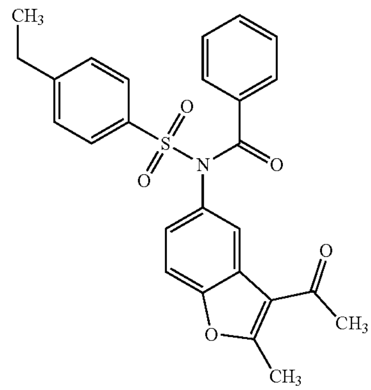 [SMILES: CCc1ccc(S(=O)(=O)N(C(=O)c2ccccc2)c2ccc3oc(C)c(C(C)=O)c3c2)cc1] | 1236 | 461.53 | C26H23NO5S |
| 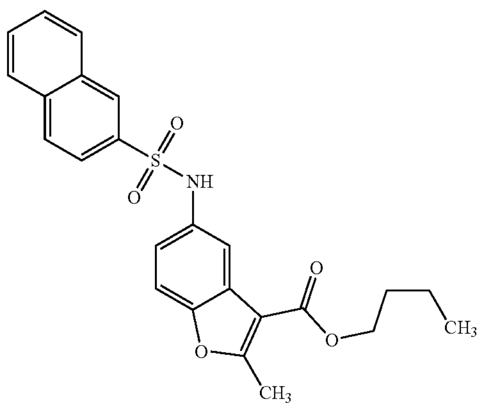 [SMILES: CCCCOC(=O)c1c(C)oc2ccc(NS(=O)(=O)c3ccc4ccccc4c3)cc12] | 1237 | 437.51 | C24H23NO5S |
| 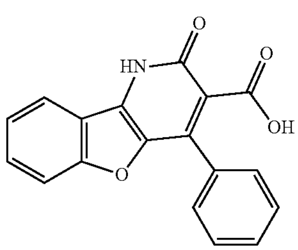 [SMILES: O=C(O)c1c(-c2ccccc2)c2oc3ccccc3c2[nH]c1=O] | 1238 | 305.28 | C18H11NO4 |
| 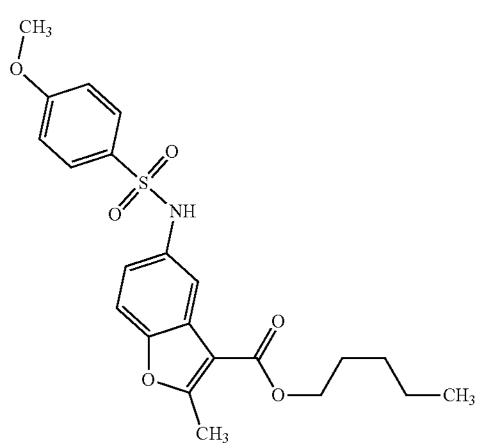 [SMILES: CCCCCOC(=O)c1c(C)oc2ccc(NS(=O)(=O)c3ccc(OC)cc3)cc12] | 1239 | 431.50 | C22H25NO6S |

TABLE 1-continued

Compounds 1001 to 1557

| Structure | Compound number | Mol Weight | Formula |
|---|---|---|---|
| 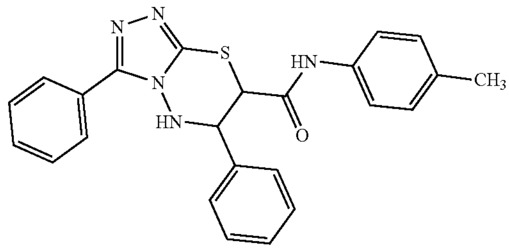 [SMILES: Cc1ccc(NC(=O)C2Sc3nnc(-c4ccccc4)n3NC2c2ccccc2)cc1] | 1240 | 431.48 | C23H18FN5OS |
| 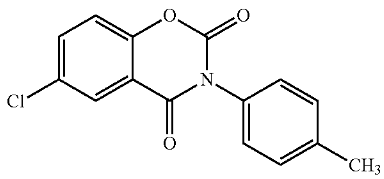 [SMILES: Cc1ccc(-n2c(=O)oc3ccc(Cl)cc3c2=O)cc1] | 1241 | 287.70 | C15H10ClNO3 |
| 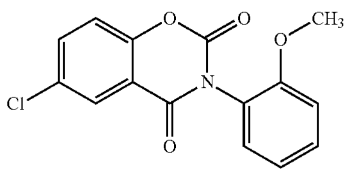 [SMILES: COc1ccccc1-n1c(=O)oc2ccc(Cl)cc2c1=O] | 1242 | 303.70 | C15H10ClNO4 |
| 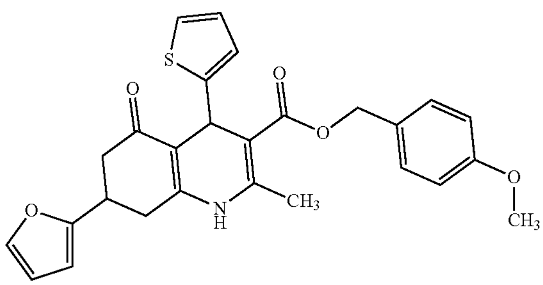 [SMILES: COc1ccc(COC(=O)C2=C(C)NC3=C(C(=O)CC(c4ccco4)C3)C2c2cccs2)cc1] | 1243 | 475.56 | C27H25NO5S |
| 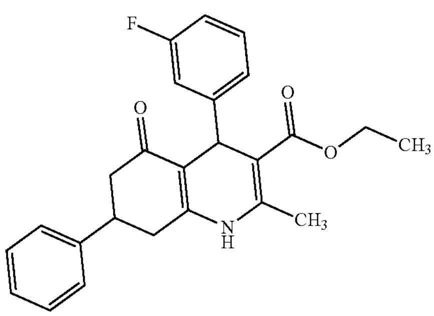 [SMILES: CCOC(=O)C1=C(C)NC2=C(C(=O)CC(c3ccccc3)C2)C1c1cccc(F)c1] | 1244 | 405.46 | C25H24FNO3 |
| 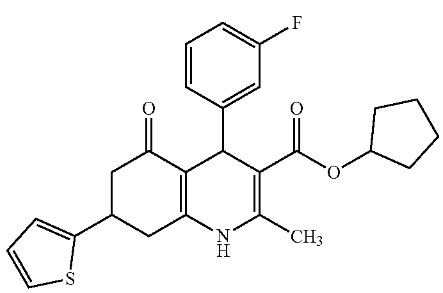 [SMILES: CC1=C(C(=O)OC2CCCC2)C(c2cccc(F)c2)C2=C(CC(c3cccs3)CC2=O)N1] | 1245 | 451.55 | C26H26FNO3S |

TABLE 1-continued

Compounds 1001 to 1557

| Structure | Compound number | Mol Weight | Formula |
|---|---|---|---|
| 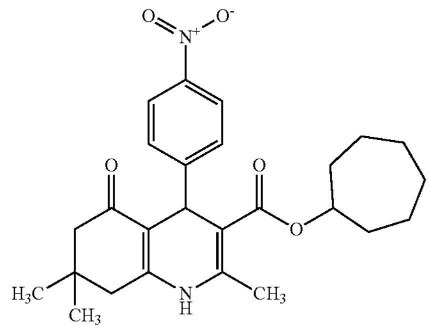 [SMILES: CC1=C(C(=O)OC2CCCCCC2)C(c2ccc([N+](=O)[O-])cc2)C2=C(CC(C)(C)CC2=O)N1] | 1246 | 452.54 | C26H32N2O5 |
| 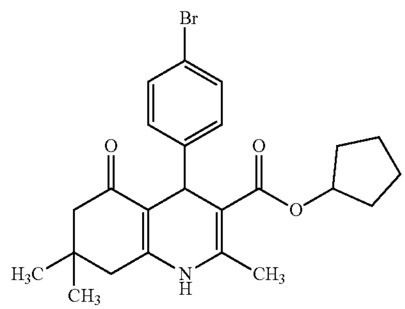 [SMILES: CC1=C(C(=O)OC2CCCC2)C(c2ccc(Br)cc2)C2=C(CC(C)(C)CC2=O)N1] | 1247 | 458.39 | C24H28BrNO3 |
| 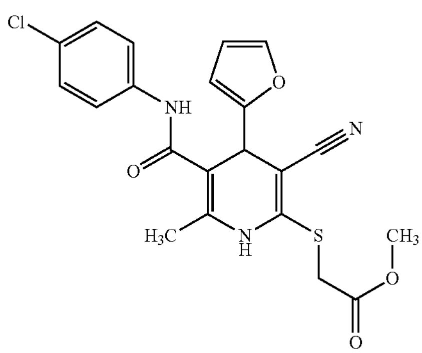 [SMILES: COC(=O)CSC1=C(C#N)C(c2ccco2)C(C(=O)Nc2ccc(Cl)cc2)=C(C)N1] | 1248 | 443.90 | C21H18ClN3O4S |
| 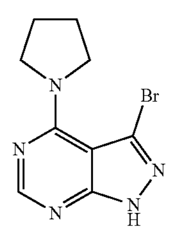 [SMILES: Brc1n[nH]c2ncnc(N3CCCC3)c12] | 1249 | 268.11 | C9H10BrN5 |
| 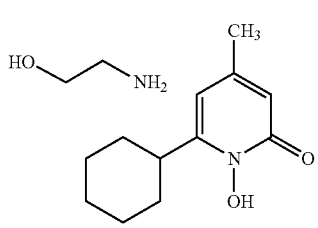 | 1250 | 268.35 | C14H24N2O3 |

TABLE 1-continued

Compounds 1001 to 1557

| Structure | Compound number | Mol Weight | Formula |
|---|---|---|---|
| 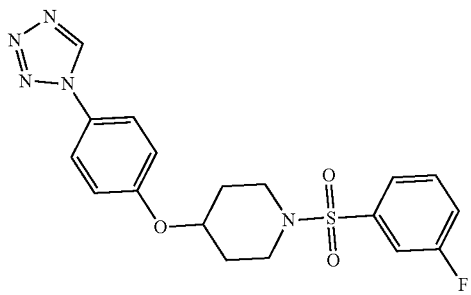 [SMILES: O=S(=O)(c1cccc(F)c1)N1CCC(Oc2ccc(-n3cnnn3)cc2)CC1] | 1251 | 403.43 | C18H18FN5O3S |
| 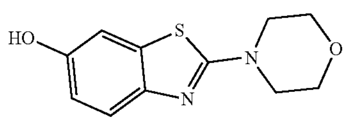 [SMILES: Oc1ccc2nc(N3CCOCC3)sc2c1] | 1252 | 236.29 | C11H12N2O2S |
| 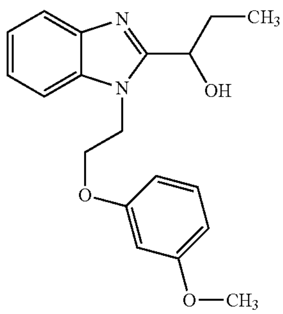 [SMILES: CCC(O)c1nc2ccccc2n1CCOc1cccc(OC)c1] | 1253 | 326.39 | C19H22N2O3 |
| 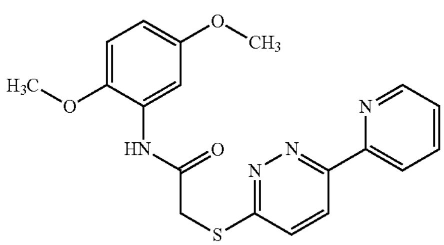 [SMILES: COc1ccc(OC)c(NC(=O)CSc2ccc(-c3ccccn3)nn2)c1] | 1254 | 382.44 | C19H18N4O3S |
| 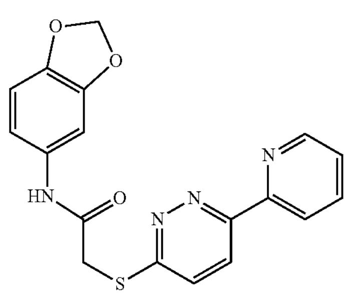 [SMILES: O=C(CSc1ccc(-c2ccccn2)nn1)Nc1ccc2c(c1)OCO2] | 1255 | 366.39 | C18H14N4O3S |

TABLE 1-continued

Compounds 1001 to 1557

| Structure | Compound number | Mol Weight | Formula |
|---|---|---|---|
| 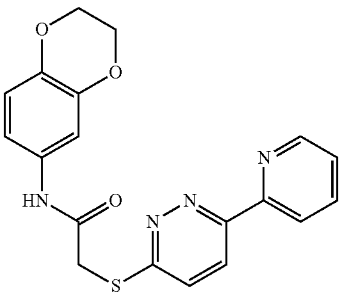 [SMILES: O=C(CSc1ccc(-c2ccccn2)nn1)Nc1ccc2c(c1)OCCO2] | 1256 | 380.42 | C19H16N4O3S |
| 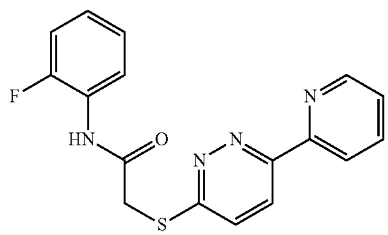 [SMILES: O=C(CSc1ccc(-c2ccccn2)nn1)Nc1ccccc1F] | 1257 | 340.38 | C17H13FN4OS |
| 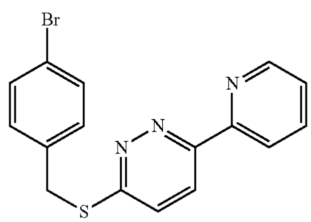 [SMILES: Brc1ccc(CSc2ccc(-c3ccccn3)nn2)cc1] | 1258 | 358.26 | C16H12BrN3S |
| 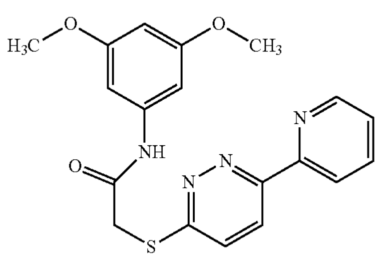 [SMILES: COc1cc(NC(=O)CSc2ccc(-c3ccccn3)nn2)cc(OC)c1] | 1259 | 382.44 | C19H18N4O3S |
| 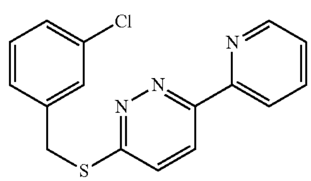 [SMILES: Clc1cccc(CSc2ccc(-c3ccccn3)nn2)c1] | 1260 | 313.80 | C16H12ClN3S |
| 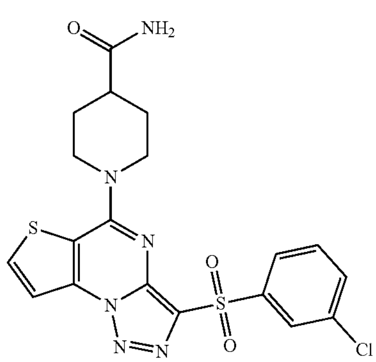 [SMILES: NC(=O)C1CCN(c2nc3c(S(=O)(=O)c4cccc(Cl)c4)nnn3c3ccsc23)CC1] | 1261 | 476.96 | C19H17ClN6O3S2 |

TABLE 1-continued

Compounds 1001 to 1557

| Structure | Compound number | Mol Weight | Formula |
|---|---|---|---|
| 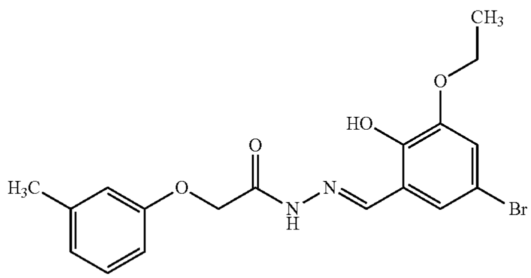 [SMILES: CCOc1cc(Br)cc(/C=N/NC(=O)COc2cccc(C)c2)c1O] | 1262 | 407.26 | C18H19BrN2O4 |
| 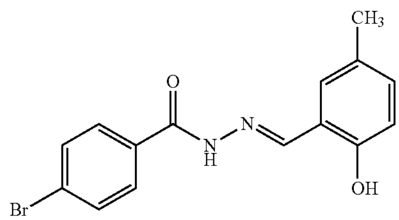 [SMILES: Cc1ccc(O)c(/C=N/NC(=O)c2ccc(Br)cc2)c1] | 1263 | 333.18 | C15H13BrN2O2 |
| 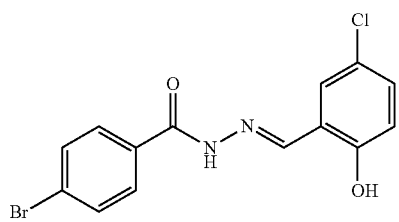 [SMILES: O=C(N/N=C/c1cc(Cl)ccc1O)c1ccc(Br)cc1] | 1264 | 353.60 | C14H10BrClN2O2 |
| 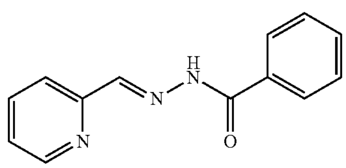 [SMILES: O=C(N/N=C/c1ccccn1)c1ccccc1] | 1265 | 225.25 | C13H11N3O |
| 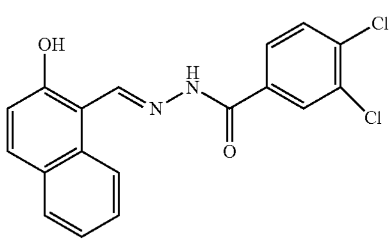 [SMILES: O=C(N/N=C/c1c(O)ccc2ccccc12)c1ccc(Cl)c(Cl)c1] | 1266 | 359.21 | C18H12Cl2N2O2 |
| 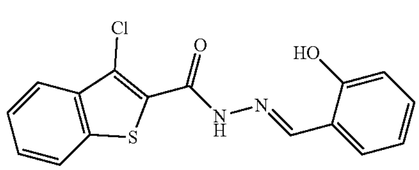 [SMILES: O=C(N/N=C/c1ccccc1O)c1sc2ccccc2c1Cl] | 1267 | 330.79 | C16H11ClN2O2S |
| 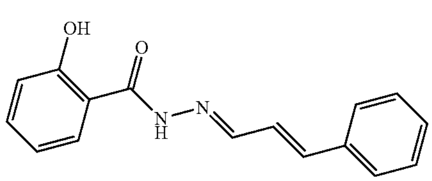 [SMILES: O=C(N/N=C/C=C/c1ccccc1)c1ccccc1O] | 1268 | 266.29 | C16H14N2O2 |

TABLE 1-continued

Compounds 1001 to 1557

| Structure | Compound number | Mol Weight | Formula |
|---|---|---|---|
| 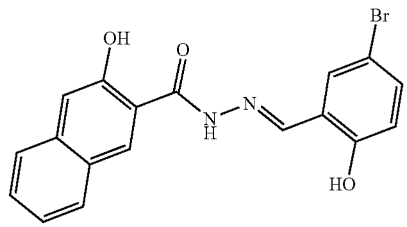 [SMILES: O=C(N/N=C/c1cc(Br)ccc1O)c1cc2ccccc2cc1O] | 1269 | 385.21 | C18H13BrN2O3 |
| 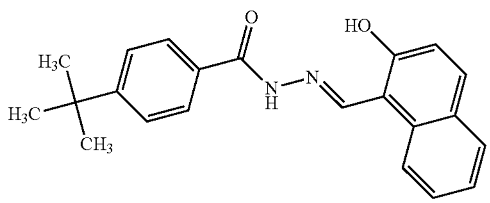 [SMILES: CC(C)(C)c1ccc(C(=O)N/N=C/c2c(O)ccc3ccccc23)cc1] | 1270 | 346.42 | C22H22N2O2 |
| 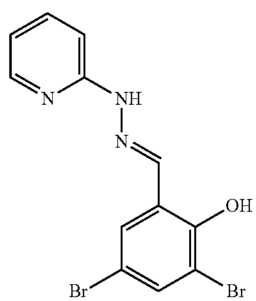 [SMILES: Oc1c(Br)cc(Br)cc1/C=N/Nc1ccccn1] | 1271 | 371.03 | C12H9Br2N3O |
| 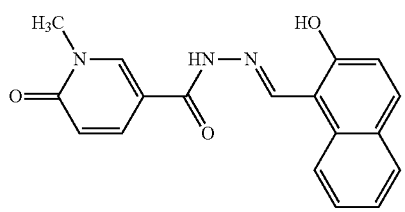 [SMILES: Cn1cc(C(=O)N/N=C/c2c(O)ccc3ccccc23)ccc1=O] | 1272 | 321.33 | C18H15N3O3 |
| 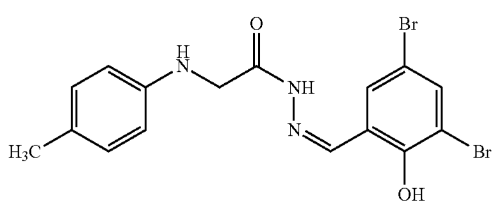 [SMILES: Cc1ccc(NCC(=O)N/N=C\c2cc(Br)cc(Br)c2O)cc1] | 1273 | 441.12 | C16H15Br2N3O2 |
| 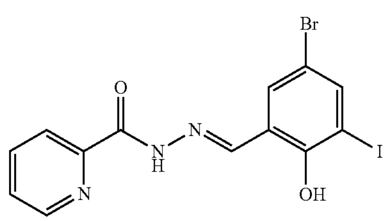 [SMILES: O=C(N/N=C/c1cc(Br)cc(I)c1O)c1ccccn1] | 1274 | 446.04 | C13H9BrIN3O2 |
| 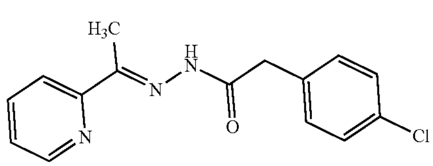 [SMILES: C/C(=N\NC(=O)Cc1ccc(Cl)cc1)c1ccccn1] | 1275 | 287.74 | C15H14ClN3O |

TABLE 1-continued

Compounds 1001 to 1557

| Structure | Compound number | Mol Weight | Formula |
|---|---|---|---|
| 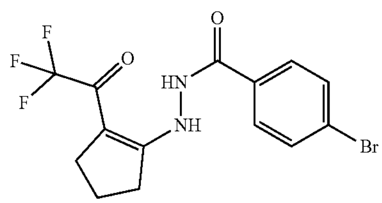 [SMILES: O=C(NNC1=C(C(=O)C(F)(F)F)CCC1)c1ccc(Br)cc1] | 1276 | 377.16 | C14H12BrF3N2O2 |
| 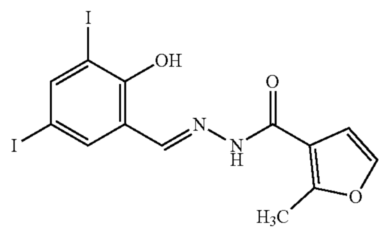 [SMILES: Cc1occc1C(=O)N/N=C/c1cc(I)cc(I)c1O] | 1277 | 496.04 | C13H10I2N2O3 |
| 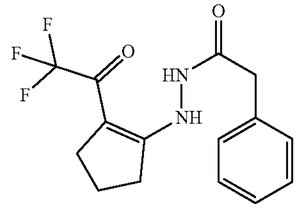 [SMILES: O=C(Cc1ccccc1)NNC1=C(C(=O)C(F)(F)F)CCC1] | 1278 | 312.29 | C15H15F3N2O2 |
| 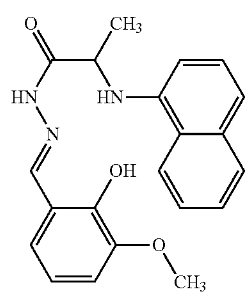 | 1279 | 363.41 | C21H21N3O3 |
| 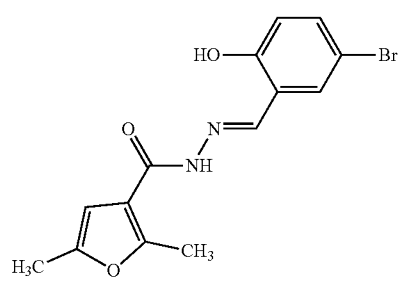 [SMILES: Cc1cc(C(=O)N/N=C/c2cc(Br)ccc2O)c(C)o1] | 1280 | 337.17 | C14H13BrN2O3 |
| 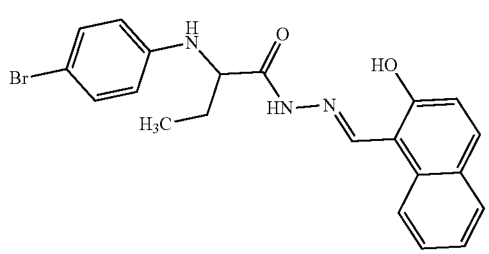 [SMILES: CCC(Nc1ccc(Br)cc1)C(=O)N/N=C/c1c(O)ccc2ccccc12] | 1281 | 426.31 | C21H20BrN3O2 |

TABLE 1-continued

Compounds 1001 to 1557

| Structure | Compound number | Mol Weight | Formula |
|---|---|---|---|
| 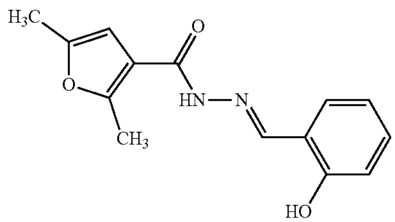 [SMILES: Cc1cc(C(=O)N/N=C/c2ccccc2O)c(C)o1] | 1282 | 258.27 | C14H14N2O3 |
| 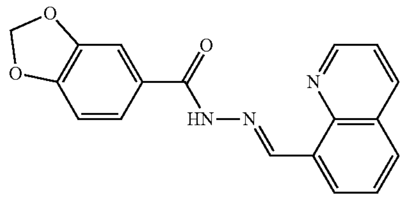 [SMILES: O=C(N/N=C/c1cccc2cccnc12)c1ccc2c(c1)OCO2] | 1283 | 319.31 | C18H13N3O3 |
| 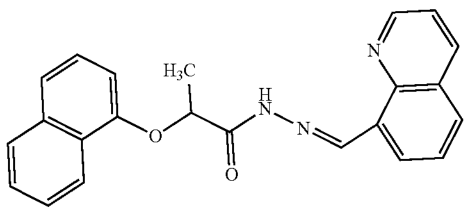 [SMILES: CC(Oc1cccc2ccccc12)C(=O)NN=Cc1cccc2cccnc12] | 1284 | 369.42 | C23H19N3O2 |
| 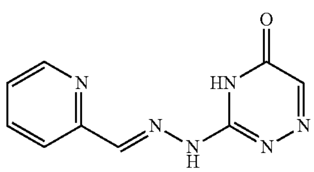 [SMILES: O=c1cnnc(N/N=C/c2ccccn2)[nH]1] | 1285 | 216.20 | C9H8N6O |
| 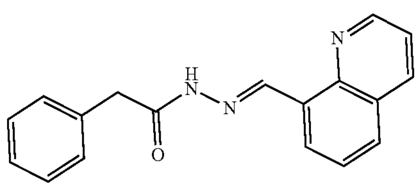 [SMILES: O=C(Cc1ccccc1)N/N=C/c1cccc2cccnc12] | 1286 | 289.33 | C18H15N3O |
| 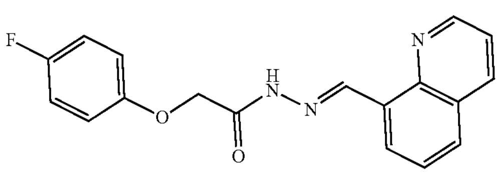 [SMILES: O=C(COc1ccc(F)cc1)N/N=C/c1cccc2cccnc12] | 1287 | 323.32 | C18H14FN3O2 |
| 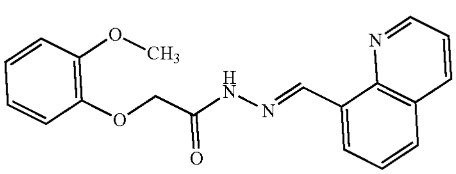 [SMILES: COc1ccccc1OCC(=O)N/N=C/c1cccc2cccnc12] | 1288 | 335.36 | C19H17N3O3 |
| 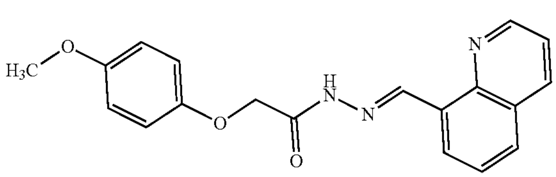 [SMILES: COc1ccc(OCC(=O)N/N=C/c2cccc3cccnc23)cc1] | 1289 | 335.36 | C19H17N3O3 |

TABLE 1-continued

Compounds 1001 to 1557

| Structure | Compound number | Mol Weight | Formula |
|---|---|---|---|
| 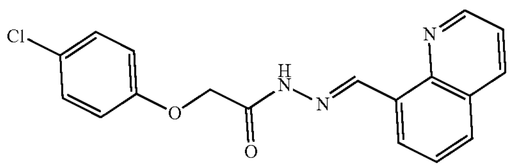 [SMILES: O=C(COc1ccc(Cl)cc1)N/N=C/c1cccc2cccnc12] | 1290 | 339.78 | C18H14ClN3O2 |
| 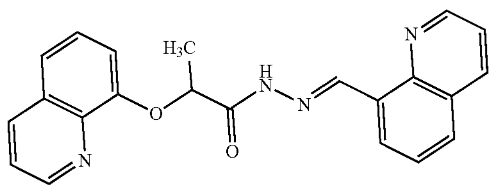 [SMILES: CC(Oc1cccc2cccnc12)C(=O)N/N=C/c1cccc2cccnc12] | 1291 | 370.40 | C22H18N4O2 |
| 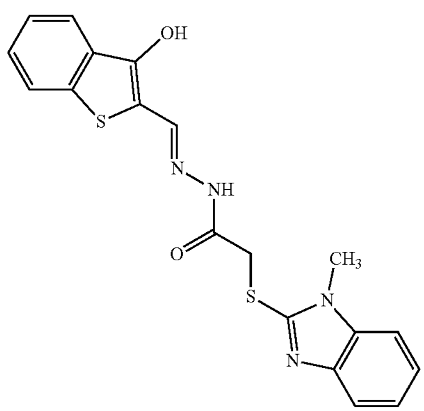 [SMILES: Cn1c(SCC(=O)N/N=C/c2sc3ccccc3c2O)nc2ccccc21] | 1292 | 396.49 | C19H16N4O2S2 |
| 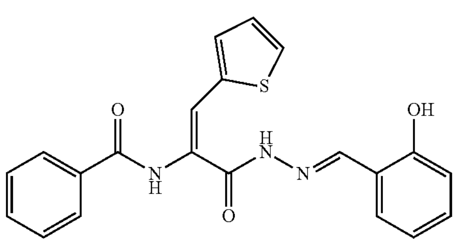 [SMILES: O=C(N/N=C/c1ccccc1O)/C(=C\c1cccs1)NC(=O)c1ccccc1] | 1293 | 391.44 | C21H17N3O3S |
| 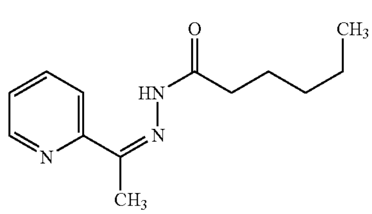 [SMILES: CCCCCC(=O)N/N=C(/C)c1ccccn1] | 1294 | 233.31 | C13H19N3O |

TABLE 1-continued

Compounds 1001 to 1557

| Structure | Compound number | Mol Weight | Formula |
|---|---|---|---|
| 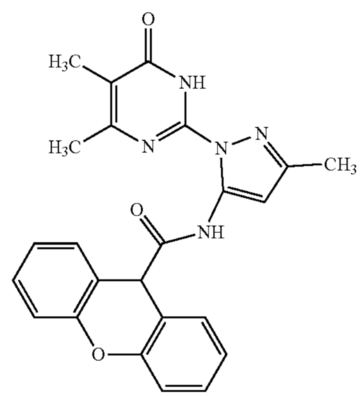 [SMILES: Cc1cc(NC(=O)C2c3ccccc3Oc3ccccc32)n(-c2nc(C)c(C)c(=O)[nH]2)n1] | 1295 | 427.46 | C24H21N5O3 |
| 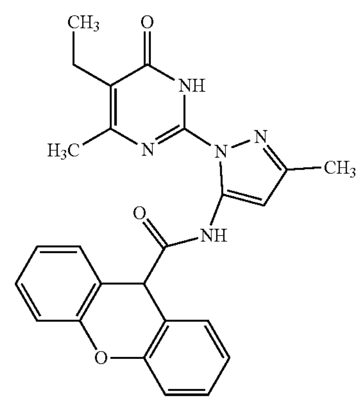 [SMILES: CCc1c(C)nc(-n2nc(C)cc2NC(=O)C2c3ccccc3Oc3ccccc32)[nH]c1=O] | 1296 | 441.48 | C25H23N5O3 |
| 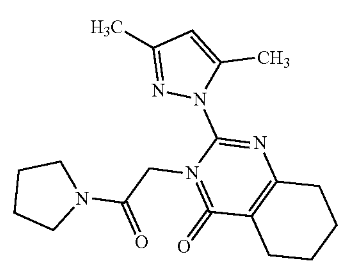 | 1297 | 355.43 | C19H25N5O2 |
| 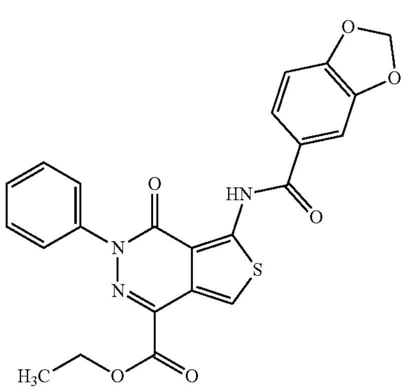 [SMILES: CCOC(=O)c1nn(-c2ccccc2)c(=O)c2c(NC(=O)c3ccc4c(c3)OCO4)scc12] | 1298 | 463.46 | C23H17N3O6S |

TABLE 1-continued

Compounds 1001 to 1557

| Structure | Compound number | Mol Weight | Formula |
|---|---|---|---|
| 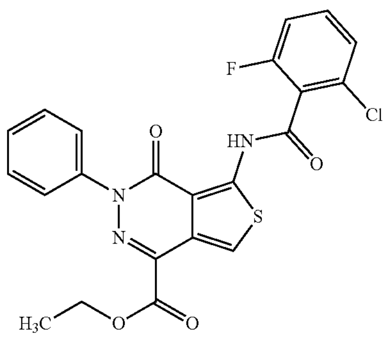 [SMILES: CCOC(=O)c1nn(-c2ccccc2)c(=O)c2c(NC(=O)c3c(F)cccc3Cl)scc12] | 1299 | 471.89 | C22H15ClFN3O4S |
| 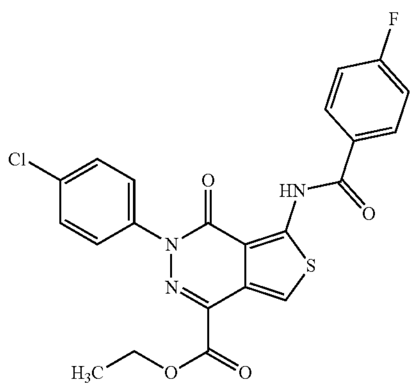 [SMILES: CCOC(=O)c1nn(-c2ccc(Cl)cc2)c(=O)c2c(NC(=O)c3ccc(F)cc3)scc12] | 1300 | 471.89 | C22H15ClFN3O4S |
| 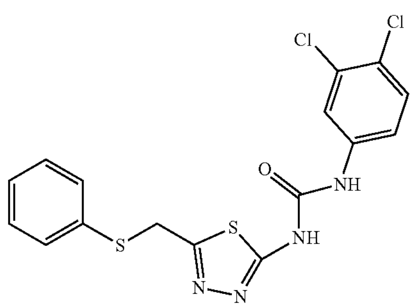 [SMILES: O=C(Nc1ccc(Cl)c(Cl)c1)Nc1nnc(CSc2ccccc2)s1] | 1301 | 411.33 | C16H12Cl2N4OS2 |
| 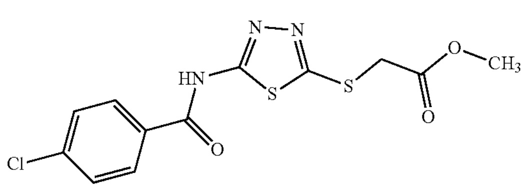 [SMILES: COC(=O)CSc1nnc(NC(=O)c2ccc(Cl)cc2)s1] | 1302 | 343.81 | C12H10ClN3O3S2 |
| 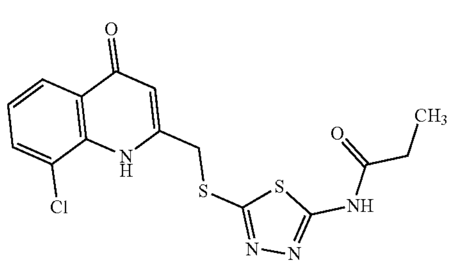 [SMILES: CCC(=O)Nc1nnc(SCc2cc(=O)c3cccc(Cl)c3[nH]2)s1] | 1303 | 380.87 | C15H13ClN4O2S2 |

165 166
TABLE 1-continued
Compounds 1001 to 1557
| Structure | Compound number | Mol Weight | Formula |
|---|---|---|---|
| 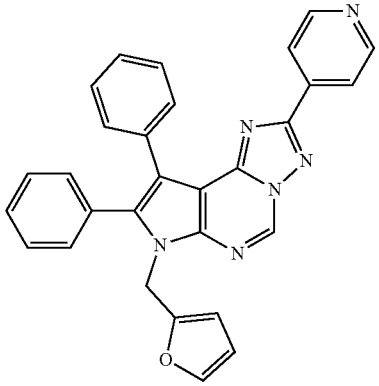 [SMILES: c1ccc(-c2c(-c3ccccc3)n(Cc3ccco3)c3ncn4nc(-c5ccncc5)nc4c23)cc1] | 1304 | 468.51 | C29H20N6O |
| 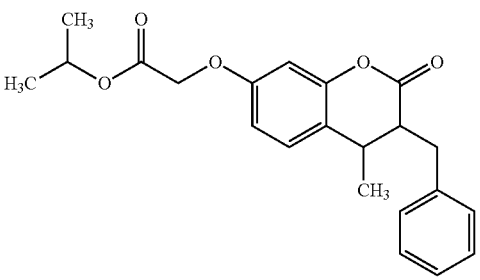 [SMILES: CC(C)OC(=O)COc1ccc2c(c1)OC(=O)C(Cc1ccccc1)C2C] | 1305 | 366.41 | C22H22O5 |
| 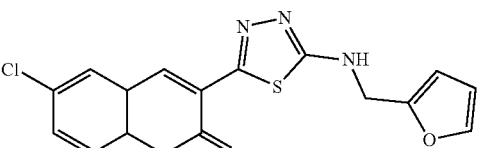 | 1306 | 359.79 | C16H10ClN3O3S |
| 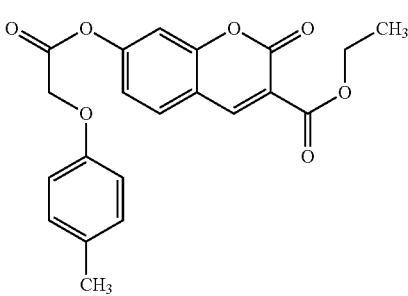 [SMILES: CCOC(=O)c1cc2ccc(OC(=O)COc3ccc(C)cc3)cc2oc1=O] | 1307 | 382.36 | C21H18O7 |
| 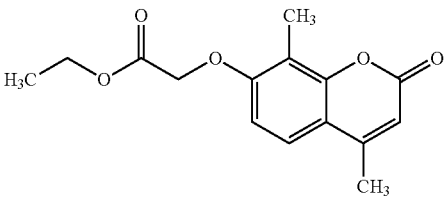 [SMILES: CCOC(=O)COc1ccc2c(C)cc(=O)oc2c1C] | 1308 | 276.28 | C15H16O5 |
| 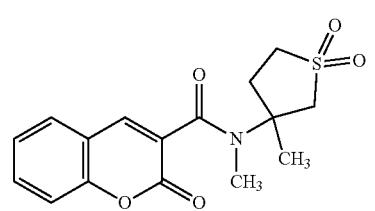 [SMILES: CN(C(=O)c1cc2ccccc2oc1=O)C1(C)CCS(=O)(=O)C1] | 1309 | 335.38 | C16H17NO5S |

TABLE 1-continued

Compounds 1001 to 1557

| Structure | Compound number | Mol Weight | Formula |
|---|---|---|---|
| 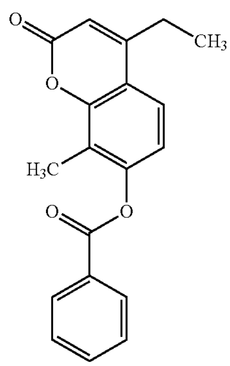 [SMILES: CCc1cc(=O)oc2c(C)c(OC(=O)c3ccccc3)ccc12] | 1310 | 308.33 | C19H16O4 |
| 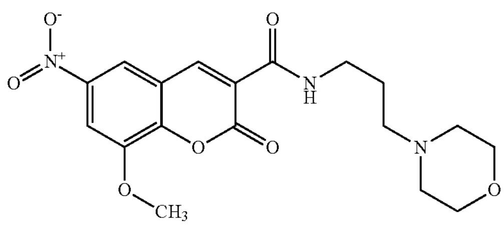 [SMILES: COc1cc([N+](=O)[O-])cc2cc(C(=O)NCCCN3CCOCC3)c(=O)oc12] | 1311 | 391.38 | C18H21N3O7 |
| 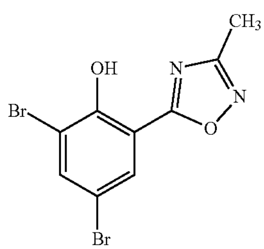 | 1312 | 333.96 | C9H6Br2N2O2 |
| 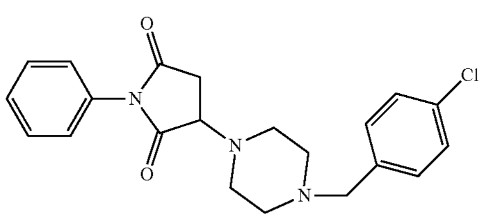 [SMILES: O=C1CC(N2CCN(Cc3ccc(Cl)cc3)CC2)C(=O)N1c1ccccc1] | 1313 | 383.87 | C21H22ClN3O2 |
| 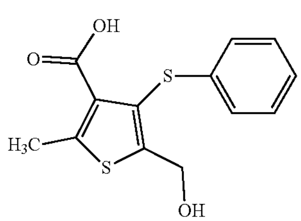 [SMILES: Cc1sc(CO)c(Sc2ccccc2)c1C(=O)O] | 1314 | 280.36 | C13H12O3S2 |

TABLE 1-continued

Compounds 1001 to 1557

| Structure | Compound number | Mol Weight | Formula |
|---|---|---|---|
| 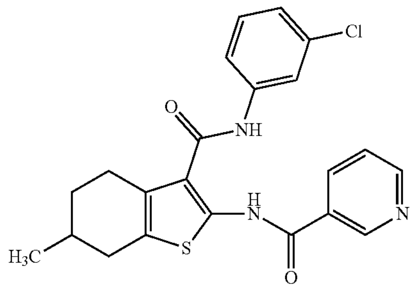 [SMILES: CC1CCc2c(sc(NC(=O)c3cccnc3)c2C(=O)Nc2cccc(Cl)c2)C1] | 1315 | 425.93 | C22H20ClN3O2S |
| 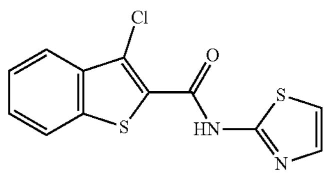 [SMILES: O=C(Nc1nccs1)c1sc2ccccc2c1Cl] | 1316 | 294.78 | C12H7ClN2OS2 |
| 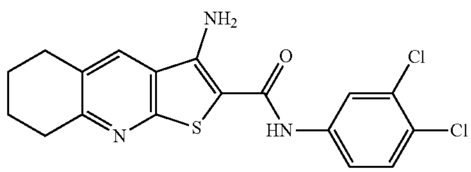 [SMILES: Nc1c(C(=O)Nc2ccc(Cl)c(Cl)c2)sc2nc3c(cc12)CCCC3] | 1317 | 392.30 | C18H15Cl2N3OS |
| 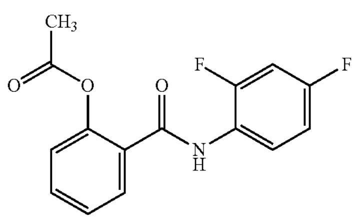 [SMILES: CC(=O)Oc1ccccc1C(=O)Nc1ccc(F)cc1F] | 1318 | 291.25 | C15H11F2NO3 |
| 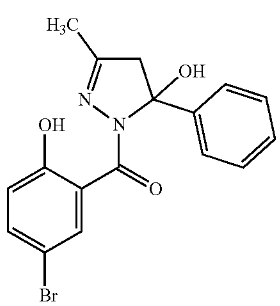 [SMILES: CC1=NN(C(=O)c2cc(Br)ccc2O)C(O)(c2ccccc2)C1] | 1319 | 375.22 | C17H15BrN2O3 |
| 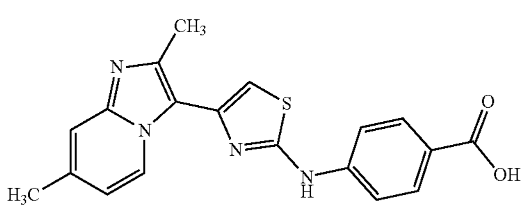 [SMILES: Cc1ccn2c(-c3csc(Nc4ccc(C(=O)O)cc4)n3)c(C)nc2c1] | 1320 | 364.42 | C19H16N4O2S |

TABLE 1-continued

Compounds 1001 to 1557

| Structure | Compound number | Mol Weight | Formula |
|---|---|---|---|
| 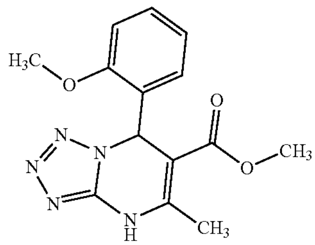 | 1321 | 301.30 | C14H15N5O3 |
| 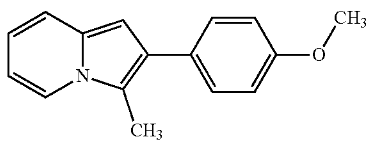 [SMILES: COc1ccc(-c2cc3ccccn3c2C)cc1] | 1322 | 237.30 | C16H15NO |
| 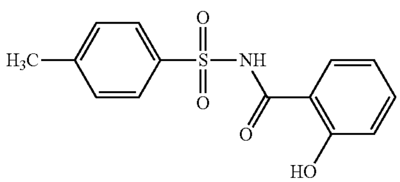 [SMILES: Cc1ccc(S(=O)(=O)NC(=O)c2ccccc2O)cc1] | 1323 | 291.32 | C14H13NO4S |
| 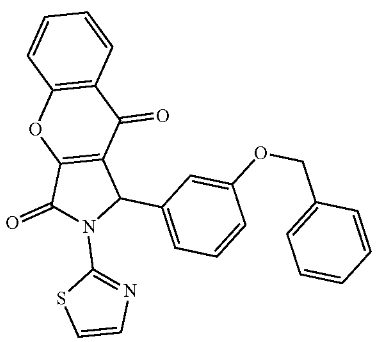 [SMILES: O=C1c2oc3ccccc3c(=O)c2C(c2cccc(OCc3ccccc3)c2)N1c1nccs1] | 1324 | 466.51 | C27H18N2O4S |
| 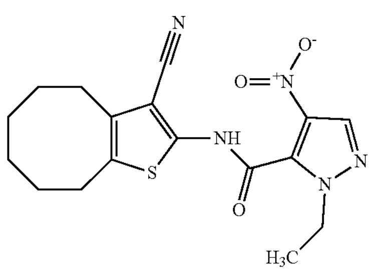 [SMILES: CCn1ncc([N+](=O)[O-])c1C(=O)Nc1sc2c(c1C#N)CCCCCC2] | 1325 | 373.43 | C17H19N5O3S |
| 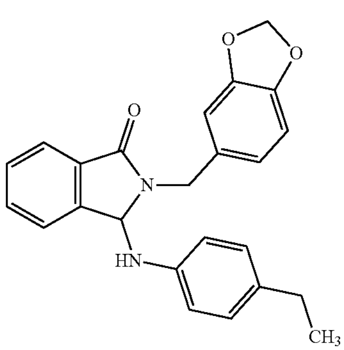 [SMILES: CCc1ccc(NC2c3ccccc3C(=O)N2Cc2ccc3c(c2)OCO3)cc1] | 1326 | 386.44 | C24H22N2O3 |

TABLE 1-continued

Compounds 1001 to 1557

| Structure | Compound number | Mol Weight | Formula |
|---|---|---|---|
| 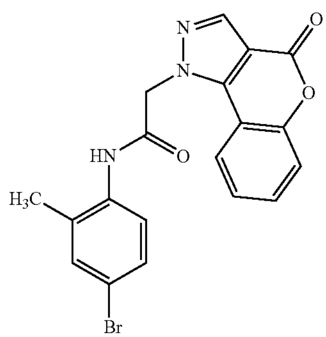 [SMILES: Cc1cc(Br)ccc1NC(=O)Cn1ncc2c(=O)oc3ccccc3c21] | 1327 | 412.24 | C19H14BrN3O3 |
| 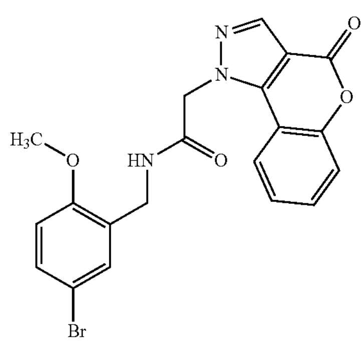 [SMILES: COc1ccc(Br)cc1CNC(=O)Cn1ncc2c(=O)oc3ccccc3c21] | 1328 | 442.26 | C20H16BrN3O4 |
| 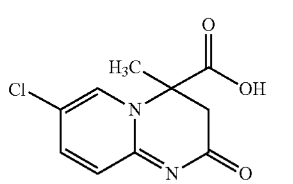 [SMILES: CC1(C(=O)O)CC(=O)N=C2C=CC(Cl)=CN21] | 1329 | 240.64 | C10H9ClN2O3 |
| 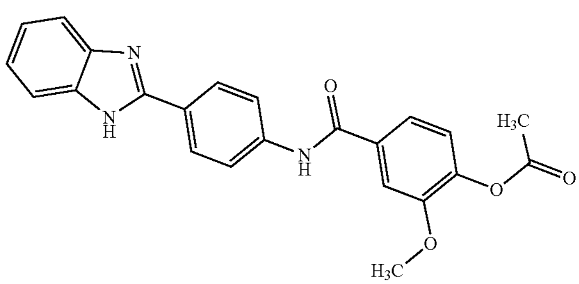 [SMILES: COc1cc(C(=O)Nc2ccc(-c3nc4ccccc4[nH]3)cc2)ccc1OC(C)=O] | 1330 | 401.41 | C23H19N3O4 |
| 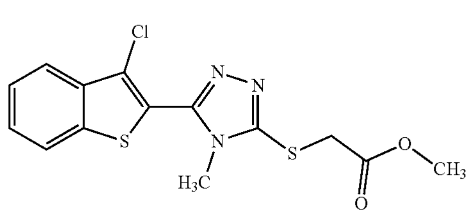 [SMILES: COC(=O)CSc1nnc(-c2sc3ccccc3c2Cl)n1C] | 1331 | 353.85 | C14H12ClN3O2S2 |

TABLE 1-continued

Compounds 1001 to 1557

| Structure | Compound number | Mol Weight | Formula |
|---|---|---|---|
| 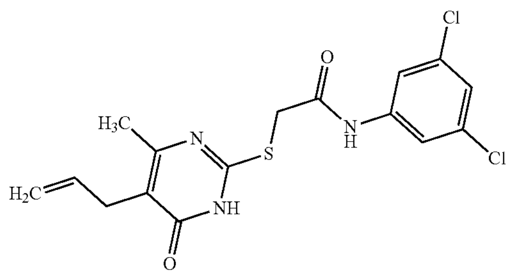 [SMILES: C=CCc1c(C)nc(SCC(=O)Nc2cc(Cl)cc(Cl)c2)[nH]c1=O] | 1332 | 384.28 | C16H15Cl2N3O2S |
| 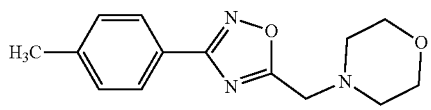 [SMILES: Cc1ccc(-c2noc(CN3CCOCC3)n2)cc1] | 1333 | 259.30 | C14H17N3O2 |
| 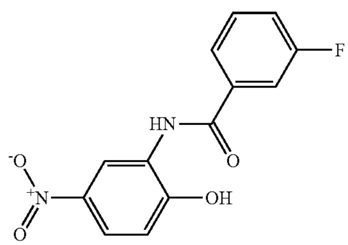 [SMILES: O=C(Nc1cc([N+](=O)[O-])ccc1O)c1cccc(F)c1] | 1334 | 276.22 | C13H9FN2O4 |
| 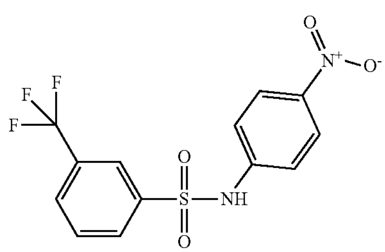 [SMILES: O=[N+]([O-])c1ccc(NS(=O)(=O)c2cccc(C(F)(F)F)c2)cc1] | 1335 | 346.28 | C13H9F3N2O4S |
| 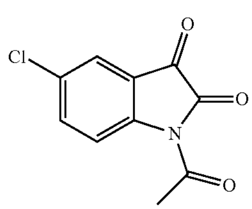 | 1336 | 223.61 | C10H6ClNO3 |
| 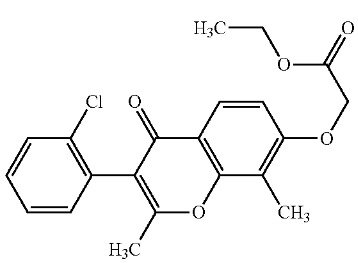 [SMILES: CCOC(=O)COc1ccc2c(=O)c(-c3ccccc3Cl)c(C)oc2c1C] | 1337 | 386.83 | C21H19ClO5 |

TABLE 1-continued

Compounds 1001 to 1557

| Structure | Compound number | Mol Weight | Formula |
|---|---|---|---|
| 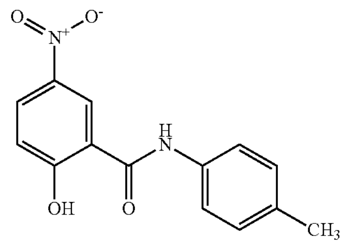 [SMILES: Cc1ccc(NC(=O)c2cc([N+](=O)[O-])ccc2O)cc1] | 1338 | 272.26 | C14H12N2O4 |
| 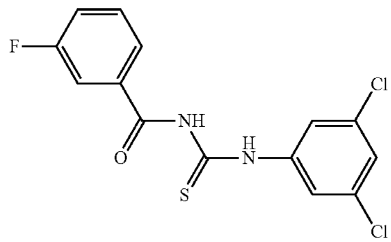 [SMILES: O=C(NC(=S)Nc1cc(Cl)cc(Cl)c1)c1cccc(F)c1] | 1339 | 343.20 | C14H9Cl2FN2OS |
| 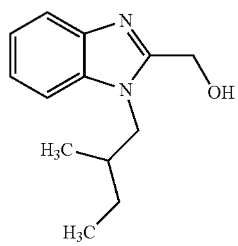 [SMILES: CCC(C)Cn1c(CO)nc2ccccc21] | 1340 | 218.29 | C13H18N2O |
| 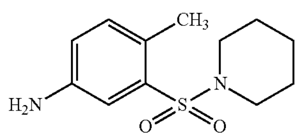 [SMILES: Cc1ccc(N)cc1S(=O)(=O)N1CCCCC1] | 1341 | 254.35 | C12H18N2O2S |
| 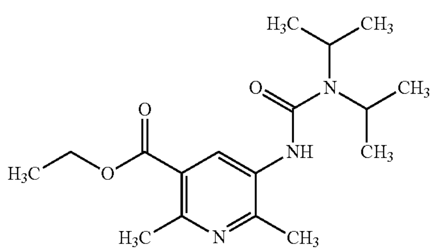 [SMILES: CCOC(=O)c1cc(NC(=O)N(C(C)C)C(C)C)c(C)nc1C] | 1342 | 321.41 | C17H27N3O3 |
| 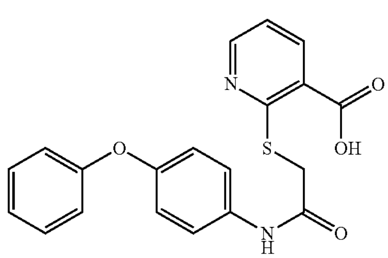 [SMILES: O=C(CSc1ncccc1C(=O)O)Nc1ccc(Oc2ccccc2)cc1] | 1343 | 380.42 | C20H16N2O4S |
| 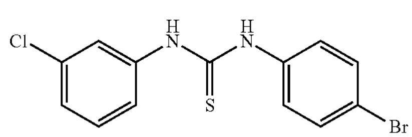 [SMILES: S=C(Nc1ccc(Br)cc1)Nc1cccc(Cl)c1] | 1344 | 341.65 | C13H10BrClN2S |

TABLE 1-continued

Compounds 1001 to 1557

| Structure | Compound number | Mol Weight | Formula |
|---|---|---|---|
| 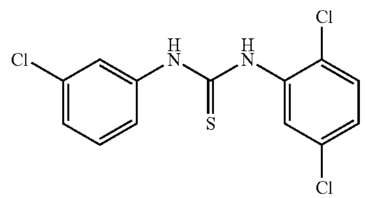 [SMILES: S=C(Nc1cccc(Cl)c1)Nc1cc(Cl)ccc1Cl] | 1345 | 331.65 | C13H9Cl3N2S |
| 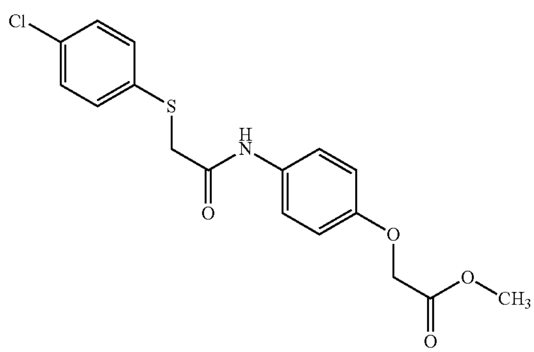 [SMILES: COC(=O)COc1ccc(NC(=O)CSc2ccc(Cl)cc2)cc1] | 1346 | 365.83 | C17H16ClNO4S |
| 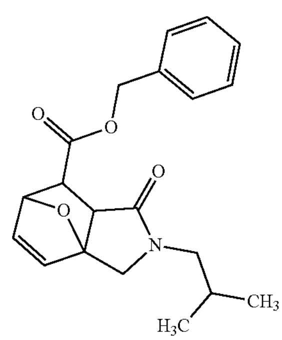 [SMILES: CC(C)CN1CC23C=CC(O2)C(C(=O)OCc2ccccc2)C3C1=O] | 1347 | 341.40 | C20H23NO4 |
| 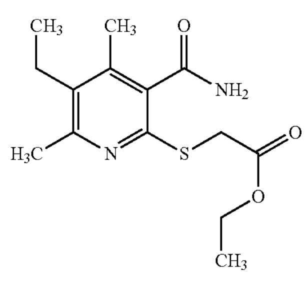 [SMILES: CCOC(=O)CSc1nc(C)c(CC)c(C)c1C(N)=O] | 1348 | 296.39 | C14H20N2O3S |
| 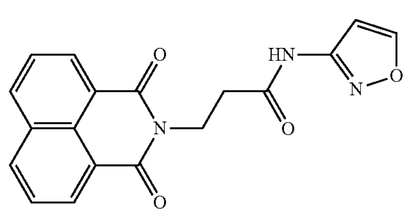 [SMILES: O=C(CCN1C(=O)c2cccc3cccc(c23)C1=O)Nc1ccon1] | 1349 | 335.31 | C18H13N3O4 |

TABLE 1-continued

Compounds 1001 to 1557

| Structure | Compound number | Mol Weight | Formula |
|---|---|---|---|
| 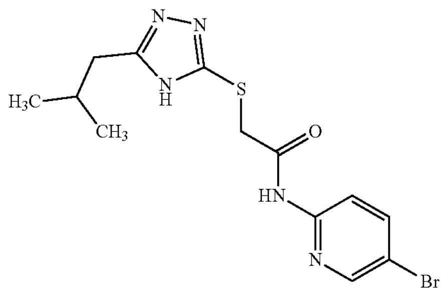 [SMILES: CC(C)Cc1nnc(SCC(=O)Nc2ccc(Br)cn2)[nH]1] | 1350 | 370.27 | C13H16BrN5OS |
| 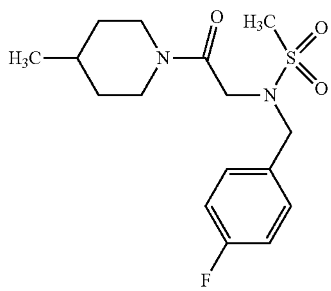 [SMILES: CC1CCN(C(=O)CN(Cc2ccc(F)cc2)S(C)(=O)=O)CC1] | 1351 | 342.43 | C16H23FN2O3S |
| 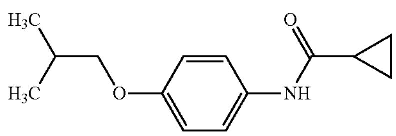 [SMILES: CC(C)COc1ccc(NC(=O)C2CC2)cc1] | 1352 | 233.31 | C14H19² |
| 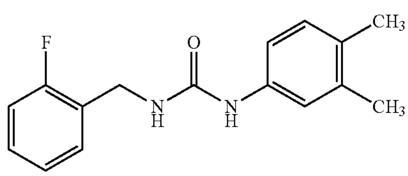 [SMILES: Cc1ccc(NC(=O)NCc2ccccc2F)cc1C] | 1353 | 272.32 | C16H17FN2O |
| 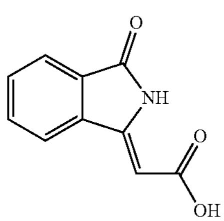 [SMILES: O=C(O)/C=C1\NC(=O)c2ccccc21] | 1354 | 189.17 | C10H7NO3 |
| 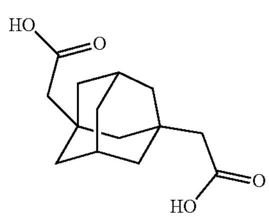 [SMILES: O=C(O)CC12CC3CC(C1)CC(CC(=O)O)(C3)C2] | 1355 | 252.31 | C14H20O4 |
| 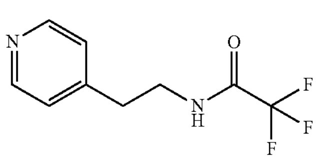 [SMILES: O=C(NCCc1ccncc1)C(F)(F)F] | 1356 | 218.18 | C9H9F3N2O |

TABLE 1-continued

Compounds 1001 to 1557

| Structure | Compound number | Mol Weight | Formula |
|---|---|---|---|
| 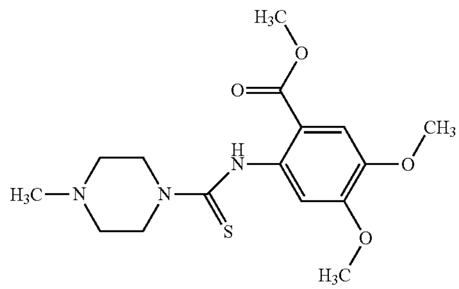 | 1357 | 353.44 | C16H23N3O4S |
| 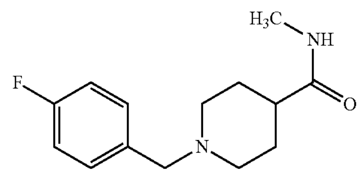 [SMILES: CNC(=O)C1CCN(Cc2ccc(F)cc2)CC1] | 1358 | 250.31 | C14H19FN2O |
| 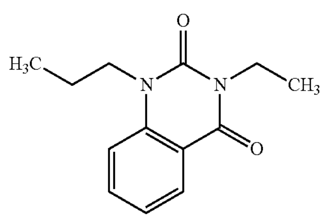 [SMILES: CCCn1c(=O)n(CC)c(=O)c2ccccc21] | 1359 | 232.28 | C13H16N2O2 |
| 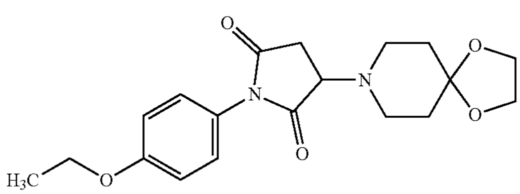 [SMILES: CCOc1ccc(N2C(=O)CC(N3CCC4(CC3)OCCO4)C2=O)cc1] | 1360 | 360.40 | C19H24N2O5 |
| 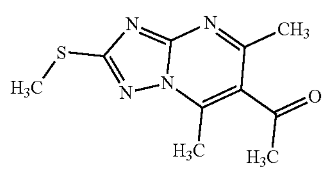 [SMILES: CSc1nc2nc(C)c(C(C)=O)c(C)n2n1] | 1361 | 236.29 | C10H12N4OS |
| 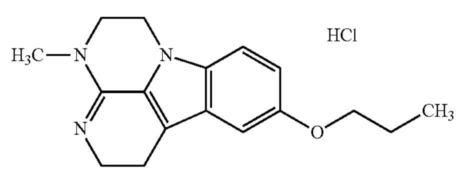 [SMILES: CCCOc1ccc2c(c1)c1c3n2CCN(C)C3=NCC1 ; Cl] | 1362 | 319.83 | C17H22ClN3O |
| 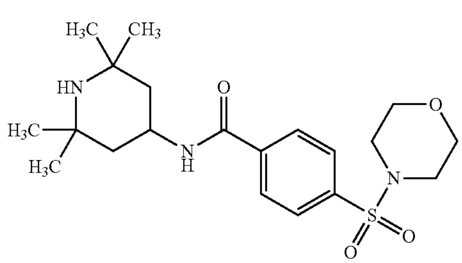 [SMILES: CC1(C)CC(NC(=O)c2ccc(S(=O)(=O)N3CCOCC3)cc2)CC(C)(C)N1] | 1363 | 409.54 | C20H31N3O4S |

TABLE 1-continued

Compounds 1001 to 1557

| Structure | Compound number | Mol Weight | Formula |
|---|---|---|---|
| 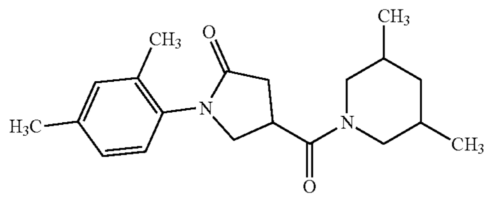 | 1364 | 328.45 | C20H28N2O2 |
| 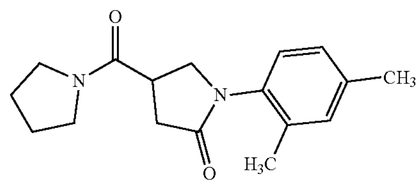 [SMILES: Cc1ccc(N2CC(C(=O)N3CCCC3)CC2=O)c(C)c1] | 1365 | 286.37 | C17H22N2O2 |
| 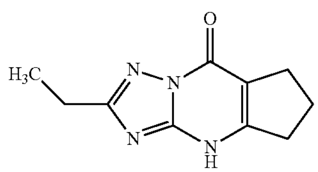 | 1366 | 204.23 | C10H12N4O |
| 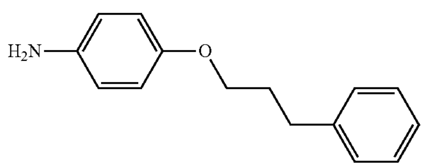 [SMILES: Nc1ccc(OCCCc2ccccc2)cc1] | 1367 | 227.30 | C15H17NO |
| 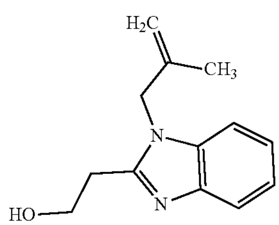 [SMILES: C=C(C)Cn1c(CCO)nc2ccccc21] | 1368 | 216.28 | C13H16N2O |
| 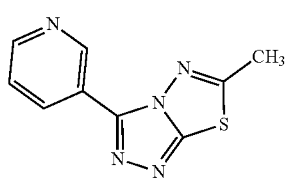 | 1369 | 217.25 | C9H7N5S |
| 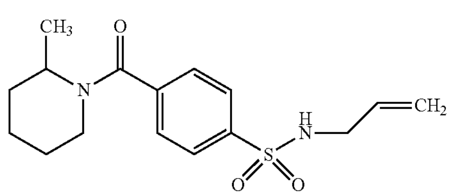 [SMILES: C=CCNS(=O)(=O)c1ccc(C(=O)N2CCCCC2C)cc1] | 1370 | 322.42 | C16H22N2O3S |
| 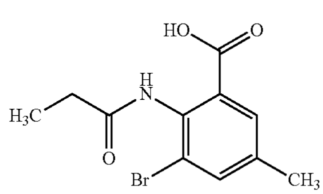 [SMILES: CCC(=O)Nc1c(Br)cc(C)cc1C(=O)O] | 1371 | 286.12 | C11H12BrNO3 |

TABLE 1-continued
Compounds 1001 to 1557
| Structure | Compound number | Mol Weight | Formula |
|---|---|---|---|
| 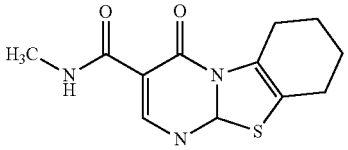 [SMILES: CNC(=O)C1=CNC2SC3=C(CCCC3)N2C1=O] | 1372 | 263.32 | C12H13N3O2S |
| 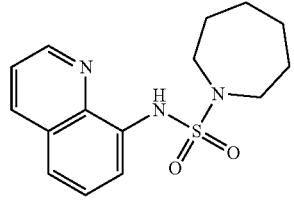 [SMILES: O=S(=O)(Nc1cccc2cccnc12)N1CCCCCC1] | 1373 | 305.39 | C15H19N3O2S |
| 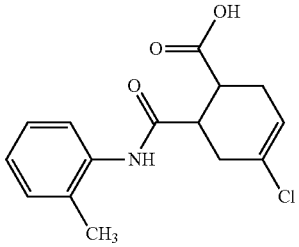 [SMILES: Cc1ccccc1NC(=O)C1CC(Cl)=CCC1C(=O)O] | 1374 | 293.74 | C15H16ClNO3 |
| 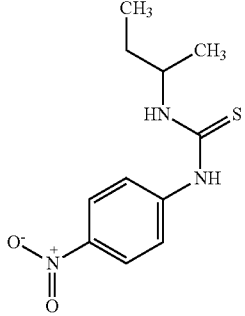 | 1375 | 253.32 | C11H15N3O2S |
| 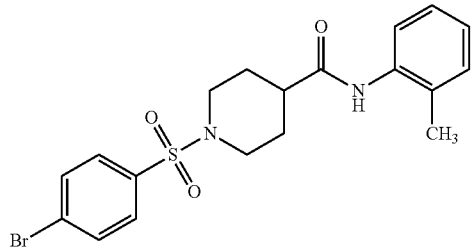 [SMILES: Cc1ccccc1NC(=O)C1CCN(S(=O)(=O)c2ccc(Br)cc2)CC1] | 1376 | 437.35 | C19H21BrN2O3S |
| 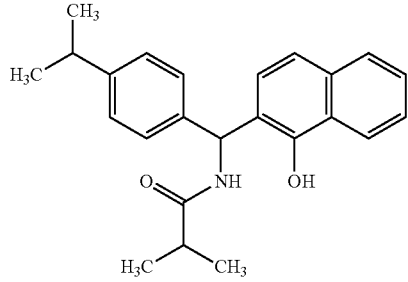 [SMILES: CC(C)C(=O)NC(c1ccc(C(C)C)cc1)c1ccc2ccccc2c1O] | 1377 | 361.48 | C24H27NO2 |

TABLE 1-continued

Compounds 1001 to 1557

| Structure | Compound number | Mol Weight | Formula |
|---|---|---|---|
| 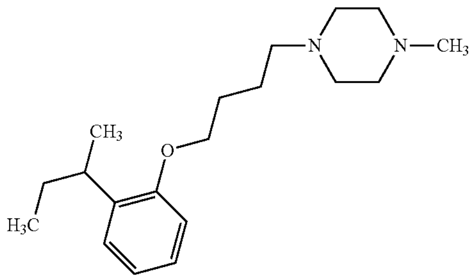 [SMILES: CCC(C)c1ccccc1OCCCCN1CCN(C)CC1] | 1378 | 304.47 | C19H32N2O |
| 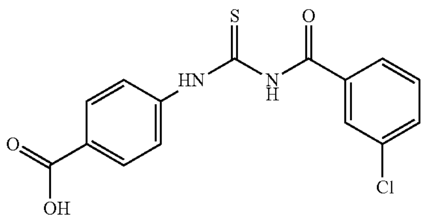 [SMILES: O=C(O)c1ccc(NC(=S)NC(=O)c2cccc(Cl)c2)cc1] | 1379 | 334.78 | C15H11ClN2O3S |
| 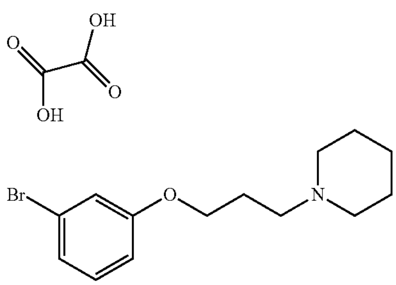 | 1380 | 388.25 | C16H22BrNO5 |
| 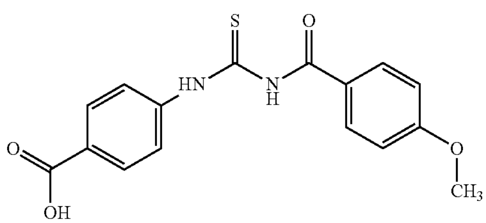 [SMILES: COc1ccc(C(=O)NC(=S)Nc2ccc(C(=O)O)cc2)cc1] | 1381 | 330.36 | C16H14N2O4S |
| 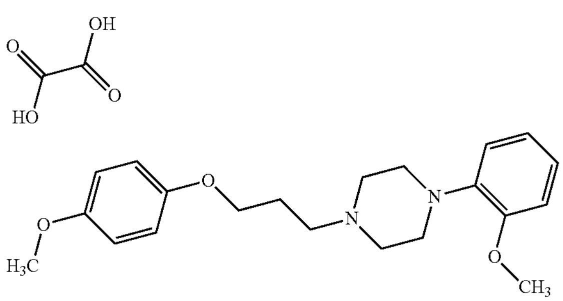 | 1382 | 446.49 | C23H30N2O7 |
| 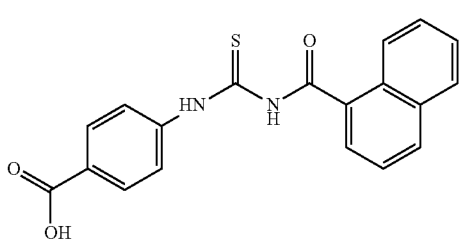 [SMILES: O=C(O)c1ccc(NC(=S)NC(=O)c2cccc3ccccc23)cc1] | 1383 | 350.39 | C19H14N2O3S |

TABLE 1-continued
Compounds 1001 to 1557
| Structure | Compound number | Mol Weight | Formula |
|---|---|---|---|
| 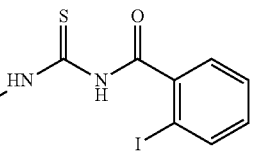 | 1384 | 426.23 | C15H11IN2O3S |
| 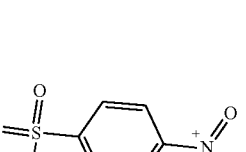 | 1385 | 328.73 | C12H9ClN2O5S |
| 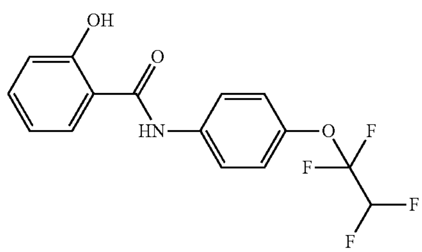 [SMILES: O=C(Nc1ccc(OC(F)(F)C(F)F)cc1)c1ccccc1O] | 1386 | 329.25 | C15H11F4NO3 |
| 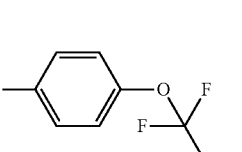 | 1387 | 339.26 | C15H9N5O5 |
| 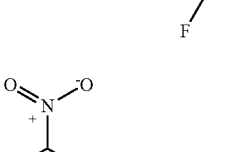 | 1388 | 465.95 | C24H20ClN3O3S |
| 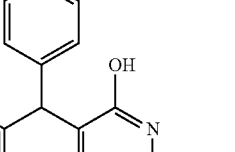 | 1389 | 303.76 | C14H19ClFNO3 | ns
TABLE 1-continued
Compounds 1001 to 1557
| Structure | Compound number | Mol Weight | Formula |
|---|---|---|---|
| 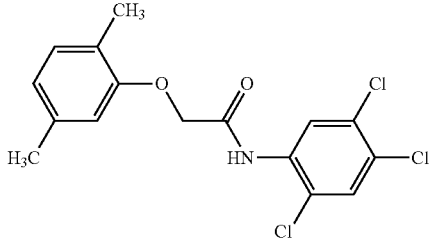 [SMILES: Cc1ccc(C)c(OCC(=O)Nc2cc(Cl)c(Cl)cc2Cl)c1] | 1390 | 358.65 | C16H14Cl3NO2 |
| 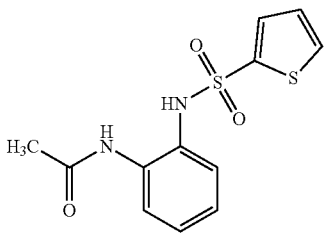 [SMILES: CC(=O)Nc1ccccc1NS(=O)(=O)c1cccs1] | 1391 | 296.36 | C12H12N2O3S2 |
| 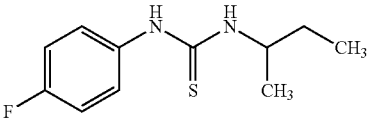 | 1392 | 226.31 | C11H15FN2S |
| 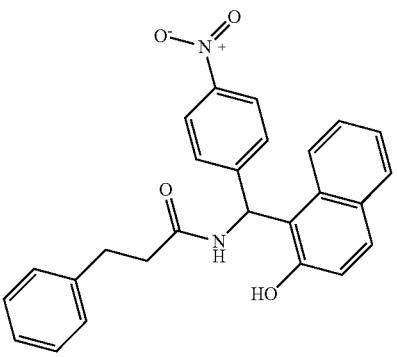 | 1393 | 426.46 | C26H22N2O4 |
| 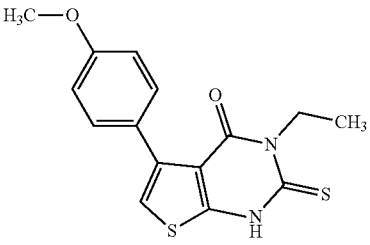 [SMILES: CCn1c(=S)[nH]c2scc(-c3ccc(OC)cc3)c2c1=O] | 1394 | 318.41 | C15H14N2O2S2 |
| 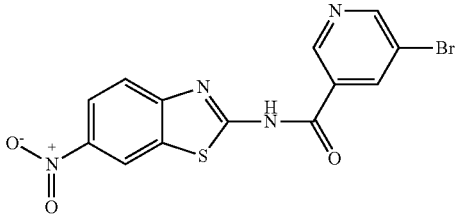 | 1395 | 379.19 | C13H7BrN4O3S |

TABLE 1-continued
Compounds 1001 to 1557
| Structure | Compound number | Mol Weight | Formula |
|---|---|---|---|
| 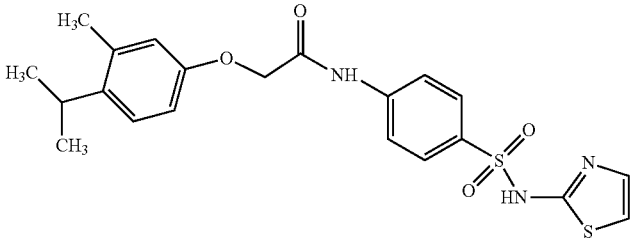 [SMILES: Cc1cc(OCC(=O)Nc2ccc(S(=O)(=O)Nc3nccs3)cc2)ccc1C(C)C] | 1396 | 445.55 | C21H23N3O4S2 |
| 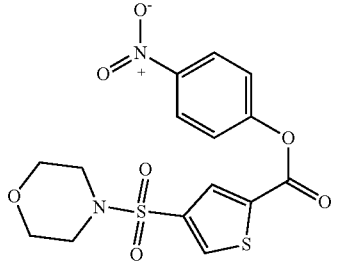 | 1397 | 398.41 | C15H14N2O7S2 |
| 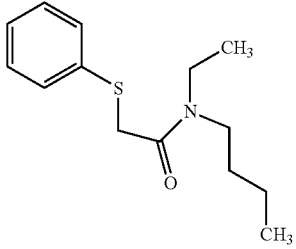 [SMILES: CCCCN(CC)C(=O)CSc1ccccc1] | 1398 | 251.39 | C14H21NOS |
| 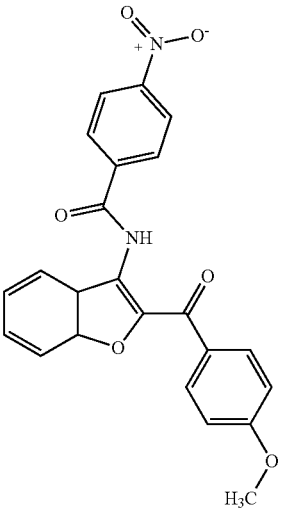 | 1399 | 416.38 | C23H16N2O6 |

TABLE 1-continued

Compounds 1001 to 1557

| Structure | Compound number | Mol Weight | Formula |
|---|---|---|---|
| 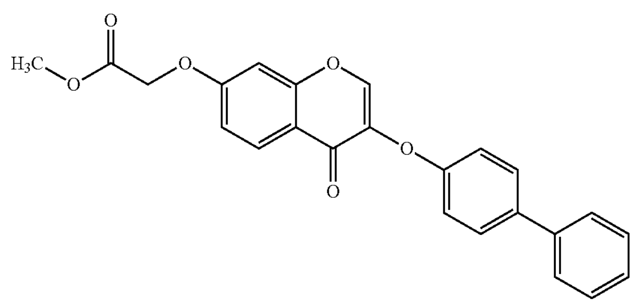 [SMILES: COC(=O)COc1ccc2c(=O)c(Oc3ccc(-c4ccccc4)cc3)coc2c1] | 1400 | 402.40 | C24H18O6 |
| 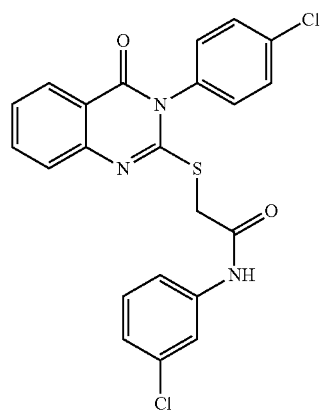 [SMILES: O=C(CSc1nc2ccccc2c(=O)n1-c1ccc(Cl)cc1)Nc1cccc(Cl)c1] | 1401 | 456.34 | C22H15Cl2N3O2S |
| 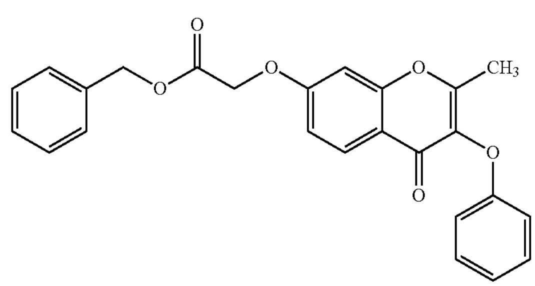 [SMILES: Cc1oc2cc(OCC(=O)OCc3ccccc3)ccc2c(=O)c1Oc1ccccc1] | 1402 | 416.42 | C25H20O6 |
| 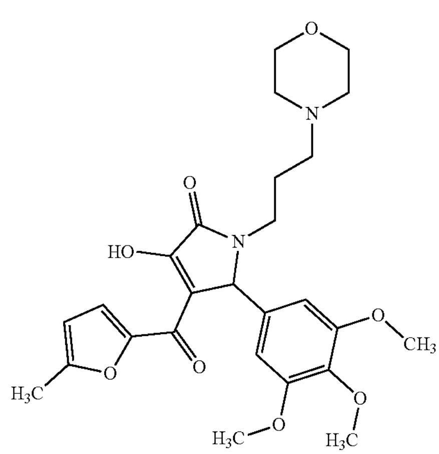 | 1403 | 500.54 | C26H32N2O8 |

TABLE 1-continued
Compounds 1001 to 1557
| Structure | Compound number | Mol Weight | Formula |
|---|---|---|---|
| 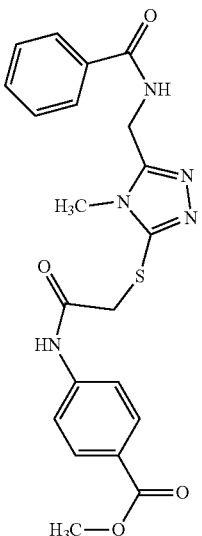 | 1404 | 439.49 | C21H21N5O4S |
| 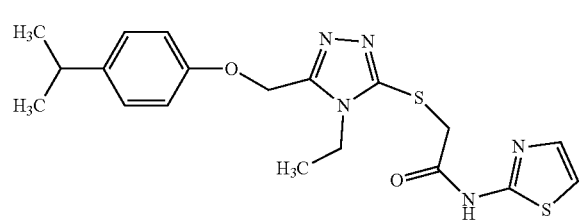 [SMILES: CCn1c(COc2ccc(C(C)C)cc2)nnc1SCC(=O)Nc1nccs1] | 1405 | 417.55 | C19H23N5O2S2 |
| 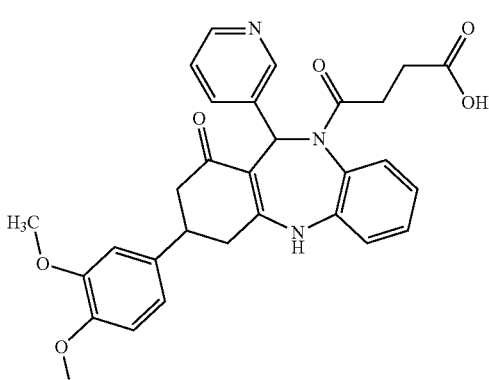 | 1406 | 527.57 | C30H29N3O6 |
| 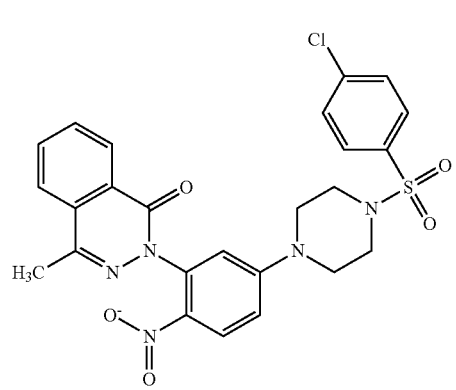 | 1407 | 539.99 | C25H22ClN5O5S |

TABLE 1-continued

Compounds 1001 to 1557

| Structure | Compound number | Mol Weight | Formula |
|---|---|---|---|
| 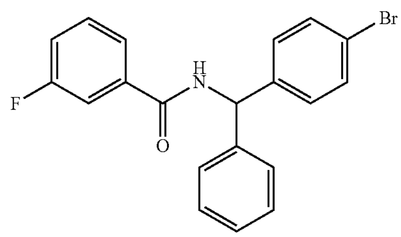 [SMILES: O=C(NC(c1ccccc1)c1ccc(Br)cc1)c1cccc(F)c1] | 1408 | 384.24 | C20H15BrFNO |
| 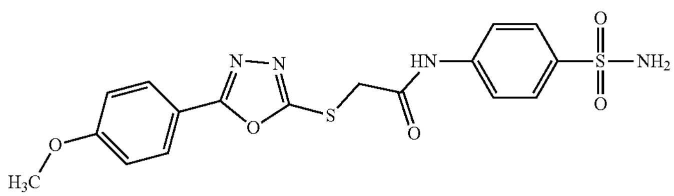 [SMILES: COc1ccc(-c2nnc(SCC(=O)Nc3ccc(S(N)(=O)=O)cc3)o2)cc1] | 1409 | 420.46 | C17H16N4O5S2 |
| 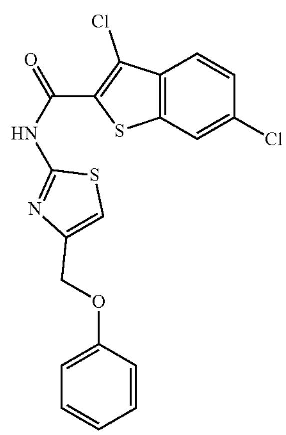 [SMILES: O=C(Nc1nc(COc2ccccc2)cs1)c1sc2cc(Cl)ccc2c1Cl] | 1410 | 435.35 | C19H12Cl2N2O2S2 |
| 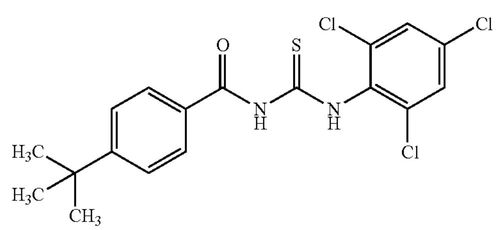 [SMILES: CC(C)(C)c1ccc(C(=O)NC(=S)Nc2c(Cl)cc(Cl)cc2Cl)cc1] | 1411 | 415.76 | C18H17Cl3N2OS |
| 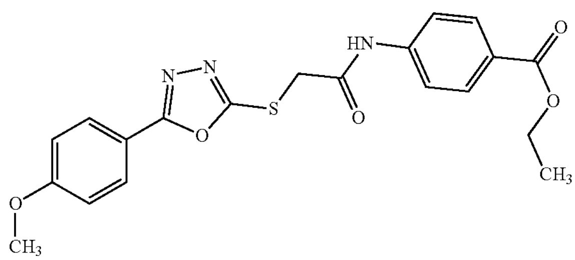 [SMILES: CCOC(=O)c1ccc(NC(=O)CSc2nnc(-c3ccc(OC)cc3)o2)cc1] | 1412 | 413.45 | C20H19N3O5S |

TABLE 1-continued

Compounds 1001 to 1557

| Structure | Compound number | Mol Weight | Formula |
|---|---|---|---|
| 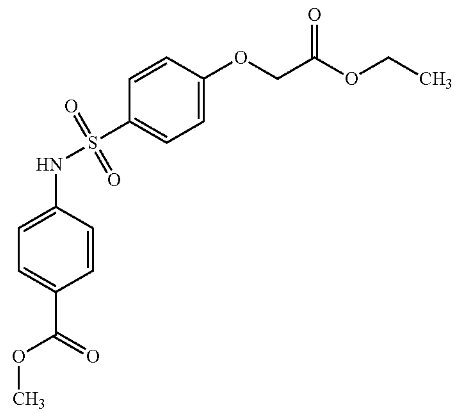 [SMILES: CCOC(=O)COc1ccc(S(=O)(=O)Nc2ccc(C(=O)OC)cc2)cc1] | 1413 | 393.41 | C18H19NO7S |
| 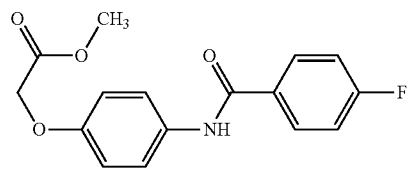 [SMILES: COC(=O)COc1ccc(NC(=O)c2ccc(F)cc2)cc1] | 1414 | 303.29 | C16H14FNO4 |
| 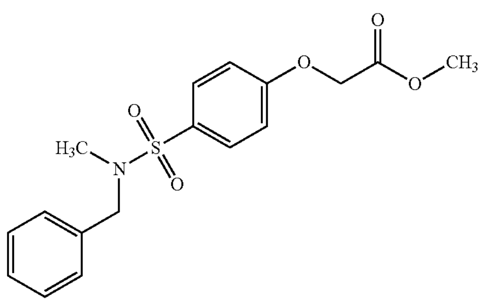 [SMILES: COC(=O)COc1ccc(S(=O)(=O)N(C)Cc2ccccc2)cc1] | 1415 | 349.40 | C17H19NO5S |
| 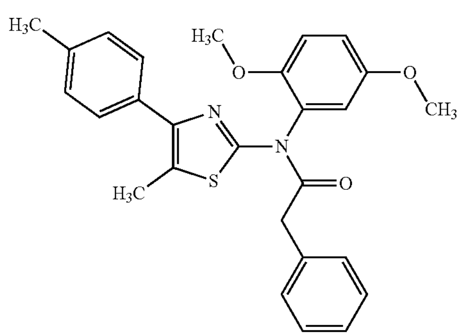 | 1416 | 458.57 | C27H26N2O3S |
| 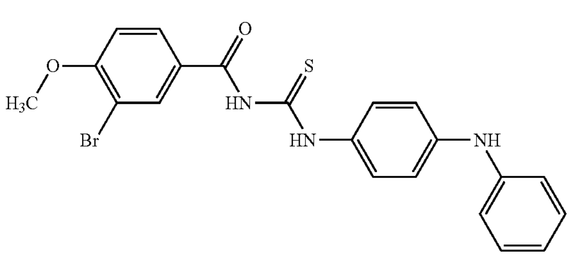 [SMILES: COc1ccc(C(=O)NC(=S)Nc2ccc(Nc3ccccc3)cc2)cc1Br] | 1417 | 456.36 | C21H18BrN3O2S |

TABLE 1-continued

Compounds 1001 to 1557

| Structure | Compound number | Mol Weight | Formula |
|---|---|---|---|
| 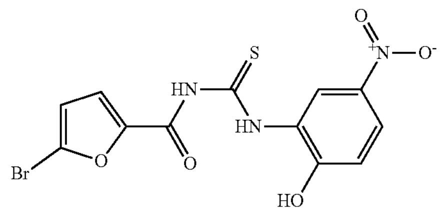 [SMILES: O=C(NC(=S)Nc1cc([N+](=O)[O-])ccc1O)c1ccc(Br)o1] | 1418 | 386.18 | C12H8BrN3O5S |
| 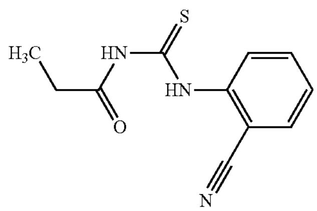 [SMILES: CCC(=O)NC(=S)Nc1ccccc1C#N] | 1419 | 233.29 | C11H11N3OS |
| 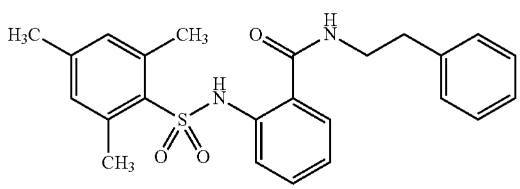 [SMILES: Cc1cc(C)c(S(=O)(=O)Nc2ccccc2C(=O)NCCc2ccccc2)c(C)c1] | 1420 | 422.54 | C24H26N2O3S |
| 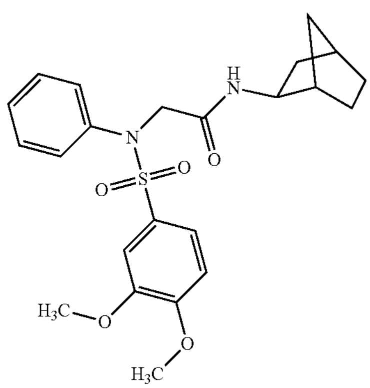 [SMILES: COc1ccc(S(=O)(=O)N(CC(=O)NC2CC3CCC2C3)c2ccccc2)cc1OC] | 1421 | 444.54 | C23H28N2O5S |
| 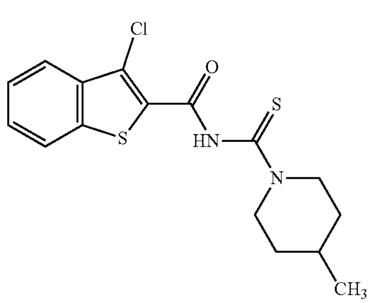 [SMILES: CC1CCN(C(=S)NC(=O)c2sc3ccccc3c2Cl)CC1] | 1422 | 352.90 | C16H17ClN2OS2 |

TABLE 1-continued

Compounds 1001 to 1557

| Structure | Compound number | Mol Weight | Formula |
|---|---|---|---|
| 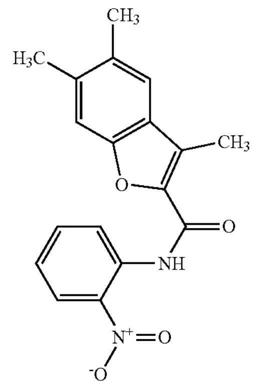 | 1423 | 324.33 | C18H16N2O4 |
| 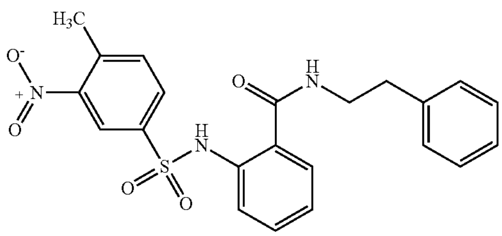 | 1424 | 439.48 | C22H21N3O5S |
| 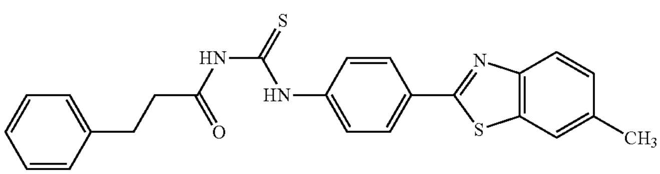 [SMILES: Cc1ccc2nc(-c3ccc(NC(=S)NC(=O)CCc4ccccc4)cc3)sc2c1] | 1425 | 431.57 | C24H21N3OS2 |
| 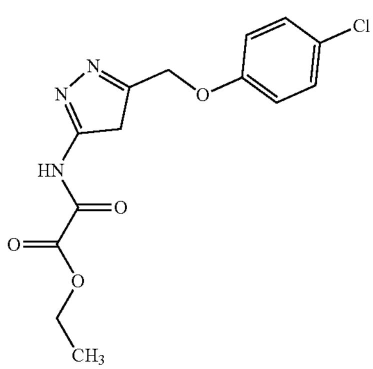 [SMILES: CCOC(=O)C(=O)NC1=NN=C(COc2ccc(Cl)cc2)C1] | 1426 | 341.77 | C13H12ClN3O4S |

TABLE 1-continued

Compounds 1001 to 1557

| Structure | Compound number | Mol Weight | Formula |
|---|---|---|---|
| 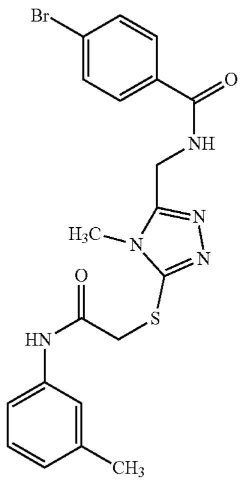 [SMILES: Cc1cccc(NC(=O)CSc2nnc(CNC(=O)c3ccc(Br)cc3)n2C)c1] | 1427 | 474.37 | C20H20BrN5O2S |
| 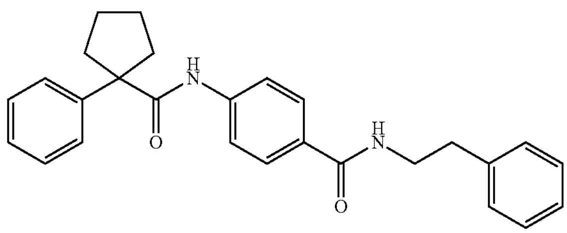 [SMILES: O=C(NCCc1ccccc1)c1ccc(NC(=O)C2(c3ccccc3)CCCC2)cc1] | 1428 | 412.52 | C27H28N2O2 |
| 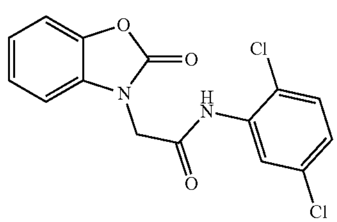 [SMILES: O=C(Cn1c(=O)oc2ccccc21)Nc1cc(Cl)ccc1Cl] | 1429 | 337.16 | C15H10Cl2N2O3 |
| 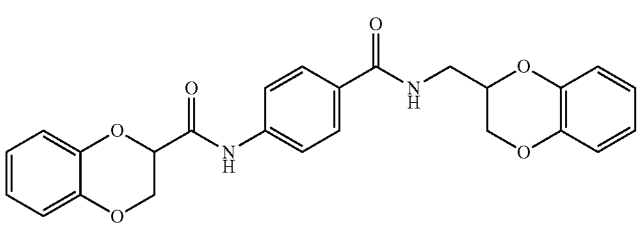 [SMILES: O=C(NCC1COc2ccccc2O1)c1ccc(NC(=O)C2COc3ccccc3O2)cc1] | 1430 | 446.45 | C25H22N2O6 |
| 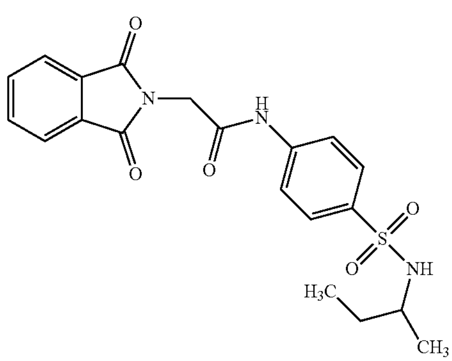 [SMILES: CCC(C)NS(=O)(=O)c1ccc(NC(=O)CN2C(=O)c3ccccc3C2=O)cc1] | 1431 | 415.46 | C20H21N3O5S |

TABLE 1-continued

Compounds 1001 to 1557

| Structure | Compound number | Mol Weight | Formula |
|---|---|---|---|
| 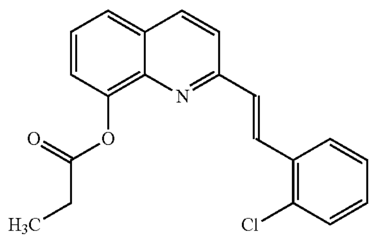 [SMILES: CCC(=O)Oc1cccc2ccc(/C=C/c3ccccc3Cl)nc12] | 1432 | 337.80 | C20H16ClNO2 |
| 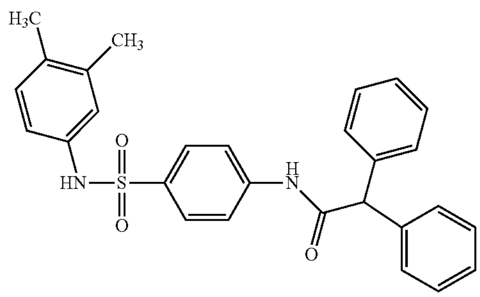 [SMILES: Cc1ccc(NS(=O)(=O)c2ccc(NC(=O)C(c3ccccc3)c3ccccc3)cc2)cc1C] | 1433 | 470.58 | C28H26N2O3S |
| 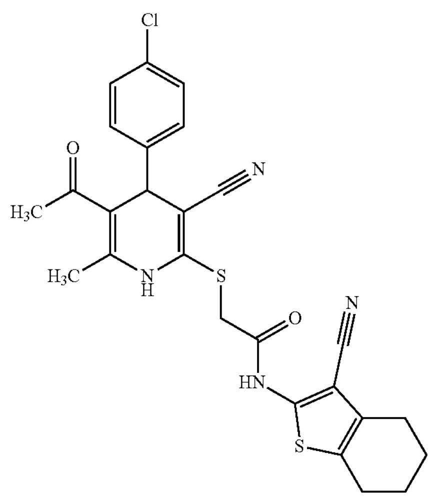 [SMILES: CC(=O)C1=C(C)NC(SCC(=O)Nc2sc3c(c2C#N)CCCC3)=C(C#N)C1c1ccc(Cl)cc1] | 1434 | 523.07 | C26H23ClN4O2S2 |
| 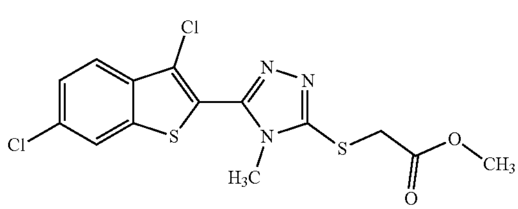 [SMILES: COC(=O)CSc1nnc(-c2sc3cc(Cl)ccc3c2Cl)n1C] | 1435 | 388.29 | C14H11Cl2N3O2S2 |
| 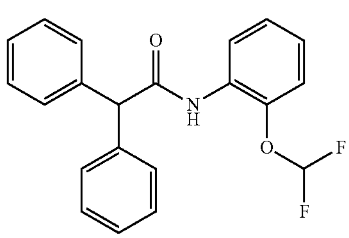 [SMILES: O=C(Nc1ccccc1OC(F)F)C(c1ccccc1)c1ccccc1] | 1436 | 353.36 | C21H17F2NO2 |

TABLE 1-continued

Compounds 1001 to 1557

| Structure | Compound number | Mol Weight | Formula |
|---|---|---|---|
| 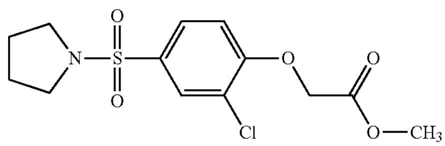 [SMILES: COC(=O)COc1ccc(S(=O)(=O)N2CCCC2)cc1Cl] | 1437 | 333.79 | C13H16ClNO5S |
| 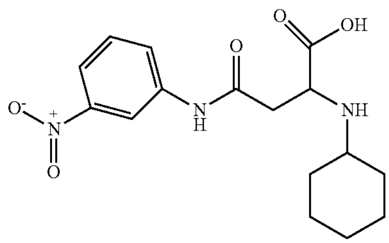 | 1438 | 335.36 | C16H21N3O5 |
| 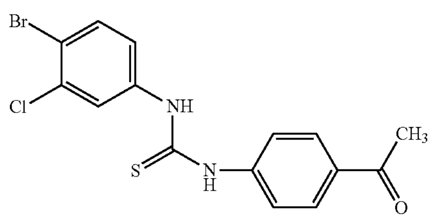 [SMILES: CC(=O)c1ccc(NC(=S)Nc2ccc(Br)c(Cl)c2)cc1] | 1439 | 383.69 | C15H12BrClN2OS |
| 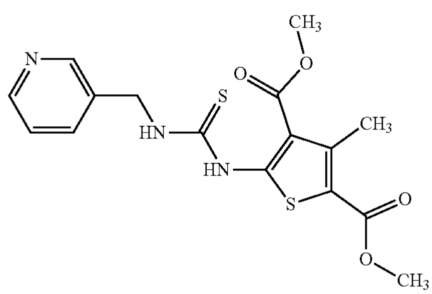 [SMILES: COC(=O)c1sc(NC(=S)NCc2cccnc2)c(C(=O)OC)c1C] | 1440 | 379.45 | C16H17N3O4S2 |
| 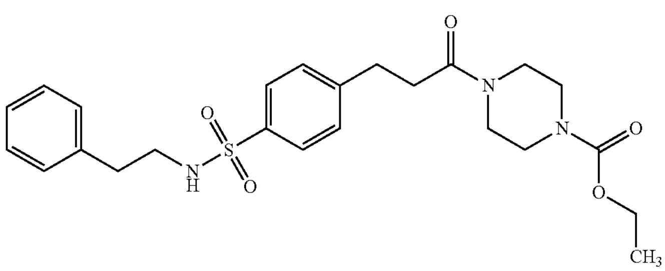 [SMILES: CCOC(=O)N1CCN(C(=O)CCc2ccc(S(=O)(=O)NCCc3ccccc3)cc2)CC1] | 1441 | 473.58 | C24H31N3O5S |
| 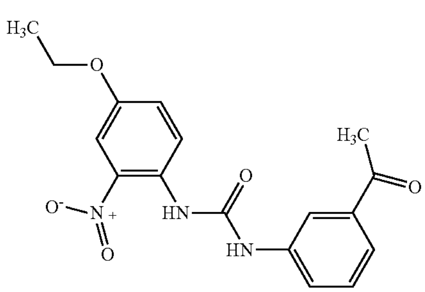 | 1442 | 343.33 | C17H17N3O5 |

TABLE 1-continued

Compounds 1001 to 1557

| Structure | Compound number | Mol Weight | Formula |
|---|---|---|---|
| 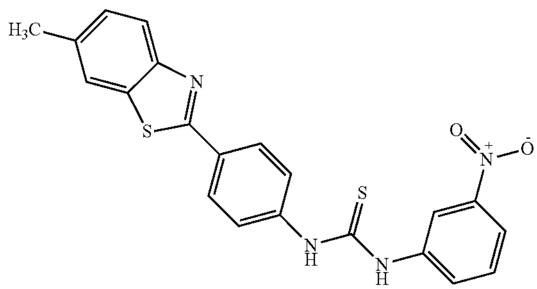 | 1443 | 420.51 | C21H16N4O2S2 |
| 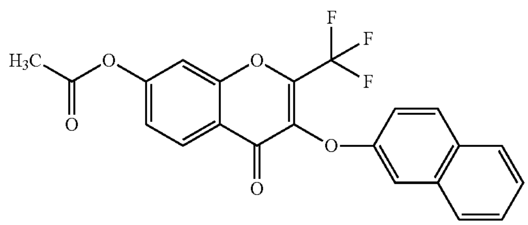 [SMILES: CC(=O)Oc1ccc2c(=O)c(Oc3ccc4ccccc4c3)c(C(F)(F)F)oc2c1] | 1444 | 414.33 | C22H13F3O5 |
| 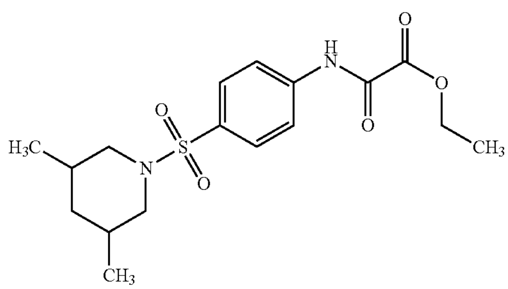 [SMILES: CCOC(=O)C(=O)Nc1ccc(S(=O)(=O)N2CC(C)CC(C)C2)cc1] | 1445 | 368.45 | C17H24N2O5S |
| 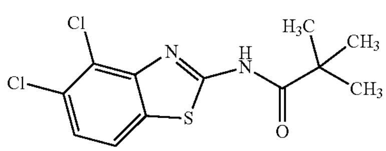 [SMILES: CC(C)(C)C(=O)Nc1nc2c(Cl)c(Cl)ccc2s1] | 1446 | 303.21 | C12H12Cl2N2OS |
| 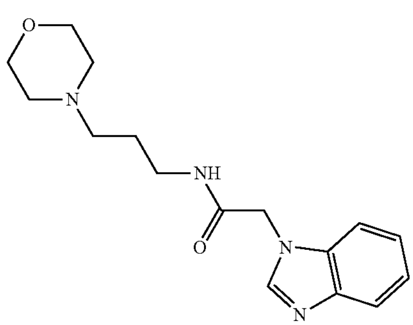 [SMILES: O=C(Cn1cnc2ccccc21)NCCCN1CCOCC1] | 1447 | 302.37 | C16H22N4O2 |
| 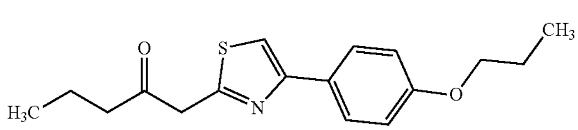 [SMILES: CCCOc1ccc(-c2csc(CC(=O)CCC)n2)cc1] | 1448 | 304.41 | C16H20N2O2S |

TABLE 1-continued

Compounds 1001 to 1557

| Structure | Compound number | Mol Weight | Formula |
|---|---|---|---|
| 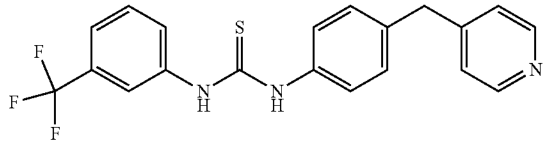 [SMILES: FC(F)(F)c1cccc(NC(=S)Nc2ccc(Cc3ccncc3)cc2)c1] | 1449 | 387.42 | C20H16F3N3S |
| 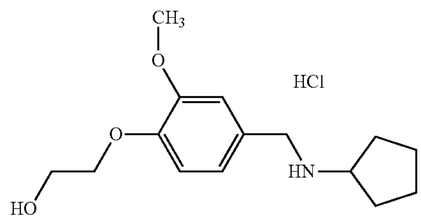 [SMILES: COc1cc(CNC2CCCC2)ccc1OCCO ; Cl] | 1450 | 301.81 | C15H24ClNO3 |
| 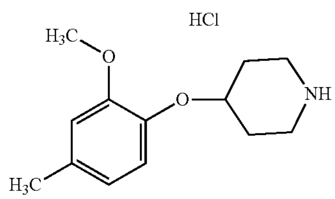 [SMILES: Cl ; COc1cc(C)ccc1OC1CCNCC1] | 1451 | 257.76 | C13H20ClNO2 |
| 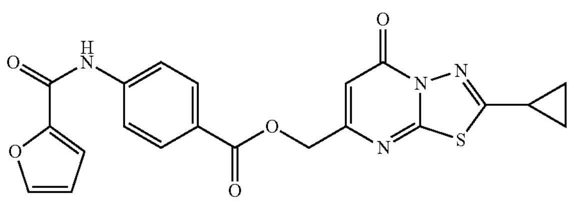 [SMILES: O=C(OCc1cc(=O)n2nc(C3CC3)sc2n1)c1ccc(NC(=O)c2ccco2)cc1] | 1452 | 436.44 | C21H16N4O5S |
| 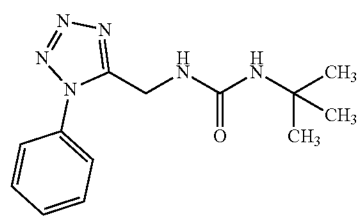 [SMILES: CC(C)(C)NC(=O)NCc1nnnn1-c1ccccc1] | 1453 | 274.32 | C13H18N6O |
| 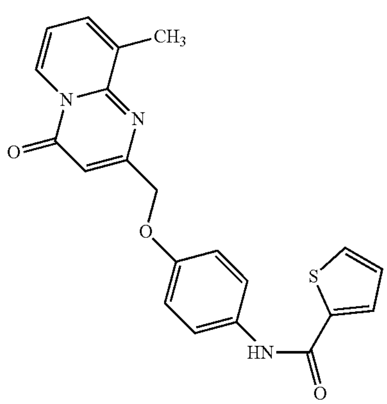 [SMILES: Cc1cccn2c(=O)cc(COc3ccc(NC(=O)c4cccs4)cc3)nc12] | 1454 | 391.44 | C21H17N3O3S |

TABLE 1-continued
Compounds 1001 to 1557
| Structure | Compound number | Mol Weight | Formula |
|---|---|---|---|
| 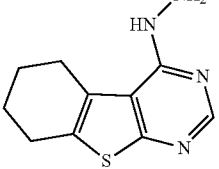 | 1455 | 220.29 | C10H12N4S |
| 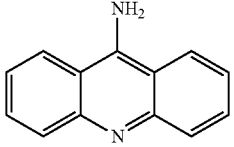 [SMILES: Nc1c2ccccc2nc2ccccc12] | 1456 | 194.23 | C13H10N2 |
| 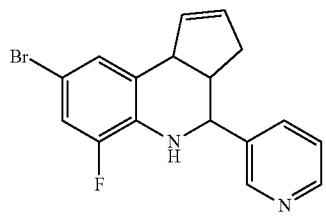 [SMILES: Fc1cc(Br)cc2c1NC(c1cccnc1)C1CC=CC21] | 1457 | 345.21 | C17H14BrFN2 |
| 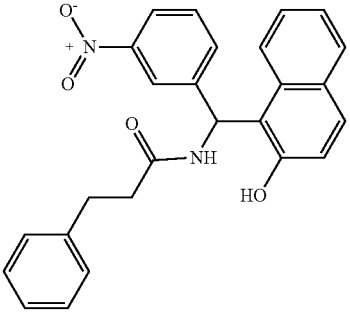 | 1458 | 426.46 | C26H22N2O4 |
| 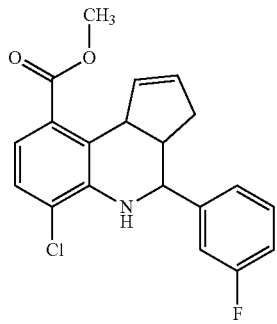 [SMILES: COC(=O)c1ccc(Cl)c2c1C1C=CCC1C(c1cccc(F)c1)N2] | 1459 | 357.81 | C20H17ClFNO2 |
| 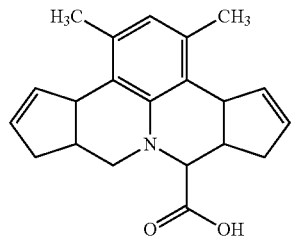 [SMILES: Cc1cc(C)c2c3c1C1C=CCC1CN3C(C(=O)O)C1CC=CC21] | 1460 | 321.41 | C21H23NO2 |

TABLE 1-continued

Compounds 1001 to 1557

| Structure | Compound number | Mol Weight | Formula |
|---|---|---|---|
| 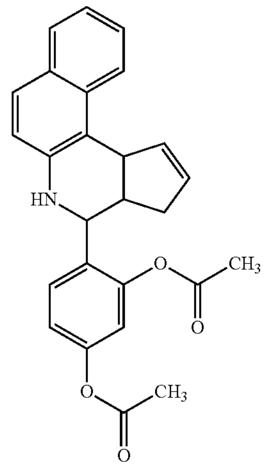 [SMILES: CC(=O)Oc1ccc(C2Nc3ccc4ccccc4c3C3C=CCC32)c(OC(C)=O)c1] | 1461 | 413.47 | C26H23NO4 |
| 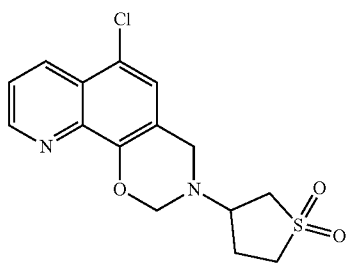 [SMILES: O=S1(=O)CCC(N2COc3c(cc(Cl)c4cccnc34)C2)C1] | 1462 | 338.81 | C15H15ClN2O3S |
| 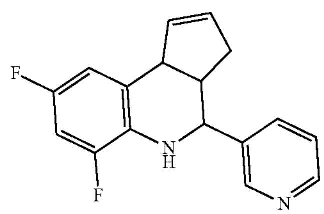 [SMILES: Fc1cc(F)c2c(c1)C1C=CCC1C(c1cccnc1)N2] | 1463 | 284.30 | C17H14F2N2 |
| 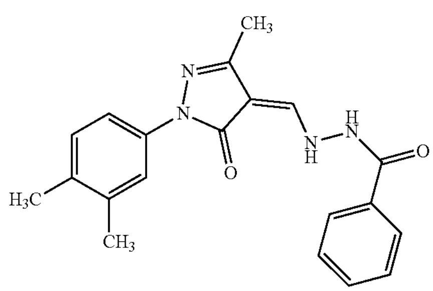 [SMILES: CC1=NN(c2ccc(C)c(C)c2)C(=O)/C1=C\NNC(=O)c1ccccc1] | 1464 | 348.40 | C20H20N4O2 |
| 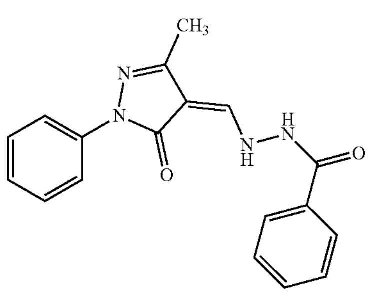 [SMILES: CC1=NN(c2ccccc2)C(=O)/C1=C\NNC(=O)c1ccccc1] | 1465 | 320.35 | C18H16N4O2 |

TABLE 1-continued

Compounds 1001 to 1557

| Structure | Compound number | Mol Weight | Formula |
|---|---|---|---|
| 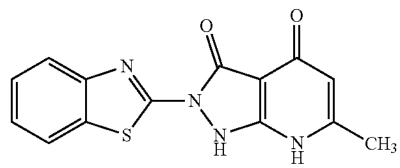 [SMILES: Cc1cc(=O)c2c(=O)n(-c3nc4ccccc4s3)[nH]c2[nH]1] | 1466 | 298.32 | C14H10N4O2S |
| 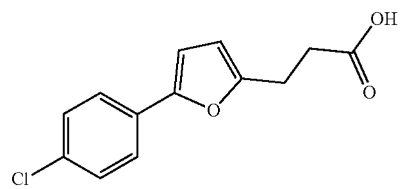 [SMILES: O=C(O)CCc1ccc(-c2ccc(Cl)cc2)o1] | 1467 | 250.68 | C13H11ClO3 |
| 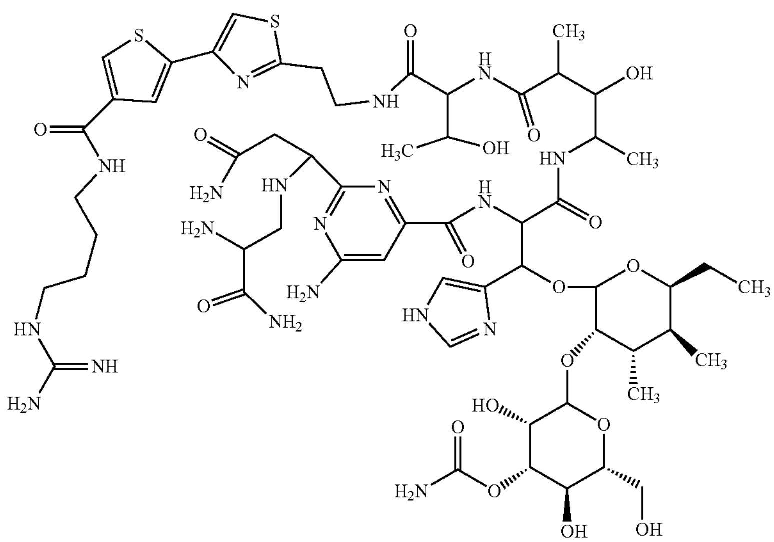 [SMILES: CC[C@@H]1OC(OC(c2c[nH]cn2)C(NC(=O)c2cc(N)nc(C(CC(N)=O)NCC(N)C(N)=O)n2)C(=O)NC(C)C(O)C(C)C(=O)NC(C(=O)NCCc2nc(-c3cc(C(=O)NCCCCCNC(=N)N)cs3)cs2)C(C)O)[C@@H](OC2O[C@H](CO)[C@@H](O)[C@H](OC(N)=O)[C@@H]2O)[C@@H](C)[C@@H]1C] | 1468 | 1615.74 | C58H94N20O26S4 |
| 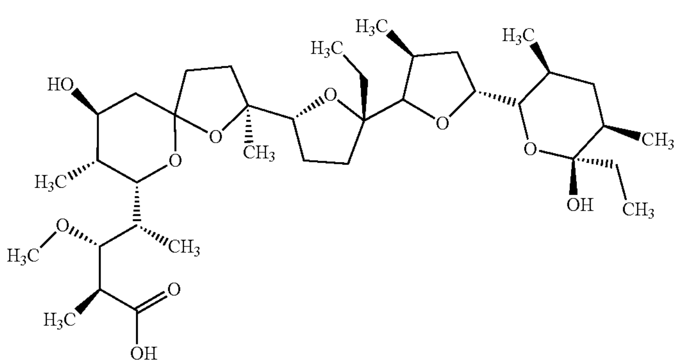 | 1469 | 690.88 | C37H63NaO10 |

TABLE 1-continued

Compounds 1001 to 1557

| Structure | Compound number | Mol Weight | Formula |
|---|---|---|---|
| 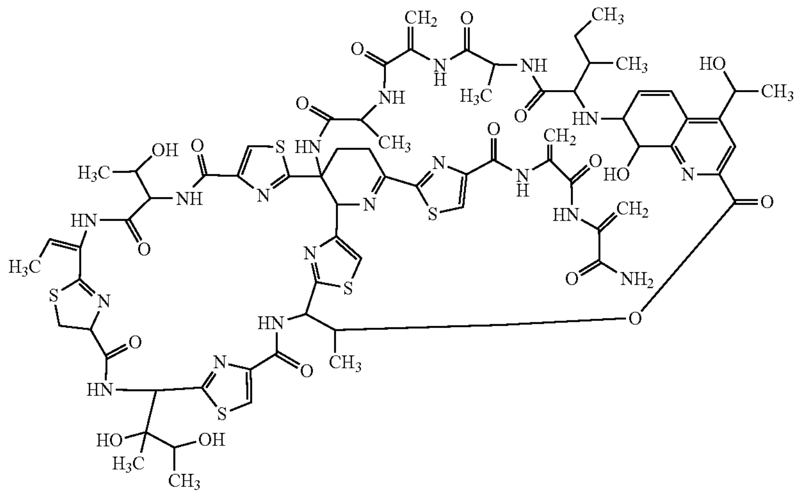 [SMILES: C=C(NC(=O)C(=C)NC(=O)c1csc(C2=NC3c4csc(n4)C4NC(=O)c5csc(n5)C(C(C)(O)C(C)O)NC(=O)C5CSC(=N5)/C(=C\C)NC(=O)C(C(C)O)NC(=O)c5csc(n5)C3(CC2)NC(=O)C(C)NC(=O)C(=C)NC(=O)C(C)NC(=O)C(C(C)CC)NC2C=Cc3c(C(C)O)cc(nc3C2O)C(=O)OCC4C)n1)C(N)=O] | 1470 | 1664.89 | C72H85N19O18S5 |
| 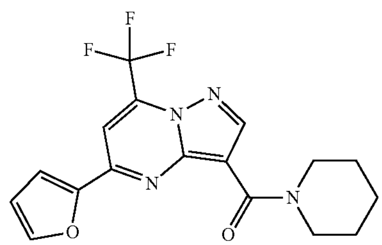 [SMILES: O=C(c1cnn2c(C(F)(F)F)cc(-c3ccco3)nc12)N1CCCCC1] | 1471 | 364.32 | C17H15F3N4O2 |
| 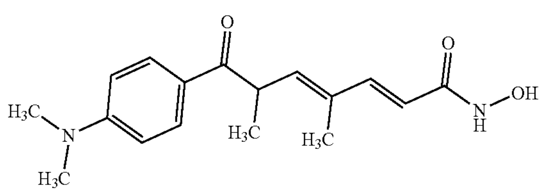 [SMILES: CC(/C=C/C(=O)NO)=C\C(C)C(=O)c1ccc(N(C)C)cc1] | 1472 | 302.37 | C17H22N2O3 |
| 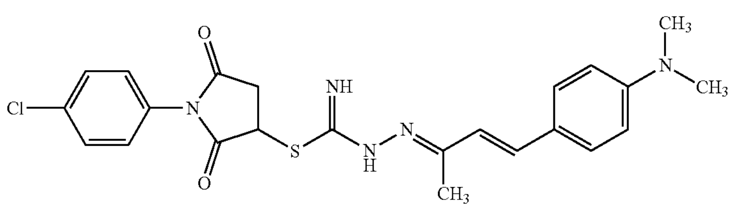 [SMILES: CC(/C=C/c1ccc(N(C)C)cc1)=N\NC(=N)SC1CC(=O)N(c2ccc(Cl)cc2)C1=O] | 1473 | 469.99 | C23H24ClN5O2S |
| 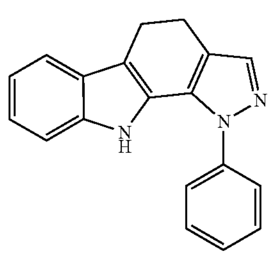 [SMILES: c1ccc(-n2ncc3c2-c2[nH]c4ccccc4c2CC3)cc1] | 1474 | 285.34 | C19H15N3 |

TABLE 1-continued

Compounds 1001 to 1557

| Structure | Compound number | Mol Weight | Formula |
|---|---|---|---|
| 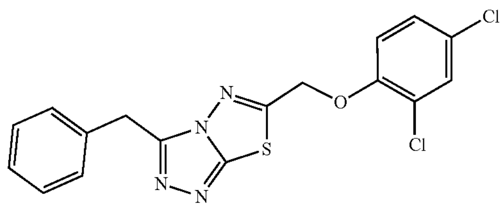 [SMILES: Clc1ccc(OCc2nn3c(Cc4ccccc4)nnc3s2)c(Cl)c1] | 1475 | 391.27 | C17H12Cl2N4OS |
| 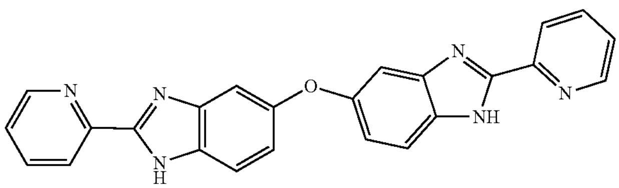 [SMILES: c1ccc(-c2nc3cc(Oc4ccc5[nH]c(-c6ccccn6)nc5c4)ccc3[nH]2)nc1] | 1476 | 404.42 | C24H16N6O |
| 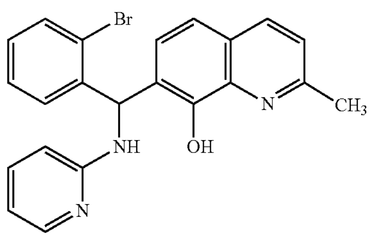 [SMILES: Cc1ccc2ccc(C(Nc3ccccn3)c3ccccc3Br)c(O)c2n1] | 1477 | 420.30 | C22H18BrN3O |
| 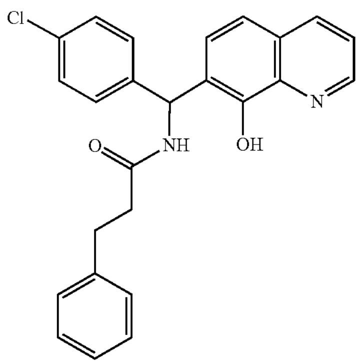 [SMILES: O=C(CCc1ccccc1)NC(c1ccc(Cl)cc1)c1ccc2cccnc2c1O] | 1478 | 416.90 | C25H21ClN2O2 |
| 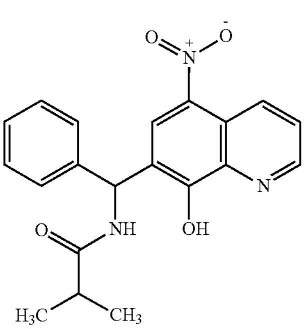 | 1479 | 365.38 | C20H19N3O4 |

TABLE 1-continued

Compounds 1001 to 1557

| Structure | Compound number | Mol Weight | Formula |
|---|---|---|---|
| 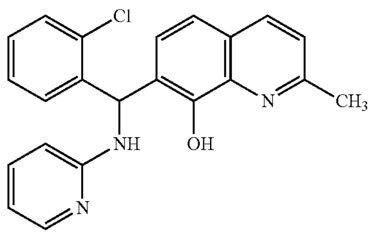 [SMILES: Cc1ccc2ccc(C(Nc3ccccn3)c3ccccc3Cl)c(O)c2n1] | 1480 | 375.85 | C22H18ClN3O |
| 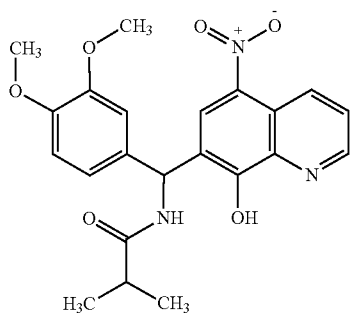 | 1481 | 425.43 | C22H23N3O6 |
| 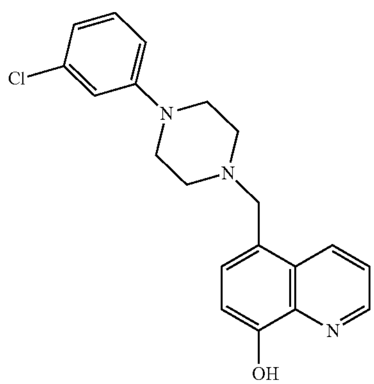 [SMILES: Oc1ccc(CN2CCN(c3cccc(Cl)c3)CC2)c2cccnc12] | 1482 | 353.85 | C20H20ClN3O |
| 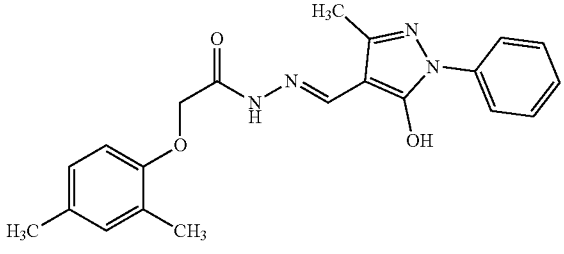 [SMILES: Cc1ccc(OCC(=O)N/N=C/c2c(C)nn(-c3ccccc3)c2O)c(C)c1] | 1483 | 378.42 | C21H22N4O3 |

TABLE 1-continued
Compounds 1001 to 1557
| Structure | Compound number | Mol Weight | Formula |
|---|---|---|---|
| 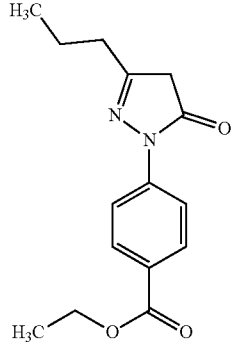 | 1484 | 274.32 | C15H18N2O3 |
| 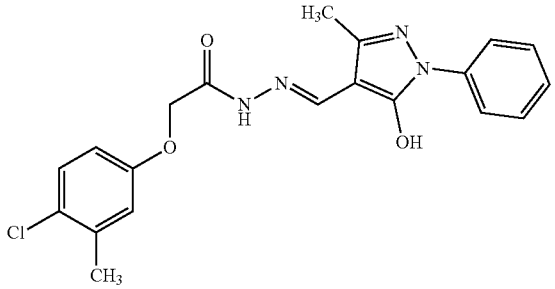 [SMILES: Cc1cc(OCC(=O)N/N=C/c2c(C)nn(-c3ccccc3)c2O)ccc1Cl] | 1485 | 398.84 | C20H19ClN4O3 |
| 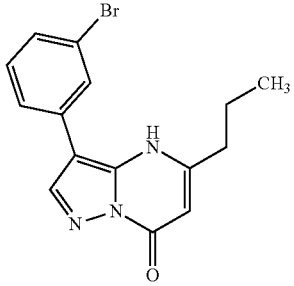 [SMILES: CCCc1cc(=O)n2ncc(-c3cccc(Br)c3)c2[nH]1] | 1486 | 332.20 | C15H14BrN3O |
| 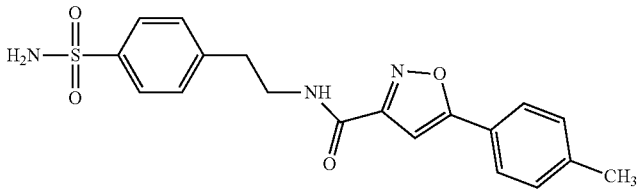 [SMILES: Cc1ccc(-c2cc(C(=O)NCCc3ccc(S(N)(=O)=O)cc3)no2)cc1] | 1487 | 385.44 | C19H19N3O4S |

TABLE 1-continued

Compounds 1001 to 1557

| Structure | Compound number | Mol Weight | Formula |
|---|---|---|---|
| 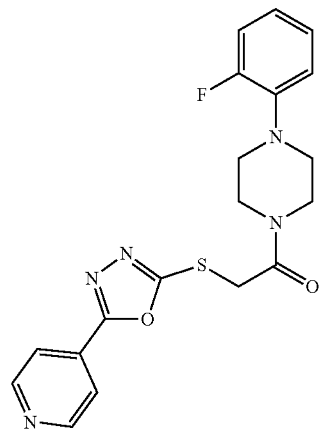 [SMILES: O=C(CSc1nnc(-c2ccncc2)o1)N1CCN(c2ccccc2F)CC1] | 1488 | 399.44 | C19H18FN5O2S |
| 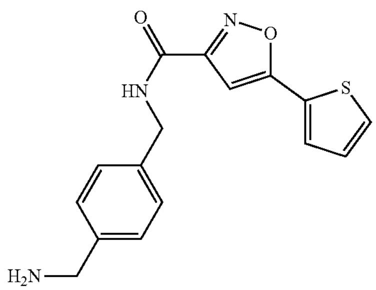 [SMILES: NCc1ccc(CNC(=O)c2cc(-c3cccs3)on2)cc1] | 1489 | 313.37 | C16H15N3O2S |
| 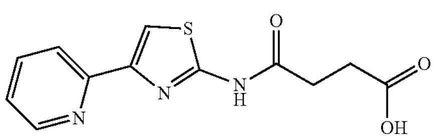 [SMILES: O=C(O)CCC(=O)Nc1nc(-c2ccccn2)cs1] | 1490 | 277.30 | C12H11N3O3S |
| 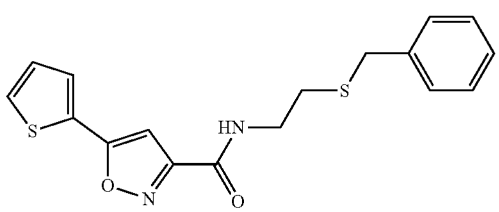 [SMILES: O=C(NCCSCc1ccccc1)c1cc(-c2cccs2)on1] | 1491 | 344.45 | C17H16N2O2S2 |
| 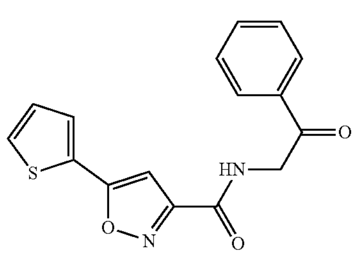 [SMILES: O=C(CNC(=O)c1cc(-c2cccs2)on1)c1ccccc1] | 1492 | 312.34 | C16H12N2O3S |

TABLE 1-continued
Compounds 1001 to 1557
| Structure | Compound number | Mol Weight | Formula |
|---|---|---|---|
| 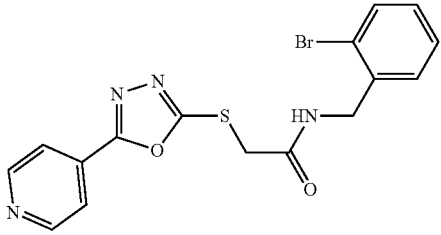 [SMILES: O=C(CSc1nnc(-c2ccncc2)o1)NCc1ccccc1Br] | 1493 | 405.27 | C16H13BrN4O2S |
| 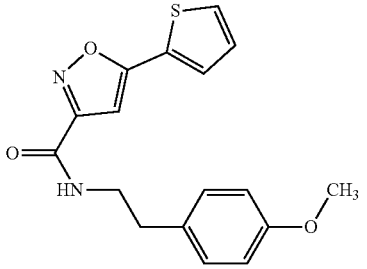 [SMILES: COc1ccc(CCNC(=O)c2cc(-c3cccs3)on2)cc1] | 1494 | 328.39 | C17H16N2O3S |
| 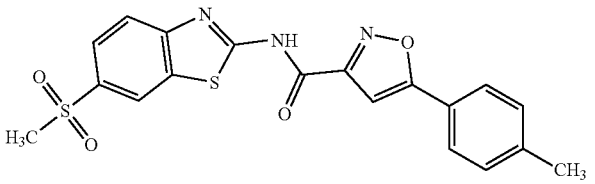 | 1495 | 413.47 | C19H15N3O4S2 |
| 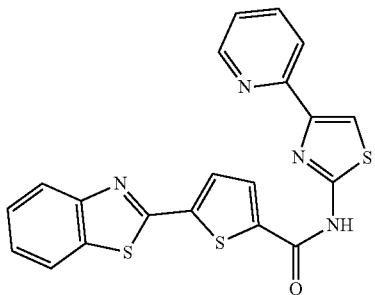 [SMILES: O=C(Nc1nc(-c2ccccn2)cs1)c1ccc(-c2nc3ccccc3s2)s1] | 1496 | 420.53 | C20H12N4OS3 |
| 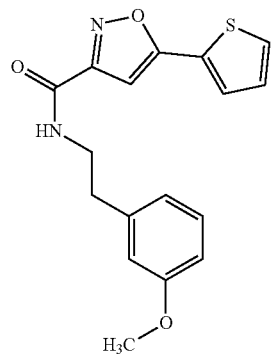 [SMILES: COc1cccc(CCNC(=O)c2cc(-c3cccs3)on2)c1] | 1497 | 328.39 | C17H16N2O3S |

TABLE 1-continued

Compounds 1001 to 1557

| Structure | Compound number | Mol Weight | Formula |
|---|---|---|---|
| 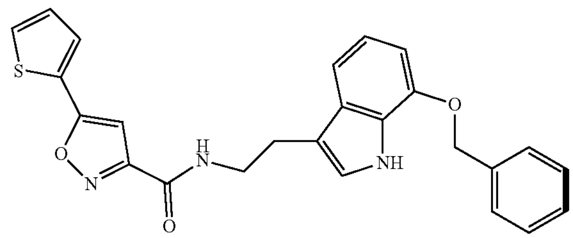 | 1498 | 443.52 | C25H21N3O3S |
| 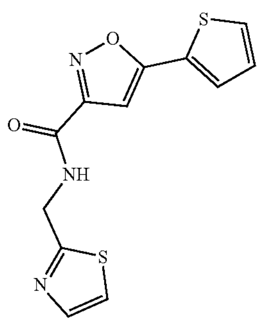 [SMILES: O=C(NCc1nccs1)c1cc(-c2cccs2)on1] | 1499 | 291.35 | C12H9N3O2S2 |
| 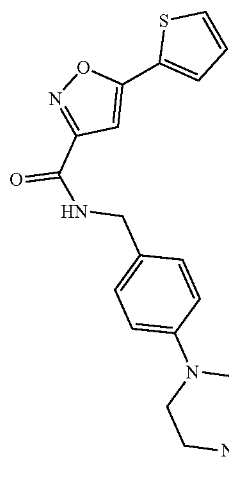 | 1500 | 382.48 | C20H22N4O2S |
| 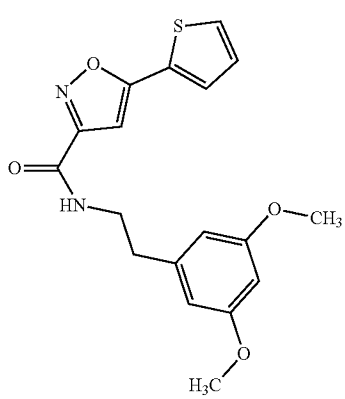 [SMILES: COc1cc(CCNC(=O)c2cc(-c3cccs3)on2)cc(OC)c1] | 1501 | 358.41 | C18H18N2O4S |

TABLE 1-continued

Compounds 1001 to 1557

| Structure | Compound number | Mol Weight | Formula |
|---|---|---|---|
| 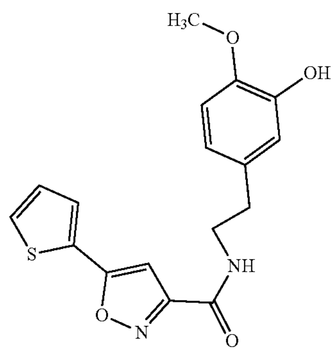 [SMILES: COc1ccc(CCNC(=O)c2cc(-c3cccs3)on2)cc1O] | 1502 | 344.39 | C17H16N2O4S |
| 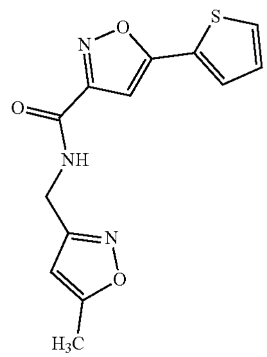 [SMILES: Cc1cc(CNC(=O)c2cc(-c3cccs3)on2)no1] | 1503 | 289.31 | C13H11N3O3S |
| 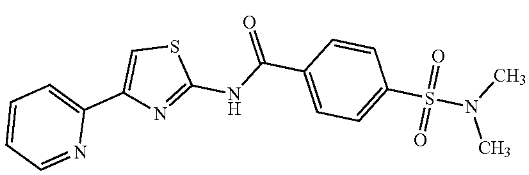 [SMILES: CN(C)S(=O)(=O)c1ccc(C(=O)Nc2nc(-c3ccccn3)cs2)cc1] | 1504 | 388.46 | C17H16N4O3S2 |
| 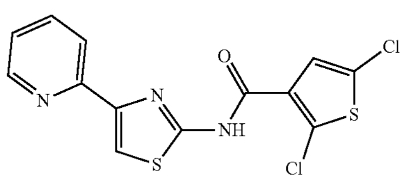 [SMILES: O=C(Nc1nc(-c2ccccn2)cs1)c1cc(Cl)sc1Cl] | 1505 | 356.25 | C13H7Cl2N3OS2 |
| 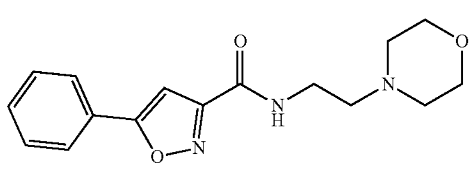 [SMILES: O=C(NCCN1CCOCC1)c1cc(-c2ccccc2)on1] | 1506 | 301.34 | C16H19N3O3 |

TABLE 1-continued

Compounds 1001 to 1557

| Structure | Compound number | Mol Weight | Formula |
|---|---|---|---|
| 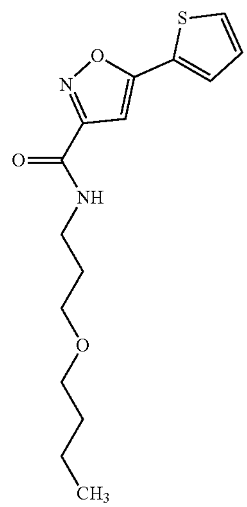 [SMILES: CCCCOCCCNC(=O)c1cc(-c2cccs2)on1] | 1507 | 308.40 | C15H20N2O3S |
| 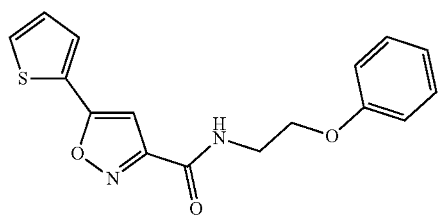 [SMILES: O=C(NCCOc1ccccc1)c1cc(-c2cccs2)on1] | 1508 | 314.36 | C16H14N2O3S |
| 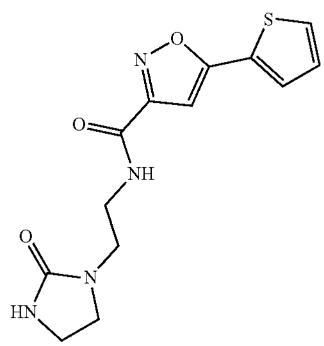 [SMILES: O=C(NCCN1CCNC1=O)c1cc(-c2cccs2)on1] | 1509 | 306.34 | C13H14N4O3S |
| 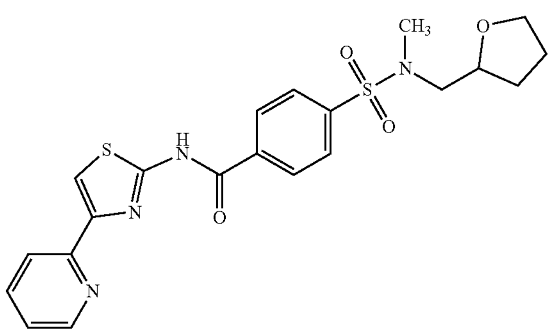 [SMILES: CN(CC1CCCO1)S(=O)(=O)c1ccc(C(=O)Nc2nc(-c3ccccn3)cs2)cc1] | 1510 | 458.55 | C21H22N4O4S2 |

TABLE 1-continued
Compounds 1001 to 1557
| Structure | Compound number | Mol Weight | Formula |
|---|---|---|---|
| 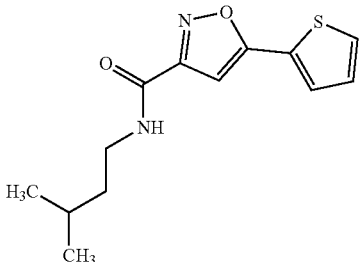 [SMILES: CC(C)CCNC(=O)c1cc(-c2cccs2)on1] | 1511 | 264.34 | C13H16N2O2S |
| 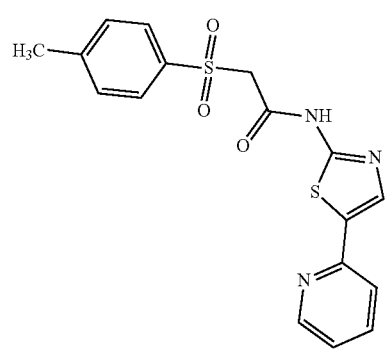 [SMILES: Cc1ccc(S(=O)(=O)CC(=O)Nc2ncc(-c3ccccn3)s2)cc1] | 1512 | 373.45 | C17H15N3O3S2 |
| 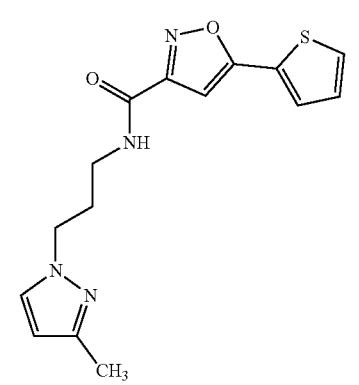 [SMILES: Cc1ccn(CCCNC(=O)c2cc(-c3cccs3)on2)n1] | 1513 | 316.38 | C15H16N4O2S |
| 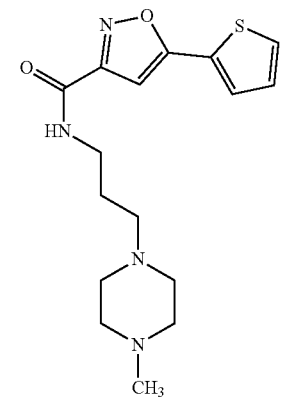 [SMILES: CN1CCN(CCCNC(=O)c2cc(-c3cccs3)on2)CC1] | 1514 | 334.44 | C16H22N4O2S |

TABLE 1-continued

Compounds 1001 to 1557

| Structure | Compound number | Mol Weight | Formula |
|---|---|---|---|
| 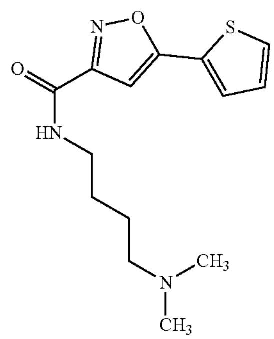 [SMILES: CN(C)CCCCNC(=O)c1cc(-c2cccs2)on1] | 1515 | 293.39 | C14H19N3O2S |
| 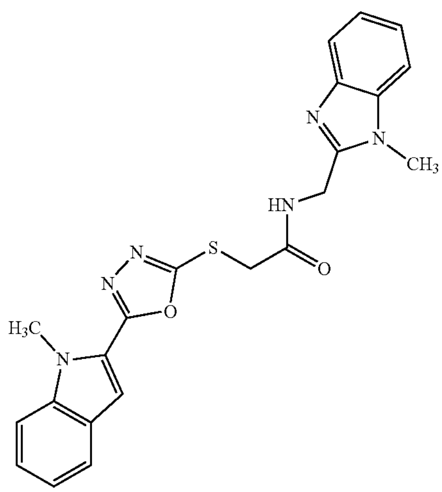 [SMILES: Cn1c(-c2nnc(SCC(=O)NCc3nc4ccccc4n3C)o2)cc2ccccc21] | 1516 | 432.50 | C22H20N6O2S |
| 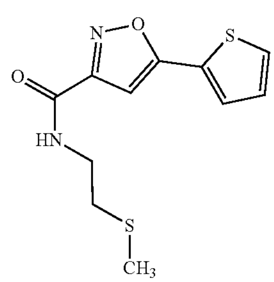 | 1517 | 268.36 | C11H12N2O2S2 |
| 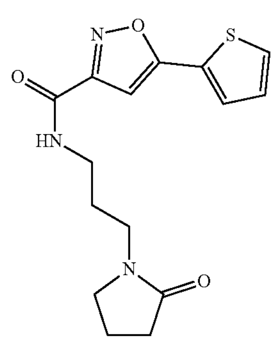 [SMILES: O=C(NCCCN1CCCC1=O)c1cc(-c2cccs2)on1] | 1518 | 319.38 | C15H17N3O3S |

TABLE 1-continued

Compounds 1001 to 1557

| Structure | Compound number | Mol Weight | Formula |
|---|---|---|---|
| 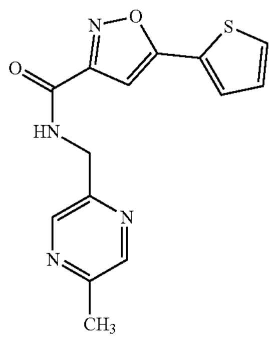 [SMILES: Cc1cnc(CNC(=O)c2cc(-c3cccs3)on2)cn1] | 1519 | 300.34 | C14H12N4O2S |
| 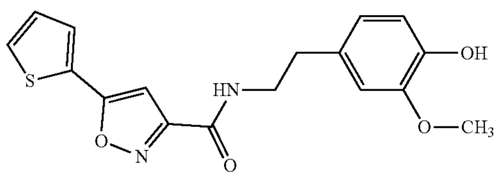 [SMILES: COc1cc(CCNC(=O)c2cc(-c3cccs3)on2)ccc1O] | 1520 | 344.39 | C17H16N2O4S |
| 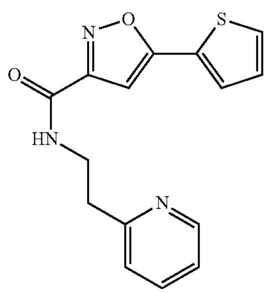 [SMILES: O=C(NCCc1ccccn1)c1cc(-c2cccs2)on1] | 1521 | 299.35 | C15H13N3O2S |
| 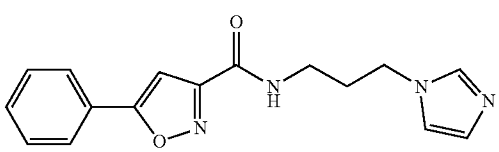 [SMILES: O=C(NCCCn1ccnc1)c1cc(-c2ccccc2)on1] | 1522 | 296.32 | C16H16N4O2 |
| 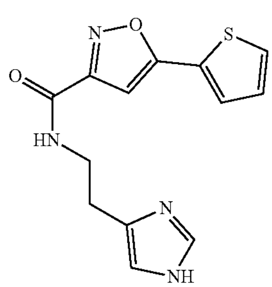 [SMILES: O=C(NCCc1c[nH]cn1)c1cc(-c2cccs2)on1] | 1523 | 288.33 | C13H12N4O2S |
| 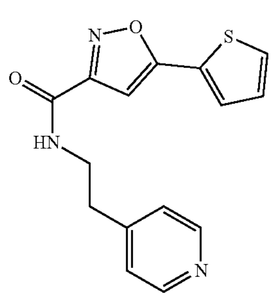 [SMILES: O=C(NCCc1ccncc1)c1cc(-c2cccs2)on1] | 1524 | 299.35 | C15H13N3O2S |

TABLE 1-continued

Compounds 1001 to 1557

| Structure | Compound number | Mol Weight | Formula |
|---|---|---|---|
| 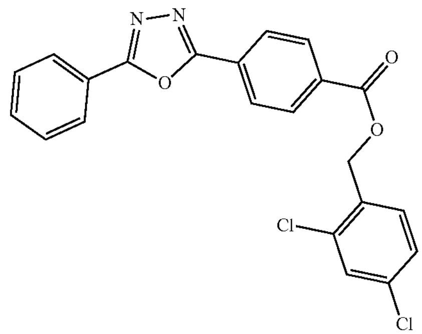 [SMILES: O=C(OCc1ccc(Cl)cc1Cl)c1ccc(-c2nnc(-c3ccccc3)o2)cc1] | 1525 | 425.26 | C22H14Cl2N2O3 |
| 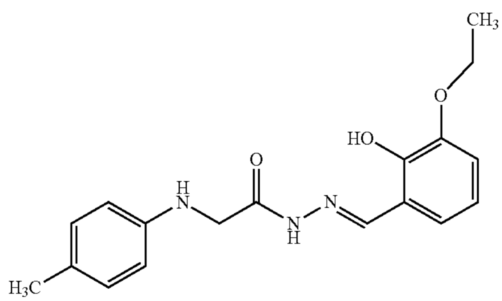 [SMILES: CCOc1cccc(/C=N/NC(=O)CNc2ccc(C)cc2)c1O] | 1526 | 327.38 | C18H21N3O3 |
| 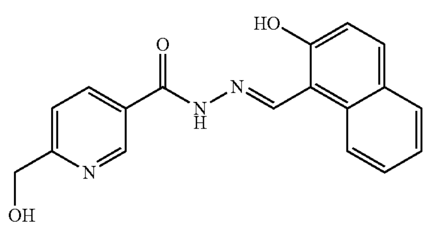 [SMILES: O=C(N/N=C/c1c(O)ccc2ccccc12)c1ccc(CO)nc1] | 1527 | 321.33 | C18H15N3O3 |
| 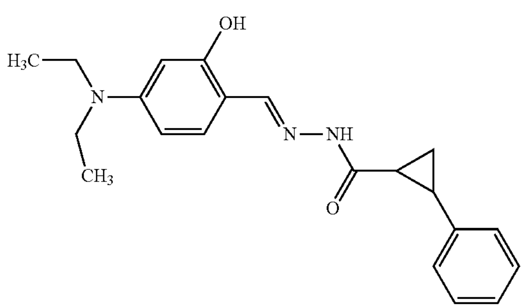 [SMILES: CCN(CC)c1ccc(/C=N/NC(=O)C2CC2c2ccccc2)c(O)c1] | 1528 | 351.44 | C21H25N3O2 |
| 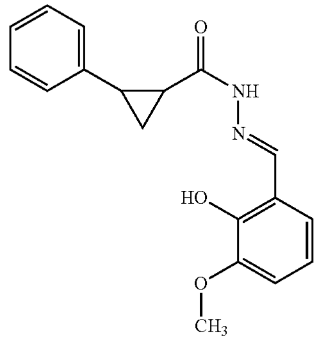 [SMILES: COc1cccc(/C=N/NC(=O)C2CC2c2ccccc2)c1O] | 1529 | 310.35 | C18H18N2O3 |

TABLE 1-continued

Compounds 1001 to 1557

| Structure | Compound number | Mol Weight | Formula |
|---|---|---|---|
| 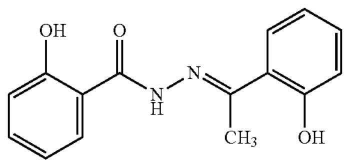 [SMILES: C/C(=N\NC(=O)c1ccccc1O)c1ccccc1O] | 1530 | 270.28 | C15H14N2O3 |
| 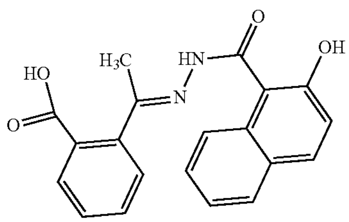 [SMILES: C/C(=N\NC(=O)c1c(O)ccc2ccccc12)c1ccccc1C(=O)O] | 1531 | 348.35 | C20H16N2O4 |
| 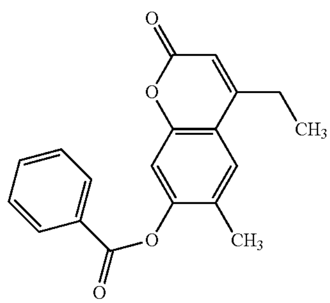 [SMILES: CCc1cc(=O)oc2cc(OC(=O)c3ccccc3)c(C)cc12] | 1532 | 328.75 | C18H13ClO4 |
| 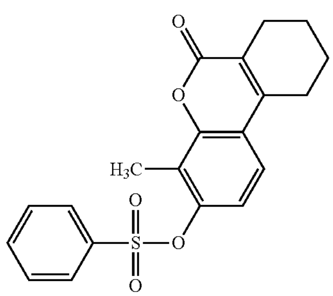 [SMILES: Cc1c(OS(=O)(=O)c2ccccc2)ccc2c3c(c(=O)oc12)CCCC3] | 1533 | 370.42 | C20H18O5S |
| 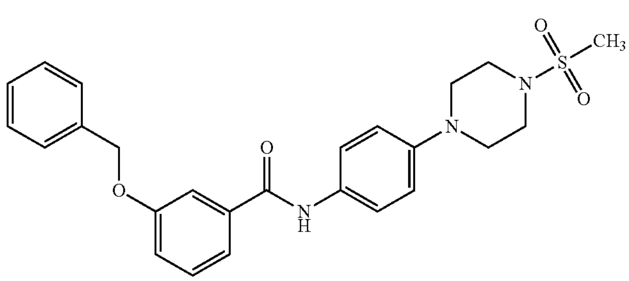 [SMILES: CS(=O)(=O)N1CCN(c2ccc(NC(=O)c3cccc(OCc4ccccc4)c3)cc2)CC1] | 1534 | 465.57 | C25H27N3O4S |
| 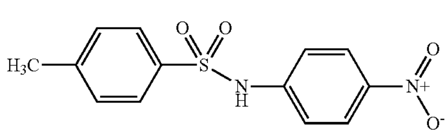 [SMILES: Cc1ccc(S(=O)(=O)Nc2ccc([N+](=O)[O-])cc2)cc1] | 1535 | 292.31 | C13H12N2O4S |

TABLE 1-continued

Compounds 1001 to 1557

| Structure | Compound number | Mol Weight | Formula |
|---|---|---|---|
| 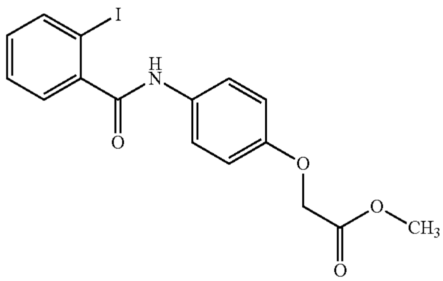 [SMILES: COC(=O)COc1ccc(NC(=O)c2ccccc2I)cc1] | 1536 | 411.19 | C16H14INO4 |
| 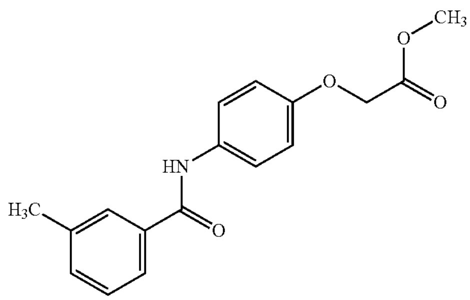 | 1537 | 299.32 | C17H17NO4 |
| 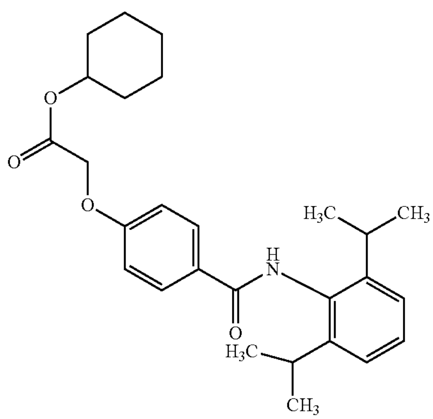 [SMILES: CC(C)c1cccc(C(C)C)c1NC(=O)c1ccc(OCC(=O)OC2CCCCC2)cc1] | 1538 | 437.57 | C27H35NO4 |
| 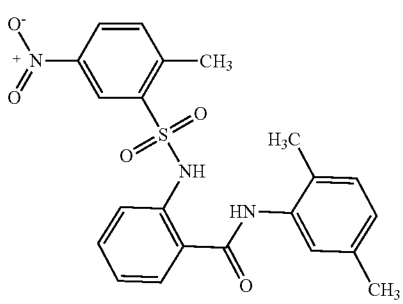 | 1539 | 439.48 | C22H21N3O5S |
| 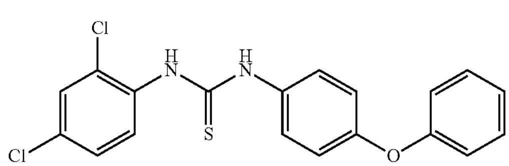 [SMILES: S=C(Nc1ccc(Oc2ccccc2)cc1)Nc1ccc(Cl)cc1Cl] | 1540 | 389.30 | C19H14Cl2N2OS |

TABLE 1-continued

Compounds 1001 to 1557

| Structure | Compound number | Mol Weight | Formula |
|---|---|---|---|
| 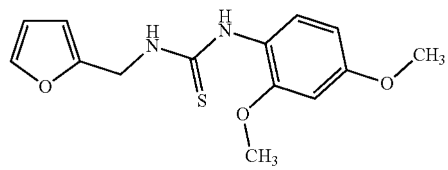 [SMILES: COc1ccc(NC(=S)NCc2ccco2)c(OC)c1] | 1541 | 292.35 | C14H16N2O3S |
| 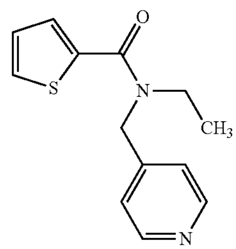 [SMILES: CCN(Cc1ccncc1)C(=O)c1cccs1] | 1542 | 246.33 | C13H14N2OS |
| 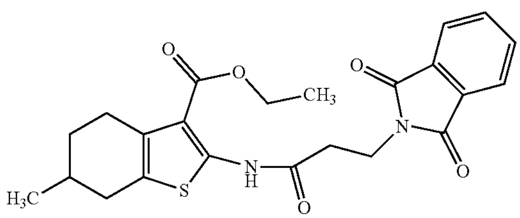 [SMILES: CCOC(=O)c1c(NC(=O)CCN2C(=O)c3ccccc3C2=O)sc2c1CCC(C)C2] | 1543 | 440.51 | C23H24N2O5S |
| 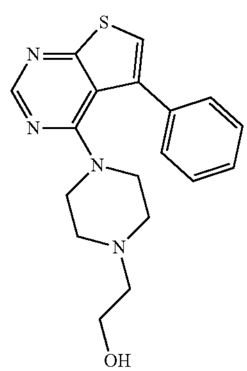 [SMILES: OCCN1CCN(c2ncnc3scc(-c4ccccc4)c23)CC1] | 1544 | 340.44 | C18H20N4OS |
| 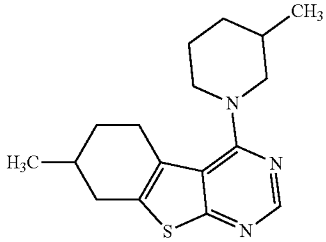 | 1545 | 301.45 | C17H23N3S |

TABLE 1-continued
Compounds 1001 to 1557
| Structure | Compound number | Mol Weight | Formula |
|---|---|---|---|
| 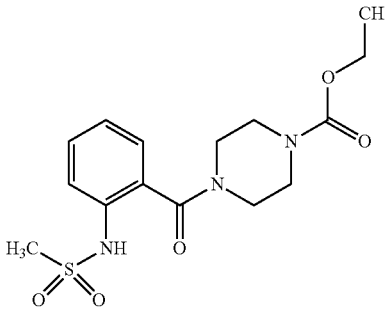 | 1546 | 369.44 | C16H23N3O5S |
| 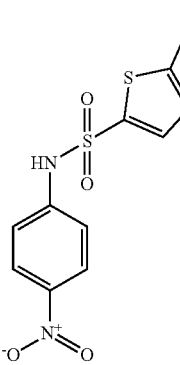 | 1547 | 363.21 | C10H7BrN2O4S2 |
| 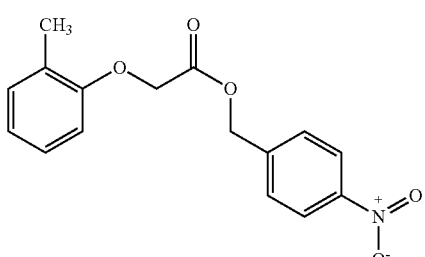 | 1548 | 301.29 | C16H15NO5 |
| 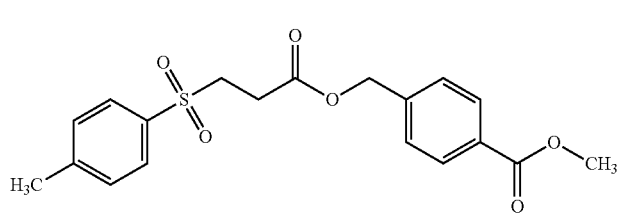 | 1549 | 376.42 | C19H20O6S |
| 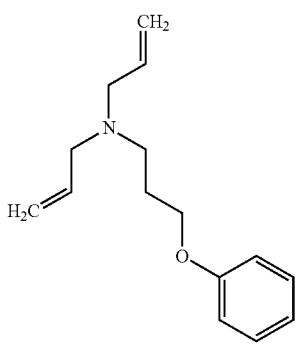 [SMILES: C=CCN(CC=C)CCCOc1ccccc1] | 1550 | 231.33 | C15H21NO |

TABLE 1-continued

Compounds 1001 to 1557

| Structure | Compound number | Mol Weight | Formula |
|---|---|---|---|
| 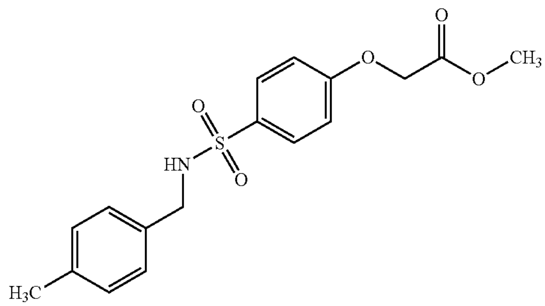 | 1551 | 349.40 | C17H19NO5S |
| 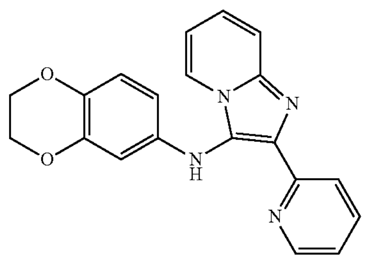 [SMILES: c1ccc(-c2nc3ccccn3c2Nc2ccc3c(c2)OCCO3)nc1] | 1552 | 344.37 | C20H16N4O2 |
| 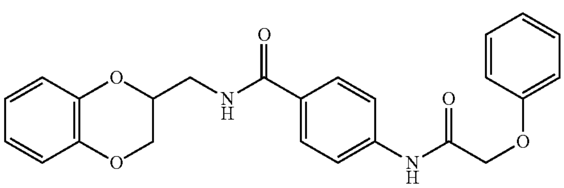 [SMILES: O=C(COc1ccccc1)Nc1ccc(C(=O)NCC2COc3ccccc3O2)cc1] | 1553 | 418.44 | C24H22N2O5 |
| 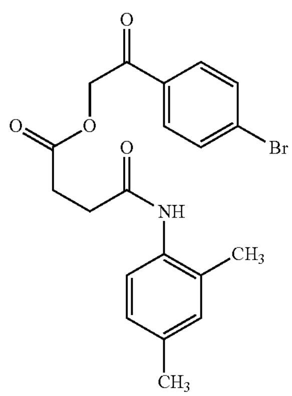 [SMILES: Cc1ccc(NC(=O)CCC(=O)OCC(=O)c2ccc(Br)cc2)c(C)c1] | 1554 | 418.28 | C20H20BrNO4 |
| 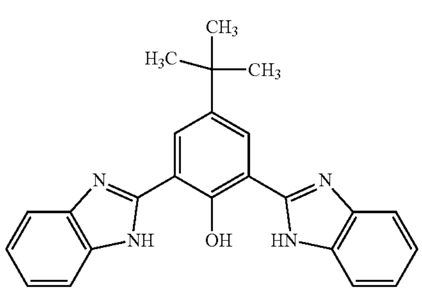 [SMILES: CC(C)(C)c1cc(-c2nc3ccccc3[nH]2)c(O)c(-c2nc3ccccc3[nH]2)c1] | 1555 | 382.46 | C24H22N4O |

TABLE 1-continued

Compounds 1001 to 1557

| Structure | Compound number | Mol Weight | Formula |
|---|---|---|---|
| 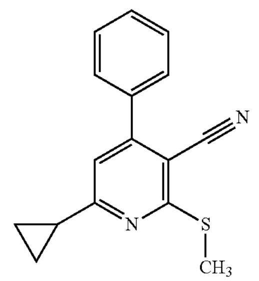 [SMILES: CSc1nc(C2CC2)cc(-c2ccccc2)c1C#N] | 1556 | 266.36 | C16H14N2S |
| 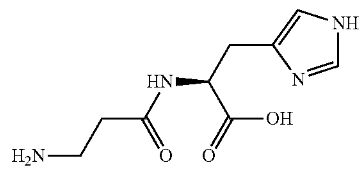 [SMILES: NCCC(=O)N[C@@H](Cc1c[nH]cn1)C(=O)O] | 1557 | 226.23 | C9H14N4O3 |

Pharmaceutical Preparations

Also provided are pharmaceutical preparations. Pharmaceutical preparations are compositions that include a TERT expression enhancing compound (for example one or more TERT expression enhancing compounds, either alone or in the presence of one or more additional active agents) present in a pharmaceutically acceptable vehicle. The term "pharmaceutically acceptable" means approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the invention is formulated for administration to a mammal. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a mammal, the compounds and compositions of the invention and pharmaceutically acceptable vehicles, excipients, or diluents may be sterile. In some instances, an aqueous medium is employed as a vehicle when the compound of the invention is administered intravenously, such as water, saline solutions, and aqueous dextrose and glycerol solutions.

Pharmaceutical compositions can take the form of capsules, tablets, pills, pellets, lozenges, powders, granules, syrups, elixirs, solutions, suspensions, emulsions, suppositories, or sustained-release formulations thereof, or any other form suitable for administration to a mammal. In some instances, the pharmaceutical compositions are formulated for administration in accordance with routine procedures as a pharmaceutical composition adapted for oral or intravenous administration to humans. Examples of suitable pharmaceutical vehicles and methods for formulation thereof are described in Remington: The Science and Practice of Pharmacy, Alfonso R. Gennaro ed., Mack Publishing Co. Easton, Pa., 19th ed., 1995, Chapters 86, 87, 88, 91, and 92, incorporated herein by reference.

The choice of excipient will be determined in part by the particular compound, as well as by the particular method used to administer the composition. Accordingly, there is a wide variety of suitable formulations of the pharmaceutical composition of the present invention.

Administration of TERT expression enhancing compounds of the invention may be systemic or local. In certain embodiments administration to a mammal will result in systemic release of a compound of the invention (for example, into the bloodstream). Methods of administration may include enteral routes, such as oral, buccal, sublingual, and rectal; topical administration, such as transdermal and intradermal; and parenteral administration. Suitable parenteral routes include injection via a hypodermic needle or catheter, for example, intravenous, intramuscular, subcutaneous, intradermal, intraperitoneal, intraarterial, intraventricular, intrathecal, and intracameral injection and non-injection routes, such as intravaginal rectal, or nasal administration. In particular embodiments, the compounds and compositions of the invention are administered orally. In particular embodiments, it may be desirable to administer one or more compounds of the invention locally to the area in need of treatment. This may be achieved, for example, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

The TERT expression enhancing compounds can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In some embodiments, formulations suitable for oral administration can include (a) liquid solutions, such as an effective amount of the compound dissolved in diluents, such as water, or saline; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can include the active ingredient in a flavor, usually sucrose and acacia or tragacanth, as well as pastilles including the active ingredient in an inert base, such as gelatin and glycerin, or sucrose and acacia, emulsions, gels, and the like containing, in addition to the active ingredient, such excipients as are described herein.

The subject formulations of the present invention can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

In some embodiments, formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration may be presented as creams, gels, pastes, or foams, containing, in addition to the active ingredient, such carriers as are appropriate. In some embodiments the topical formulation contains one or more components selected from a structuring agent, a thickener or gelling agent, and an emollient or lubricant. Frequently employed structuring agents include long chain alcohols, such as stearyl alcohol, and glyceryl ethers or esters and oligo(ethylene oxide) ethers or esters thereof. Thickeners and gelling agents include, for example, polymers of acrylic or methacrylic acid and esters thereof, polyacrylamides, and naturally occurring thickeners such as agar, carrageenan, gelatin, and guar gum. Examples of emollients include triglyceride esters, fatty acid esters and amides, waxes such as beeswax, spermaceti, or carnauba wax, phospholipids such as lecithin, and sterols and fatty acid esters thereof. The topical formulations may further include other components, e.g., astringents, fragrances, pigments, skin penetration enhancing agents, sunscreens (i.e., sunblocking agents), etc.

For use in wound healing or treatment of other acute or chronic conditions of the epidermis, a compound of the invention may be formulated for topical administration. The vehicle for topical application may be in one of various forms, e.g. a lotion, cream, gel, ointment, stick, spray, or paste. They may contain various types of carriers, including, but not limited to, solutions, aerosols, emulsions, gels, and liposomes. The carrier may be formulated, for example, as an emulsion, having an oil-in-water or water-in-oil base. Suitable hydrophobic (oily) components employed in emulsions include, for example, vegetable oils, animal fats and oils, synthetic hydrocarbons, and esters and alcohols thereof, including polyesters, as well as organopolysiloxane oils. Such emulsions also include an emulsifier and/or surfactant, e.g. a nonionic surfactant to disperse and suspend the discontinuous phase within the continuous phase.

Suppository formulations are also provided by mixing with a variety of bases such as emulsifying bases or water-soluble bases. Formulations suitable for vaginal administration may be presented as pessaries, tampons, creams, gels, pastes, foams.

A compound of the invention may also be formulated as a dietary supplement or nutraceutical, e.g., for oral administration. For a nutraceutical formulation, or an oral pharmaceutical formulation, suitable excipients include pharmaceutical grades of carriers such as mannitol, lactose, glucose, sucrose, starch, cellulose, gelatin, magnesium stearate, sodium saccharine, and/or magnesium carbonate. For use in oral liquid formulations, the composition may be prepared as a solution, suspension, emulsion, or syrup, being supplied either in solid or liquid form suitable for hydration in an aqueous carrier, such as, for example, aqueous saline, aqueous dextrose, glycerol, or ethanol, preferably water or normal saline. If desired, the composition may also contain minor amounts of non-toxic auxiliary substances such as wetting agents, emulsifying agents, or buffers. A compound of the invention may also be incorporated into existing nutraceutical formulations, such as are available conventionally, which may also include an herbal extract.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may include the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Dose levels can vary as a function of the specific compound, the nature of the delivery vehicle, and the like. Desired dosages for a given compound are readily determinable by a variety of means.

The dose administered to an animal, particularly a human, in the context of the present invention should be sufficient to effect a prophylactic or therapeutic response in the animal over a reasonable time frame, e.g., as described in greater detail below. Dosage will depend on a variety of factors including the strength of the particular compound employed, the condition of the animal, and the body weight of the animal, as well as the severity of the illness and the stage of the disease. The size of the dose will also be determined by the existence, nature, and extent of any adverse side-effects that might accompany the administration of a particular compound.

In pharmaceutical dosage forms, the TERT expression enhancing compounds may be administered in the form of a free base, their pharmaceutically acceptable salts, or they may also be used alone or in appropriate association, as well as in combination, with other pharmaceutically active compounds.

METHODS OF USE

Aspects of the invention further include methods of using TERT expression enhancing compounds, e.g., as described above, to enhance TERT expression in a target cell population. In practicing methods of the invention, the cells of interest are contacted with an effective amount of a TERT expression enhancing compound, e.g., as described above. By effective amount is meant an amount of the TERT expression enhancing compound that is sufficient to enhance TERT expression in the target cell population to a desired level. By enhancing TERT expression is meant that the expression level of the TERT coding sequence is increased by 2-fold or more, such as by 5-fold or more and including by 25-, 50-, 100-fold or more, such as by 300-fold or more, as compared to a control, i.e., expression from an expression system that is not subjected to the methods of the present invention. Alternatively, in cases where expression of the TERT gene is so low that it is undetectable, expression of the TERT gene is considered to be enhanced if expression is increased to a level that is easily detectable.

In practicing methods of the invention, the cells of interest may be contacted with the effective amount of the TERT expression enhancing compound in an in vitro or ex vivo culture system, or in vivo. For example, a TERT expression enhancing compound may be contacted to primary cells grown under standard tissue culture conditions or alternatively to cells that are part of a whole animal (e.g., administered to a subject). As such, the target cell or collection of cells may vary, where the collection of cells may be cultured cells, a whole animal or portion thereof, e.g., tissue, organ, etc. As such, the target cell(s) may be a host animal or portion thereof, or may be a therapeutic cell (or cells) which is to be introduced into a multi-cellular organism, e.g., a cell employed in gene therapy. In such methods, an effective amount of an active agent is administered to the target cell or cells, e.g., by contacting the cells with the agent, by administering the agent to the animal, etc. By effective amount is meant a dosage sufficient to modulate TERT expression in the target cell(s), as desired.

In the subject methods, the TERT expression enhancing compound may be contacted with the target cells using any convenient protocol that results in the desired enhancement of TERT expression. Thus, the TERT expression enhancing compound can be incorporated into a variety of pharmaceutical compositions for therapeutic administration, e.g., as described above. For example, the TERT expression enhancing compound can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments (e.g., skin creams), solutions, suppositories, injections, inhalants and aerosols, such as described above. As such, administration of the TERT expression enhancing compounds can be achieved in various ways, including oral, buccal, rectal, parenteral, intraperitoneal, intradermal, transdermal, intracheal, etc., administration.

The subject methods find use in the treatment of a variety of different conditions in which the enhancement of TERT expression in the host is desired. By treatment is meant that at least an amelioration of the symptoms associated with the condition afflicting the host is achieved, where amelioration is used in a broad sense to refer to at least a reduction in the magnitude of a parameter, e.g. symptom (such as inflammation), associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Also provided are methods of screening TERT expression enhancing compounds, e.g., as described above, for their ability to inhibit binding of a transcriptional repressor protein/protein complex to a TERT promoter that includes at least one of Site C binding site. Aspects of these screening methods may include determining whether a candidate TERT expression enhancing compound is capable of inhibiting binding of the transcriptional repressor protein/protein complex to the Site C binding site. Screening methods may include screening for TERT expression enhancing activity in a cell containing a TERT expression system that includes at least one Site C binding site in its promoter. Such methods may include: (i) contacting the cell with an effective amount of a candidate TERT expression enhancing compound; and (ii) determining whether the candidate compound inhibits binding of a transcriptional repressor protein/protein complex to the Site C binding site.

The determining step may be carried out by any one or more of a variety a protocols for characterizing TERT expression and/or the inhibition of binding of the transcriptional repressor protein/protein complex to the Site C binding site of the TERT expression system. For example, screening may be a reconstitution assay, cell-based assay, enzyme assay, ELISA assay or other related biological assay for assessing TERT expression and/or the inhibition of binding of the transcriptional repressor protein/protein complex to the Site C binding site of the TERT expression system, and the determining or assessment step suitable for application in such assays are well known and involve routine protocols. Screening may also include in silico approaches, in which one or more physical and/or chemical attributes of a compound of interest are expressed in a computer-readable format and evaluated by any one or more of a variety molecular modeling and/or analysis programs and algorithms suitable for this purpose.

Thus the screening methods of the invention can be carried out in vitro or in vivo. For example, when the TERT promoter is in a cell, the cell may be in vitro or in vivo, and the determining of whether the compound is capable of inhibiting binding includes: (i) contacting the cell with an effective amount of the candidate TERT expression enhancing compound; and (ii) assessing whether the candidate compound inhibits binding of the transcriptional repressor protein/protein complex to the Site C binding site. In certain embodiments, inhibition of binding of the transcriptional repressor protein/protein complex to the Site C binding site increases the proliferative capacity of the cell. In some embodiments, inhibition of binding of the transcriptional repressor protein/protein complex to the Site C binding site delays the senescence of the cell. In yet additional embodiments, the TERT expression enhancing compound inhibits binding of the transcriptional repressor protein/protein complex to the Site C binding site. As such, determining whether a candidate TERT expression enhancing compound is capable of inhibiting binding of the transcriptional repressor protein/protein complex to the Site C binding site may be carried out by any number of methods, as well as combinations thereof.

In certain embodiments, the screening protocol is or includes part of an assay selected from a potency assay, a compound or product release assay, and combinations thereof. The potency assay characterizes one or more biological activities of a compound of interest, where biological activity is characterized in general by TERT expression levels and/or inhibiting binding of the transcriptional repressor protein/protein complex to the Site C binding site of a TERT expression system. Such a potency assay may also be exploited in the development and/or validation of assays, as well as for a compound release assay. The compound release assay involves assessment of one or more of sterility, safety, purity, identity and potency of a compound of interest.

Thus, in some embodiments, when the screening method employs a TERT expression enhancing compound that inhibits binding of the transcriptional repressor protein/protein complex to the Site C binding site, the TERT expression enhancing compound may be present as a pharmaceutical composition, e.g., as described above. In certain embodiments, the screening is a release assay for the pharmaceutical composition. In some embodiments, the screening is a potency assay for the pharmaceutical composition.

Accordingly, in certain embodiments, the screening methods of the invention are carried out for compound release, such as to demonstrate and/or confirm that a compound, such as a pharmaceutical composition including the compound, is one or more of safe, pure, potent, effective and stable. As such, the screening methods of the invention may include demonstration of manufacturing and product consistency, including characterization for product release involving assessment of one or more of sterility, safety, purity, identity and potency.

Of interest are screening methods of the invention that assess potency of a TERT expression enhancing compound of interest. By "potency" is intended the specific ability or capacity of a compound to effect a given result. Tests for potency may consist of either in vitro or in vivo tests, or both, which have been specifically adapted for each product so as to indicate its potency. Thus, potency assays indicate biological activity(s) specific/relevant to the product of interest. As noted above, the potency assays may include the generation of data regarding TERT expression and/or inhibition of binding of the transcriptional repressor protein/protein complex to the Site C binding site. Such data may include, but is not limited to, qualitative and/or quantitative results for compound activity, lot release, predefined acceptance and/or rejection criteria (demonstrate lot to lot consistency), include appropriate reference material/controls, be validated for licensure, measure activity of one or more components that may be necessary for product activity, and/or indicate product stability.

Potency measurements can be direct (e.g., biological assay) or indirect (e.g., surrogate assay(s) correlated to biological activity that may include one of many assays that measure product quality). For example, potency can be measured by simple identity markers that exhibit minimal variability from assay to assay over time, including functional biomarkers that correlate with cellular differentiation and senescence. This includes measurement of one or more of cellular proliferation, cellular survival, and/or senescence, as well as biomarkers from analytic, genomic and/or proteomic-based techniques that correlate to the biological activity of interest. For instance, determining expression of TERT and/or inhibition of binding of the transcriptional repressor protein/protein complex to the Site C binding site can include various approaches for indirect potency measurements, including analytical assays such as a non-bioassay method correlated to a unique and/or specific activity of the compound (e.g., immunochemical procedures such as ELISA, ELISPOT, Q-flow cytometry, quantitative western blots; and molecular and biochemical procedures such as enzymatic assays, Q-PCR, RT-PCR, microarray/genomics, proteomics).

Thus potency measurement may be carried out in vivo in animal models or from clinical data (e.g., assessment of gene function, cell survival and so forth), and in vitro such as in cell and/or tissue culture (e.g., assessment of signaling pathways, proliferation, enzymatic activity, cell survival and so forth).

Utility

The TERT expression enhancing compounds, e.g., as described above, find use in a variety of applications. Applications of interest include, but are not limited to: therapeutic applications, research and manufacturing applications, and screening applications. Each of these different applications are now reviewed in greater details below.

Therapeutic Applications

TERT expression enhancing compounds of the invention find use in a variety of therapeutic applications. Therapeutic applications of interest include those applications in which reduced activity or expression of TERT (or shortened telomeres) is the cause or a compounding factor in disease progression. As such, the subject compounds find use in the treatment of a variety of different conditions in which the enhancement of TERT expression in the host is desired. Examples of disease conditions which may be treated with compounds of the invention include, but are not limited to: cancer, progeria, atherosclerosis, cardiovascular diseases, osteoarthritis, osteoporosis, Alzheimer's disease, macular degeneration, muscular dystrophy, dyskeratosis congenital, idiopathic pulmonary fibrosis, Cri du Chat syndrome, down's syndrome, Fanconi's Anemia, tuberous sclerosis, Werner's syndrome, conditions related to cell and tissue transplants, liver cirrhosis, rheumatoid arthritis, immune senescence, skin rejuvenation, bone marrow disorders, anemia, leukemia, lymphoma, and AIDS.

One disease condition where compounds of the invention find use is Progeria. Progeria is a collection of syndromes all of which exhibit varying forms of premature aging. In many ways progeria parallels aging itself. The two most publicized forms of progeria are Hutchinson-Gilford syndrome, which strikes in early childhood, and Werner syndrome, which is an adult-onset disease. Children with Hutchinson-Gilford syndrome live an average of just under 13 years, dying primarily from atherosclerosis, usually cardiac or cardiovascular. People with Werner syndrome are usually diagnosed in their thirties and die in their forties. The progerias have been linked directly to premature telomere loss in a variety of cell types. Dyskeratosis congenita is rare progressive congenital disorder which results in premature aging as seen in progeria. It is thought to be primarily a disorder of poor telomere maintenance. The subject methods can be used in such conditions to further delay natural telomeric shortening and/or increase telomeric length, thereby treating these currently incurable syndromes. Administration of TERT enhancing compounds of the invention to subjects suffering from this condition in accordance with methods of the invention, e.g., as described above, results in treatment of the subject for this condition.

Another disease condition in which the subject compounds find use is Fanconi anemia (FA). FA is a genetic disease that affects children and adults from all ethnic backgrounds. FA is characterized by short stature, skeletal anomalies, increased incidence of solid tumors and leukemias, bone marrow failure (aplastic anemia), and cellular sensitivity to DNA damaging agents such as mitomycin C. FA is known to affect DNA repair and FA patients are more likely to develop bone marrow failure, myelodysplastic syndromes (MDS) and acute myeloid leukemia (AML). Administration of TERT enhancing compounds of the invention to subjects suffering from this condition in accordance with methods of the invention, e.g., as described above, results in treatment of the subject for this condition.

Another disease condition in which the subject compounds find use is in immune senescence. The effectiveness of the immune system decreases with age. Part of this decline is due to fewer T-lymphocytes in the system, a result of lost replicative capacity. Many of the remaining T-lymphocytes experience loss of function as their telomeres shorten and they approach senescence. The subject methods can be employed to inhibit immune senescence due to telomere loss. Because hosts with aging immune systems are at greater risk of developing pneumonia, cellulitis, influenza, and many other infections, the subject methods reduce morbidity and mortality due to infections. Administration of TERT enhancing compounds of the invention to subjects suffering from this condition in accordance with methods of the invention, e.g., as described above, results in treatment of the subject for this condition.

Another disease condition in which the subject compounds find use is AIDS. HIV, the virus that causes AIDS, invades white blood cells, particularly CD4 lymphocyte cells, and causes them to reproduce high numbers of the HIV virus, ultimately killing cells. In response to the loss of immune cells (typically about a billion per day), the body produces more CD8 cells to be able to suppress infection. This rapid cell division accelerates telomere shortening, ultimately hastening immune senescence of the CD8 cells. Anti-retroviral therapies have successfully restored the immune systems of AIDS patients, but survival depends upon the remaining fraction of the patient's aged T-cells. Once shortened, telomere length has not been naturally restored within cells. The subject methods can be employed to restore this length and/or prevent further shortening. As such the subject methods can spare telomeres and is useful in conjunction with the anti-retroviral treatments currently available for HIV/AIDS. Administration of TERT enhancing compounds of the invention to subjects suffering from this condition in accordance with methods of the invention, e.g., as described above, results in treatment of the subject for this condition.

Yet another type of disease condition in which the invention finds use is cardiovascular disease. The compounds of the invention can be employed to extend telomere length and replicative capacity of endothelial cells lining blood vessel walls (DeBono, Heart 80:110-1, 1998). Endothelial cells form the inner lining of blood vessels and divide and replace themselves in response to stress. Stresses include high blood pressure, excess cholesterol, inflammation, and flow stresses at forks in vessels. As endothelial cells age and can no longer divide sufficiently to replace lost cells, areas under the endothelial layer become exposed. Exposure of the underlying vessel wall increases inflammation, the growth of smooth muscle cells, and the deposition of cholesterol. As a result, the vessel narrows and becomes scarred and irregular, which contributes to even more stress on the vessel (Cooper, Cooke and Dzau, J Gerontol Biol Sci 49: 191-6, 1994). Aging endothelial cells also produce altered amounts of trophic factors (hormones that affect the activity of neighboring cells). These too contribute to increased clotting, proliferation of smooth muscle cells, invasion by white blood cells, accumulation of cholesterol, and other changes, many of which lead to plaque formation and clinical cardiovascular disease (Ibid.). By extending endothelial cell telomeres, the subject methods can be employed to combat the stresses contributing to vessel disease. Many heart attacks may be prevented if endothelial cells were enabled to continue to divide normally and better maintain cardiac vessels. The occurrence of strokes caused by the aging of brain blood vessels may also be significantly reduced by employing the subject methods to help endothelial cells in the brain blood vessels to continue to divide and perform their intended function. Administration of TERT enhancing compounds of the invention to subjects suffering from this condition in accordance with methods of the invention, e.g., as described above, results in treatment of the subject for this condition.

Yet another disease condition in which the subject compounds find use is the treatment of osteoporosis. Two types of cells interplay in osteoporosis: osteoblasts make bone and osteoclasts destroy it. Normally, the two are in balance and maintain a constant turnover of highly structured bone. In youth, bones are resilient, harder to break, and heal quickly. In old age, bones are brittle, break easily, and heal slowly and often improperly. Bone loss has been postulated to occur because aged osteoblasts, having lost much of their replicative capacity, cannot continue to divide at the rate necessary to maintain balance (Hazzard et al. PRINCIPLES OF GERIATRIC MEDICINE AND GERONTOLOGY, 2d ed. McGraw-Hill, New York City, 1994). The subject compounds can be employed to lengthen telomeres of osteoblast and osteoclast stem cells, thereby encouraging bone replacement and proper remodeling and reinforcement. The resultant stronger bone improves the quality of life for the many sufferers of osteoporosis and provides savings from fewer fracture treatments. The subject compounds and methods are generally part of a comprehensive treatment regime that also includes calcium, estrogen, and exercise. Administration of TERT enhancing compounds of the invention to subjects suffering from this condition in accordance with methods of the invention, e.g., as described above, results in treatment of the subject for this condition.

Yet another disease condition in which the subject compounds find use in the treatment of bone marrow disorders. The target may be a cell or population of cells which are treated according to the subject methods and then introduced into a multi-cellular organism for therapeutic effect. For example, the subject methods may be employed in bone marrow transplants for the treatment of cancer and skin grafts for burn victims. In these cases, cells are isolated from a human donor and then cultured for transplantation back into human recipients. During the cell culturing, the cells normally age and senesce, decreasing their useful lifespans. Bone marrow cells, for instance, lose approximately 40% of their replicative capacity during culturing. This problem is aggravated when the cells are first genetically engineered (Decary, Mouly et al. Hum Gene Ther 7(11): 1347-50, 1996). In such cases, the therapeutic cells must be expanded from a single engineered cell. By the time there are sufficient cells for transplantation, the cells have undergone the equivalent of 50 years of aging (Decary, Mouly et al. Hum Gene Ther 8(12): 1429-38, 1997). Use of the subject methods spares the replicative capacity of bone marrow cells and skin cells during culturing and expansion and thus significantly improves the survival and effectiveness of bone marrow and skin cell transplants. Any transplantation technology requiring cell culturing can benefit from the subject methods, including ex vivo gene therapy applications in which cells are cultured outside of the animal and then administered to the animal, as described in U.S. Pat. Nos. 6,068,837; 6,027,488; 5,824,655; 5,821,235; 5,770,580; 5,756,283; 5,665,350; the disclosures of which are herein incorporated by reference.

The subject compounds further find use cell therapy treatment applications. Cell therapy involves the isolation of healthy human cells, the expansion of those cells ex vivo, and the reinfusion of the expanded cells into a patient. Cell therapy has application in the treatment of cancer and organ transplantation and many other disease states or conditions. For instance, bone marrow therapy takes advantage of the fact that bone marrow, the major organ of the immune system, is responsible for production of various cells in the blood from hematopoietic stem cells. Physicians treat hematological disorders such as anemia, leukemia, and lymphoma through bone marrow transplantation, in which bone marrow is removed from a donor (allogenic transplant) or a patient (autologous transplant) through general surgery, frozen and stored, and then transfused into the patient at a later date. Once transfused into the patient, the bone marrow cells gravitate to the bone marrow and engraft, eventually producing new blood cells either to increase the number of such cells in the anemic patient or to reconstitute the bone marrow destroyed as a result of chemotherapy or radiation therapy.

Yet another disease condition in which the subject compounds find use is macular degeneration. Macular degeneration results in the gradual loss of central vision, ultimately leading to blindness. Some evidence points to the senescence of retinal pigment epithelial cells as the cause of macular degeneration. Applications of interest therefore include the treatment of macular degeneration by enhancing TERT expression in these cells. Similarly, the senescence of ocular keratocytes correlates with the development of cataracts and is another target for compounds of the invention. Administration of TERT enhancing compounds of the invention to subjects suffering from this condition in accordance with methods of the invention, e.g., as described above, results in treatment of the subject for this condition.

Yet another disease condition in which the subject compounds find use is hepatic cirrhosis. Hepatic cirrhosis causes many deaths each year and has no effective treatment. Liver cells normally turn over slowly and have excellent regenerative characteristics. In cirrhosis, however, regeneration is insufficient and abnormal leading ultimately to liver failure. Relengthening telomeres in liver cells with compounds of the invention delays or prevents loss of liver function and failure. Administration of TERT enhancing compounds of the invention to subjects suffering from this condition in accordance with methods of the invention, e.g., as described above, results in treatment of the subject for this condition.

Yet another disease condition in which the subject compounds find use is Alzheimer's disease. Most current research on this degenerative disease of the brain focuses on amyloid plaques and neurofibrillary tangles. Amyloid plaques are found outside the neurons, neurofibrillary plaques are found inside the neurons. Neuron cells do not divide at any significant rate so many people discount the role of telomere shortening in Alzheimer's disease and other dementias. However, neurons depend on glial and microglial cells for support, and these cells do divide continually. Relengthening of glial telomeres addresses the underlying cause of neuronal damage, and provides a treatment of Alzheimer's disease. Administration of TERT enhancing compounds of the invention to subjects suffering from this condition in accordance with methods of the invention, e.g., as described above, results in treatment of the subject for this condition.

Additional disease conditions in which the subject methods find use are described in WO 99/35243, the disclosures of which are herein incorporated by reference.

The subject compounds also find use in skin rejuvenation. The skin is the first line of defense of the immune system and shows the most visible signs of aging (West, Arch Dermatol 130(1):87-95, 1994). As skin ages, it thins, develops wrinkles, discolors, and heals poorly. Skin cells divide quickly in response to stress and trauma; but, over time, there are fewer and fewer actively dividing skin cells. Compounding the loss of replicative capacity in aging skin is a corresponding loss of support tissues. The number of blood vessels in the skin decreases with age, reducing the nutrients that reach the skin. Also, aged immune cells less effectively fight infection. Nerve cells have fewer branches, slowing the response to pain and increasing the chance of trauma. In aged skin, there are also fewer fat cells, increasing susceptibility to cold and temperature changes. Old skin cells respond more slowly and less accurately to external signals. They produce less vitamin D, collagen, and elastin, allowing the extracellular matrix to deteriorate. As skin thins and loses pigment with age, more ultraviolet light penetrates and damages skin. To repair the increasing ultraviolet damage, skin cells need to divide to replace damaged cells, but aged skin cells have shorter telomeres and are less capable of dividing (Fossel, REVERSING HUMAN AGING. William Morrow & Company, New York City, 1996).

By practicing the subject methods, e.g., via administration of a compound of the invention topically, one can extend telomere length, and slow the downward spiral that skin experiences with age. Such a product not only helps protect a person against the impairments of aging skin; it also permits rejuvenated skin cells to restore youthful immune resistance and appearance. As such, compounds and methods of the invention may be employed to reduce the appearance of aging, e.g., by reducing the appearance of fine lines and wrinkles of the face and other locations of the body. The subject compounds and methods can be used for both medical and cosmetic skin rejuvenation applications.

The subject compounds also find use in treatment of wounds and acute or chronic skin conditions, by increasing telomerase activity, cell proliferation or migration at the treatment site, epithelialization of the surface, closure of a wound if present, or restoration of normal physiological function. The subject compounds also find use in increasing the density of epithelial cells at the treatment site as a result of the applied therapy. The subject compounds also find use increasing telomerase activity in cells surrounding a wound to enhance wound healing. The subject compounds and methods can be used for skin rejuvenation and wound treatment applications. A topical composition including a compound may be used for treatment of acute or chronic conditions of the epidermis or for wound treatment and healing, e.g., such as a lotion, cream, gel, ointment, stick, spray, or paste.

Compounds of the invention may be used for treating decubitus ulcers, sepsis, hypothermic stress, and other conditions of poor wound healing. Compounds could also be valuable in the production and use of skin grafts for severe burns and other conditions of traumatic skin loss.

The subject compounds also find use in protecting cells against the harmful effects of exposure to UV and γ-radiation. Telomere dysfunction is linked to impaired DNA repair and radiosensitvity, and as such activation of TERT may counter or protect against the harmful effects of radiation induced stress on skin cells. The subject compounds and methods can be used for skin protection applications. A topical composition including a compound may be used as a sunscreen e.g., a lotion, cream, gel, ointment, stick, spray, or past; and optionally include a UV absorbing compound, a moisturizer, and other common components of sunscreens.

The subject compounds also find use to induce the proliferation of hair follicles for growth of hair. Induction of TERT in skin epithelium causes a rapid transition from telogen, the resting phase of the hair follicle cycle, to anagen, the active phase, thereby facilitating robust hair growth. The subject compounds and methods can be used for hair rejuvenation applications. A topical or a nutraceutical composition including a compound may enhance hair growth, density or color, e.g., a shampoo, cream, hair gel, or hair spray.

In addition to the above-described uses, the subject compounds can also be used to extend the lifespan of a mammal. By extend the lifespan is meant to increase the time during which the animal is alive, where the increase is generally 1% or more, such as 5% or more and including 10% or more as compared to a control.

As indicated above, instead of a multicellular animal, the target may be a cell or population of cells which are treated according to the subject methods and then introduced into a multicellular organism for therapeutic effect. For example, the subject compounds may be employed in bone marrow transplants for the treatment of cancer and skin grafts for burn victims. In these cases, cells are isolated from a human donor and then cultured for transplantation back into human recipients. During the cell culturing, the cells normally age and senesce, decreasing their useful lifespans. Bone marrow cells, for instance, lose approximately 40% of their replicative capacity during culturing. This problem is aggravated when the cells are first genetically engineered (Decary, Mouly et al. Hum Gene Ther 7(11): 1347-50, 1996). In such cases, the therapeutic cells must be expanded from a single engineered cell. By the time there are sufficient cells for transplantation, the cells have undergone the equivalent of 50 years of aging (Decary, Mouly et al. Hum Gene Ther 8(12): 1429-38, 1997). Use of the subject compounds spares the replicative capacity of bone marrow cells and skin cells during culturing and expansion and thus significantly improves the survival and effectiveness of bone marrow and skin cell transplants. Any transplantation technology requiring cell culturing can benefit from the subject methods, including ex vivo gene therapy applications in which cells are cultured outside of the animal and then administered to the animal, as described in U.S. Pat. Nos. 6,068,837; 6,027, 488; 5,824,655; 5,821,235; 5,770,580; 5,756,283; 5,665, 350; the disclosures of which are herein incorporated by reference.

The subject compounds also find use in countering the harmful effects of oxidative stress induced in the cells of newborn infants during the first 4 months of age. Newborns, and especially those delivered preterm, are more prone to oxidative stress than individuals later in life. Factors such as oxidative stress are modulators of telomere length. Telomere length has also been implicated as a modulating factor of genetic damage in newborns. Telomere dysfunction is linked to impaired DNA repair. As such, the subject compounds and methods can be used to protect against the harmful effects of oxidative stress. A composition (e.g. a topical or neutraceutical composition) including a compound may be used for treatment of oxidative stress injuries, e.g. a nutritional supplement for use in baby food or vitamin products, or a lotion, cream, shampoo, etc.

The subject compounds also find use in countering the effects of abnormal or diminished levels of TERT activity in spermatogonia cells, their progenitors or descendants. The subject compounds and methods can be used in fertility applications, for example, by reversing abnormal or diminished levels of TERT activity in spermatogonia cells. A composition including a compound may be used for the treatment of infertility or disorders of reproduction.

Research and Manufacturing Applications

TERT expression enhancing compounds of the invention may find use in a variety addition applications, include research and manufacturing applications. For example, TERT expression enhancing compounds find use in applications for increasing the proliferative capacity of cells grown in vitro (e.g., immortalizing cells). As such, compounds of the invention find use in expanding cells for a variety uses, including expanding cells for use in diagnostic assays, expanding cells for use in preparative protocols (e.g., expanding antibody-producing cells or cells expressing a protein/factor of interest), expanding cells to facilitate studying the cells themselves (e.g., expanding rare stem cells harvested from a subject). The primary method of producing monoclonal antibodies requires the creation of immortalized antibody producing cells, called hybridomas, made by fusing B-lymphocytes (which secrete antibodies) with immortal (cancerous) myeloma cells to extend their life span. The fusion process can take from 8 to 12 months and represents approximately 25% of the cost of production. A compound of the invention could be used to extend the life span of B-lymphocytes directly, reducing the production startup time to, for example, 2 to 3 months.

In addition, the compounds of the invention can be used to expand cells that will themselves be administered to a subject for experimental or therapeutic purposes, for example in expanding cells for genetic alteration (e.g., gene therapeutic purposes). As such, the compounds and methods of the invention are useful in any application in which an increase in cellular proliferation or a reduction in cellular senescence is advantageous.

The subject compounds also find use in countering the effects of premature aging of cloned animals. A cloned animal inherits its age from its cell donor, thus being born old and die early. The length of the telomeres is related to the ageing problems of clones. Early embryonic telomere elongation is telomerase dependent, such that activation may lead to a rejuvenation of telomeres in cloned bovine embryos. The subject compounds also find use in cloning applications and may be used in a composition for use in agricultural cloning, such as in cloning of a cow or a sheep.

Screening Applications

The screening methods, e.g., as described above, find use in a variety of applications, including identifying and/or testing candidate TERT expression enhancing compounds use in a wide range of research and therapeutic applications, such as pharmaceutical development, manufacturing, and quality assurance/control, as well as immortalization of cell lines and treating conditions in a subject characterized by cellular senescence. Applications of interest include use of the screening methods of the invention for performing research, as well as for pharmaceutical compliance related to GLP ("Good Laboratory Practice") and GMP ("Good Manufacturing Practice" also referred to as "cGMP" or "current Good Manufacturing Practice")) and laboratory services. Thus the screening methods of the invention find broad use in research and lead development, sample analysis, as well as assay development, validation, drug regulatory submissions and compliance for new drug substances and drug products, drug product release and compound auditing in general. By "compound auditing" is meant quality assurance and/or quality control of a compound.

Compound auditing in accordance with the subject screening methods may be exploited in multiple settings. One example is in assay development or simply to transfer an assay from one location to another, whether or not it requires GLP and/or GMP compliance. This aspect may include the use of the subject screening methods to ensure that a compound of interest performs consistently and provides continuity in an assay over time. Statistical data analysis and related relevant data analysis tools can be exploited to best match the compound and use of interest. For instance, the screening method can be performed under "research level" protocols to identify those parameters such as the limit of detection (LOD), the limit of quantitation (LOQ) and the linear range necessary for assay validation and/or transfer. As such, the screening methods find use in compiling and executing SOPs ("Standard Operating Procedure" or "Standard Operating Protocol") which can be used for compound auditing.

Additional uses of the screening methods of the invention include the generation and/or execution one or more GLP or GMP protocols that assess one or more of linearity, accuracy, precision, specificity, robustness, ruggedness and system suitability for one or more compounds of interest for a given end use. Generation of such protocols may include assays for identifying as well as testing of a compound of interest, including QA and/or QC, as well as generating controls that may be aliquoted under GLP or GMP compliance which may be used over several years depending upon the stability of the compound of interest.

The subject screening methods may be used in qualitative and/or quantitative potency assays for routine lot release, lot comparisons, sampling, and stability assessment of a compound of interest.

The screening methods may also be used in a multiple assay approach (i.e., assay matrix), such as when it is desirable to develop or use more than a single assay (e.g., an assay matrix often finds use when there is limited knowledge of product and mechanism of action, the product has multiple components with multiple biological activities, time is constrained due to limited product stability, biological assay is not quantitative and the like). Thus the subject screening methods may find use in a combination of assays where the combined results constitute an acceptable product release and/or potency assay (e.g., a quantitative physical assay along with a qualitative bioassay).

Combination Therapy

Aspects of the invention further include combination therapies. By combination therapy is meant that a compound of the invention can be used in a combination with another therapeutic agent to treat a single disease or condition. In particular embodiments, a compound of the invention is administered concurrently with the administration of another therapeutic agent, which can be administered as a component of a composition including the compound of the invention or as a component of a different composition. In particular embodiments, a composition including a compound of the invention is administered prior or subsequent to administration of another therapeutic agent.

The compounds of the present invention can be administered in combination with other therapeutic agents in a variety of therapeutic applications. Therapeutic applications of interest for combination therapy include those applications in which reduced activity or expression of TERT (or shortened telomeres) is the cause or a compounding factor in disease progression. As such, the subject compounds find use in combination therapies in which the enhancement of TERT expression in the host is desired. Examples of disease conditions which may be treated by a combination therapy including a compound of the invention include, but are not limited to: cancer, progeria, atherosclerosis, cardiovascular diseases, osteoarthritis, osteoporosis, Alzheimer's disease, macular degeneration, muscular dystrophy, dyskeratosis congenital, idiopathic pulmonary fibrosis, Cri du Chat syndrome, down's syndrome, Fanconi's Anemia, tuberous sclerosis, Werner's syndrome, conditions related to cell and tissue transplants, liver cirrhosis, rheumatoid arthritis, immune senescence, skin rejuvenation, bone marrow disorders, anemia, leukemia, lymphoma, and AIDS. For example, combinations for anti-aging and AIDS therapy are discussed below.

Combinations for Anti-Aging Therapy

The compounds of the present invention can be administered in combination with other therapeutic agents as an anti-aging therapy.

Over time, cell membranes may be damaged by reactive oxygen species and other free radicals, resulting, for example, in cross-linkage or cleavage of proteins and lipoproteins, and oxidation of membrane lipids and lipoproteins. Damage to the cell membrane can result in myriad changes including loss of cell permeability, increased intercellular ionic concentration, and decreased cellular capacity to excrete or detoxify waste products. As the intercellular ionic concentration of potassium increases, colloid density increases and m-RNA and protein synthesis are hampered, resulting in decreased cellular repair. Some cells become so dehydrated they cannot function at all. In aging, the regularity of tissue structure is lost, and individual cells enlarge, but the total number of cells decreases approximately 30%.

To treat some effects of aging, for example as described above, compounds of the invention can be used in combination with an antioxidant. Examples of antioxidants include vitamin E, vitamin C, superoxide dismutase, glutathione, resveratrol, lipoic acid, carnosine, sulforaphane, and pioglitazone.

Other compounds that have anti-aging effects and can be used in combination with compounds of the invention include (-)deprenyl (selegeline), 6-furfurylamino purine (kinetin), and 6-benzylamino purine (BAP). (-)Deprenyl (selegeline) can increase the formation of natural antioxidant enzymes SuperOxide Dismutase (SOD) and catalase. Cytokinins, such as 6-furfurylamino purine (kinetin) and 6-benzylamino purine (BAP), are known to be growth stimulators. Kinetin promotes cell division.

In some instances, compounds of the invention are administered in conjunction with resveratrol, or an analog thereof. 3,4',5-trihydroxystilbene commonly known as resveratrol is found in grapes. Resveratrol is found to exhibit antioxidative and antimutagenic properties. Resveratrol is also an inducer of phase II drug metabolizing enzymes. In humans, resveratrol consumption is found to inhibit peroxidation of plasma low density lipoprotein and this effect has been proposed to protect against the development of atherosclerosis. The above referenced bioprotective properties of resveratrol are attributed to the presence of phenolic groups in its structure. Also of interest are resveratrol analogs, such as those describe din U.S. Pat. No. 7,026,518; the disclosure of which is herein incorporated by reference.

Combinations for AIDS Therapy

The compounds of the present invention can be administered jointly with other therapeutics in order to enhance antiviral efficacy. The present compounds can be administered with antiviral agents, including (but not limited to) agents acting on any suitable target in the virus replication process, such as reverse transcriptase inhibitors, viral protease inhibitors and glycosylation inhibitors, etc; antiviral agents acting on different targets all through the virus spreading process; antiviral agents acting on different sites of the same molecule; and antiviral agents capable of preventing or reducing the development of the drug resistance.

In certain embodiments, compounds of the invention can be administered jointly with retrovirus inhibitors, including (but not limited to) nucleoside analogs. The nucleoside derivatives, in the absence of any 3'-substituent that can be bound to other nucleosides, can suppress the synthesis of cDNA catalyzed by reverse transcriptase and thereby terminate the viral DNA replication. This is why they become anti-HIV therapeutic agents. For example, AZT and ddT, both of them can suppress HIV-1 replication in vivo and in vitro, had been approved as remedies for HIV infection and AIDS.

The present compounds can be administered jointly with nucleoside derivatives and non-nucleoside derivatives. The nucleoside derivatives include (but not limited to): 2',3'-dideoxyadenosine (ddA); 2',3'-diseoxyguanosine (ddG); 2',3'-dideoxyinosine (ddI); 2',3'-dideoxycytidine (ddC); 2',3'-dideoxythymidine (ddT); 2',3'-dideoxy-dideoxythymidine (d4T) and 3'-azide2',3'-dideoxycytidine (AZT). According to an embodiment of the present invention, the nucleoside derivatives are halonucleoside, preferably 2' 3'-dideoxy-2'-fluoronuceotides, including (but not limited to): 2',3'-dideoxy-2'-fluoroadenosine; 2',3'-dideoxy-2'-fluoroinosine; 2',3'-dideoxy-2'-fluorothymidine; 2',3'-dideoxy-2'-fluorocytidine; and 2',3'-dideoxy-2',3'-didehydro-2'-fluoronuceotides, including (but not limited to): 2',3'-dideoxy-2', 3'-didehydro-2'fluorothymidine (Fd4T).

The present compounds can also be administered jointly with inhibitors of uridine phosphorylating enzyme, including (but not limited to) acyclouridine compounds, including benzylacyclouridine (BAU); benzoxybenzylacyclouridine (BBAU); amethobenzylacyclouridine (AMBAU); amethobenzoxybenzylacyclouridine (AMB-BAU); hydroxymethylbenzylacyclouridine (HMBAU); and hydroxymethylbenzoxybenzylacyclouridine (HMBBAU).

The present compounds can also be administered jointly with cytokines or cytokine inhibitors, including (but not limited to): rIFNα, rIFNβ, and rIFNγ, TNFα inhibitors, MNX-160, human r interferon αA, human r interferonβ, and human r interferonγ.

Protease inhibitors prevent the virus from maturing mainly during the viral assembly period or after the assembly period (namely during the viral budding). Protease inhibitors show an antiviral activity both in vivo and in vitro. After being administered protease inhibitors, the AIDS patient HIV-level exhibits an exponential decline and their CD4 lymphocytes rise in number (Deeks, et al., 1997, JAMA 277:145-53). Aspects of the present invention provide for administration of the present compounds together with a protease inhibitor, the latter including (but not limited to): Indinavir, Invirase, Norvir, Viracept, and Agenerase.

The present compounds can also be used jointly with anti-HIV drugs that disturb 5'-mRNA processing, such as virazole. The acting mechanism of virazole is unknown yet and presumed to be competing with guanine in forming the mRNA capping structure, and/or disturbing the methylation of these molecules.

In addition, the present compounds can be administered jointly with amphotericin B. Amphotericin B is a polyene antifungal antibiotic that can bind irreversibly with sterol. Amphotericin B and its formate have an inhibiting effect against many lipid envelop viruses including HIV.

The present compounds can also be administered jointly with the glycoprotein processing inhibitor castanospermine, which is a vegetable alkaloid capable of inhibiting glycol protein processing. HIV envelope contains two large glycoproteins gp120 and gp41. The glycosylation of proteins plays an important role in the interactions between gp120 and CD4. The progeny virus synthesized in the presence of castanospermine has a weaker infectivity than the parental virus.

Drug combinations of interest include the present compounds, and at least one of other antiviral agents, such as reverse transcriptase inhibitors, protease inhibitors, mRNA processing inhibitors, protein glycosylation inhibitors, virus adsorbent, CD4 receptor inhibitors, chemokine co-receptor inhibitors, neutralizing antibody, integrase inhibitors, and other fusion inhibitors, including (but not limited to) nucleoside analogs or chain terminators; chemokine co-receptor inhibitors AMD-3100 (Tremblay, C. L. et al., 2000, J. AIDS 1:25(2)99-10).

According to an embodiment of the present invention, therapeutic agents that can be used jointly with the present compounds include (but not limited to): 2-deoxy-D-glucose (2dG1c), deoxynojirimycinacycloguanosine, virazole, rifadin, adamantanamine, rifabutine, ganciclover (DHPG), famciclove, buciclover (DHBG), fluoroiodoaracytosine, iodoxuridine, trifluorothymidine, ara-A, ara-AMP, bromovinyldeoxyuridine, BV-arau, 1-b-D-glycoarabinofuranoside-E-5-[2-bromovinyl]uracil, adamantethylamine, hydroxyurea, phenylacetic heptanedione, diarylamidine, (S)-(p-nitrobenzyl)-6-thioinosine and phosphonoformate.

Systems and Kits

Also provided are systems and kits that include compounds of the invention. Systems of the invention are collections of active agents brought together, e.g., by a health care practitioner, for administration to a subject, such as a patient. Such systems may include TERT expression enhancing compound of the invention and one or more additional active agents. Kits that include TERT expression enhancing compounds of the invention are also provided. Kits of the invention may include one or more dosages of a TERT expression enhancing compound, and optionally one or more dosages of one or more additional active agents. Conveniently, the formulations may be provided in a unit dosage format. In such kits, in addition to the containers containing the formulation(s), e.g. unit doses, is an informational package insert describing the use of the subject formulations in the methods of the invention, e.g., instructions for using the subject unit doses to treat cellular proliferative disease conditions.

These instructions may be present in the subject systems and kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are offered by way of illustration and not by way of limitation.

EXPERIMENTAL

Telomerase is a ribonucleoprotein complex composed of the catalytic protein subunit (human telomerase reverse transcriptase or hTERT) and the RNA template. hTERT expression level can be measured by PCR.

Quantitative Reverse Transcription PCR

Quantitative Reverse Transcription PCR can be run according to procedures outlined in Yajima et al. (Yajima, T. et al. Quantitative Reverse Transcription-PCR Assay of the RNA Component of Human Telomerase Using the TaqMan Fluorogenic Detection System Clinical Chemistry, 44:12, 2441-2445, 1998).

Real-Time PCR.

The principle of real-time PCR was first described by Heid et al. (Heid C. A., Stevens J., Livak K. J., Williams P. M. Real time quantitative PCR. Genome Res., 6:986-994, 1996). Briefly, amplification of the target sequence is monitored per PCR cycle by detecting the fluorescence signal emitted by an internal probe that is degraded by the 5' nuclease activity of the Taq polymerase. The emission signal accumulates in each sample, and the $C_t$ required to reach a given fluorescence threshold is determined ($C_t$ stands for Cycle Threshold and is a measure of the number of PCR cycles that are required to amplify a target—thus, a lower $C_t$ score means that there is more abundant hTERT mRNA). Thus, the $C_t$ value of a sample inversely correlates to the quantity of the starting cDNA which correlates to the number of mRNA transcripts. Using the cDNA of known quantity, a standard curve can be generated and used to determine the starting amount of mRNA transcripts based on the $C_1$ value of each sample.

Quantitative real-time PCR can be done on cDNA from test compound-treated and nontreated cells by use of a ABI Prism 7900 Sequence Detection System (PE Applied Biosystems, Foster City, CA) following the Assays-on-Demand protocol (PE Applied Biosystems, Foster City, CA). Quantitative data can be analyzed using the Sequence Detection System software version 2.1 (PE Applied Biosystems).

Cell Viability Assay

Cell viability is determined using a homogeneous method, such as CellTiter-Glo® Luminescent Cell Viability Assay (Promega Corporation, Madison, WI.) to determine the number of viable cells in culture These assays are based on quantitation of the ATP present, which signals the presence of metabolically active cells. Luminescent values of compound treated cells are compared to that of cells treated with vehicle alone to determine the average cell viability as a percent of control.

The following compounds were tested in assays designed to identify compounds that enhance human TERT expression. The compounds turned on human TERT expression in these assays.

TABLE 2

Results of assays

| Compound number | Average Number of hTERT Transcripts | Number of hTERT Transcripts Standard Deviation | Average Cell Viability after 24 Hours (% DMSO) | Cell Viability after 24 Hours Standard Deviation |
| --- | --- | --- | --- | --- |
| 1001 | 12.47 | 11.42 | 44.55 | 1.71 |
| 1002 | 14.79 | 12.60 | 57.70 | 3.79 |
| 1003 | 10.05 | 8.45 | 73.53 | 1.15 |
| 1004 | 12.11 | 11.82 | 54.71 | 4.60 |
| 1005 | 55.17 | 37.10 | 64.80 | 2.81 |
| 1006 | 25.82 | 25.11 | 69.78 | 2.50 |
| 1007 | 18.02 | 7.88 | 68.00 | 1.53 |
| 1008 | 43.18 | 16.58 | 67.58 | 4.73 |
| 1009 | 50.29 | 26.34 | 68.59 | 2.23 |
| 1010 | 35.70 | 14.30 | 86.63 | 9.62 |
| 1011 | 14.20 | 12.27 | 64.50 | 5.64 |
| 1012 | 12.01 | 10.39 | 60.73 | 7.00 |
| 1013 | 40.42 | 29.90 | 74.96 | 7.68 |
| 1014 | 11.55 | 15.60 | 28.33 | 6.32 |
| 1015 | 63.93 | 21.41 | 74.68 | 4.45 |
| 1016 | 10.90 | 10.21 | 42.84 | 6.09 |
| 1017 | 96.98 | 36.78 | 75.48 | 7.40 |
| 1018 | 105.41 | 58.80 | 56.90 | 5.97 |
| 1019 | 271.75 | 69.45 | 35.74 | 1.84 |
| 1020 | 45.03 | 30.62 | 25.10 | 17.34 |
| 1021 | 60.68 | 59.27 | Not Tested | Not Tested |
| 1022 | 60.01 | 18.19 | 63.83 | 2.04 |
| 1023 | 160.65 | 46.80 | 75.33 | 5.22 |
| 1024 | 165.68 | 142.55 | 95.15 | 2.55 |
| 1025 | 113.98 | 31.60 | 93.50 | 4.31 |
| 1026 | 11.55 | 3.83 | 52.03 | 4.58 |
| 1027 | 19.72 | 6.85 | 62.71 | 2.92 |
| 1028 | 65.66 | 28.84 | 80.69 | 3.03 |
| 1029 | 5.30 | 6.13 | 32.00 | 6.32 |
| 1030 | 26.47 | 21.32 | 73.78 | 5.85 |
| 1031 | 44.80 | 37.60 | 76.88 | 10.27 |
| 1032 | 39.96 | 16.25 | 75.67 | 6.49 |
| 1033 | 28.91 | 16.07 | 84.43 | 7.43 |
| 1034 | 44.71 | 24.55 | 83.39 | 9.68 |
| 1035 | 66.72 | 49.05 | 62.45 | 2.36 |
| 1036 | 65.00 | 27.21 | 73.28 | 8.26 |
| 1037 | 55.41 | 20.76 | 67.96 | 3.61 |
| 1038 | 28.95 | 11.94 | 80.33 | 7.47 |
| 1039 | 30.90 | 7.64 | 72.76 | 9.79 |
| 1040 | 25.16 | 17.82 | 61.11 | 7.11 |
| 1041 | 20.78 | 10.69 | 72.82 | 14.19 |
| 1042 | 10.53 | 12.70 | 55.51 | 5.51 |
| 1043 | 15.13 | 11.14 | 47.47 | 11.07 |
| 1044 | 92.93 | 47.32 | 85.35 | 6.65 |
| 1045 | 13.86 | 8.06 | 60.30 | 4.10 |
| 1046 | 158.46 | 22.17 | 78.00 | 4.74 |
| 1047 | 43.89 | 13.20 | 69.78 | 4.31 |
| 1048 | 58.04 | 31.74 | 70.37 | 3.55 |
| 1049 | 49.12 | 23.61 | 65.63 | 4.08 |
| 1050 | 47.68 | 23.93 | 62.77 | 2.65 |
| 1051 | 45.24 | 36.17 | 65.27 | 2.75 |
| 1052 | 12.07 | 11.00 | 60.80 | 2.04 |
| 1053 | 47.54 | 25.67 | 59.77 | 3.58 |
| 1054 | 8.59 | 2.47 | 46.45 | 4.58 |
| 1055 | 28.89 | 24.73 | 57.43 | 3.41 |
| 1056 | 62.15 | 24.86 | 65.75 | 5.76 |
| 1057 | 12.42 | 11.58 | 50.02 | 5.23 |
| 1058 | 47.99 | 19.95 | 69.11 | 4.26 |
| 1059 | 26.79 | 21.38 | 53.52 | 1.33 |
| 1060 | 65.91 | 37.44 | 63.44 | 2.44 |
| 1061 | 128.91 | 76.19 | 62.27 | 6.57 |
| 1062 | 47.98 | 14.52 | 60.77 | 10.00 |
| 1063 | 205.20 | 73.14 | 85.12 | 9.17 |
| 1064 | 52.74 | 27.36 | 67.37 | 7.01 |
| 1065 | 24.47 | 21.02 | 61.72 | 5.27 |
| 1066 | 43.68 | 26.51 | 72.46 | 4.79 |

TABLE 2-continued

Results of assays

| Compound number | Average Number of hTERT Transcripts | Number of hTERT Transcripts Standard Deviation | Average Cell Viability after 24 Hours (% DMSO) | Cell Viability after 24 Hours Standard Deviation |
|---|---|---|---|---|
| 1067 | 16.20 | 11.84 | 49.62 | 6.88 |
| 1068 | 21.41 | 20.36 | 61.20 | 2.24 |
| 1069 | 101.80 | 27.98 | 80.34 | 8.85 |
| 1070 | 68.65 | 52.81 | 69.71 | 3.89 |
| 1071 | 70.74 | 43.22 | 81.62 | 6.95 |
| 1072 | 93.44 | 12.76 | 78.35 | 6.09 |
| 1073 | 103.42 | 26.48 | 80.10 | 3.19 |
| 1074 | 49.89 | 29.98 | 75.55 | 13.70 |
| 1075 | 83.26 | 34.81 | 82.63 | 4.53 |
| 1076 | 61.45 | 26.99 | 62.85 | 5.85 |
| 1077 | 15.88 | 12.10 | 38.99 | 11.80 |
| 1078 | 36.96 | 7.43 | 67.66 | 6.48 |
| 1079 | 98.36 | 38.69 | 71.22 | 3.48 |
| 1080 | 26.36 | 18.61 | 72.44 | 9.94 |
| 1081 | 18.87 | 11.18 | 70.69 | 5.65 |
| 1082 | 7.54 | 5.75 | 56.92 | 13.57 |
| 1083 | 18.44 | 23.08 | 74.39 | 11.63 |
| 1084 | 11.54 | 11.11 | 65.08 | 10.69 |
| 1085 | 59.41 | 41.30 | 61.83 | 2.17 |
| 1086 | 48.77 | 38.78 | 56.53 | 2.95 |
| 1087 | 240.41 | 68.79 | 72.33 | 2.58 |
| 1088 | 191.81 | 64.36 | 55.87 | 4.02 |
| 1089 | 38.29 | 10.92 | 89.98 | 4.09 |
| 1090 | 29.08 | 31.41 | 27.89 | 2.35 |
| 1091 | 91.89 | 13.87 | 94.30 | 16.44 |
| 1092 | 96.33 | 50.83 | 66.43 | 6.22 |
| 1093 | 160.48 | 43.93 | 66.50 | 3.87 |
| 1094 | 32.08 | 37.61 | 56.64 | 3.37 |
| 1095 | 3.46 | 4.10 | 56.93 | 3.68 |
| 1096 | 48.25 | 56.62 | 67.13 | 5.68 |
| 1097 | 77.36 | 82.40 | 78.08 | 4.20 |
| 1098 | 102.70 | 58.19 | 68.58 | 2.48 |
| 1099 | 67.59 | 51.68 | 64.22 | 1.72 |
| 1100 | 9.12 | 10.95 | 56.10 | 2.68 |
| 1101 | 24.80 | 29.27 | 76.69 | 2.94 |
| 1102 | 351.44 | 311.36 | 68.56 | 4.06 |
| 1103 | 70.50 | 61.20 | 58.35 | 4.80 |
| 1104 | 19.27 | 24.19 | 71.14 | 0.98 |
| 1105 | 51.56 | 40.50 | 58.63 | 9.94 |
| 1106 | 68.17 | 22.45 | 79.49 | 4.11 |
| 1107 | 67.06 | 13.21 | 98.68 | 5.33 |
| 1108 | 79.20 | 52.09 | 94.50 | 3.64 |
| 1109 | 35.79 | 27.88 | 67.53 | 3.32 |
| 1110 | 86.68 | 25.60 | 100.67 | 10.23 |
| 1111 | 18.99 | 15.09 | 47.04 | 4.83 |
| 1112 | 112.20 | 84.13 | 77.30 | 3.45 |
| 1113 | 66.98 | 63.35 | 89.80 | 3.66 |
| 1114 | 148.58 | 77.87 | 89.40 | 2.35 |
| 1115 | 59.18 | 40.24 | 81.68 | 11.09 |
| 1116 | 102.70 | 87.57 | 75.26 | 4.07 |
| 1117 | 57.88 | 26.57 | 84.16 | 18.09 |
| 1118 | 54.45 | 41.50 | 73.41 | 6.61 |
| 1119 | 125.15 | 45.24 | 62.38 | 2.35 |
| 1120 | 118.82 | 40.40 | 52.50 | 0.58 |
| 1121 | 119.73 | 50.10 | 52.77 | 5.14 |
| 1122 | 13.40 | 11.37 | 66.57 | 4.30 |
| 1123 | 58.23 | 30.79 | 79.37 | 4.89 |
| 1124 | 34.96 | 20.20 | 87.04 | 3.05 |
| 1125 | 82.95 | 45.61 | 78.39 | 9.93 |
| 1126 | 75.66 | 46.02 | 95.13 | 2.72 |
| 1127 | 20.86 | 10.19 | 92.15 | 2.29 |
| 1128 | 42.25 | 26.90 | 86.93 | 2.85 |
| 1129 | 54.36 | 28.19 | 68.77 | 3.54 |
| 1130 | 31.93 | 37.43 | 70.45 | 16.11 |
| 1131 | 95.19 | 29.40 | 75.57 | 5.67 |
| 1132 | 81.62 | 79.10 | 91.26 | 9.12 |
| 1133 | 108.84 | 55.84 | 77.29 | 3.93 |
| 1134 | 127.97 | 61.53 | 87.25 | 4.27 |
| 1135 | 23.88 | 14.58 | 88.69 | 7.68 |
| 1136 | 135.61 | 107.37 | 90.51 | 6.21 |
| 1137 | 81.62 | 20.83 | 81.10 | 2.01 |
| 1138 | 162.66 | 43.39 | 87.23 | 6.72 |
| 1139 | 19.61 | 16.21 | 74.45 | 17.21 |
| 1140 | 95.37 | 65.43 | 79.69 | 3.47 |
| 1141 | 19.39 | 22.90 | 71.38 | 2.88 |
| 1142 | 112.51 | 47.06 | 44.56 | 1.16 |
| 1143 | 22.65 | 15.92 | 35.07 | 5.31 |
| 1144 | 54.47 | 29.42 | 40.68 | 2.79 |
| 1145 | 76.07 | 29.26 | 63.03 | 1.37 |
| 1146 | 57.84 | 16.27 | 63.23 | 2.23 |
| 1147 | 29.83 | 5.88 | 61.72 | 3.88 |
| 1148 | 108.34 | 37.96 | 88.31 | 7.49 |
| 1149 | 91.14 | 48.85 | 87.19 | 4.82 |
| 1150 | 80.37 | 60.06 | 86.82 | 5.10 |
| 1151 | 164.58 | 54.99 | 77.04 | 9.15 |
| 1152 | 64.86 | 15.33 | 73.68 | 5.75 |
| 1153 | 5.84 | 6.78 | 88.39 | 7.61 |
| 1154 | 48.37 | 23.81 | 69.15 | 8.75 |
| 1155 | 15.30 | 16.30 | 80.19 | 3.27 |
| 1156 | 45.97 | 14.62 | 61.07 | 5.84 |
| 1157 | 16.13 | 9.16 | 71.08 | 5.20 |
| 1158 | 71.35 | 21.49 | 62.57 | 2.33 |
| 1159 | 5.22 | 7.17 | 55.24 | 5.47 |
| 1160 | 54.13 | 38.70 | 59.19 | 6.80 |
| 1161 | 139.82 | 43.35 | 62.93 | 6.77 |
| 1162 | 113.08 | 47.20 | 65.07 | 3.28 |
| 1163 | 68.40 | 22.92 | 70.88 | 3.09 |
| 1164 | 56.66 | 11.40 | 71.68 | 4.36 |
| 1165 | 132.12 | 18.78 | 55.73 | 2.24 |
| 1166 | 152.34 | 64.54 | 77.99 | 11.63 |
| 1167 | 66.71 | 9.04 | 97.27 | 3.14 |
| 1168 | 79.80 | 19.43 | 63.67 | 4.61 |
| 1169 | 122.92 | 44.09 | 56.42 | 3.57 |
| 1170 | 102.53 | 25.36 | 36.74 | 8.23 |
| 1171 | 22.66 | 18.65 | 56.61 | 5.18 |
| 1172 | 28.72 | 45.21 | 88.81 | 1.87 |
| 1173 | 43.63 | 25.28 | 86.99 | 2.38 |
| 1174 | 12.12 | 8.84 | 73.06 | 1.38 |
| 1175 | 29.54 | 28.84 | 74.43 | 3.29 |
| 1176 | 8.56 | 6.69 | 67.72 | 1.00 |
| 1177 | 4.00 | 4.76 | 73.09 | 1.36 |
| 1178 | 63.78 | 64.46 | 83.07 | 5.92 |
| 1179 | 3.70 | 4.31 | 97.79 | 6.98 |
| 1180 | 56.10 | 21.93 | 81.47 | 3.48 |
| 1181 | 24.74 | 5.02 | 85.44 | 3.70 |
| 1182 | 19.03 | 13.70 | 87.44 | 3.10 |
| 1183 | 37.61 | 20.83 | 88.76 | 3.89 |
| 1184 | 73.49 | 29.98 | 88.36 | 8.64 |
| 1185 | 20.89 | 24.87 | 80.02 | 2.80 |
| 1186 | 367.36 | 51.59 | 94.79 | 1.74 |
| 1187 | 61.19 | 47.91 | 95.94 | 5.37 |
| 1188 | 295.07 | 157.07 | 88.71 | 8.66 |
| 1189 | 73.15 | 20.59 | 83.26 | 3.40 |
| 1190 | 41.79 | 11.57 | 96.27 | 5.13 |
| 1191 | 164.47 | 26.62 | 95.11 | 5.87 |
| 1192 | 279.74 | 44.36 | 95.64 | 5.72 |
| 1193 | 3.56 | 4.12 | 22.74 | 5.62 |
| 1194 | 6.20 | 4.98 | 76.71 | 5.36 |
| 1195 | 220.50 | 31.52 | 95.66 | 1.42 |
| 1196 | 163.15 | 61.18 | 98.07 | 5.41 |
| 1197 | 168.54 | 57.19 | 88.24 | 5.23 |
| 1198 | 104.02 | 107.63 | 64.75 | 6.94 |
| 1199 | 110.78 | 185.02 | 57.55 | 16.22 |
| 1200 | 198.48 | 143.78 | 74.03 | 2.65 |
| 1201 | 49.55 | 8.88 | 74.59 | 3.58 |
| 1202 | 141.08 | 14.92 | 72.91 | 1.86 |
| 1203 | 119.23 | 24.50 | 73.09 | 3.80 |
| 1204 | 76.87 | 18.94 | 55.98 | 1.04 |
| 1205 | 114.55 | 54.85 | 86.42 | 4.09 |
| 1206 | 80.15 | 38.98 | 83.74 | 4.76 |
| 1207 | 275.25 | 33.11 | 87.06 | 4.15 |
| 1208 | 380.09 | 155.89 | 70.93 | 1.12 |
| 1209 | 21.73 | 11.78 | 91.26 | 4.51 |
| 1210 | 26.56 | 31.06 | 62.70 | 8.41 |

TABLE 2-continued

Results of assays

| Compound number | Average Number of hTERT Transcripts | Number of hTERT Transcripts Standard Deviation | Average Cell Viability after 24 Hours (% DMSO) | Cell Viability after 24 Hours Standard Deviation |
|---|---|---|---|---|
| 1211 | 52.31 | 64.62 | 81.77 | 5.00 |
| 1212 | 38.44 | 52.53 | 80.54 | 4.02 |
| 1213 | 5.90 | 4.57 | 69.85 | 4.54 |
| 1214 | 32.75 | 18.83 | 55.08 | 3.18 |
| 1215 | 7.76 | 6.11 | 52.19 | 2.90 |
| 1216 | 5.19 | 6.27 | 42.91 | 6.71 |
| 1217 | 10.04 | 7.11 | 45.00 | 5.92 |
| 1218 | 3.35 | 3.93 | 82.36 | 5.88 |
| 1219 | 14.25 | 8.63 | 56.01 | 2.91 |
| 1220 | 6.37 | 5.08 | 48.07 | 3.51 |
| 1221 | 68.62 | 9.33 | 86.33 | 13.52 |
| 1222 | 15.04 | 24.18 | 102.27 | 5.78 |
| 1223 | 24.63 | 28.47 | 44.16 | 3.00 |
| 1224 | 89.52 | 10.04 | Not Tested | Not Tested |
| 1225 | 88.29 | 21.13 | 37.89 | 2.68 |
| 1226 | 31.01 | 38.01 | 77.96 | 1.07 |
| 1227 | 72.86 | 12.22 | 77.50 | 1.02 |
| 1228 | 48.23 | 25.29 | 73.46 | 1.88 |
| 1229 | 17.57 | 6.80 | 79.23 | 5.16 |
| 1230 | 17.54 | 16.66 | 72.00 | 3.43 |
| 1231 | 61.08 | 42.37 | 37.70 | 0.97 |
| 1232 | 23.68 | 6.07 | 112.57 | 17.63 |
| 1233 | 41.94 | 13.29 | 61.61 | 4.07 |
| 1234 | 62.81 | 46.71 | 53.62 | 5.60 |
| 1235 | 153.66 | 23.13 | 75.75 | 0.85 |
| 1236 | 5.24 | 6.85 | 86.61 | 6.56 |
| 1237 | 43.79 | 16.11 | 71.28 | 2.34 |
| 1238 | 5.16 | 6.64 | 89.10 | 6.57 |
| 1239 | 31.94 | 32.44 | 66.47 | 10.00 |
| 1240 | 19.66 | 30.17 | 66.43 | 6.22 |
| 1241 | 39.79 | 32.55 | 77.91 | 4.37 |
| 1242 | 56.42 | 36.28 | 80.60 | 13.34 |
| 1243 | 5.18 | 6.10 | 99.98 | 2.33 |
| 1244 | 9.34 | 14.02 | 80.52 | 3.50 |
| 1245 | 8.42 | 7.49 | 79.22 | 10.39 |
| 1246 | 27.65 | 6.55 | 83.08 | 9.43 |
| 1247 | 74.16 | 52.54 | 95.77 | 0.69 |
| 1248 | 4.69 | 3.14 | 57.47 | 8.27 |
| 1249 | 27.87 | 25.28 | 77.92 | 3.41 |
| 1250 | 184.64 | 33.04 | 67.25 | 12.25 |
| 1251 | 23.22 | 20.84 | 65.10 | 5.68 |
| 1252 | 4.21 | 5.16 | 96.63 | 1.86 |
| 1253 | 3.09 | 3.57 | 91.13 | 3.08 |
| 1254 | 47.45 | 19.68 | 66.42 | 2.65 |
| 1255 | 56.91 | 14.73 | 76.32 | 2.48 |
| 1256 | 33.82 | 10.86 | 73.30 | 3.34 |
| 1257 | 37.50 | 20.24 | 82.05 | 4.04 |
| 1258 | 12.89 | 15.03 | 53.72 | 3.39 |
| 1259 | 10.70 | 3.19 | 60.54 | 5.65 |
| 1260 | 17.25 | 16.58 | 60.48 | 6.03 |
| 1261 | 40.28 | 29.33 | 85.18 | 2.73 |
| 1262 | 8.78 | 6.64 | 57.61 | 8.60 |
| 1263 | 53.36 | 74.68 | 64.51 | 4.03 |
| 1264 | 33.41 | 23.10 | 64.22 | 3.85 |
| 1265 | 4.42 | 5.38 | 81.94 | 3.50 |
| 1266 | 14.59 | 10.31 | 50.17 | 2.87 |
| 1267 | 3.76 | 4.41 | 38.10 | 3.37 |
| 1268 | 14.70 | 4.26 | 80.84 | 5.49 |
| 1269 | 93.93 | 57.44 | 68.44 | 2.92 |
| 1270 | 34.64 | 25.01 | 59.66 | 4.31 |
| 1271 | 38.63 | 14.54 | 57.70 | 0.59 |
| 1272 | 33.61 | 16.33 | 57.10 | 4.00 |
| 1273 | 40.65 | 31.57 | 75.55 | 1.52 |
| 1274 | 20.59 | 10.47 | 75.52 | 4.13 |
| 1275 | 127.83 | 69.95 | 71.98 | 1.96 |
| 1276 | 9.73 | 9.66 | 92.70 | 5.04 |
| 1277 | 24.11 | 34.00 | 68.53 | 4.98 |
| 1278 | 35.46 | 13.32 | 74.57 | 1.74 |
| 1279 | 25.71 | 16.18 | 63.90 | 3.32 |
| 1280 | 9.80 | 2.95 | 59.52 | 8.06 |
| 1281 | 8.35 | 7.61 | 56.81 | 2.17 |
| 1282 | 27.61 | 10.42 | 68.67 | 1.70 |
| 1283 | 18.81 | 5.40 | 68.25 | 1.96 |
| 1284 | 44.70 | 22.02 | 73.23 | 1.51 |
| 1285 | 97.75 | 53.38 | 65.50 | 0.98 |
| 1286 | 29.62 | 8.52 | 75.11 | 2.18 |
| 1287 | 12.08 | 14.00 | 67.01 | 4.65 |
| 1288 | 18.81 | 7.24 | 78.28 | 4.51 |
| 1289 | 21.50 | 9.03 | 84.79 | 3.61 |
| 1290 | 9.13 | 9.11 | 62.81 | 5.52 |
| 1291 | 47.89 | 8.94 | 77.64 | 3.94 |
| 1292 | 39.11 | 11.38 | 69.51 | 4.54 |
| 1293 | 37.88 | 31.25 | 89.97 | 4.50 |
| 1294 | 105.99 | 90.78 | 74.63 | 2.83 |
| 1295 | 45.40 | 18.10 | 66.62 | 5.50 |
| 1296 | 60.31 | 18.77 | 73.20 | 4.65 |
| 1297 | 40.67 | 18.56 | 103.22 | 1.62 |
| 1298 | 8.68 | 12.07 | 101.83 | 3.65 |
| 1299 | 2.95 | 3.41 | 69.64 | 3.36 |
| 1300 | 6.98 | 5.53 | 62.52 | 1.38 |
| 1301 | 65.14 | 16.23 | 63.90 | 1.60 |
| 1302 | 41.43 | 9.76 | 70.75 | 5.39 |
| 1303 | 4.51 | 5.85 | 80.90 | 3.34 |
| 1304 | 59.37 | 33.89 | 89.74 | 3.11 |
| 1305 | 90.46 | 99.10 | 67.59 | 6.75 |
| 1306 | 8.36 | 13.09 | 97.90 | 8.08 |
| 1307 | 8.66 | 4.17 | 80.83 | 4.67 |
| 1308 | 3.16 | 3.65 | 90.12 | 3.12 |
| 1309 | 10.58 | 13.79 | 119.29 | 1.99 |
| 1310 | 5.00 | 6.14 | 105.11 | 4.91 |
| 1311 | 4.38 | 5.36 | 92.83 | 1.72 |
| 1312 | 51.29 | 33.19 | 67.76 | 8.80 |
| 1313 | 7.45 | 9.17 | 112.79 | 3.00 |
| 1314 | 8.82 | 11.17 | 109.57 | 5.67 |
| 1315 | 26.20 | 20.65 | 58.86 | 2.16 |
| 1316 | 13.39 | 17.06 | 73.91 | 13.32 |
| 1317 | 10.56 | 9.77 | 88.17 | 6.60 |
| 1318 | 13.40 | 2.52 | 59.35 | 7.15 |
| 1319 | 15.04 | 11.08 | 61.93 | 13.18 |
| 1320 | 8.00 | 6.35 | 90.39 | 5.08 |
| 1321 | 22.30 | 16.98 | 124.73 | 4.62 |
| 1322 | 20.10 | 10.66 | 81.69 | 8.98 |
| 1323 | 11.00 | 8.30 | 121.47 | 4.39 |
| 1324 | 8.42 | 10.38 | 57.19 | 3.90 |
| 1325 | 29.36 | 29.87 | 94.20 | 3.95 |
| 1326 | 8.73 | 8.13 | 86.99 | 2.94 |
| 1327 | 4.67 | 6.10 | 101.34 | 5.08 |
| 1328 | 5.42 | 7.49 | 71.81 | 0.67 |
| 1329 | 3.63 | 4.25 | 94.31 | 1.43 |
| 1330 | 3.59 | 4.26 | 97.84 | 7.48 |
| 1331 | 32.92 | 19.31 | 90.44 | 3.33 |
| 1332 | 12.68 | 10.68 | 94.78 | 6.92 |
| 1333 | 3.71 | 4.29 | 96.79 | 6.79 |
| 1334 | 31.04 | 4.77 | 75.50 | 10.49 |
| 1335 | 11.78 | 9.07 | 75.24 | 3.75 |
| 1336 | 7.64 | 6.01 | 100.05 | 4.11 |
| 1337 | 30.15 | 9.70 | 67.33 | 8.12 |
| 1338 | 49.42 | 7.23 | 80.45 | 9.94 |
| 1339 | 7.09 | 6.23 | 68.94 | 4.74 |
| 1340 | 4.37 | 5.15 | 106.88 | 4.67 |
| 1341 | 4.50 | 5.30 | 110.20 | 6.14 |
| 1342 | 4.48 | 5.21 | 103.16 | 5.93 |
| 1343 | 4.57 | 5.90 | 103.75 | 1.95 |
| 1344 | 7.86 | 6.86 | 42.95 | 7.64 |
| 1345 | 24.88 | 12.22 | 45.42 | 6.40 |
| 1346 | 31.23 | 17.87 | 56.33 | 7.27 |
| 1347 | 12.01 | 8.13 | 118.20 | 1.84 |
| 1348 | 5.97 | 7.92 | 106.19 | 4.53 |
| 1349 | 12.52 | 8.56 | 76.50 | 4.86 |
| 1350 | 5.91 | 6.99 | 98.43 | 7.45 |
| 1351 | 5.17 | 6.16 | 98.19 | 3.68 |
| 1352 | 5.61 | 7.37 | 83.84 | 3.66 |
| 1353 | 3.61 | 4.37 | 87.98 | 7.75 |
| 1354 | 14.31 | 13.44 | 96.80 | 5.34 |

TABLE 2-continued

Results of assays

| Compound number | Average Number of hTERT Transcripts | Number of hTERT Transcripts Standard Deviation | Average Cell Viability after 24 Hours (% DMSO) | Cell Viability after 24 Hours Standard Deviation |
|---|---|---|---|---|
| 1355 | 4.95 | 5.91 | 95.78 | 4.15 |
| 1356 | 5.18 | 6.68 | 101.39 | 2.91 |
| 1357 | 9.07 | 2.60 | 95.29 | 2.51 |
| 1358 | 7.53 | 8.75 | 111.88 | 6.28 |
| 1359 | 13.21 | 16.91 | 104.81 | 6.09 |
| 1360 | 16.98 | 5.72 | 108.82 | 7.33 |
| 1361 | 17.57 | 8.83 | 109.24 | 5.90 |
| 1362 | 15.20 | 8.47 | 75.90 | 4.65 |
| 1363 | 32.11 | 23.63 | 89.56 | 10.42 |
| 1364 | 9.06 | 11.13 | 104.57 | 4.76 |
| 1365 | 10.67 | 14.52 | 99.89 | 2.70 |
| 1366 | 10.02 | 6.81 | 99.48 | 4.26 |
| 1367 | 7.25 | 8.40 | 94.27 | 9.94 |
| 1368 | 9.25 | 10.49 | 106.63 | 6.32 |
| 1369 | 15.35 | 15.37 | 98.38 | 0.97 |
| 1370 | 11.58 | 9.96 | 107.18 | 4.30 |
| 1371 | 5.46 | 7.49 | 105.87 | 2.73 |
| 1372 | 5.43 | 7.44 | 94.06 | 2.67 |
| 1373 | 37.20 | 13.90 | 65.74 | 3.56 |
| 1374 | 5.48 | 7.30 | 107.65 | 5.16 |
| 1375 | 11.45 | 10.74 | 92.06 | 12.61 |
| 1376 | 4.72 | 6.08 | 88.77 | 11.44 |
| 1377 | 10.23 | 7.57 | 67.09 | 3.31 |
| 1378 | 11.15 | 9.57 | 89.06 | 2.77 |
| 1379 | 12.37 | 14.38 | 82.14 | 2.30 |
| 1380 | 5.98 | 7.49 | 104.34 | 2.80 |
| 1381 | 8.62 | 6.62 | 87.38 | 5.39 |
| 1382 | 6.08 | 7.24 | 98.31 | 4.64 |
| 1383 | 53.78 | 22.61 | 74.00 | 3.00 |
| 1384 | 7.88 | 9.71 | 84.52 | 3.66 |
| 1385 | 21.71 | 4.37 | 78.86 | 3.07 |
| 1386 | 11.93 | 11.28 | 30.71 | 10.55 |
| 1387 | 9.00 | 13.97 | 100.57 | 5.93 |
| 1388 | 42.56 | 27.21 | 29.68 | 1.37 |
| 1389 | 9.17 | 11.78 | 93.93 | 9.56 |
| 1390 | 4.81 | 6.32 | 106.51 | 1.50 |
| 1391 | 4.95 | 6.36 | 87.67 | 17.46 |
| 1392 | 4.99 | 6.04 | 102.61 | 2.51 |
| 1393 | 23.22 | 20.29 | 62.25 | 7.30 |
| 1394 | 7.00 | 8.19 | 100.14 | 3.87 |
| 1395 | 39.44 | 15.41 | 63.84 | 0.83 |
| 1396 | 12.14 | 4.36 | 88.25 | 4.91 |
| 1397 | 5.00 | 6.52 | 96.05 | 8.88 |
| 1398 | 8.01 | 6.02 | 87.02 | 10.64 |
| 1399 | 5.19 | 6.42 | 70.99 | 2.33 |
| 1400 | 12.41 | 10.74 | 80.39 | 1.32 |
| 1401 | 7.24 | 8.36 | 96.20 | 7.71 |
| 1402 | 29.82 | 12.71 | 86.55 | 3.27 |
| 1403 | 9.95 | 8.54 | 95.26 | 3.22 |
| 1404 | 10.87 | 10.44 | 104.14 | 4.14 |
| 1405 | 3.33 | 3.92 | 110.82 | 7.02 |
| 1406 | 4.62 | 6.09 | 105.29 | 9.64 |
| 1407 | 3.38 | 3.91 | 109.75 | 8.43 |
| 1408 | 3.47 | 4.02 | 89.70 | 5.98 |
| 1409 | 18.63 | 6.03 | 86.13 | 3.64 |
| 1410 | 8.90 | 8.43 | 75.12 | 2.31 |
| 1411 | 10.04 | 9.85 | 92.66 | 4.58 |
| 1412 | 6.19 | 7.69 | 92.98 | 4.01 |
| 1413 | 25.20 | 11.03 | 80.11 | 5.59 |
| 1414 | 203.88 | 44.48 | 69.42 | 4.07 |
| 1415 | 30.51 | 20.34 | 79.96 | 5.84 |
| 1416 | 15.42 | 10.72 | 95.26 | 10.09 |
| 1417 | 5.13 | 6.02 | 92.17 | 7.45 |
| 1418 | 42.80 | 19.53 | 94.19 | 4.23 |
| 1419 | 5.40 | 6.57 | 87.51 | 3.17 |
| 1420 | 57.36 | 19.89 | 73.35 | 5.92 |
| 1421 | 6.96 | 8.24 | 104.42 | 4.13 |
| 1422 | 19.95 | 5.65 | 102.65 | 8.25 |
| 1423 | 8.22 | 6.61 | 99.62 | 2.66 |
| 1424 | 37.45 | 18.17 | 94.37 | 7.10 |
| 1425 | 17.07 | 16.56 | 79.15 | 1.46 |
| 1426 | 8.07 | 9.62 | 84.07 | 4.94 |
| 1427 | 5.16 | 6.09 | 107.40 | 6.01 |
| 1428 | 7.81 | 6.98 | 92.20 | 4.91 |
| 1429 | 13.70 | 15.72 | 83.97 | 5.38 |
| 1430 | 23.55 | 11.47 | 88.00 | 4.00 |
| 1431 | 9.12 | 12.44 | 100.20 | 1.36 |
| 1432 | 19.46 | 10.04 | 86.95 | 11.74 |
| 1433 | 45.43 | 21.15 | 75.77 | 13.30 |
| 1434 | 25.17 | 3.93 | 72.00 | 12.00 |
| 1435 | 48.10 | 25.86 | 60.23 | 6.46 |
| 1436 | 8.14 | 6.42 | 82.48 | 9.23 |
| 1437 | 22.13 | 4.32 | 79.26 | 6.38 |
| 1438 | 8.29 | 6.42 | 97.89 | 4.45 |
| 1439 | 11.63 | 10.14 | 51.61 | 9.44 |
| 1440 | 13.85 | 4.70 | 99.11 | 3.17 |
| 1441 | 5.06 | 6.33 | 101.03 | 2.27 |
| 1442 | 7.65 | 8.97 | 84.87 | 2.76 |
| 1443 | 7.82 | 9.03 | 77.16 | 5.14 |
| 1444 | 16.54 | 3.29 | 64.02 | 15.46 |
| 1445 | 6.33 | 8.29 | 87.20 | 4.47 |
| 1446 | 46.62 | 31.93 | 65.61 | 3.17 |
| 1447 | 5.30 | 7.04 | 96.56 | 4.56 |
| 1448 | 10.17 | 3.01 | 96.46 | 1.31 |
| 1449 | 48.57 | 13.53 | 53.58 | 4.25 |
| 1450 | 8.24 | 6.67 | 96.61 | 3.43 |
| 1451 | 5.80 | 8.29 | 96.84 | 2.96 |
| 1452 | 7.45 | 6.63 | 81.09 | 4.43 |
| 1453 | 11.03 | 12.70 | 97.19 | 2.13 |
| 1454 | 3.99 | 4.73 | 97.09 | 4.03 |
| 1455 | 130.06 | 26.28 | 84.96 | 5.64 |
| 1456 | 92.07 | 66.43 | 57.96 | 1.51 |
| 1457 | 12.20 | 7.16 | 57.76 | 10.86 |
| 1458 | 10.26 | 7.15 | 62.79 | 6.05 |
| 1459 | 11.14 | 13.09 | 72.75 | 12.16 |
| 1460 | 46.47 | 51.81 | 89.11 | 5.21 |
| 1461 | 29.65 | 36.07 | 55.44 | 1.02 |
| 1462 | 7.97 | 6.04 | 62.26 | 4.98 |
| 1463 | 174.29 | 71.94 | 62.06 | 3.49 |
| 1464 | 18.97 | 9.56 | 67.60 | 1.37 |
| 1465 | 20.29 | 13.61 | 80.62 | 2.39 |
| 1466 | 97.31 | 46.28 | 75.47 | 6.92 |
| 1467 | 108.02 | 96.08 | 79.50 | 6.51 |
| 1468 | 95.88 | 39.86 | 72.48 | 5.36 |
| 1469 | 59.72 | 54.24 | 60.18 | 1.23 |
| 1470 | 13.16 | 19.21 | 43.17 | 2.71 |
| 1471 | 148.88 | 19.15 | 90.01 | 18.20 |
| 1472 | 76.60 | 22.82 | 82.14 | 3.94 |
| 1473 | 32.72 | 11.77 | 69.29 | 5.67 |
| 1474 | 17.37 | 12.79 | 80.47 | 7.74 |
| 1475 | 17.56 | 5.10 | 67.26 | 6.17 |
| 1476 | 25.18 | 27.09 | 86.51 | 4.22 |
| 1477 | 31.13 | 15.64 | 76.49 | 5.74 |
| 1478 | 34.36 | 11.36 | 72.44 | 6.90 |
| 1479 | 35.19 | 16.57 | 68.20 | 6.47 |
| 1480 | 35.20 | 40.84 | 79.43 | 4.74 |
| 1481 | 58.99 | 14.91 | 78.30 | 4.17 |
| 1482 | 29.15 | 7.78 | 80.49 | 5.18 |
| 1483 | 5.19 | 6.14 | 81.33 | 7.82 |
| 1484 | 16.52 | 5.61 | 62.51 | 6.83 |
| 1485 | 48.25 | 27.58 | 112.70 | 15.86 |
| 1486 | 51.80 | 39.32 | 73.20 | 6.04 |
| 1487 | 1.93 | 3.86 | 95.31 | 4.15 |
| 1488 | 3.19 | 3.69 | 86.72 | 3.65 |
| 1489 | 3.77 | 3.26 | 107.24 | 4.08 |
| 1490 | 3.91 | 3.40 | 111.59 | 4.21 |
| 1491 | 5.09 | 4.81 | 102.96 | 0.67 |
| 1492 | 6.45 | 5.96 | 91.36 | 5.46 |
| 1493 | 6.84 | 5.20 | 100.09 | 1.32 |
| 1494 | 9.18 | 9.19 | 110.08 | 3.60 |
| 1495 | 10.81 | 7.30 | 85.84 | 2.02 |
| 1496 | 11.43 | 22.87 | 12.76 | 14.36 |
| 1497 | 14.74 | 13.95 | 92.73 | 19.16 |
| 1498 | 16.50 | 13.56 | 94.63 | 4.71 |

TABLE 2-continued

Results of assays

| Compound number | Average Number of hTERT Transcripts | Number of hTERT Transcripts Standard Deviation | Average Cell Viability after 24 Hours (% DMSO) | Cell Viability after 24 Hours Standard Deviation |
|---|---|---|---|---|
| 1499 | 17.01 | 17.04 | 119.54 | 3.63 |
| 1500 | 17.14 | 2.98 | 110.86 | 4.23 |
| 1501 | 24.13 | 9.59 | 99.31 | 3.41 |
| 1502 | 28.74 | 13.81 | 91.65 | 1.32 |
| 1503 | 28.94 | 15.72 | 108.11 | 3.06 |
| 1504 | 40.27 | 7.39 | 76.43 | 2.59 |
| 1505 | 43.28 | 8.17 | 70.89 | 4.93 |
| 1506 | 52.39 | 23.75 | 84.31 | 1.83 |
| 1507 | 58.76 | 38.92 | 102.58 | 7.65 |
| 1508 | 59.45 | 22.44 | 94.22 | 5.64 |
| 1509 | 72.08 | 48.02 | 73.34 | 8.05 |
| 1510 | 76.03 | 45.66 | 83.99 | 1.68 |
| 1511 | 88.76 | 34.31 | 75.76 | 20.55 |
| 1512 | 102.66 | 35.49 | 81.39 | 4.34 |
| 1513 | 102.76 | 30.12 | 82.67 | 14.79 |
| 1514 | 102.98 | 5.41 | 98.72 | 1.70 |
| 1515 | 113.63 | 52.62 | 96.89 | 4.02 |
| 1516 | 127.39 | 63.25 | 87.09 | 3.59 |
| 1517 | 140.89 | 22.53 | 112.40 | 3.67 |
| 1518 | 302.69 | 32.49 | 104.12 | 8.12 |
| 1519 | 303.81 | 178.38 | 110.34 | 0.79 |
| 1520 | 322.93 | 136.92 | 98.51 | 7.66 |
| 1521 | 329.90 | 68.35 | 106.64 | 1.01 |
| 1522 | 345.10 | 140.69 | 80.72 | 2.89 |
| 1523 | 513.46 | 126.07 | 87.71 | 0.85 |
| 1524 | 562.51 | 200.08 | 103.34 | 5.41 |
| 1525 | 7.73 | 10.88 | 83.30 | 10.10 |
| 1526 | 8.14 | 5.84 | 79.56 | 8.35 |
| 1527 | 15.53 | 8.41 | 89.01 | 17.44 |
| 1528 | 24.18 | 14.01 | 69.89 | 0.97 |
| 1529 | 29.94 | 15.40 | 102.67 | 1.24 |
| 1530 | 30.46 | 6.83 | 96.99 | 13.67 |
| 1531 | 32.70 | 12.37 | 110.91 | 13.38 |
| 1532 | 4.42 | 2.96 | 88.55 | 6.01 |
| 1533 | 35.76 | 27.57 | 99.57 | 4.18 |
| 1534 | 3.18 | 3.68 | 90.05 | 2.87 |
| 1535 | 3.69 | 4.27 | 88.02 | 4.78 |
| 1536 | 7.34 | 7.32 | 65.12 | 5.58 |
| 1537 | 9.58 | 8.49 | 67.92 | 4.21 |
| 1538 | 10.53 | 14.61 | 74.17 | 5.68 |
| 1539 | 37.11 | 14.37 | 65.11 | 4.90 |
| 1540 | 9.11 | 4.09 | 68.10 | 1.84 |
| 1541 | 3.41 | 3.94 | 104.75 | 3.40 |
| 1542 | 3.43 | 4.10 | 111.82 | 6.25 |
| 1543 | 3.71 | 4.42 | 82.75 | 2.38 |
| 1544 | 3.85 | 4.48 | 104.59 | 2.43 |
| 1545 | 4.40 | 5.21 | 43.72 | 17.14 |
| 1546 | 4.63 | 5.95 | 101.47 | 3.40 |
| 1547 | 5.38 | 3.61 | 86.92 | 3.37 |
| 1548 | 5.77 | 4.24 | 99.62 | 3.32 |
| 1549 | 8.60 | 8.48 | 99.71 | 3.94 |
| 1550 | 12.90 | 15.13 | 96.87 | 5.30 |
| 1551 | 16.60 | 15.92 | 40.32 | 5.98 |
| 1552 | 21.09 | 13.25 | 64.55 | 7.14 |
| 1553 | 23.58 | 11.85 | 77.33 | 3.09 |
| 1554 | 46.62 | 36.87 | 71.31 | 8.52 |
| 1555 | 52.10 | 13.97 | 90.08 | 3.82 |
| 1556 | 85.40 | 37.52 | 90.02 | 8.07 |
| 1557 | 54.80 | 35.45 | 97.77 | 17.35 |

Although the particular embodiments have been described in some detail by way of illustration and example for purposes of clarity of understanding, it is readily apparent in light of the teachings of this invention that certain changes and modifications may be made thereto without departing from the spirit or scope of the appended claims.

Accordingly, the preceding merely illustrates the principles of the invention. Various arrangements may be devised which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method for enhancing telomerase reverse transcriptase (TERT) expression in an individual, the method comprising:

administering to the individual an azole compound described by one of the following structures:

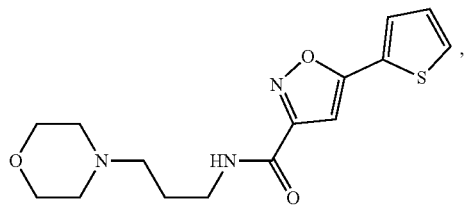

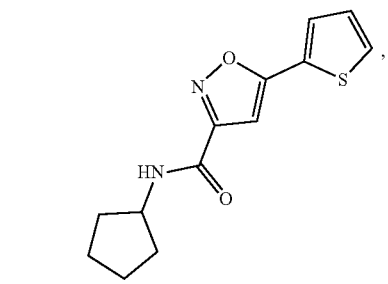

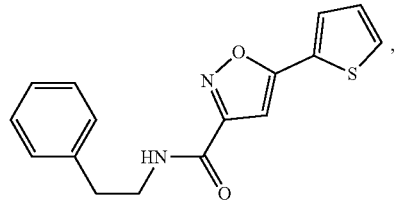

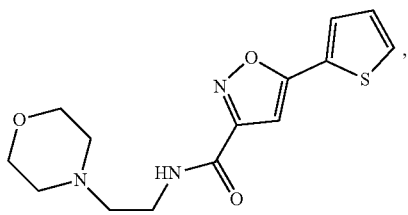

-continued

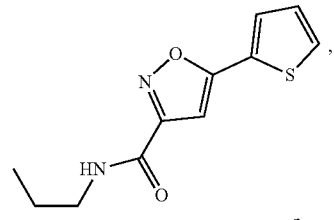

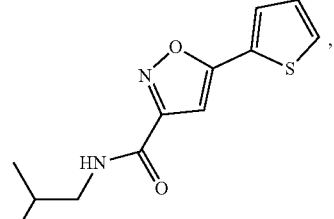

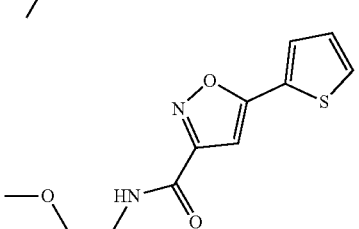

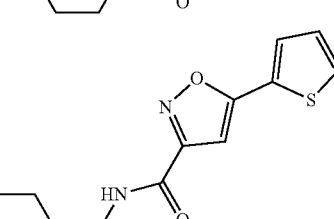

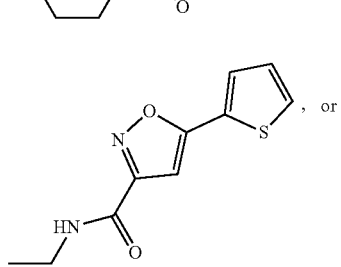

-continued

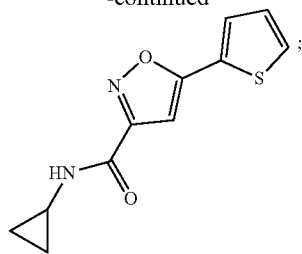

determining the amount of expression of TERT in a cell of the individual after administration with the compound.

2. The method according to claim 1, wherein the proliferative capacity of one or more cells of the individual is increased.

3. The method according to claim 1, wherein senescence of one or more cells of the individual is delayed.

4. The method according to claim 1, wherein the azole compound is described by one of the following structures:

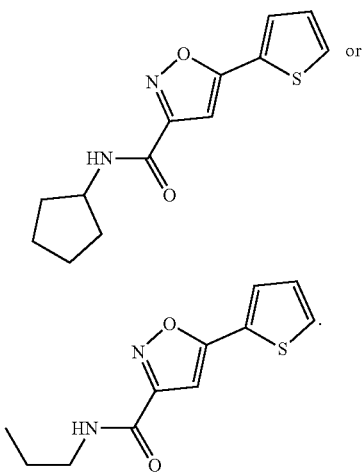

* * * * *

UNITED STATES PATENT AND TRADEMARK OFFICE
CERTIFICATE OF CORRECTION

| | |
|---|---|
| PATENT NO. | : 12,404,304 B1 |
| APPLICATION NO. | : 16/879075 |
| DATED | : September 2, 2025 |
| INVENTOR(S) | : William H. Andrews et al. |

It is certified that error appears in the above-identified patent and that said Letters Patent is hereby corrected as shown below:

In the Specification

Please move ""Cyano" refers to a -CN group." (Column 3, Lines 37-38) as an independent paragraph (Column 3, Line 38).

Please replace "LBP1 b." with -- LBP1b. -- (Column 8, Line 15).

Please replace "$R_{10}$," with -- $R^{10}$, -- (Column 15, Line 27).

Please replace "$R_{10}$," with -- $R^{10}$, -- (Column 15, Line 31).

Please replace "$R^{II}$" with -- $R^{11}$ -- (Column 15, Line 31).

Please replace "$R_{10}$," with -- $R^{10}$, -- (Column 15, Line 36).

Please replace "$R^{II}$" with -- $R^{11}$ -- (Column 15, Line 36).

Please replace "$R_{10}$," with -- $R^{10}$, -- (Column 15, Line 39).

Please replace "$R^{II}$" with -- $R^{11}$ -- (Column 15, Line 39).

Please replace " 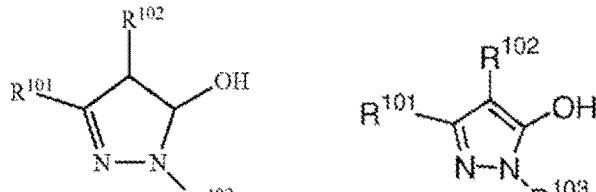 " with -- 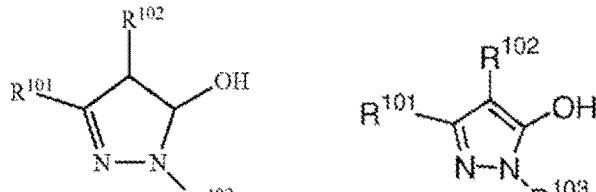 -- (Column 18, Lines 36-43).

Please replace "$R^{21}$," with -- $R^{211}$, -- (Column 28, Line 28).

Signed and Sealed this
Eighteenth Day of November, 2025

John A. Squires
*Director of the United States Patent and Trademark Office*

CERTIFICATE OF CORRECTION (continued)
U.S. Pat. No. 12,404,304 B1

Please replace "$R^{21}$" with -- $R^{211}$ -- (Column 29, Line 42).

Please replace "$R^{31}$" with -- $R^{311}$ -- (Column 30, Line 48).

Please replace " 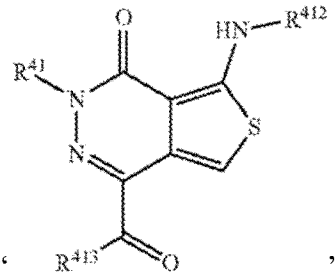 " with -- 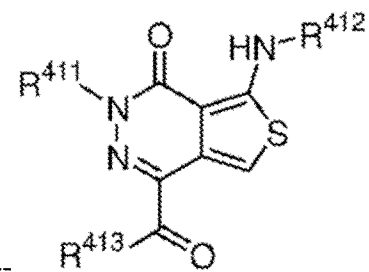 -- (Column 41, Line 5).

In the Claims

Please replace "; determining" in Claim 1 with -- ; and determining -- (Column 291, Lines 2-13).